US010060846B2

(12) United States Patent
Wanders et al.

(10) Patent No.: US 10,060,846 B2
(45) Date of Patent: Aug. 28, 2018

(54) HEMATOLOGY SYSTEMS AND METHODS

(71) Applicant: Iris International, Inc., Chatsworth, CA (US)

(72) Inventors: Bart J. Wanders, Trabuco Canyon, CA (US); Gregory A. Farrell, Ridgewood, NJ (US); Thomas H. Adams, Encinitas, CA (US); Warren Groner, Somers, NY (US); Xiaodong Zhao, San Diego, CA (US); Brett Jordan, Los Angeles, CA (US); Jack Cremins, Waterbury, CT (US); Carol Quon, Newbury Park, CA (US)

(73) Assignee: Iris International, Inc., Brea, CA (US)

( * ) Notice: Subject to any disclaimer, the term of this patent is extended or adjusted under 35 U.S.C. 154(b) by 0 days.

(21) Appl. No.: 15/645,710

(22) Filed: Jul. 10, 2017

(65) Prior Publication Data
US 2017/0370820 A1 Dec. 28, 2017

Related U.S. Application Data

(63) Continuation of application No. 14/775,448, filed as application No. PCT/US2014/030942 on Mar. 18, 2014, now Pat. No. 9,702,806.
(Continued)

(51) Int. Cl.
*G01N 15/14* (2006.01)
*G01N 33/50* (2006.01)
(Continued)

(52) U.S. Cl.
CPC .......... *G01N 15/1404* (2013.01); *G01N 1/30* (2013.01); *G01N 15/147* (2013.01);
(Continued)

(58) Field of Classification Search
CPC ........... G01N 15/1468; G01N 15/1459; G01N 15/1404; G01N 15/1434
(Continued)

(56) References Cited

U.S. PATENT DOCUMENTS 3,819,270 A * 6/1974 Hirschfeld ............... G01N 1/38
356/343
3,822,095 A * 7/1974 Hirschfeld ......... G01N 15/1434
250/573
(Continued)

FOREIGN PATENT DOCUMENTS

CA 2349995 A1 12/2001
EP 0286088 A2 10/1988
(Continued)

OTHER PUBLICATIONS

JP 2016-502595 filed Mar. 18, 2014, received an office action dated Jan. 9, 2018, 20 pages.
(Continued)

*Primary Examiner* — Roy M Punnoose
(74) *Attorney, Agent, or Firm* — Kilpatrick Townsend & Stockton LLP

(57) ABSTRACT

Aspects and embodiments of the instant disclosure provide a particle and/or intracellular organelle alignment agent for a particle analyzer used to analyze particles contained in a sample. An exemplary particle and/or intracellular organelle alignment agent includes an aqueous solution, a viscosity modifier, and/or a buffer. Embodiments also encompass systems, compositions, and methods for analyzing a sample containing particles. Parrticles such as blood cells can be categorized and counted by a digital image processor. A digital microscope camera can be directed, for example using certain focusing techniques, into a flowcell defining a symmetrically narrowing flowpath in which the sample stream flows in a ribbon flattened by flow and viscosity
(Continued)

parameters between layers of sheath fluid. Blood cell images can be collected and analyzed using dynamic range extension processes and systems.

20 Claims, 60 Drawing Sheets

Related U.S. Application Data

(60) Provisional application No. 61/799,152, filed on Mar. 15, 2013.

(51) Int. Cl.
    *G01N 33/49* (2006.01)
    *G01N 21/53* (2006.01)
    *G01N 1/30* (2006.01)
    *G01N 33/80* (2006.01)
    G01N 21/05 (2006.01)
    G01N 15/10 (2006.01)
    G01N 15/00 (2006.01)

(52) U.S. Cl.
    CPC ..... *G01N 15/1434* (2013.01); *G01N 15/1463* (2013.01); *G01N 15/1468* (2013.01); *G01N 15/1475* (2013.01); *G01N 21/53* (2013.01); *G01N 33/49* (2013.01); *G01N 33/4915* (2013.01); *G01N 33/5091* (2013.01); *G01N 33/5094* (2013.01); *G01N 33/80* (2013.01); G01N 2015/0065 (2013.01); G01N 2015/1037 (2013.01); G01N 2015/1411 (2013.01); G01N 2015/1413 (2013.01); G01N 2015/1452 (2013.01); G01N 2015/1486 (2013.01); G01N 2021/058 (2013.01)

(58) Field of Classification Search
    USPC .......................................................... 356/39
    See application file for complete search history.

(56) References Cited

U.S. PATENT DOCUMENTS

| | | | |
|---|---|---|---|
| 4,338,024 A | 7/1982 | Bolz et al. | |
| 4,393,466 A | 7/1983 | Deindorfer et al. | |
| 4,428,669 A * | 1/1984 | Bessis | G01N 15/0205 356/39 |
| 4,606,631 A * | 8/1986 | Anno | G01N 15/1404 250/574 |
| 4,732,479 A | 3/1988 | Tanaka et al. | |
| 5,007,732 A * | 4/1991 | Ohki | G01N 15/1404 356/39 |
| 5,159,403 A * | 10/1992 | Kosaka | G01N 15/1459 250/201.2 |
| 5,412,466 A * | 5/1995 | Ogino | G01N 15/1404 356/246 |
| 5,436,978 A | 7/1995 | Kasdan | |
| 5,457,526 A | 10/1995 | Kosaka | |
| 5,585,246 A | 12/1996 | Dubrow et al. | |
| 5,619,032 A | 4/1997 | Kasdan | |
| 5,633,503 A | 5/1997 | Kosaka | |
| 5,690,895 A * | 11/1997 | Matsumoto | G01N 15/1404 356/246 |
| 5,812,419 A | 9/1998 | Chupp et al. | |
| 5,822,447 A | 10/1998 | Kasdan | |
| 5,880,835 A * | 3/1999 | Yamazaki | G01N 15/147 356/336 |
| 6,184,978 B1 | 2/2001 | Kasdan et al. | |
| 6,424,415 B1 | 7/2002 | Kasdan et al. | |
| 6,441,894 B1 | 8/2002 | Manian et al. | |
| 6,590,646 B2 | 7/2003 | Kasdan et al. | |
| 6,825,926 B2 | 11/2004 | Turner et al. | |
| 6,947,586 B2 | 9/2005 | Kasdan et al. | |
| 7,041,952 B2 | 5/2006 | Iffland et al. | |
| 7,071,451 B2 | 7/2006 | Ishikawa et al. | |
| 7,236,623 B2 | 6/2007 | Chapoulaud et al. | |
| 7,319,907 B2 | 1/2008 | Kasdan et al. | |
| 7,324,694 B2 | 1/2008 | Chapoulaud et al. | |
| 7,486,329 B2 | 2/2009 | Endo | |
| 7,822,276 B2 | 10/2010 | Turner et al. | |
| 7,825,360 B2 | 11/2010 | Karasawa et al. | |
| 7,855,831 B2 | 12/2010 | Wolleschensky et al. | |
| 8,174,686 B2 | 5/2012 | Namba et al. | |
| 8,362,409 B2 | 1/2013 | Cooper et al. | |
| 9,316,635 B2 * | 4/2016 | Farrell | G01N 33/5091 |
| 9,322,752 B2 * | 4/2016 | Wanders | G01N 33/5094 |
| 9,702,806 B2 | 7/2017 | Wanders et al. | |
| 2004/0070757 A1 * | 4/2004 | Moore | G01N 15/1404 356/339 |
| 2004/0180444 A1 | 9/2004 | Rannikko et al. | |
| 2005/0180885 A1 | 8/2005 | Tateishi | |
| 2006/0050946 A1 | 3/2006 | Mitchison | |
| 2006/0148028 A1 | 7/2006 | Noda et al. | |
| 2007/0209938 A1 | 9/2007 | Zhang | |
| 2008/0019584 A1 | 1/2008 | Lindberg et al. | |
| 2008/0138852 A1 | 6/2008 | Winkelman et al. | |
| 2008/0283722 A1 | 11/2008 | Uchiyama et al. | |
| 2009/0011430 A1 | 1/2009 | Ateya et al. | |
| 2009/0269799 A1 | 10/2009 | Winkelman et al. | |
| 2010/0178666 A1 | 7/2010 | Leshansky et al. | |
| 2010/0284602 A1 | 11/2010 | Winkelman et al. | |
| 2011/0014645 A1 | 1/2011 | Winkelman et al. | |
| 2011/0070606 A1 | 3/2011 | Winkelman et al. | |
| 2012/0035061 A1 | 2/2012 | Bransky et al. | |
| 2012/0301883 A1 | 11/2012 | Pagano et al. | |
| 2013/0070249 A1 | 3/2013 | Choi et al. | |
| 2014/0273067 A1 * | 9/2014 | Wanders | G01N 33/5094 435/29 |
| 2014/0273068 A1 * | 9/2014 | Wanders | G01N 33/5094 435/29 |
| 2014/0273076 A1 | 9/2014 | Adams et al. | |
| 2014/0315238 A1 * | 10/2014 | Farrell | G01N 15/1468 435/29 |
| 2014/0329265 A1 * | 11/2014 | Wanders | G01N 15/1468 435/29 |

FOREIGN PATENT DOCUMENTS

| | | |
|---|---|---|
| EP | 0468100 A1 | 1/1992 |
| EP | 0486747 A2 | 5/1992 |
| EP | 0556971 A2 | 8/1993 |
| EP | 0708334 A2 | 4/1996 |
| EP | 0949498 A2 | 10/1999 |
| EP | 1264205 A2 | 12/2002 |
| EP | 1761817 A1 | 3/2007 |
| EP | 2028264 A1 | 2/2009 |
| EP | 2030062 A1 | 3/2009 |
| EP | 2083268 A1 | 7/2009 |
| GB | 1557691 A | 12/1979 |
| GB | 2121976 A | 1/1984 |
| GB | 2167880 A | 6/1986 |
| GB | 1471976 A | 4/1997 |
| JP | H04188042 A | 7/1992 |
| JP | H05296915 A | 11/1993 |
| JP | H09089753 A | 4/1997 |
| JP | 2003/005088 A | 1/2003 |
| JP | 2016-519758 A | 7/2016 |
| JP | 2016-520805 A | 7/2016 |
| JP | 2016-520806 A | 7/2016 |
| WO | 97/43620 A1 | 11/1997 |
| WO | 99/05504 A2 | 2/1999 |
| WO | 00/011449 A1 | 2/2000 |
| WO | 01/048455 A2 | 7/2001 |
| WO | 2004/045488 A2 | 6/2003 |
| WO | 2014/146063 A9 | 11/2014 |

OTHER PUBLICATIONS

Anonymous, "Coulter VCS Reticulocyte method", Internet Citation, Oct. 25, 1996, pp. 1-2, retrieved from: www.cyto.purdue.edu/cdroms/cyto2/6/coulter/ss000126.html.

(56) References Cited

OTHER PUBLICATIONS

Cubaud et al.: "High-viscosity fluid threads in weakly diffusive microfluidic systems", New Journal of Physics, Jul. 31, 2009, p. 75029, vol. 11, No. 7, Institute of Physics Publishing, Bristol, GB.
Kachel et al: "Uniform Lateral Orientation, Caused by Flow Forces, or Flat Particles in Flow-Through Systems", Journal of Histochemistry and Cytochemistry, Jan. 1, 1977, pp. 774-780, vol. 25, No. 7, Histochemical Society, New York, NY, US.
Wietzorrek, et al. "A New Multiparameter Flow Cytometer: Optical and Electrical Cell Analysis in Combination With Video Microscopy in Flow", Apr. 1, 1999 retrieved from: http://onlinelibrary.wiley.com/store , 11 pages.
Wu et al: "Rapid Mixing Using Two-Phase Hydraulic Focusing in Microchannels", Biomedical Microdevices, Mar. 1, 2005, pp. 13-20, vol. 7, No. 1, Kluwer Academic Publishes, BO.
International Search Report and Written Opinion of PCT/US/2014/030850 dated Jun. 27, 2014, 22 pages.
International Search Report and Written Opinion of PCT/US2014/030902 dated Jun. 18, 2014, 15 pages.
International Search Report and Written Opinion from PCT/US2014/030928 dated Jun. 18, 2014, 13 pages.
International Search Report and Written Opinion of PCT/US2014/030939 dated Jul. 7, 2014, 15 pages.
Form PCT/ISA 206 from PCT/US2014/030940 dated Jul. 21, 2014, 6 pages.
International Search Report and Written Opinion from PCT/US2014/030940 dated Oct. 23, 2014, 25 pages.
International Search Report and Written Opinion from Patent Application No. PCT/US2014/030942 dated Oct. 14, 2014, 30 pages.
International Preliminary Report on Patentability from Patent Application No. PCT/US2014/030942 dated Sep. 24, 2015, 24 pages.

* cited by examiner

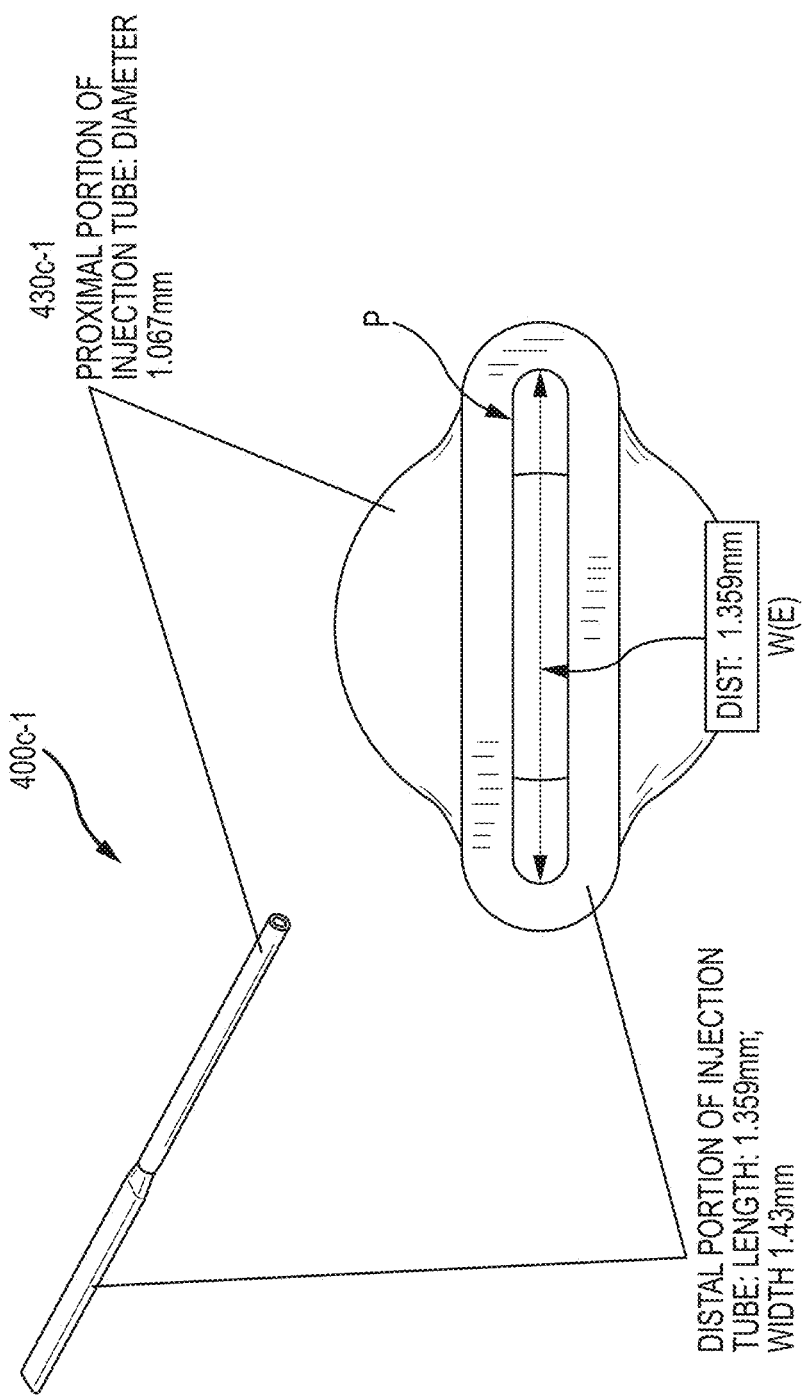

RBCs IN SAMPLE STREAM
WITH CONVENTIONAL SHEATH

RBCs IN SAMPLE STREAM
WITH PIOAL

RBCs IN SAMPLE STREAM AT 20X
MAGNIFICATION WITH CONVENTIONAL SHEATH

RBCs IN SAMPLE STREAM AT 20X
MAGNIFICATION WITH PIOAL

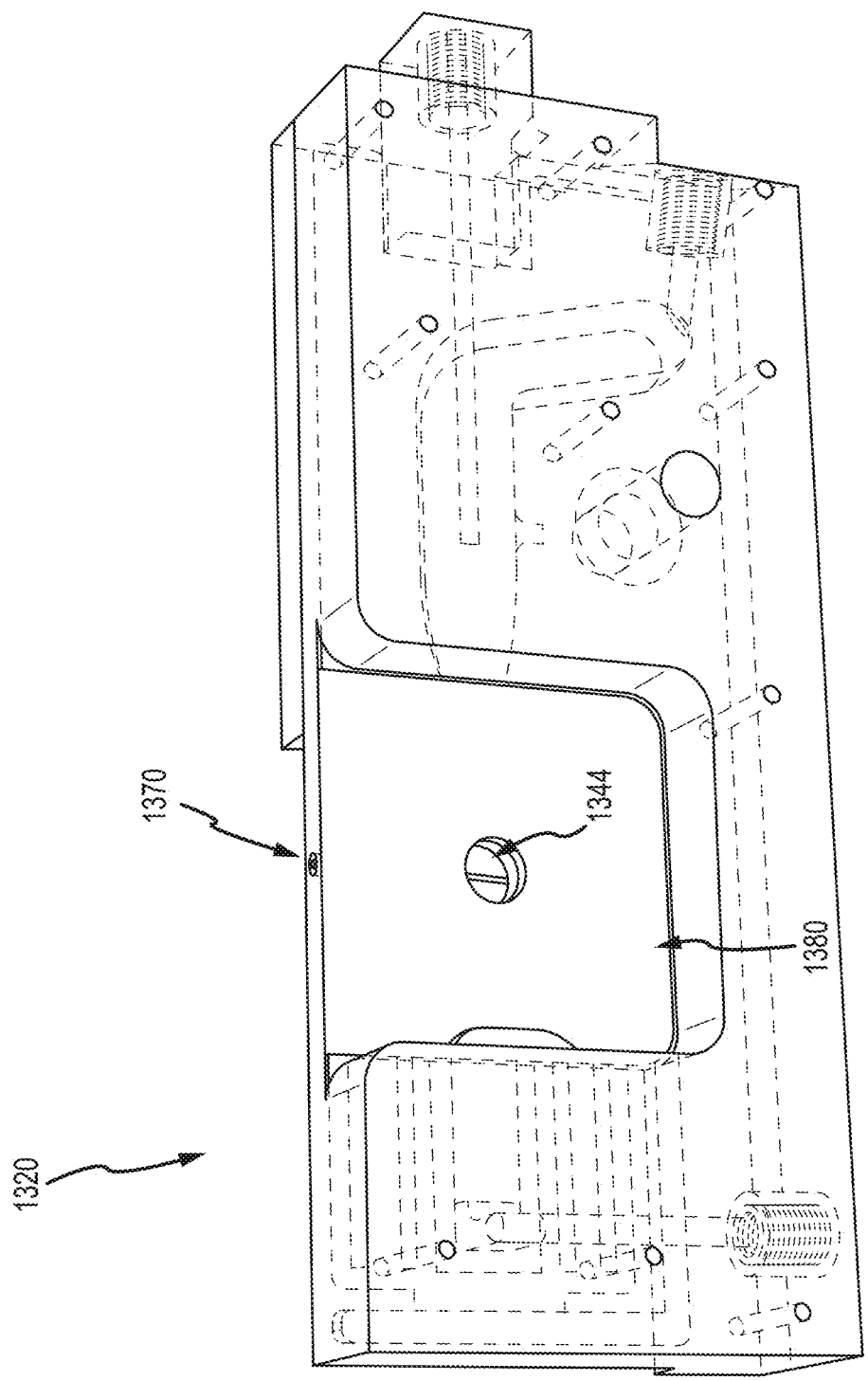

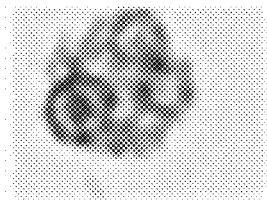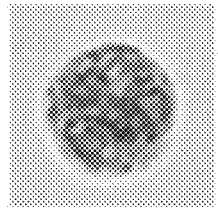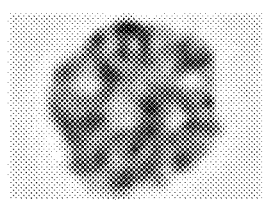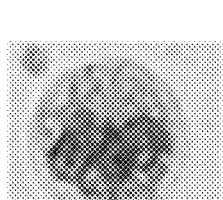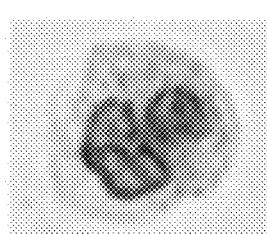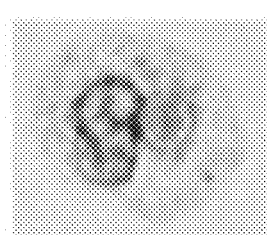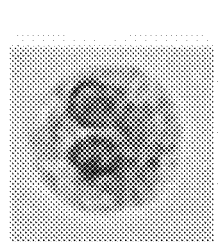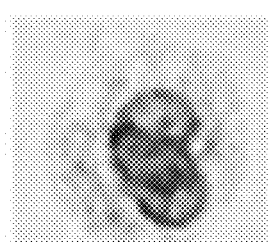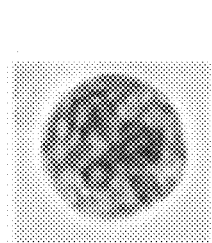
FIG. 30          FIG. 31

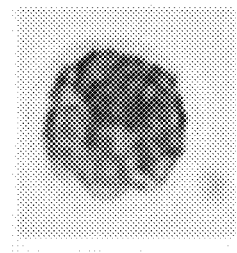
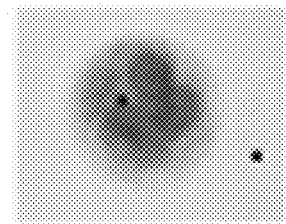
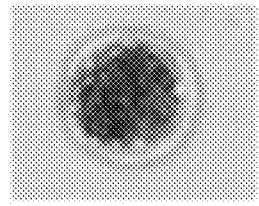
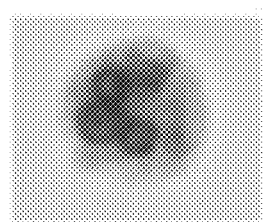
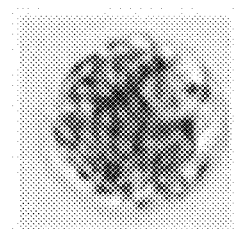
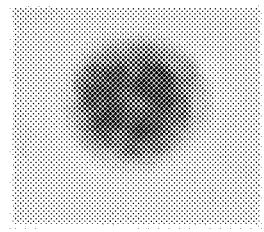
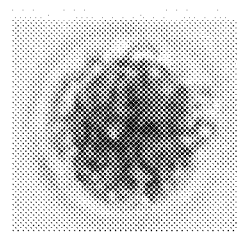
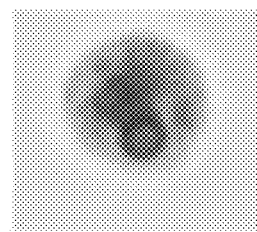
FIG. 32        FIG. 33

HEMATOLOGY SYSTEMS AND METHODS

CROSS-REFERENCES TO RELATED APPLICATIONS

This application is a continuation of U.S. patent application Ser. No. 14/775,448, filed Sep. 11, 2015, which is a U.S. National Stage Entry under § 371 of PCT International Patent Application No. PCT/US2014/030942, filed Mar. 18, 2014, which claims the benefit of priority to U.S. Provisional Patent Application No. 61/799,152 filed Mar. 15, 2013, the contents of which are incorporated herein by reference. This application is also related to U.S. patent application Ser. Nos. 14/215,834, 14/216,533, 14/216,339, 14/216,811 and 14/217,034; and PCT International Patent Application Nos. PCT/US2014/030851, PCT/US2014/030902, PCT/US2014/030850, and PCT/US2014/030928, all filed Mar. 17, 2014. The content of each of these filings is incorporated herein by reference.

BACKGROUND OF THE INVENTION

This disclosure relates to the field of apparatus, systems, compositions, and methods for analysis of particles, including imaging of particles in fluid samples, using wholly or partly automated devices to discriminate and quantify particles such as blood cells in the sample. The present disclosure also relates to a particle and/or intracellular organelle alignment liquid (PIOAL) useful for analyzing particles in a sample from a subject, methods for producing the liquid, and methods for using the liquid to detect and analyze particles. Compositions, systems, devices and methods useful for conducting image-based biological fluid sample analysis are also disclosed. The compositions, systems, devices, and methods of the present disclosure are also useful for detecting, counting and characterizing particles in biological fluids such as red blood cells, reticulocytes, nucleated red blood cells, platelets, and for image and morphologically-based white blood cell differential counting, categorization, sub-categorization, characterization and/or analysis.

Blood cell analysis is one of the most commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, five major types or subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity and other causes. Red blood cell subclasses may include reticulocytes and nucleated red blood cells.

A blood cell count estimating the concentration of RBCs, WBCs or platelets can be done manually or using an automatic analyzer. When blood cell counts are done manually, a drop of blood is applied to a microscope slide as a thin smear. Traditionally, manual examination of a dried, stained smear of blood on a microscope slide has been used to determine the number or relative amounts of the five types of white blood cells. Histological dyes and stains have been used to stain cells or cellular structures. For example, Wright's stain is a histologic stain that has been used to stain blood smears for examination under a light microscope. A Complete Blood Count (CBC) can be obtained using an automated analyzer, one type of which counts the number of different particles or cells in a blood sample based on impedance or dynamic light scattering as the particles or cells pass through a sensing area along a small tube. The automated CBC can employ instruments or methods to differentiate between different types of cells that include RBCs, WBCs and platelets (PLTs), which can be counted separately. For example, a counting technique requiring a minimum particle size or volume might be used to count only large cells. Certain cells such as abnormal cells in the blood may not be counted or identified correctly. Small cells that adhere to one another may be erroneously counted as a large cell. When erroneous counts are suspected, manual review of the instrument's results may be required to verify and identify cells.

Automated blood cell counting techniques can involve flow cytometry. Flow cytometry involves providing a narrow flow path, and sensing and counting the passage of individual blood cells. Flow cytometry methods have been used to detect particles suspended in a fluid, such as cells in a blood sample, and to analyze the particles as to particle type, dimension, and volume distribution so as to infer the concentration of the respective particle type or particle volume in the blood sample. Examples of suitable methods for analyzing particles suspended in a fluid include sedimentation, microscopic characterization, counting based on impedance, and dynamic light scattering. These tools are subject to testing errors. On the other hand, accurate characterization of types and concentration of particles may be critical in applications such as medical diagnosis.

In counting techniques based on imaging, pixel data images of a prepared sample that may be passing through a viewing area are captured using a microscopy objective lens coupled to a digital camera. The pixel image data can be analyzed using data processing techniques, and also displayed on a monitor.

Aspects of automated diagnosis systems with flowcells are disclosed in U.S. Pat. No. 6,825,926 to Turner et al. and in U.S. Pat. Nos. 6,184,978; 6,424,415; and 6,590,646, all to Kasdan et al., which are hereby incorporated by reference as if set forth fully herein.

Automated systems using dynamic light scattering or impedance have been used to obtain a complete blood count (CBC): total white blood cell count (WBC), total cellular volume of red blood cells (RBC distribution), hemoglobin HGB (the amount of hemoglobin in the blood); mean cell volume (MCV) (mean volume of the red cells); MPV (mean PLT volume); hematocrit (HCT); MCH (HGB/RBC) (the average amount of hemoglobin per red blood cell); and MCHC (HGB/HCT) (the average concentration of hemoglobin in the cells). Automated or partially automated processes have been used to facilitate white blood cell five part differential counting and blood sample analyses.

Although such currently known particle analysis systems and methods, along with related medical diagnostic techniques, can provide real benefits to doctors, clinicians, and patients, still further improvements are desirable. For example, there is a continuing need for improved methods and compositions useful for particle and/or intracellular organelle alignment when performing image-based sample analysis using automated systems. Embodiments of the present invention provide solutions for at least some of these outstanding needs.

BRIEF SUMMARY OF THE INVENTION

Embodiments of the present invention relate to apparatus, systems, compositions, and methods for analyzing a prepared sample containing particles. In some aspects the system comprises an analyzer which may be a visual analyzer. In some aspects, the apparatus contains a visual analyzer and a processor. In one aspect, this disclosure relates to an automated particle imaging system in which a liquid sample containing particles of interest is caused to flow through a flowcell having a viewport through which a high optical resolution imaging device captures an image. In some aspects the high optical resolution imaging device comprises a camera such as a digital camera. In one aspect the high optical resolution imaging device comprises an objective lens.

The flowcell is coupled to a source of sample fluid, such as a prepared sample, and to a source of particle and/or intracellular organelle alignment liquid (PIOAL). The system permits capture of focused images of particles in a sample in flow. In some embodiments the images can be used in automated, high throughput processes for categorizing and subcategorizing particles. An exemplary visual analyzer may include a processor to facilitate automated analysis of the images. In some cases, the visual analyzer can be used in methods of this disclosure to provide automated image-based WBC differential counting or other blood sample particle analysis protocols. In some cases, the methods of this disclosure relate to automated identification of morphological abnormalities for determining, diagnosing, prognosing, predicting, and/or supporting a diagnosis of whether a subject is healthy or has a disease, condition, abnormality and/or infection and for monitoring whether a subject is responsive or non-responsive to treatment.

The PIOAL aligns non-spherical particles in a plane substantially parallel to the flow direction, which results in image optimization. The PIOAL also assists spherical cells in positioning, repositioning and/or better-positioning of intracellular structures, organelles or lobes substantially parallel to the direction of flow. In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles.

Embodiments of the present invention provide systems, methods, and sheath fluid compositions useful for particle and/or intracellular organelle alignment in cells treated with particle contrast agent compositions. Such techniques overcome certain difficulties associated with conventional sheath fluids used in flow cytometry that may suffer from the disadvantages of maintaining cell morphology and/or not providing for the capture of optimized images which permit determination of one or more blood components.

In certain embodiments, a viscosity difference and/or speed difference between a ribbon-shaped sample stream and a sheath fluid and/or a thickness of the ribbon-shaped sample stream, for example in combination with a geometric focusing effect provided by a narrowing flowpath transition zone, can introduce shear forces to act on the particles while in flow thereby causing the particles to align or remain in alignment throughout an imaging process in a visual analyzer. In some embodiments the sample will be contrast enhanced. In some embodiments the sheath fluid may comprise up to 100% of a viscosity agent. In another embodiment, the sheath fluid has up to 60% v/v of a viscosity agent. Depending on the types of viscosity agent used, in some embodiments the sheath fluid may comprise a viscosity agent that is commercially available in dry form at a concentration of about 5 to 7%, or more specifically at 6.5% (w/v).

In other embodiments, this disclosure relates to a sheath fluid that can be used in image based analysis of particles in samples such as cells and other particle features in other biological fluids such as cerebrospinal fluid and effusions associated with particular conditions. Cell category and/or subcategory counts as described for use in blood samples in this disclosure as nonlimiting examples of the sort of samples that may be analyzed. In some embodiments, cells present in samples may also include bacterial or fungal cells as well as white blood cells, red blood cells or platelets. In some embodiments, particle suspensions obtained from tissues or aspirates may be analyzed.

In some embodiments a stream of sample fluid can be injected through a cannula with a flattened opening to establish a flowpath with a considerable width. The sheath fluid can be introduced into the flowcell and carries the sample fluid along through the imaging area, then toward a discharge. A sheath fluid has a different viscosity, e.g., higher, than the sample fluid, and, optionally, a different flow rate at the point of injection to the ribbon-shaped sample stream results in the sample fluid flattening into a thin ribbon shape. The thin ribbon of sample fluid is carried along with the sheath fluid, through a narrowing flowpath transition zone, to pass in front of a viewing port where a high optical resolution imaging device and a light source are arranged to view the ribbon-shaped sample stream.

In one embodiment, the viscosity of the sheath fluid can be higher than the viscosity of the sample. The viscosity of the sheath fluid, the viscosity of the sample material, the flow rate of the sheath fluid and the flow rate of the sample material are coordinated, for example in combination with a ribbon compression effect provided by a narrowing transition zone, to provide the flow in a ribbon-shaped sample stream with predetermined dimensional characteristics, such as an advantageous ribbon-shaped sample stream thickness. Maintaining an advantageous ribbon-shaped sample stream thickness provides, as an example, a high percentage of in-focus cells or in-focus cellular components.

Embodiments of the instant disclosure are based at least in part on the discovery that the addition of a suitable amount of a viscosity agent in the sheath fluid significantly improves particle/cell alignment in a flowcell, for example in a flowcell having a narrowing transition zone, and increases in-focus intracellular contents of cells, resulting in higher quality images of cells in flow compared to use of a non viscosity-modified conventional sheath fluid used in flow cytometry. The addition of the viscosity agent increases the shear forces on elongate or nonspherical particles or cells like red blood cells (RBCs) which then aligns the cells in a plane substantially parallel to the flow direction, which results in image optimization. For cells like white blood cells (WBCs), this also results in positioning, repositioning, and/or better-positioning of intracellular structures, organelles or lobes substantially parallel to the direction of flow. For example, the white blood cells can be compressible or deformable in response to the shear forces conferred by the viscosity agent or differential, thus leading to particle elongation or compression and alignment under shear.

Alignment of particles that are smaller in diameter than the flow stream may be obtained by increasing the viscosity of the sheath fluid. This results in improved alignment of those particles in a plane substantially parallel to the direction of the flow.

The ribbon-shaped sample stream thickness can be affected by the relative viscosities and flow rates of the sample fluid and the sheath fluid, for example in combination with the geometry of the narrowing transition zone of the flowcell. The feed source of the sample and/or the feed source of the sheath fluid, for example comprising precision displacement pumps, can be configured to provide the sample and/or the sheath fluid at stable flow rates for optimizing the dimensions of the ribbon-shaped sample stream, namely as a thin ribbon at least as wide as the field of view of the imaging device.

An exemplary sheath fluid embodiment is used in a flowcell for particle analysis. A sample is enveloped in the stream of the sheath fluid and passed through the flowcell of the analyzer device. Then information from the sample when passing through the detection area is collected, enabling an analyzer to analyze particles/cells contained in the sample. The use of the sheath fluid on such an analyzer allows accurate categorization and subcategorization and counting of cells and/or particles contained in samples.

As used herein, sheath fluid is useful in obtaining information relating to following cells and/or particles related thereto: including for example; neutrophil, lymphocyte, monocyte, eosinophil, basophil, platelet, reticulocyte, nucleated RBC, blast, promyelocyte, myelocyte, and/or a metamyelocyte.

The present disclosure provides novel compositions and methods of use thereof for conducting particle analysis. In particular, the present disclosure relates to a particle and/or intracellular organelle alignment liquid (PIOAL) used in a analyzer for analyzing particles in a sample. The terms sheath fluid and PIOAL can be used interchangeably throughout this disclosure. The present disclosure further provides methods for producing the PIOAL and methods for using the PIOAL to analyze particles. The PIOAL of this invention is useful, as an example, in methods for automated categorization and subcategorization of particles in a sample.

In one aspect, embodiments of the present invention encompass methods for imaging a plurality of particles using a particle analysis system. The system can be configured for combined viscosity and geometric hydrofocusing. The particles can be included in a blood fluid sample having a sample fluid viscosity. Exemplary methods can include flowing a sheath fluid along a flowpath of a flowcell, and the sheath fluid can have a sheath fluid viscosity that differs from the sample fluid viscosity by a viscosity difference in a predetermined viscosity difference range. Methods can also include injecting the blood fluid sample into the flowing sheath fluid within the flowcell so as to provide a sample fluid stream enveloped by the sheath fluid. Further, methods can include flowing the sample fluid stream and the sheath fluid through a reduction in flowpath size toward an imaging site, such that a viscosity hydrofocusing effect induced by an interaction between the sheath fluid and the sample fluid stream associated with the viscosity difference, in combination with a geometric hydrofocusing effect induced by an interaction between the sheath fluid and the sample fluid stream associated with the reduction in flowpath size, is effective to provide a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid. What is more, methods may include imaging the plurality of particles at the imaging site. In some cases, the sheath fluid has an index of refraction n=1.3330. In some cases, the sheath fluid has an index of refraction that is the same as the index of refraction of water. In some cases, the interaction between the sheath fluid and the sample fluid stream associated with the reduction in flowpath size contributes to providing the target imaging state by producing a shear force on the plurality of particles. In some cases, the target imaging state includes a target orientation of one or more target particles in the flow relative to a focal plane of an imaging device used to acquire images at the imaging site.

According to some embodiments, the flowpath at the imaging site defines a plane that is substantially parallel to the focal plane. In some cases, the target orientation corresponds to a target alignment relative to the focal plane at the imaging site. In some cases, the target alignment corresponds to a target particle alignment relative to the focal plane at the imaging site. In some cases, the target alignment corresponds to a target intraparticle structure alignment relative to the focal plane at the imaging site. In some cases, the target orientation corresponds to a target position relative to the focal plane at the imaging site. In some cases, the target position corresponds to a target particle position relative to a focal plane at the imaging site. In some cases, the target position corresponds to a target intraparticle structure position relative to a focal plane at the imaging site. In some cases, the target position is within the focal plane. In some cases, the target position is at a distance from the focal plane, the distance corresponding to a positional tolerance. In some cases, the target orientation corresponds to a target alignment relative to the focal plane and a target position relative to the focal plane. In some cases, the target imaging state corresponds to a target orientation of one or more target intraparticle structures in the flow relative to a focal plane of an imaging device used to acquire images at the imaging site. In some cases, the flowpath at the imaging site defines a plane that is substantially parallel to the focal plane. In some cases, the target orientation corresponds to a target alignment relative to the focal plane at the imaging site. In some cases, the target alignment corresponds to a target particle alignment relative to the focal plane at the imaging site. In some cases, the target alignment corresponds to a target intraparticle structure alignment relative to the focal plane at the imaging site. In some cases, the target orientation corresponds to a target position relative to the focal plane at the imaging site. In some cases, the target position corresponds to a target particle position relative to a focal plane at the imaging site. In some cases, the target position corresponds to a target intraparticle structure position relative to a focal plane at the imaging site. In some cases, the target position is within the focal plane. In some cases, the target position is at a distance from the focal plane, the distance corresponding to a positional tolerance. In some cases, the target orientation corresponds to a target alignment relative to the focal plane and a target position relative to the focal plane. In some cases, the target imaging state corresponds to a target deformation of one or more target particles or of one or more target intraparticle structures.

According to some embodiments, the process of injecting the blood fluid sample is performed by directing a stream of the blood fluid sample through a sample injection tube with a sample fluid velocity. The injection tube can have a port within the flowpath. The port can devine a width, a thickness, and a flow axis extending along the flowpath. The width can be being greater than the thickness so that the sample stream has opposed major surfaces transverse to the imaging path adjacent the imaging site. In some cases, the sheath fluid flowing along the flowpath of the flowcell extends along the major surfaces of the sample stream and has a sheath fluid velocity different than the sample fluid velocity. In some cases, an interaction between the sheath fluid and the sample fluid associated with the differing velocities, in combination with the interaction between the sheath fluid and the sample fluid associated with the differing viscosities, provides the target imaging state. According to some embodiments, the plurality of particles can include a red blood cell, a white blood cell, and/or a platelet. According to some embodiments, the plurality of particles can include a cell having an intraparticle structure. In some cases, an intraparticle structure can be an intracellular structure, an organelle, or a lobe.

In some embodiments, the sheath fluid has a viscosity between 1 and 10 centipoise (cP). In some cases, the predetermined viscosity difference has an absolute value within a range from about 0.1 to about 10 centipoise (cP). In some cases, the predetermined viscosity difference has an absolute value within a range from about 1.0 to about 9.0 centipoise (cP). In some cases, the predetermined viscosity difference has an absolute value within a range from about 1.0 to about 5.0 centipoise (cP). In some cases, predetermined viscosity difference has an absolute value of about 3.0 centipoise (cP). In some cases, the viscosity agent of the sheath fluid includes glycerol, glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the viscosity agent of the sheath fluid includes glycerol at a concentration between about 1 to about 50% (v/v). In some cases, the viscosity agent of the sheath fluid includes glycerol and polyvinylpyrrolidone (PVP). In some cases, the viscosity agent of the sheath fluid includes glycerol at a concentration of 5% (v/v) and glycerol and polyvinylpyrrolidone (PVP) at a concentration of 1% (w/v). In some cases, the viscosity agent of the sheath fluid includes glycerol present at a final concentration between about 3 to about 30% (v/v) under operating conditions. In some cases, the viscosity agent of the sheath fluid includes glycerol present at a final concentration of about 30% (v/v) under operating conditions. In some cases, the viscosity agent of the sheath fluid includes glycerol present at a final concentration of about 6.5% v/v under operating conditions. In some cases, the viscosity agent of the sheath fluid includes glycerol present at a final concentration of about 5% (v/v) and polyvinylpyrrolidone (PVP) present at a concentration of about 1% (w/v) under operating conditions.

According to some embodiments, the blood fluid sample at the imaging site has a linear velocity within a range from 20 to 200 mm/second. In some cases, the blood fluid sample at the imaging site has a linear velocity within a range from 50 to 150 mm/second. In some cases, the blood fluid sample has a sample stream thickness of up to 7 µm and a sample stream width within a range from 500 to 3000 µm at the imaging site. In some cases, the blood fluid sample has sample stream thickness within a range from 2 to 4 µm and a sample stream width within a range from 1000 to 2000 µm at the imaging site. In some cases, the plurality of particles includes a set of non-spherical particles, the blood fluid sample has a direction of flow at the imaging site, and more than 75% of the set of non-spherical particles are aligned substantially in a plane parallel to the direction of flow such a major surface of each aligned non-spherical particle is parallel to the plane parallel to the direction of flow. In some cases, the plurality of particles includes a set of non-spherical particles, the blood fluid sample has a direction of flow at the imaging site, and at least 90% of the set of non-spherical particles are aligned within 20 degrees from a plane substantially parallel to the direction of flow. In some cases, the plurality of particles includes intraparticle structures, the blood fluid sample has a direction of flow at the imaging site, and at least 92% of the intraparticle structures are substantially parallel to the direction of flow.

In another aspect, embodiments of the present invention encompass systems for imaging a plurality of particles in a blood fluid sample having a sample fluid viscosity. The system can be configured for use with a sheath fluid having a sheath fluid viscosity that differs from the sample fluid viscosity by a viscosity difference in a predetermined viscocity difference range. Exemplary systems can include a flowcell having a flowpath and a sample fluid injection tube, the flowpath having a reduction in flowpath size, a sheath fluid input in fluid communication with the flowpath of the flowcell so as to transmit a flow of the sheath fluid along the flowpath of the flowcell, and a blood fluid sample input in fluid communication with the injection tube of the flowcell so as to inject a flow of the blood fluid sample into the flowing sheath fluid within the flowcell, such that as the sheath fluid and the sample fluid flow through the reduction in flowpath size and toward an imaging site, a viscosity hydrofocusing effect induced by an interaction between the sheath fluid and the sample fluid associated with the viscosity difference, in combination with a geometric hydrofocusing effect induced by an interaction between the sheath fluid and the sample fluid associated with the reduction in flowpath size, provides a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid. Systems can further include an imaging device that images the plurality of particles at the imaging site.

According to some embodiments, the target imaging state corresponds to a target orientation of one or more target particles in the flow relative to a focal plane of an imaging device used to acquire images at the imaging site. In some cases, the plurality of particles includes a member selected from the group consisting of a red blood cell, a white blood cell, and a platelet. In some cases, the plurality of particles includes a cell having an intraparticle structure. An intracellular structure can be an intracellular structure, an organelle, or a lobe. In some cases, the predetermined viscosity difference has an absolute value within a range from about 0.1 to about 10 centipoise (cP). In some cases, the viscosity agent of the sheath fluid includes glycerol, a glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the viscosity agent of the sheath fluid includes glycerol at a concentration between about 1 to about 50% (v/v). In some cases, the viscosity agent of the sheath fluid includes glycerol and polyvinylpyrrolidone (PVP). In some cases, the viscosity agent of the sheath fluid includes glycerol at a concentration of 5% (v/v) and glycerol and polyvinylpyrrolidone (PVP) at a concentration of 1% (w/v).

According to some embodiments, the plurality of particles includes a set of non-spherical particles, the blood fluid sample has a direction of flow at the imaging site, and at least 90% of the set of non-spherical particles are aligned within 20 degrees from a plane substantially parallel to the direction of flow. In some cases, the target orientation corresponds to a target particle orientation relative to a focal plane at the imaging site. A particle may be a red blood cell, an white blood cell, or a platelet, in some embodiments. In some cases, the target orientation corresponds to a target intraparticle structure orientation relative to a focal plane at the imaging site. (e.g. intraparticle structure can be an intracellular structure, an organelle, or a lobe). In some cases, the flowpath at the imaging site defines a plane that is substantially parallel to the focal plane. In some cases, the target orientation corresponds to a target alignment relative to the focal plane at the imaging site. In some cases, the target alignment corresponds to a target particle alignment relative to a focal plane at the imaging site. In some cases, the target alignment corresponds to a target intraparticle structure alignment relative to a focal plane at the imaging site. In some cases, the target orientation corresponds to a target position relative to the focal plane at the imaging site. In some cases, the target position corresponds to a target particle position relative to a focal plane at the imaging site. In some cases, the target position corresponds to a target intraparticle structure position relative to a focal plane at the imaging site. In some cases, the target position is within the focal plane. In some cases, the target position is at a distance from the focal plane, the distance corresponding to a positional tolerance. In some cases, the target orientation corresponds to a target alignment relative to the focal plane and a target position relative to the focal plane. In some cases, the target imaging state corresponds to a target deformation at the imaging site.

According to some embodiments, a blood fluid sample source can be configured to provide the blood fluid sample a sample fluid velocity into the flowing sheath fluid, such that the sheath fluid has a sheath fluid velocity that is different from the sample fluid velocity. In some cases, an interaction between the sheath fluid and the sample fluid associated with the differing velocities, in combination with the interaction between the sheath fluid and the sample fluid associated with the differing viscosities, provides the target imaging state.

According to some embodiments, the flowpath of the flowcell includes a zone with a change in flowpath size, and an interaction between the sheath fluid and the sample fluid associated with the change in flowpath size, in combination with the interaction between the sheath fluid and the sample fluid associated with the differing viscosities, provides the target imaging state. In some cases, the interaction between the sheath fluid and the sample fluid associated with the change in flowpath size contributes to providing the target imaging state by producing a lateral fluid compression force. In some cases, the plurality of particles includes a red blood cell, a white blood cell, and/or a platelet. In some cases, the plurality of particles includes a cell having an intraparticle structure, and the structure can be an intracellular structure, an organelle, or a lobe.

According to some embodiments, the predetermined viscosity difference has an absolute value within a range from about 0.1 to about 10 centipoise (cP). In some cases, the predetermined viscosity difference has an absolute value within a range from about 1.0 to about 9.0 centipoise (cP). In some cases, the predetermined viscosity difference has an absolute value within a range from about 1.0 to about 5.0 centipoise (cP). In some cases, the predetermined viscosity difference has an absolute value of about 3.0 centipoise (cP). In some cases, the sheath fluid includes a viscosity agent which can include glycerol, a glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the sheath fluid comprises glycerol at a concentration between about 1 to about 50% (v/v).

According to some embodiments, the blood fluid sample at the imaging site has a linear velocity within a range from 20 to 200 mm/second. In some cases, the blood fluid sample at the imaging site has a linear velocity within a range from 50 to 150 mm/second. In some cases, the blood fluid sample has a sample stream thickness of up to 7 µm and a sample stream width of over 500 µm at the imaging site. In some cases, the blood fluid sample has a sample stream thickness within a range from 2 to 4 µm and a sample stream width within a range from 1000 to 2000 µm at the imaging site. In some cases, the plurality of particles includes a set of non-spherical particles, the blood fluid sample has a direction of flow at the imaging site, and at least 90% of the set of non-spherical particles are aligned and/or positioned substantially in a plane parallel to the direction of flow. In some cases, the plurality of particles includes a set of non-spherical particles, the blood fluid sample has a direction of flow at the imaging site, and at least 95% of the set of non-spherical particles are aligned within 20 degrees from a plane substantially parallel to the direction of flow. In some cases, the plurality of particles include intraparticle structures, the blood fluid sample has a direction of flow at the imaging site, and at least 92% of the intraparticle structures are substantially parallel to the direction of flow.

In another aspect, embodiments of the present invention encompass a particle and intracellular organelle alignment liquid (PIOAL) for use in a combined viscosity and geometric hydrofocusing analyzer. The PIOAL can direct flow of a blood sample fluid of a given viscosity that is injected into a narrowing flowcell transition zone of the visual analyzer so as to produce a sample fluid stream enveloped by the PIOAL. The PIOAL can include a fluid having a higher viscosity than the viscosity of the blood sample fluid. A viscosity hydrofocusing effect induced by an interaction between the PIOAL fluid and the sample fluid associated with the viscosity difference, in combination with a geometric hydrofocusing effect induced by an interaction between the PIOAL fluid and the sample fluid associated with the narrowing flowcell transition zone, is effective to provide a target imaging state in at least some of the plurality of particles at an imaging site of the visual analyzer while a viscosity agent in the PIOAL retains viability of cells in the sample fluid stream leaving structure and content of the cells intact when the cells extend from the sample fluid stream into the flowing sheath fluid. In some cases, the viscosity agent of the sheath fluid includes glycerol, a glycerol derivative, ethylene glycol, propylene glycol (dihydroxypropane), polyethylene glycol, polyvinylpyrrolidone (PVP), carboxymethylcellulose (CMC), water soluble polymer(s), and/or dextran. In some cases, the viscosity agent of the sheath fluid includes glycerol at a concentration between about 1 to about 50% (v/v). In some cases, the viscosity agent of the sheath fluid includes polyvinylpyrrolidone (PVP). In some cases, the polyvinylpyrrolidone (PVP) is at a concentration of 1% (w/v). In some cases, the viscosity agent of the sheath fluid further includes glycerol. In some cases, the viscosity agent of the sheath fluid includes glycerol at a concentration of 5% (v/v) and glycerol and polyvinylpyrrolidone (PVP) at a concentration of 1% (w/v). In some cases, the PIOAL has a viscosity of between about 1-10 cP.

In yet another aspect, embodiments of the present invention encompass a particle and intracellular organelle alignment liquid (PIOAL) for use in a visual analyzer configured to direct flow of a sample of a given viscosity in a flow path. The PIOAL can include a fluid having a higher viscosity than the viscosity of the sample. The PIOAL can be effective to support the flow of the sample and to align particles and increase the in-focus content of particles and intracellular organelles of cells flowing in the flowpath, whereby the aligned particles and intracellular organelles of cells can be imaged. In some cases, the PIOAL further includes a viscosity agent. In some cases, the PIOAL further includes a buffer, a pH adjusting agent, an antimicrobial agent, an ionic strength modifier, a surfactant, and/or a chelating agent. In some cases, the particle and intracellular organelle alignment liquid is isotonic. In some cases, the particle and intracellular organelle alignment liquid includes sodium chloride. In some cases, wherein the sodium chloride is present at a concentration of about 0.9%. In some cases, the pH of the PIOAL sample is between about 6.0 to about 8.0 under operating conditions. In some cases, the pH of the PIOAL sample mixture is between about 6.5 to about 7.5 under operating conditions. In some cases, the PIOAL includes a pH adjusting agent for adjusting the pH is between about 6.8 to about 7.2 under operating conditions. In some cases, the PIOAL liquid has a target viscosity of between about 1-10 centipoise under operating conditions.

In still yet another aspect, embodiments of the present invention encompass a stock solution of concentrated PIOAL. In some cases, the concentrated stock solution can be diluted to achieve the target viscosity. In some cases, the concentration of the stock solution is present at least about 1.1× to at least about 100× concentration of the PIOAL under operating conditions. In some cases, 139. The PIOAL of claim 127, wherein the viscosity agent is selected from at least one of glycerol, glycerol derivative; PVP, CMC, ethylene glycol; propylene glycol (dihydroxypropane); polyethylene glycol; water soluble polymer and dextran. In some cases, the viscosity agent includes glycerol. In some cases, the viscosity agent includes glycerol and polyvinylpyrrolidone (PVP). In some cases, the viscosity agent includes glycerol and carboxymethylcellulose (CMC). In some cases, the viscosity agent includes glycerol and dextran sulfate. In some cases, the viscosity agent includes a glycerol derivative. In some cases, the viscosity agent includes PVP. In some cases, the viscosity agent includes propylene glycol (dihydroxypropane). In some cases, the viscosity agent includes polyethylene glycol. In some cases, the viscosity agent includes water soluble dextran. In some cases, the glycerol is present at a final concentration between about 1 to about 50% (v/v) under operating conditions. In some cases, said glycerol is present at a final concentration between about 3 to about 30% (v/v) under operating conditions. In some cases, said glycerol is present at a final concentration of about 30% (v/v) under operating conditions. In some cases, said glycerol is present at a final concentration of about 6.5% v/v under operating conditions. In some cases, said glycerol is present at a final concentration of about 5% v/v and the PVP is present at a concentration of about 1% w/v under operating conditions. In some cases, said PVP is present at a final concentration of about 1% w/v under operating conditions. In some cases, embodiments of the present invention encompass kits that include a PIOAL as disclosed herein.

In another aspect, embodiments of the present invention encompass methods for analyzing a plurality of cells in a blood fluid sample having a sample fluid viscosity, the cells having opposed major surfaces. Exemplary methods can include flowing a sheath fluid along a flowpath of a flowcell. The sheath fluid can have a sheath fluid viscosity higher than the sample fluid viscosity. Methods can also include injecting the blood fluid sample into the flowing sheath fluid within the flowcell. The plurality of cells can include a first subset with major surfaces oriented transverse to an orientation of an imaging path. Methods can also include imaging the particles along the imaging path at an imaging site while the plurality of cells include a second subset with the major surfaces oriented trasverse to the imaging path, the second subset being more numerous than the first subset. Methods can also include directing the fluid blood sample and the sheath fluid through a reduction in flowpath size such that an interaction between the sheath fluid and the sample fluid associated with the differing viscosities reorients at least some of the plurality of cells such that the second subset is more numerous than the first subset.

In another aspect, embodiments of the present invention encompass systems for imaging a plurality of cells in a blood fluid sample having a sample fluid viscosity. Systems can be configured for use with a sheath fluid having a sheath fluid viscosity higher than the sample fluid viscosity, the cells having opposed major surfaces. Exemplary systems can include a flowcell having a flowpath and a sample fluid injection tube, a sheath fluid input in fluid communication with the flowpath of the flowcell so as to transmit a flow of the sheath fluid along the flowpath of the flowcell, and a blood fluid sample input in fluid communication with the injection tube of the flowcell so as to inject a flow of the blood fluid sample into the flowing sheath fluid within the flowcell such that the plurality of the injected cells including a first subset with major surfaces aligned transverse to an orientation of an imaging path. In some cases, the flowpath of the flowcell can have a zone with a change in flowpath size configured such that an interaction between the sheath fluid and the blood sample fluid associated with the differing viscosities reorients at least some of the particles. Systems can also include an imaging device that images the plurality of particles along the imaging path at an imaging site while the major surfaces of the second subset of the plurality of cells are oriented transverse to the imaging path.

In one aspect, this invention relates to a method for imaging a particle comprising: treating particles in a sample using the particle contrast agent compositions of this disclosure; illuminating the stained particle with light in a visual analyzer comprising a flowcell and autofocus apparatus; obtaining a digitized image of the particle enveloped in a particle and/or intracellular organelle alignment liquid (PIOAL); and; analyzing a particle in the sample based on the image information. In some embodiments, the particle is selected from at least one of neutrophil, lymphocyte, monocyte, eosinophil, basophil, platelet, reticulocyte, nucleated red blood cell (RBC), blast, promyelocyte, myelocyte, metamyelocyte, red blood cell (RBC), platelet, cell, bacteria, particulate matter, cell clump, or cellular fragment or component. For example, in some embodiments, the apparatus may be used for automated image based white blood cell (WBC) differential counting, as well as automated identification of morphological abnormalities useful in determining, diagnosing, prognosing, predicting, and/or supporting a diagnosis of whether a subject is healthy or has a disease, condition, or infection and/or is responsive or non-responsive to treatment.

In one aspect, embodiments of the present invention encompass methods for imaging particles using a particle analysis system that is configured for combined viscosity and geometric hydrofocusing. The particles can be included within first and second sample fluids of a blood fluid sample. Exemplary methods may include flowing a sheath fluid along a flowpath of a flowcell of the particle analyzer, and the sheath fluid can have a viscosity that is different from a viscosity of the blood fluid sample. In some cases, the sheath fluid has a sheath fluid viscosity that differs from the sample fluid viscosity by a viscosity difference, and the viscosity difference has a value in a predetermined viscosity difference range. Methods may also include injecting the first sample fluid from a sample fluid injection tube into the flowing sheath fluid within the flowcell so as to provide a sample fluid stream having a first thickness adjacent the injection tube. The flowpath of the flowcell can have a decrease in flowpath size such that thickness of the sample fluid stream decreases from the initial thickness to a second thickness adjacent an image capture site. Methods can further include imaging a first plurality of the particles from the first sample fluid at the image capture site of the flowcell, and initiating sample fluid transients by terminating injection of the first sample fluid into the flowing sheath fluid and injecting the second sample fluid into the flowing sheath fluid. What is more, methods can include imaging a second plurality of the particles from the second sample fluid at the image capture site of the flowcell. The imaging of the second plurality of particles can be performed substantially after the sample fluid transients and within 4 seconds of the imaging of the first plurality of the particles. In some cases, the decrease in flowpath size is defined by a proximal flowpath portion having a proximal thickness, and distal flowpath portion having a distal thickness less than the proximal thickness. A downstream end of the sample fluid injection tube can be positioned distal to the proximal flowpath portion. The viscosity difference between the sheath and blood fluid samples, in combination with the decrease in flowpath size, can be effective to hydrofocus the first and second sample fluids at the image capture site, while a viscosity agent in the sheath fluid retains viability of cells in the first and second sample fluids leaving structure and content of the cells intact when the cells extend from the sample fluid stream into the flowing sheath fluid.

In some methods, the injection tube can include an internal volume based on a ratio of a flow area cross-section of the injection tube to a flow area cross-section of the flowcell, a ratio of the flow area cross-section of the injection tube to an outer diameter of the flowcell, or a ratio of the flow area cross-section of the injection tube to a flow area cross-section of the sample stream. In some cases, the decrease in flowpath size can be defined by opposed walls of the flowpath angling radially inwardly along the flowpath generally symmetric about a transverse plane that bisects the sample fluid stream first and second thicknesses. In some cases, symmetry in the decrease in flowpath size is effective to limit red blood cells imaging orientation misalignment in the blood fluid sample to less than about 20%. In some cases, the blood fluid sample includes spherical particles, and a viscosity differential between the sample fluid and the sheath fluid is effective to align intracellular organelles of the spherical particles within a focal plane at the image capture site of the flowcell. In some cases, a distal portion of the sample fluid injection tube is positioned at an axial separation distance from the image capture site, and the axial separation distance has a value within a range from about 16 mm to about 26 mm. In some cases, the injection tube has an internal volume of less than about 30 µL.

In some methods, the injection tube has a proximal portion having a first flow cross-section area and a distal portion having a second flow cross-section area, and the flow cross-section area of the proximal portion is greater than 1.5 times the flow cross-section area of the distal portion. In some methods, the injection tube has a central portion disposed between the proximal portion and the distal portion, the central portion has a third flow cross-section, and the third flow cross section is greater than the first and second flow cross-sections.

In some methods, a distal portion of the sample fluid injection tube includes an outlet port having a height and a width, and the height can be less than the width. In some cases, the height is about 150 µm and the width is about 1350 µm. In some cases, the height has a value within a range from about 50 µm to about 250 µm and the width has a value within a range from about 500 µm to about 3000 µm.

In some methods, a ratio of the sheath fluid flow rate to the sample fluid flow rate is about 70. In some cases, the ratio of the sheath fluid flow rate to the sample fluid flow rate is about 200. In some cases, the sheath fluid has a flow rate of about 35 µL/s and the sample fluid has a flow rate of about 0.5 µL/s. In some cases, the sample fluid has a velocity of between about 20 and 200 mm/second at the image capture site. In some cases, the sheath fluid velocity and the fluid sample velocity may differ at a flowpath position near the injection tube tube exit port, and the sheath fluid velocity and the fluid sample velocity may be the same at the image capture site. In some cases, the first thickness of the sample fluid stream is about 150 µm, for example where the sample fluid exits the injection tube. In some cases, the second thickness of the sample fluid stream is within a range from about 2 µm to about 10 µm, for example where the sample fluid stream flows through the image capture site. In some cases, the second thickness of the sample fluid stream is within a range from about 2 µm to about 4 µm. In some cases, a ratio of the first thickness of the sample fluid stream to the second thickness of the sample fluid stream has a value within a range from about 20:1 to about 70:1. In some cases, a ratio of the first thickness of the sample fluid stream to the second thickness of the sample fluid stream has a value within a range from about 5:1 to about 200:1. In some cases, a ratio of the proximal thickness of the proximal flowpath portion to the distal thickness of the distal flowpath portion has a geometric thinning value selected from the group consisting of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, and 200:1. In some cases, the flowcell has a minimum compression ratio of about 50:1 and a maximum compression ratio of about 125:1.

In some methods, the flowcell is oriented so that the sample fluid and the sheath fluid flowing within the flowcell flow against gravity. In some cases, the flowcell is oriented so that the sample fluid and the sheath fluid flowing within the flowcell flow with gravity. Exemplary methods may also include removing bubbles from the flowing sample fluid. In some cases, the first sample fluid reaches a stabilized state within about 1 to 3 seconds following injection of the first sample fluid from the sample fluid injection tube into the flowing sheath fluid. In some cases, the first sample fluid reaches a stabilized state within less than 1 second following injection of the first sample fluid from the sample fluid injection tube into the flowing sheath fluid. In some cases, the first sample fluid reaches a stabilized state within about 1.8 seconds from injection of the first sample fluid from the sample fluid injection tube into the flowing sheath fluid. In some cases, the sample fluid has a transit time through the flowcell within a range from about 2 to 4 seconds. In some cases, the image capture site has a field of view of between about 150 µm×150 µm and 400 µm×400 µm. In some cases, the first sample fluid has a volume in a range from about 50 to about 150 µL. In some cases, a proximal portion of the injection tube is coupled to a sample port of a sample inlet fitting.

In another aspect, embodiments of the present invention encompass particle analysis systems that perform combined viscosity and geometric hydrofocusing for imaging particles in a blood fluid sample. The particles can be included within first and second sample fluids. Exemplary systems can include a flowcell having a flowpath configured for transmitting a flow of the sheath fluid. The sheath fluid can have a viscosity that is different from a viscosity of the blood fluid sample. In some cases the sheath fluid viscosity is greater than the blood fluid sample viscosity. In some cases, the sheath fluid has a sheath fluid viscosity that differs from the sample fluid viscosity by a viscosity difference, and the viscosity difference has a value in a predetermined viscosity difference range. Systems may also include a sample fluid injection system in fluid communication with the flowpath. The sample fluid injection system can be configured for injecting the sample fluids into the flowing sheath fluid within the flowcell so as to provide a sample fluid stream having a first thickness adjacent the injection tube. The flowpath of the flowcell can have a decrease in flowpath size such that thickness of the sample fluid stream decreases from the initial thickness to a second thickness adjacent an image capture site. Further, systems can include an image capture device aligned with the image capture site so as to image a first plurality of the particles from the first sample fluid at the image capture site of the flowcell. What is more, systems can include a processor coupled with the sample fluid injector system and the image capture device. The processor can be configured to terminate injection of the first sample fluid into the flowing sheath fluid and injecting the second sample fluid into the flowing sheath fluid such that sample fluid transients are initiated, and to image a second plurality of the particles from the second sample fluid at the image capture site of the flowcell after the sample fluid transients and within 4 seconds of the imaging of the first plurality of the particles. In exemplary systems, the viscosity difference between the sheath and blood fluid samples, in combination with the decrease in flowpath size, is effective to hydrofocus the first and second sample fluids at the image capture site of the flowcell, while a viscosity agent in the sheath fluid retains viability of cells in the first and second sample fluids leaving structure and content of the cells intact when the cells extend from the sample fluid stream into the flowing sheath fluid.

In some systems, the injection tube includes an internal volume based on a ratio of a flow area cross-section of the injection tube to a flow area cross-section of the flowcell, a ratio of the flow area cross-section of the injection tube to an outer diameter of the flowcell, or a ratio of the flow area cross-section of the injection tube to a flow area cross-section of the sample stream. In some cases, the decrease in flowpath size is defined by opposed walls of the flowpath angling radially inwardly along the flowpath generally symmetric about a transverse plane that bisects the sample fluid stream first and second thicknesses. In some cases, symmetry in the decrease in flowpath size is effective to limit red blood cells imaging orientation misalignment in the blood fluid sample to less than about 20%. In some cases, a distal portion of the sample fluid injection tube is positioned at an axial separation distance from the image capture site, and the axial separation distance has a value within a range from about 16 mm to about 26 mm. In some cases, the injection tube includes a proximal portion having a first flow cross-section area and a distal portion having a second flow cross-section area, and the flow cross-section area of the proximal portion is greater than 1.5 times the flow cross-section area of the distal portion. In some cases, the sample fluid has a transit time through the flowcell within a range from about 2 to 4 seconds. In some cases, the flowcell is configured to receive the sheath fluid from a sheath fluid source into the flowpath in a first flow direction that is perpendicular to second flow direction of the sheath fluid along the flowpath at the imaging site. In some cases, the flowcell includes an autofocus target for the image capture device.

Embodiments of the present invention encompass systems and methods for quantifying cells or particles present in a blood fluid sample, using exemplary dynamic or detection range extension techniques.

For example, exemplary embodiments encompass techniques for correcting inaccurate particle counts associated with at least one detection range, based on a parameter such as particle volume. By operating the apparatus as described in the present disclosure, the particles outside the detection range for concentration and/or by volume can be detected and measured accurately.

As used herein, the term "detection limit" or "outside of detection range" associated with a particle counter made in this disclosure will be understood to encompass a range, within which the particle count is more accurate and/or outside of which the particle count is less accurate or even inoperable. A detection range may include an upper and/or a lower detection limit, typically expressed as a maximum or minimum concentration, but also possibly expressed as a maximum or minimum frequency at which particles are counted within a given tolerance of accuracy. Hence, embodiments of the present invention emcompass systems and methods for parallel flowcell and impedance analysis of blood fluid samples for quantification of sparse and/or copious species counts.

A detection range can be based on the concentration, which may include a local concentration, and/or other specified criterion or criteria. For example, a particle such as a blood cell or fragment smaller than a normal PLT (i.e., having a diameter less than 2 µm) may be difficult to detect and count accurately in a particle counter. An abnormal cell larger than a regular white cell (i.e., having a diameter higher than 15 µm) may be difficult to detect and count accurately in a particle counter. In addition, in high concentrations, RBCs and PLTs may be difficult to count accurately. Even after dilution, RBCs and PLTs may aggregate to form clumps, resulting in false readings of particle counts obtained using a particle counter. Furthermore, it is difficult to provide an accurate count of some immature or abnormal blood cells present in the sample at low concentrations.

As an example, by using the apparatus described herein, the detection range of measurement, the upper detection limit for WBCs can be extended up to 300,000, 400,000, 500,000, 600,000, 700,000, 800,000, 900,000, or 1,000,000 per (unit volume) in some embodiments. The lower detection limit for PLTs can be extended lower than 20,000, 19,000, 18,000,17,000, 16,000, 15,000, 14,000, 13,000, 12,000, 11,000, 10,000, 9,500, 9,000, 8,500, 8,000, 7,500, 7,000, 6,500, 6,000, 5,500, 5,000, 4,500, 4,000, 3,500, 3,000, 2,500, 2,000, 1,500 or 1,000, or 500 per µl in some embodiments.

Relatedly, exemplary embodiments encompass techniques for correcting inaccurate results obtained in a particle counter by differentiating different classes (including members of each class) of particles detected in one channel. As described herein, some particles have similar volume or morphology and may be detected in one channel. For example, "giant" PLTs, PLT aggregates or clumps, and nucleated RBCs may be counted as "WBCs" in one channel designed to detect WBCs. In addition, other species such as unlysed cells, cryoglobulin, heinz bodies, and malaria parasite may be counted as "WBCs" to give a WBC count higher than that actually exists in the sample. Similarly, high concentration of WBCs and giant PLTs may be counted as "RBCs" and result in a RBC count higher than the actual value. Presence of microcytic red cells, red cell inclusions, white cell fragments, dust particles, hemolysis/Schistocytes and even electronic/electric noises may result in a count of PLTs higher than actual. On the other hand, clotting and smudge cells within the same class or confusion of one class of cells with another class may result in inaccurate and lower count of the corresponding class of cells on the particle counter.

In some aspects of the methods of this disclosure a first category and/or subcategory of particles is present in the sample at a concentration above a detection range applicable to the first category and/or subcategory of particles; and a second category and/or subcategory of particles is present in the sample within a detection range applicable to the second category and/or subcategory of particles. In other aspects of the methods of this invention, the first category and/or subcategory of particles is present in the sample at a concentration below a detectable range applicable to the first category and/or subcategory of particles, and the second category and/or subcategory of particles is present in the sample within a detection range applicable to the second category and/or subcategory of particles. In other aspects, the first category and/or subcategory of particles comprises at least one type of abnormal blood cells, immature blood cells, clumped blood cells, blood cells having diameter larger than 15 microns, and blood cells having diameter smaller than 2 microns; and the second category and/or subcategory of particles comprises white blood cells.

By operating the apparatus as described in this disclosure, those particles which are miscounted as another type of particle in one channel of the particle counter can be measured separately and accurately. Exemplary methods can be also used to determine particle count or concentrations of particles which cannot be detected accurately on the particle counter. These particles include but are not limited to the particles outside normal volume ranges and/or particles present at concentrations near or outside the high or low end of concentrations detectable on the particle counter. Relatedly, by operating a system apparatus as described, especially comprising a particle counter and an image analyzer in combination with the exemplary particle contrast agent compositions and PIOAL as described in this disclosure, some particles which may be miscounted as another type of particle in one channel of the particle counter can be measured separately and accurately. The methods of this invention can be also used in some instances to determine particle count or concentrations of particles which cannot be detected accurately on the particle counter. These particles include but are not limited to the particles outside a detection range and/or particles present at concentrations near or beyond the high or low end of concentrations detectable on the particle counter. This is done by applying information obtained from the image analyzer.

Overall, by operating an apparatus as disclosed herein, for example using exemplary particle contrast agent compositions and PIOAL sheath fluids, analysis of a sample containing particles such as blood cells or other fragments can be performed in detection ranges that are outside the nominal detection range for a particle counter. Relatedly, using systems and compositions as described herein, analysis of a blood fluid sample can be performed in extended detection ranges based on a parameter such as concentration or particle volume. The extended detection ranges can outside the detection range for a particle counter.

In some embodiments, a system or apparatus can include a particle counter. In other embodiments this particle counter has at least one detection range. In certain aspects, the analyzer and the processor can be configured to provide additional information to correct testing errors associated with the particle counter, and further determine accurate particle count or concentration of different categories and/or subcategories of particles in the sample. Provided that information is available from the particle counter and the analyzer about the counts, one or more ratios, and/or distribution over at least two of the categories and/or subcategories of particles, then errors in counts, categorization and/or subcategorization from the particle counter can be corrected, and counts, categories and/or subcategories can be derived that were not initially reported by the particle counter.

Embodiments of the present invention encompass certain focusing techniques that allow hematology systems and methods to produce high quality images of particles that are present in fluid blood samples. Such high quality images provide the foundation for achieving high levels of discrimination which are useful to accurately classify cells allows for the use of optical systems having a high magnification and high numerical aperture objective. Exemplary optical alignment or focusing techniques facilitate the production of images with high level of resolution, with a short depth of field that corresponds to a thin ribbon of fluid sample which carries the particles.

In some cases, hematology systems may be re-focused on a regular basis to adjust for changes in local temperature and other factors. For example, autofocus techniques as discussed herein can compensate for thermal expansion or other factors present in a hematology analyzer which change the distance between an imaging objective and a flowcell and therefore negatively impact imaging results, for example by producing an image which is out of focus. Embodiments of the present invention also encompass autofocus systems and methods for hematology instruments that involve automatically focusing an imaging system without the need for a focusing liquid or solution or other user intervention. For example, exemplary autofocus techniques can involve obtaining an initial focus on a target fixed relative to the flowcell, rather than using techniques that are based on maximizing the contrast of the subject itself that appears in the image.

Certain embodiments of the present invention are based at least in part on the observation that the stream position within the flowcell does not change in response to temperature fluctuations, and may involve focusing on a target somewhere in the flowcell and then using a fixed offset to achieve good focus on the sample stream. Such approaches can be implemented without the use of a focusing solution that is flowed through the flowcell, and can be performed automatically and totally transparently to the user.

According to some embodiments, this disclosure relates to a visual analyzer for imaging a sample comprising particles suspended in a liquid, in which the apparatus includes a flowcell coupled to a source of the sample and to a source of a PIOAL, wherein the flowcell defines an internal flowpath, the flowcell being configured to direct a flow of a ribbon-shaped sample stream enveloped with the PIOAL through a viewing zone in the flowcell. An objective lens associated with a high optical resolution imaging device is disposed on an optical axis that intersects the ribbon-shaped sample stream. The relative distance between the objective and the flowcell is variable by operation of a motor drive coupled to a controller, for resolving and collecting a digitized image on a photosensor array. An autofocus pattern or imaging target is provided at a position fixed relative to the flowcell, the autofocus pattern being located at a predetermined distance from the plane of the prepared ribbon-shaped sample stream. A light source illuminates the ribbon-shaped sample stream and the autofocus pattern. At least one digital processor is associated with the controller coupled to operate the motor drive. The processor is also arranged to analyze the digitized image. The processor determines a focus position of the autofocus pattern to generate a focused image and then relatively displaces the objective and the flowcell over the predetermined distance (e.g. a displacement distance) from the focused position, to focus the high optical resolution imaging device on the ribbon-shaped sample stream.

In one aspect, embodiments of the present invention encompass methods for imaging particles in a blood fluid sample using a particle analysis system. The particle analysis system can be configured for geometric hydrofocusing. In some cases, the system can be configured for combined viscosity and geometric hydrofocusing. In some cases, the particles can be included in a blood fluid sample having a sample fluid viscosity. Exemplary methods can include flowing a sheath fluid along a flowpath of a flowcell of the particle analysis system. In some cases, the sheath fluid can have a sheath fluid viscosity that differs from the sample fluid viscosity by a viscosity difference in a predetermined viscosity difference range. Methods can also include injecting the blood fluid sample into the flowing sheath fluid within the flowcell so that the blood fluid sample fluid flows in a sample flowstream with a flowstream width greater than a flowstream thickness, the sample flowstream flowing through a decrease in flowpath size and traversing an imaging axis. Further, methods can include focusing an image capture device by imaging an imaging target having a position fixed relative to the flowcell. What is more, methods can include acquiring a focused image of the particles, suitable for particle characterization and counting, within the flowstream with the image capture device, where the image capture device is focused on the sample flowstream using a displacement distance. According to some embodiments, a viscosity difference between the sheath fluid and blood fluid sample, in combination with the decrease in flowpath size, is effective to hydrofocus the sample flowstream at the imaging axis while a viscosity agent in the sheath fluid retains viability of cells in the sample flowstream leaving structure and content of the cells intact when the cells extend from the sample flowstream into the flowing sheath fluid. In some cases, the sample flowstream has a thickness at the imaging axis within a range from about 2 μm to about 10 μm. In some cases, the flowpath has a thickness of about 150 μm at the imaging axis. In some cases, the imaging target is located on a viewport window disposed between the sample flowstream and the image capture device. In some cases, the imaging target is located on an illumination window, and the sample flowstream is disposed between the illumination window and the image capture device. In some cases, the displacement distance is zero. In some cases, the imaging target is located between an illumination window and a viewport window. In some cases, in the acquiring step, the image capture device is focused on the on the sample flowstream by adjusting a focal distance of the image capture device based on the displacement distance.

According to some embodiments, the process of acquiring the focused image includes adjusting a distance between the image capture device and the flowcell using the displacement distance. In some cases, adjusting the distance between the image capture device and the flowcell includes moving a component of the image capture device. The component of the image capture device can be a zoom lens, a mirror of the image capture device, or an assembly that includes the image capture device. In some cases, adjusting the distance between the image capture device and the flowcell includes moving the flowcell. In some cases, adjusting the distance between the image capture device and the flowcell includes moving at least an optical element of the image capture device and the flowcell. In some cases, the displacement distance is a distance along the imaging axis between the imaging target and the sample flowstream. In some cases, displacement distance is a distance difference between a first focal distance between the image capture device and the target and a second focal distance between the image capture device and the sample flowstream. In some cases, methods include an autofocusing step that involves injecting a test fluid sample into the sheath fluid to form a test sample flowstream within the flow cell, obtaining a first focused image of the imaging target using the image capture device, such that the focused imaging target and the image capture device define a first focal distance, obtaining a second focused image of the test sample flowstream using the image capture device, such that the focused test sample flow stream and the image capture device defining a second focal distance, and obtaining the displacement distance by calculating a difference between the first focal distance and the second focal distance. In some cases, the test fluid sample is the same blood fluid sample and the test sample flowstream is the same as the sample flowstream. In some cases, the autofocusing step establishes a focal plane associated with the image capture device, and the focal plane remains stationary relative to the image capture device. In some cases, the image capture device is focused on the sample flowstream using a temperature such as a sample fluid temperature, a sheath fluid temperature, a flowcell temperature, or an image capture device temperature. In some cases, the image capture device can be focused on the sample flowstream using a temperature, such as a flowcell temperature at the imaging site, a flowcell temperature at a location upstream of the imaging site, and a flowcell temperature at a location downstream of the imaging site. In some cases, the image capture device can be focused on the sample flowstream using a temperature rate of change, such as a sample fluid temperature rate of change, a sheath fluid temperature rate of change, a flowcell temperature rate of change, or an image capture device temperature rate of change.

According to some embodiments, methods may include detecting an autofocus re-initiation signal, and repeating autofocusing and image acquisition steps in response to the auto-focus re-initiation signal. In some cases, the autofocus re-initiation signal includes or is based on a change in temperature, a decrease in focus quality, a lapsed time interval, or a user-input. In some cases, the focusing of the image capture device on the sample flowstream is performed independently of a temperature of the image capture device. In some cases, the imaging target includes a scale for use in positioning the imaging axis of the image capture device relative to the sample flowstream. In some cases, the imaging target includes an iris aligned relative to the imaging axis, such that the imaged particles are disposed within an aperture defined by the iris, and one or more edge portions of the iris are imaged during autofocusing. In some cases, the image capture device is focused on the sample flowstream by implementing axial rotation of the image capture device about the imaging axis, axial rotation of the flowcell about an axis extending along the imaging axis and within the field of view of the imaging device, tip rotation of the image capture device about an axis extending along the flowpath, tip rotation of the flowcell about an axis extending along and within the flowpath, tilt rotation of the image capture device about an axis traversing the flowpath and the imaging axis, and/or tilt rotation of the flowcell about an axis traversing the flowpath and the imaging axis and within the field of view of the image capture device. In some cases, the image capture device is focused on the sample flowstream by implementing a rotation of the flowcell, the rotation centered in the field of view of the image capture device. In some cases, the autofocusing of the image capture device includes determining an optimal focus position from among a plurality of focus positions.

In another aspect, embodiments of the present invention encompass methods for imaging particles in a blood fluid sample. Exemplary methods can include flowing a sheath fluid along a flowpath of a flowcell, and injecting the blood fluid sample into the flowing sheath fluid within the flowcell so that the blood fluid sample flows in a sample flowstream with a flowstream width greater than a flowstream thickness. The flowcell can have an associated temperature. Methods can also include focusing an image capture device, along an imaging axis, on the flowstream to a first focal state while the temperature associated with the flowcell is at a first temperature, and acquiring a first focused image of a first subset of the particles within the flowstream with the image capture device at the first focal state. Methods can further include determining that the temperature associated with the flowcell has undergone a change from the first temperature to a second temperature, and automatically adjusting focus of the image capture device from the first focal state to a second focal state in response to the change in temperature and a known relationship between flowcell temperature and desired focus. Further, methods can include acquiring a second focused image of a second subset of the particles within the flowstream with the image capture device at the second focal state. In some cases, adjusting focus of the image capture device involves adjusting a distance between the image capture device and the flowcell using the change in temperature and the known relationship between flowcell temperature and desired focus. In some cases, adjusting focus of the image capture device involves adjusting a focal distance of the image capture device using the change in temperature and the known relationship between flowcell temperature and desired focus. In some cases, adjusting focus of the image capture device involves implementing axial rotation of the image capture device about the imaging axis, axial rotation of the flowcell about an axis extending along the imaging axis and within the field of view of the imaging device, tip rotation of the image capture device about an axis extending along the flowpath, tip rotation of the flowcell about an axis extending along and within the flowpath, tilt rotation of the image capture device about an axis traversing the flowpath and the imaging axis, and/or tilt rotation of the flowcell about an axis traversing the flowpath and the imaging axis and within the field of view of the image capture device. In some cases, the image capture device is focused on the sample flowstream by implementing a rotation of the flowcell, the rotation centered in the field of view of the image capture device.

In another aspect, embodiments of the present invention encompass particle analysis systems that perform geometric hydrofocusing, or in some cases combined viscosity and geometric hydrofocusing, for imaging particles in a blood fluid sample. Exemplary systems can include a flowcell having a flowpath with an injection tube and an imaging window with an imaging axis therethrough. The flowpath of the flowcell can have a decrease in flowpath size. Systems can also include a sheath fluid input in fluid communication with the flowpath. Further, systems can include a blood fluid input in fluid communication with the infection tube. The blood fluid input can be configured for injecting the blood fluid sample into the flowing sheath fluid within the flowcell so that the blood fluid sample flows in a sample flowstream with a flowstream width greater than a flowstream thickness. In some cases, the sheath fluid can have a viscosity that is greater than a viscosity of the blood fluid sample. What is more, systems can include an image capture device, a focusing mechanism configured to set a focal state of the image capture device relative to the flowcell, and an imaging target having a position fixed relative to the flowcell. In some cases, the imaging target and sample flowstream can define a displacement distance along the imaging axis. Further, systems can include a processor, and a focusing module having a tangible medium embodying machine-readable code executed on the processor for operating the focusing mechanism to set the focal state of the image capture device, suitable for particle characterization and counting, using the displacement distance. In some cases, a viscosity difference between the sheath fluid and blood fluid sample, in combination with the decrease in flowpath size, is effective to hydrofocus the sample flowstream at the imaging axis while a viscosity agent in the sheath fluid retains viability of cells in the sample flowstream leaving structure and content of the cells intact when the cells extend from the sample flowstream into the flowing sheath fluid. In some cases, the focusing mechanism can include a drive motor configured to adjust a distance between the image capture device and the flowcell. In some cases, the imaging target is located on a viewport window disposed between the sample flowstream and the image capture device. In some cases, the imaging target is located on an illumination window, and the sample flowstream is disposed between the illumination window and the image capture device. In some cases, the system is configured to perform an acquiring step that includes focusing the image capture device on the sample flowstream by adjusting a focal distance of the image capture device based on the displacement distance. In some cases, the system is configured to perform an acquiring step for obtaining a focused image by adjusting a distance between the image capture device and the flowcell using the displacement distance. In some cases, the system is configured to adjust the distance between the image capture device and the flowcell by moving the flowcell. In some cases, the system is configured to perform an autofocusing step that includes injecting a test fluid sample into the sheath fluid to form a test sample flowstream within the flow cell, obtaining a first focused image of the imaging target using the image capture device, such that the focused imaging target and the image capture device define a first focal distance, obtaining a second focused image of the test sample flowstream using the image capture device, such that the focused test sample flow stream and the image capture device define a second focal distance, and obtaining the displacement distance by calculating a difference between the first focal distance and the second focal distance. In some cases, the system is configured to focus the image capture device on the sample flowstream using a temperature, such as a sample fluid temperature, a sheath fluid temperature, a flowcell temperature, or an image capture device temperature. In some cases, the system is configured to detect an autofocus re-initiation signal, and repeat autofocusing and image acquisition steps in response to the auto-focus re-initiation signal.

In another aspect, embodiments of the present invention encompass systems for imaging particles in a blood fluid sample. Exemplary systems can include a flowcell having a flowpath with an injection tube and an imaging window with an imaging axis therethrough, a sheath fluid input in fluid communication with the flowpath, and a blood fluid input in fluid communication with the injection tube. The blood fluid input can be configured for injecting the blood fluid sample into the flowing sheath fluid within the flowcell so that the blood fluid sample flows in a sample flowstream with a flowstream width greater than a flowstream thickness. Systems can also include an image capture device, a focusing mechanism configured to set a focal state of the image capture device relative to the flowcell, a temperature sensor thermally coupled to the flowcell, a processor, and a focusing module. The focusing module can include a tangible medium embodying machine-readable code executed on the processor for operating the focusing mechanism to set the focal state of the image capture device, suitable for particle characterization and counting, in response to a change in temperature sensed by the temperature sensor and a known relationship between temperature and desired focus. In some cases, the focusing mechanism includes a drive motor configured to adjust a distance between the image capture device and the flowcell.

In another aspect, embodiments of the present invention encompass methods for the analysis of cells in a blood fluid sample. Exemplary methods can include flowing a sheath fluid along a flowpath of a flowcell, and injecting the blood fluid sample into the flowing sheath fluid within the flowcell so that the blood fluid sample fluid flows in a sample flowstream with a flowstream width wider than a flowstream thickness. The sample flowstream can be offset, along an imaging axis, from an imaging window of the flowcell by a first distance. Methods can also include autofocusing an image capture device by imaging an imaging target affixed to the flowcell. The imaging target can be positioned at a second distance from the imaging window along the imaging axis. Further, methods can include acquiring focused images of the cells, suitable for cell characterization and counting, within the flowstream with the image capture device. In some cases, the image capture device can be focused on the sample flowstream using the autofocusing step and a known relationship between the first distance and the second distance.

In another aspect, embodiments of the present invention encompass systems for the analysis of cells in a blood fluid sample. Exemplary systems can include a flowcell having a flowpath with an injection tube and an imaging window with an imaging axis therethrough. Systems can also include a sheath fluid input in fluid communication with the flowpath, and a blood fluid input in fluid communication with the infection tube. The blood fluid input can be configured for injecting the blood fluid sample into the flowing sheath fluid within the flowcell so that the blood fluid sample flows in a sample flowstream with a flowstream width greater than a flowstream thickness. The sample flowstream can be offset, along the imaging axis, from the imaging window of the flowcell by a first distance. Systems can also include an image capture device orientable along the imaging axis. The image capture device can include a focusing mechanism. Further, systems can include an imaging target affixed to the flowcell. The imaging target can be at a second distance from the imaging window surface along the imaging axis. What is more, systems can include a processor coupled to the focusing mechanism. The processor can be configured to acquire focused images of the particles within the flowstream, sufficient for characterization and counting of the cells, by focusing the image capture device on the target, and by using a known relationship between the first distance and the second distance.

In yet another aspect, embodiments of the present invention encompass systems for the analysis of cells in a blood fluid sample. Exemplary systems can include a flowcell having a flowpath with an injection tube and an imaging window with an imaging axis therethrough. Further, systems can include a sheath fluid input in fluid communication with the flowpath, and a blood fluid sample input in fluid communication with the injection tube. The sample fluid input can be configured for injecting the blood fluid sample into the flowing sheath fluid within the flowcell so that the blood fluid sample flows in a sample flowstream with a flowstream width greater than a flowstream thickness. Further, systems can include an image capture device orientable along the imaging axis, and the image capture device can include a focusing mechanism. Systems can also include a temperature sensor thermally coupled to the flowcell, and a processor coupled to the temperature sensor and the focusing mechanism. In some cases, the processor is configured to adjust focus of the image capture device, sufficient for characterization and counting of the cells, in response to a change in temperature and a known relationship between temperature and desired focus.

According to some embodiments, a visual analyzer can include a flowcell coupled to a source of a sample and to a source of a sheath fluid. The flowcell can define an internal flowpath, and can be configured to direct a flow of the sample enveloped with the sheath fluid through a viewing zone in the flowcell. The analyzer can also include a high optical resolution imaging device with an objective on an optical axis that intersects the ribbon-shaped sample stream, and a relative distance between the objective and the flowcell can be variable by operation of a motor drive, for resolving and collecting a digitized image on a photosensor array. The analyzer can also include an autofocus pattern having a position fixed relative to the flowcell, the autofocus pattern being located at a displacement distance from the plane of the ribbon-shaped sample stream. The displacement distance can be predetermined. The analyzer can also include a light source configured to illuminate the ribbon-shaped sample stream and the autofocus pattern. Further, the analyzer can include at least one digital processor coupled to operate the motor drive and to analyze the digitized image. The processor can be configured to determine a focus position of the autofocus pattern and to relatively displace a high optical resolution imaging device and the flowcell over the displacement distance from the focused position, whereby the high optical resolution imaging device becomes focused on the ribbon-shaped sample stream. According to some embodiments, the autofocus pattern includes forms with limited size and the displacement distance is sufficient that the forms are substantially invisible in the digitized image when focused on the ribbon-shaped sample stream. In some cases, the optical axis is substantially perpendicular to the ribbon-shaped sample stream.

In another aspect, embodiments of the present invention encompass methods of focusing a visual analyzer for sample analysis. Exemplary methods can include focusing a high optical resolution imaging device on an autofocus pattern fixed relative to a flowcell, the autofocus pattern being located at a displacement distance from a ribbon-shaped sample stream that is predetermined, the high optical resolution imaging device with an objective on an optical axis that intersects the ribbon-shaped sample stream, a relative distance between the high optical resolution imaging device and the flowcell being variable by operation of a motor drive, the high optical resolution imaging device configured to resolve and collect a digitized image on a photosensor array. Further, methods can include operating the motor drive over the displacement distance to focus the high optical resolution imaging device on the ribbon-shaped sample stream.

In another aspect, embodiments of the present invention encompass methods of imaging particles in a sample. Exemplary methods can include providing a visual analyzer for a sample comprising particles suspended in a liquid, establishing a flow having laminar sections that are of higher and lower viscosity in the visual analyzer. The analyzer can include a flowcell coupled to a source of the sample and to a source of a PIOAL having a higher viscosity than the viscosity of the sample. The flowcell can define an internal flowpath, and can direct a flow of the sample enveloped with the PIOAL through a viewing zone in the flowcell. The analyzer can also include a high optical resolution imaging device with an objective on an optical axis that intersects the ribbon-shaped sample stream, a relative distance between the high optical resolution imaging device and the flowcell being variable by operation of a motor drive, for resolving and collecting a digitized image on a photosensor array. The analyzer can also include an autofocus pattern having a position fixed relative to the flowcell, the autofocus pattern being located at a displacement distance from the plane of the ribbon-shaped sample stream that has been predetermined, a light source configured to illuminate the ribbon-shaped sample stream and the autofocus pattern, at least one digital processor coupled to operate the motor drive and to analyze the digitized image, where the processor is configured to determine a focus position of the autofocus pattern and to relatively displace the high optical resolution imaging device and the flowcell over the displacement distance from the focused position, whereby the high optical resolution imaging device becomes focused on the ribbon-shaped sample stream. In some cases, an analyzer can include a flowcell coupled to a source of the sample and to a source of a PIOAL where the flowcell defines an internal flowpath and is configured to direct a flow of the sample enveloped with the PIOAL through a viewing zone in the flowcell, a high optical resolution image device with an objective on an optical axis that intersects the ribbon-shaped sample stream, a relative distance between the objective and the flowcell being variable by operation of a motor drive, for resolving and collecting a digitized image on a photosensor array, an autofocus pattern having a position fixed relative to the flowcell, the autofocus pattern being located at a displacement distance from the plane of the ribbon-shaped sample stream that has been predetermined, a light source configured to illuminate the ribbon-shaped sample stream and the autofocus pattern, and at least one digital processor coupled to operate the motor drive and to analyze the digitized image, where the processor is configured to determine a focus position of the autofocus pattern and to relatively displace the high optical resolution imaging device and the flowcell over the displacement distance from the focused position, whereby the high optical resolution imaging device becomes focused on the ribbon-shaped sample stream.

A particle contrast agent composition is disclosed for staining a blood fluid sample being imaged in an automated particle analysis system. The particle contrast agent composition can include at least one particle contrast agent selected from the group consisting of Crystal Violet, New Methylene Blue, Methyl Green, Eosin Y, and Safranin O. The particle contrast agent composition can further include a permeabilizing agent selected from the group consisting of a surfactant, a saponin, a quarternary ammonium salt, a nonionic surfactant, a detergent; and a zwitterionic surfactant. The particle contrast agent composition can further include a fixing agent selected from the group consisting of gluteraldehyde and formaldehyde.

In one embodiment, the permeabilizing agent can be saponin present in amounts sufficient to result in concentrations between about 50 mg/L and about 750 mg/L under staining conditions. The fixing agent can be gluteraldehyde present in amounts sufficient to result in concentrations at or below 0.1% under staining conditions.

In one embodiment, the at least one particle contrast agent can include Crystal Violet, New Methylene Blue, and Eosin-Y. The ratio of the Crystal Violet to the New Methylene Blue can be between about 1:90 to about 1:110 under staining conditions. The Eosin-Y can be present in amounts sufficient to result in concentrations of about 3 µM to about 300 µM under staining conditions.

In one embodiment, the Crystal Violet can be present in amounts sufficient to result in concentrations of about 6 µM to about 10 µM under staining conditions. The New Methylene Blue can be present in amounts sufficient to result in concentrations of about 70 µM to about 2.4 mM under staining conditions. The Eosin-Y can be present in amounts sufficient to result in concentrations of about 10 µM to about 50 µM under staining conditions.

In some embodiments, the Crystal Violet is approximately 90% pure or greater. The New Methylene Blue can be approximately 70% pure or greater. The Eosin-Y can be approximately 80% pure or greater.

In some embodiments, the Crystal Violet is present in amounts sufficient to result in concentrations of about 7.8 µM under staining conditions. The New Methylene Blue is present in amounts sufficient to result in concentrations of about 735 µM under staining conditions. The Eosin-Y can be present in amounts sufficient to result in concentrations of about 27 µM under staining conditions. In some embodiments, the particle contrast agent composition can additionally include buffer components.

A method is disclosed for treating particles of a blood fluid sample which will be imaged using an automated particle analysis system. The method can include combining the blood fluid sample with a particle contrast agent composition to obtain a sample mixture and incubating the sample mixture at a temperature between about 37° Celsius and about 60° Celsius for fewer than 90 seconds. The particle contrast agent composition include at least one particle contrast agent selected from the group consisting of Crystal Violet, New Methylene Blue, Methyl Green, Eosin Y, and Safranin O; a permeabilizing agent selected from the group consisting of a surfactant, a saponin, a quarternary ammonium salt, a nonionic surfactant, a detergent; and a zwitterionic surfactant; and a fixing agent selected from the group consisting of gluteraldehyde and formaldehyde.

In some embodiments, the particle contrast agent can include Crystal Violet New Methylene Blue in amounts sufficient to result in a ratio of the Crystal Violet to the New Methylene Blue between about 1:1 to about 1:500 under staining conditions. The saponin can be included in amounts sufficient to result in concentrations between about 50 mg/L and about 750 mg/L under staining conditions. The gluteraldehyde can be included in amounts sufficient to result in concentrations at or below 0.1% under staining conditions. The method can include the sample mixture being incubated for fewer than 60 seconds.

In some embodiments, the particle contrast agent composition can include Crystal Violet present in amounts sufficient to result in concentrations at about 6 μM to about 10 μM under staining conditions. The New Methylene Blue can be present in amounts sufficient to result in concentrations of about 70 μM to about 2.4 mM under staining conditions. The Eosin-Y can be present in amounts sufficient to result in concentrations of about 10 μM to about 50 μM under staining conditions. The blood fluid sample can be combined with the particle contrast agent composition at a ratio of the blood fluid sample to the particle contrast agent composition of about 1:2 to about 1:10.

In some embodiments, the method can include heating the sample mixture to between 46° C. and about 49° C. for between 40 and 50 seconds.

In some embodiment, the Crystal Violet can be approximately 90% pure or greater. The New Methylene Blue can be approximately 70% pure or greater. The Eosin-Y can be approximately 80% pure or greater.

In some embodiments, the particle contrast agent can include Crystal Violet present in amounts sufficient to result in concentrations at about 7.8 μM under staining conditions; New Methylene Blue present in amounts sufficient to result in concentrations of about 735 μM under staining conditions; and Eosin-Y present in amounts sufficient to result in concentrations of about 27 μM under staining conditions. The particle contrast agent composition can further include buffer components. The blood fluid sample can be combined with the particle contrast agent composition at a ratio of the blood fluid sample to the particle contrast agent composition of about 1:3 to about 1:4. The sample mixture can be heated to about 47° C. for about 45 seconds.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIG. 4B-1 and 4B-2 show aspects of flowcell flowpaths according to embodiments of the present invention.

FIGS. 4A-1 and 4A-2 illustrate changes in sample stream dimensions according to embodiments of the present invention.

FIG. 4C-1 shows an exemplary cannula or sample feed tube according to embodiments of the present invention.

FIG. 4D-1 shows an exemplary cannula or sample feed tube according to embodiments of the present invention.

FIGS. 4K-1, 4K-2, and 4K-3 show the target imaging site according to embodiments of the present invention.

FIG. 4L-1 shows parabolic flow profiles according to embodiments of the present invention.

FIGS. 13A, 13B, and 13C, depict views of a flowcell temperature sensor according to embodiments of the present invention.

FIG. 30 is a representative illustration of stained cells according to an early Example 3.

FIG. 31 is a representative illustration of stained cells according to an early Example 4.

FIG. 32 is a representative illustration of stained cells according to an early example.

FIG. 33 is a representative illustration of stained cells according to an early Example 5.

DETAILED DESCRIPTION OF THE INVENTION

The present disclosure relates to apparatus, systems, compositions, and methods for analyzing a sample containing particles. In one embodiment, the invention relates to an automated particle imaging system which comprises an analyzer which may be, for example, a visual analyzer. In some embodiments, the visual analyzer may further comprise a processor to facilitate automated analysis of the images.

According to this disclosure, a system comprising a visual analyzer is provided for obtaining images of a sample comprising particles suspended in a liquid. The system may be useful, for example, in characterizing particles in biological fluids, such as detecting and quantifying erythrocytes, reticulocytes, nucleated red blood cells, platelets, and white blood cells, including white blood cell differential counting, categorization and subcategorization and analysis. Other similar uses such as characterizing blood cells from other fluids are also encompassed by embodiments of the present invention. Typically, the blood fluid sample is introduced into a flowing sheath fluid, and the combined sheath and sample fluids are compressed with a narrowing flowpath transition zone that reduces the thickness of the sample ribbon fluid flow. Hence, particles such as cells can be oriented and/or compressed within the blood fluid sample by the surrounding viscous sheath fluid, for example in combination with a geometric focusing effect provided by a narrowing transition zone. Similarly, internal features within blood cells can be aligned an oriented as a result of a viscosity differential between the sample fluid and the sheath fluid, for example in combination with a geometric focusing effect provided by a narrowing transition zone.

To facilitate the capacity, speed and effectiveness by which particles such as cells are categorized and/or subcategorized, it is advantageous to provide clear high quality images of the blood cells for automated analysis by the data processing system. According to the present disclosure, a prepared sample stream is arranged in a thin ribbon having a stable position between opposite walls of a flowcell. The positioning of the sample stream and its flattening into a thin ribbon shape may be achieved by flow between layers of a PIOAL introduced into the flowcell that differs in viscosity from the sample fluid and is flowed through a symmetrical narrowing transition zone of a flow channel.

Hematology—Particle Analysis System

Figure 1:
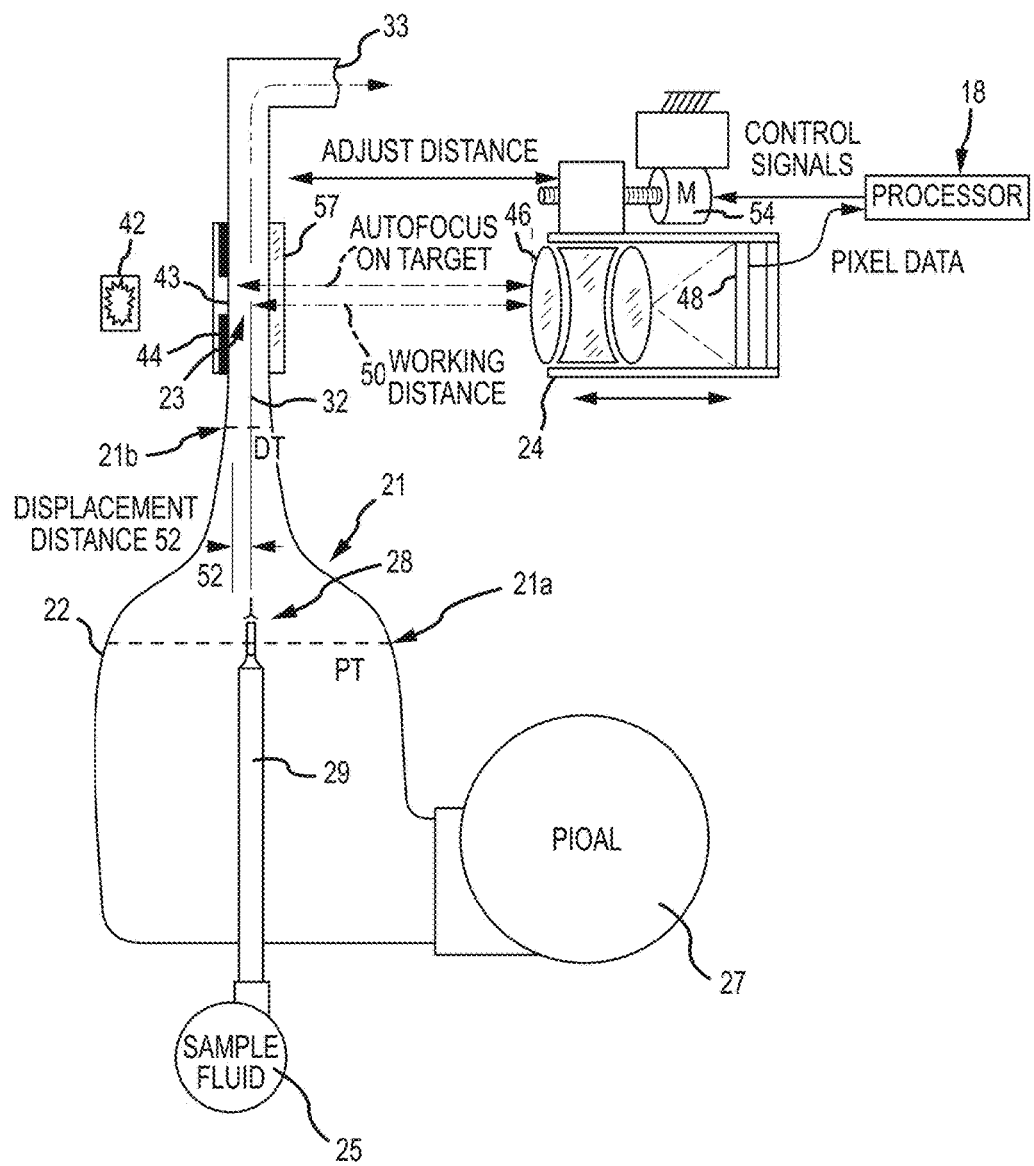
FIG. 1 is a schematic illustration, partly in section and not to scale, showing operational aspects of an exemplary flowcell, and autofocus system and high optical resolution imaging device for sample image analysis using digital image processing according to embodiments of the present invention.

Turning now to the drawings, FIG. 1 schematically shows an exemplary flowcell 22 for conveying a sample fluid through a viewing zone 23 of a high optical resolution imaging device 24 in a configuration for imaging microscopic particles in a sample flow stream 32 using digital image processing. Flowcell 22 is coupled to a source 25 of sample fluid which may have been subjected to processing, such as contact with a particle contrast agent composition and heating. Flowcell 22 is also coupled to one or more sources 27 of a particle and/or intracellular organelle alignment liquid (PIOAL), such as a clear glycerol solution having a viscosity that is greater than the viscosity of the sample fluid.

The sample fluid is injected through a flattened opening at a distal end 28 of a sample feed tube 29, and into the interior of the flowcell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by precision metering pumps that move the PIOAL with the injected sample fluid along a flowpath that narrows substantially. The PIOAL envelopes and compresses the sample fluid in the zone 21 where the flowpath narrows. Hence, the decrease in flowpath thickness at zone 21 can contribute to a geometric focusing of the sample stream 32. The sample fluid ribbon 32 is enveloped and carried along with the PIOAL downstream of the narrowing zone 21, passing in front of, or otherwise through the viewing zone 23 of, the high optical resolution imaging device 24 where images are collected, for example, using a CCD 48. Processor 18 can receive, as input, pixel data from CCD 48. The sample fluid ribbon flows together with the PIOAL to a discharge 33.

As shown here, the narrowing zone 21 can have a proximal flowpath portion 21a having a proximal thickness PT and a distal flowpath portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid can enter the PIOAL envelope as the PIOAL stream is compressed by the zone 21, wherein the sample fluid injection tube has a distal exit port through which sample fluid is injected into flowing sheath fluid, the distal exit port bounded by the decrease in flowpath size of the flowcell.

The digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

According to some embodiments, the system can operate to hydrofocus the sample fluid ribbon 32. The term hydrofocus or hydrofocusing can refer to a focusing effect which is influenced by a viscosity difference between the sheath and sample fluids, a geometric narrowing transition zone of the flowcell, and a velocity difference between the the sheath and sample fluids. Hydrodynamic flow results from the velocity difference between the sample and sheath fluid streams, which affects the flow ribbon thickness and shape.

The present disclosure provides a technique for automatically achieving a correct working position of the high optical resolution imaging device 24 for focusing on the ribbon-shaped sample stream 32. The flowcell structure 22 can be configured such that the ribbon-shaped sample stream 32 has a fixed and dependable location within the flowcell defining the flow path of sample fluid, in a thin ribbon between layers of PIOAL, passing through a viewing zone 23 in the flowcell 22. In certain flowcell embodiments, the cross section of the flowpath for the PIOAL narrows symmetrically at the point at which the sample is inserted through a flattened orifice such as a tube 29 with a rectangular lumen at the orifice, or cannula. The narrowing flowpath (for example geometrically narrowing in cross sectional area by a ratio of 20:1, or by a ratio between 20:1 to 70:1) along with a differential viscosity between the PIOAL and sample fluids, and optionally, a difference in linear speed of the PIOAL compared to the flow of the sample, cooperate to compress the sample cross section by a ratio of about 20:1 to 70:1. In some embodiments the cross section thickness ratio may be 40:1.

In one aspect, the symmetrical nature of the flowcell 22 and the manner of injection of the sample fluid and PIOAL provide a repeatable position within the flowcell 22 for the ribbon-shaped sample stream 32 between the two layers of the PIOAL. As a result, process variations such as the specific linear velocities of the sample and the PIOAL; do not tend to displace the ribbon-shaped sample stream from its location in the flow. Relative to the structure of the flowcell 22, the ribbon-shaped sample stream 32 location is stable and repeatable.

However, the relative positions of the flowcell 22 and the high optical resolution imaging device 24 of the optical system may be subject to change and may benefit from occasional position adjustments to maintain an optimal or desired distance between the high optical resolution imaging device 24 and the ribbon-shaped sample stream 32, thus providing a quality focus image of the enveloped particles in the ribbon-shaped sample stream 32. According to some embodiments, there can be an optimal or desired distance between the high optical resolution imaging device 24 and the ribbon-shaped sample stream 32 for obtaining focused images of the enveloped particles. The optics can first be positioned accurately relative to the flowcell 22 by autofocus or other techniques to locate the high optical resolution imaging device 24 at the optimal or desired distance from an autofocus target 44 with a fixed position relative to the flowcell 22. The displacement distance between the autofocus target 44 and the ribbon-shaped sample stream 32 is known precisely, for example as a result of initial calibration steps. After autofocusing on the autofocus target 44, the flowcell 22 and/or high optical resolution imaging device 24 is then displaced over the known displacement distance between the autofocus target 44 and the ribbon-shaped sample stream 32. As a result, the objective lens of the high optical resolution imaging device 44 is focused precisely on the ribbon-shaped sample stream 32 containing the enveloped particles.

Exemplary embodiments of the present invention involve autofocusing on the focus or imaging target 44, which is a high contrast figure defining a known location along the optical axis of the high optical resolution imaging device or the digital image capture device 24. The target 44 can have a known displacement distance relative to the location of the ribbon-shaped sample stream 32. A contrast measurement algorithm can be employed specifically on the target features. In one example, the position of the high optical resolution imaging device 24 can be varied along a line parallel to the optical axis of the high optical resolution imaging device or the digital image capture device, to find the depth or distance at which one or more maximum differential amplitudes are found among the pixel luminance values occurring along a line of pixels in the image that is known to cross over an edge of the contrast figure. In some cases, the autofocus pattern has no variation along the line parallel to the optical axis, which is also the line along which a motorized control operates to adjust the position of the high optical resolution imaging device 24 to provide the recorded displacement distance.

In this way, it may not be necessary to autofocus or rely upon an image content aspect that is variable between different images, that is less highly defined as to contrast, or that might be located somewhere in a range of positions, as the basis for determining a distance location for reference. Having found the location of optimal or desired focus on the autofocus target 44, the relative positions of the high optical resolution imaging device objective 24 and the flowcell 22 can be displaced by the recorded displacement distance to provide the optimal or desired focus position for particles in the ribbon-shaped sample stream 32.

According to some embodiments, the high optical resolution imaging device 24 can resolve an image of the ribbon-shaped sample stream 32 as backlighted by a light source 42 applied through an illumination opening (window) 43. In the embodiments shown in FIG. 1, the perimeter of the illumination opening 43 forms an autofocusing target 44. However the object is to collect a precisely focused image of the ribbon-shaped sample stream 32 through high optical resolution imaging device optics 46 on an array of photosensitive elements, such as an integrated charge coupled device.

The high optical resolution imaging device 24 and its optics 46 are configured to resolve an image of the particles in the ribbon-shaped sample stream 32 that is in focus at distance 50, which distance can be a result of the dimensions of the optical system, the shape of the lenses, and the refractive indices of their materials. In some cases, the optimal or desired distance between the high optical resolution imaging device 24 and the ribbon-shaped sample stream 32 does not change. In other cases, the distance between the flowcell 22 and the high optical resolution imaging device and its optics 46 can be changed. Moving the high optical resolution imaging device 24 and/or flowcell 22 closer or further apart, relative to one another (e.g. by adjusting distance 51 between the imaging device 24 and the flowcell 22), moves the location of the focusing point at the end of distance 50 relative to the flowcell.

According to embodiments of the present invention, a focus target 44 can be located at a distance from the ribbon-shaped sample stream 32, in this case fixed directly to the flowcell 22 at the edges of the opening 43 for light from illumination source 42. The focus target 44 is at a constant displacement distance 52 from the ribbon-shaped sample stream 32. Often, the displacement distance 52 is constant because the location of the ribbon-shaped sample stream 32 in the flowcell remains constant.

An exemplary autofocus procedure involves adjusting the relative positions of the high optical resolution imaging device 24 and flowcell 22 using a motor 54 to arrive at the appropriate focal length thereby causing the high optical resolution imaging device 24 to focus on the autofocus target 44. In this example, the autofocus target 44 is behind the ribbon-shaped sample stream 32 in the flowcell. Then the high optical resolution imaging device 24 is moved toward or away from flowcell 22 until autofocus procedures establish that the image resolved on photosensor is an accurately focused image of autofocus target 44. Then motor 54 is operated to displace the relative positions of high optical resolution imaging device 24 and flowcell 22 to cause the high optical resolution imaging device to focus on the ribbon-shaped sample stream 32, namely by moving the high optical resolution imaging device 24 away from flowcell 22 , precisely by the span of the displacement distance 52. In this exemplary embodiment, imaging device 24 is shown to be moved by motor 54 to get to a focus position. In other embodiments, flowcell 22 is moved or both the flowcell 22 and imaging device 24 are moved by similar means to obtain focused images.

These directions of movement would of course be reversed if the focus target 44 was located on the front viewport window as opposed to the rear illumination window 43. In that case, the displacement distance would be the span between the ribbon-shaped sample stream 32 and a target 44 at the front viewport (not shown).

The displacement distance 52, which is equal to the distance between ribbon-shaped sample stream 32 and autofocus target 44 along the optical axis of the high optical resolution imaging device 24, can be established in a factory calibration step or established by a user. Typically, once established, the displacement distance 52 does not change. Thermal expansion variations and vibrations may cause the precise position of the high optical resolution imaging device 24 and flowcell 22 to vary relative to one another, thus necessitating re-initiation of the autofocus process. But autofocusing on the target 44 provides a position reference that is fixed relative to the flowcell 22 and thus fixed relative to the ribbon-shaped sample stream 32. Likewise, the displacement distance is constant. Therefore, by autofocusing on the target 44 and displacing the high optical resolution imaging device 24 and flowcell 22 by the span of the displacement distance, the result is the high optical resolution imaging device being focused on the ribbon-shaped sample stream 32.

According to some embodiments, the focusing target is provided as a high contrast circle printed or applied around the illumination opening 43. Alternative focusing target configurations are discussed elsewhere herein. When a square or rectangular image is collected in focus on the target 44, a high contrast border appears around the center of illumination. Seeking the position at which the highest contrast is obtained in the image at the inner edges of the opening automatically focuses the high optical resolution imaging device at the working location of the target 44. According to some embodiments, the term "working distance" can refer to the distance between the objective and its focal plane and the term "working location" can refer to the focal plane of the imaging device. The highest contrast measure of an image is where the brightest white and darkest black measured pixels are adjacent to one another along a line through an inner edge. The highest contrast measure can be used to evaluate whether the focal plane of the imaging device is in the desired position relative to the target 44. Other autofocus techniques can be used as well, such as edge detection techniques, image segmentation, and integrating the differences in amplitude between adjacent pixels and seeking the highest sum of differences. In one technique, the sum of differences is calculated at three distances that encompass working positions on either side of the target 44 and matching the resulting values to a characteristic curve, wherein the optimal distance is at the peak value on the curve. Relatedly, exemplary autofocus techniques can involve collecting images of the flow cell target at different positions and analyzes the images to find the best focus position using a metric that is largest when the image of the target is sharpest. During a first step (coarse) the autofocus technique can operate to find a preliminary best position from a set of images collected at 2.5 µm intervals. From that position the autofocus technique can then involve collecting a second set of images (fine) at 0.5 µm intervals, and calculating the final best focus position on the target.

In some cases, the focus target (autofocus pattern) can reside on the periphery of the area of view in which the sample is to appear. It is also possible that the focus target could be defined by contrasting shapes that reside in the field of view, such at that depicted in FIG. 15. Typically, the autofocus target is mounted on the flowcell or attached rigidly in fixed position relative to the flowcell. Under power of a positioning motor controlled by a detector responsive to maximizing the contrast of the image of the autofocusing target, the apparatus autofocuses on the target as opposed to the ribbon-shaped sample stream. Then by displacing the flowcell and/or the high optical resolution imaging device relative to one another, by the displacement distance known to be the distance between the autofocus target and the ribbon-shaped sample stream, the working position or the focal plane of the high optical resolution imaging device is displaced from the autofocus target to the ribbon-shaped sample stream. As a result, the ribbon-shaped sample stream appears in focus in the collected digital image.

In order to distinguish particle types by data processing techniques, such as categories and/or subcategories of red and white blood cells, it is advantageous to record microscopic pixel images that have sufficient resolution and clarity to reveal the aspects that distinguish one category or subcategory from the others. It is an object of the invention to facilitate autofocus techniques as described.

Figure 1A:
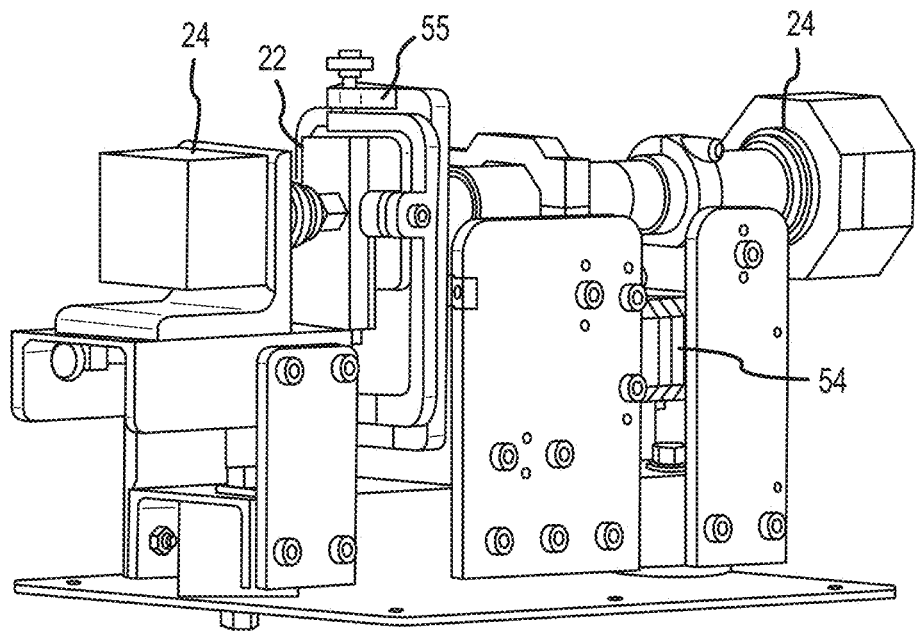
FIGS. 1A and 1B show an optical bench arrangement according to embodiments of the present invention.
Figure 1B:
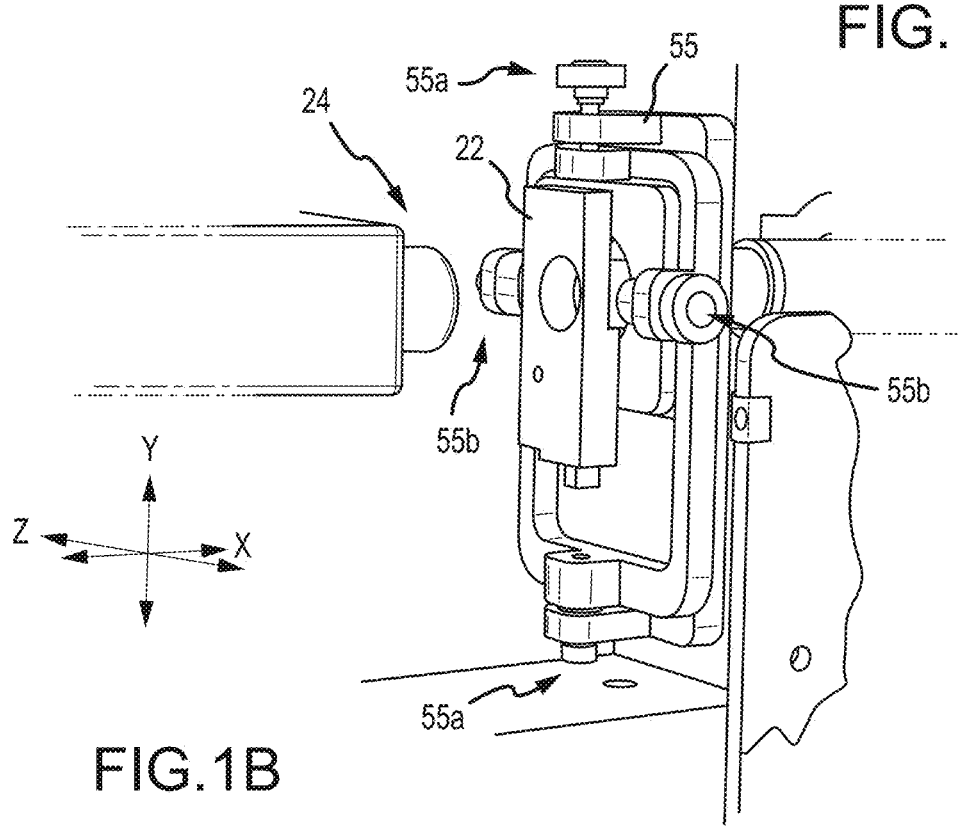

In a practical embodiment, the apparatus can be based on an optical bench arrangement such as shown in FIG. 1A and as enlarged in FIG. 1B, having a source of illumination 42 directed onto a flowcell 22 mounted in a gimbaled or flowcell carrier 55, backlighting the contents of the flowcell 22 in an image obtained by a high optical resolution imaging device 24. Carrier 55 is mounted on a motor drive so as to be precisely movable toward and away from the high optical resolution imaging device 24. Carrier 55 also allows a precise alignment of the flowcell relative to the optical viewing axis of the high optical resolution imaging device or the digital image capture device, so that the ribbon-shaped sample stream flows in a plane normal to the viewing axis in the zone where the ribbon-shaped sample stream is imaged, namely between the illumination opening 43 and viewing port 57 as depicted in FIG. 1. The focus target 44 can assist in adjustment of carrier 55, for example to establish the plane of the ribbon-shaped sample stream normal to the optical axis of the high optical resolution imaging device or the digital image capture device.

Hence, carrier 55 provides for very precise linear and angular adjustment of the position and orientation of flowcell 22, for example relative to the image capture device 24 or the image capture device objective. As shown here, the carrier 55 includes two pivot points 55a, 55b to facilitate angular adjustment of the carrier and flowcell relative to the image capture device. Angular adjustment pivot points 55a, 55b are located in the same plane and centered to the flow cell channel (e.g. at the image capture site). This allows for adjustment of the angles without causing any linear translation of the flow cell position. The carrier 55 can be rotated about an axis of pivot point 55a or about an axis of pivot point 55b, or about both axes. Such rotation can be controlled by a processor and a flowcell movement control mechanism, such as processor 440 and flowcell control mechanism 442 depicted in FIG. 4.

With returning reference to FIG. 1B, it can be seen that either or both of the image capture device 24 and the carrier 55 (along with flowcell 22) can be rotated or translated along various axes (e.g. X, Y, Z) in three dimensions. Hence, an exemplary technique for adjusting focus of the image capture device can include implementing axial rotation of the image capture device 24 about the imaging axis, for example by rotating device 24 about axis X. Focus adjustment can also be achieved by axial rotation of the flowcell 22 and/or carrier carrier 55 about an axis extending along the imaging axis, for example about axis X, and within the field of view of the imaging device. In some cases, focus adjustment may include tip rotation (e.g. rotation about axis Y) of the image capture device. In some cases, focus adjustment may include tip rotation (e.g. rotation about axis Y, or about pivot point 55a) of the flowcell. As depicted here, pivot point 55a corresponds to a Y axis that extends along and within the flowpath of the flowcell. In some cases, focus adjustment can include tilt rotation (e.g. rotation about axis Z) of the image capture device. In some cases, focus adjustment may include tilt rotation (e.g. rotation about axis Z, or about pivot point 55b) of the flowcell. As depicted here, pivot point 55b corresponds to a Z axis that traverses the flowpath and the imaging axis. In some cases, the image capture device can be focused on the sample flowstream by implementing a rotation of the flowcell (e.g. about axis X), such that the rotation is centered in the field of view of the image capture device. The three dimensional rotational adjustments described herein can be implemented so as to account for positional drift in one or more components of the analyzer system. In some cases, the three dimensional rotational adjustments can be implemented so as to account for temperature fluctuations in one or more components of the analyzer system. In some cases, adjustment of an analyzer system may include translating imaging device 24 along axis X. In some cases, adjustment of analyzer sysetm may include translating carrier 55 or flowcell 22 along axis X.

According to some embodiments, a visual analyzer for obtaining images of a sample containing particles suspended in a liquid includes flowcell 22, coupled to a source 25 of the sample and to a source 27 of PIOAL material as depicted in FIG. 1. As seen in the section view of FIG. 3, the flowcell 22 defines an internal flowpath that narrows symmetrically in the flow direction (right to left in FIG. 3 or bottom to top in FIG. 1). The flowcell 22 is configured to direct a flow 32 of the sample enveloped with the PIOAL through a viewing zone in the flowcell, namely behind viewing port 57.

Referring again to FIG. 1, the digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

The autofocus pattern 44, having a position that is fixed relative to the flowcell 22, is located at a displacement distance 52 from the plane of the ribbon-shaped sample stream 32. In the embodiment shown, the autofocus pattern (target 44) is applied directly to the flowcell 22 at a location that is visible in the image collected by the high optical resolution imaging device 24. In another embodiment, the target can be carried on a part that is rigidly fixed in position relative to the flowcell 22 and the ribbon-shaped sample stream 32 therein, if not applied directly to the body of the flowcell in an integral manner.

The light source 42, which can be a steady source or can be a strobe that is flashed in time with operation of the high optical resolution imaging device photosensor, is configured to illuminate the ribbon-shaped sample stream 32 and also to contribute to the contrast of the target 44. In the depicted embodiment, the illumination is from back-lighting.

Figure 1C:
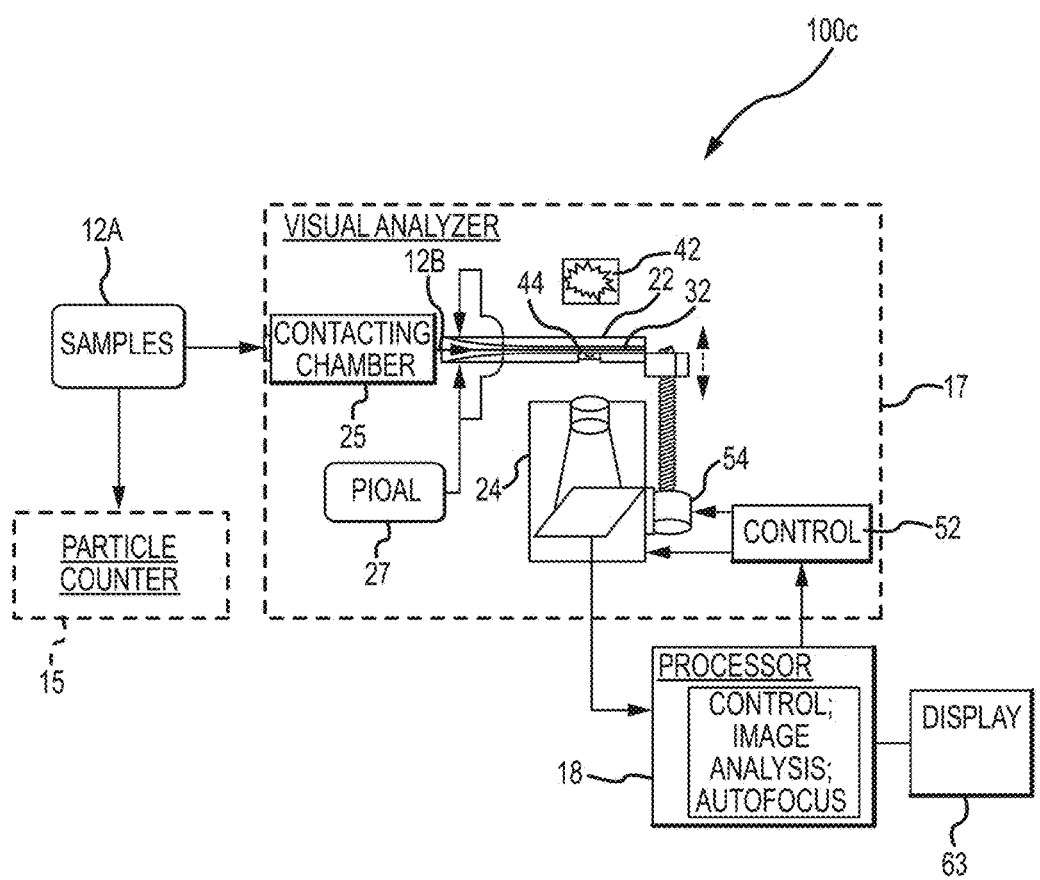
FIG. 1C is a block diagram of a hematology analyzer according to embodiments of the present invention.

FIG. 1C provides a block diagram showing additional aspects of an exemplary hematology analyzer. As shown here, the analyzer 100c includes at least one digital processor 18 coupled to operate the motor drive 54 and to analyze the digitized image from the photosensor array as collected at different focus positions relative to the target autofocus pattern 44. The processor 18 is configured to determine a focus position of the autofocus pattern 44, i.e., to autofocus on the target autofocus pattern 44 and thus establish an optimal distance between the high optical resolution imaging device 24 and the autofocus pattern 44. This can be accomplished by image processing steps such as applying an algorithm to assess the level of contrast in the image at a first distance, which can apply to the entire image or at least at an edge of the autofocus pattern 44. The processor moves the motor 54 to another position and assesses the contrast at that position or edge, and after two or more iterations determines an optimal distance that maximizes the accuracy of focus on the autofocus pattern 44 (or would optimize the accuracy of focus if moved to that position). The processor relies on the fixed spacing between the autofocus target autofocus pattern 44 and the ribbon-shaped sample stream, the processor 18 then controls the motor 54 to move the high optical resolution imaging device 24 to the correct distance to focus on the ribbon-shaped sample stream 32. More particularly, the processor operates the motor to displace the distance between the high optical resolution imaging device and the ribbon-shaped sample stream 32 by the displacement distance 52 (for example as depicted in FIG. 1) by which the ribbon-shaped sample stream is displaced from the target autofocus pattern 44. In this way, the high optical resolution imaging device is focused on the ribbon-shaped sample stream.

The motor 54 can comprise a geared stepping motor with precision somewhat smaller than the distinguishing features imaged by the high optical resolution imaging device or the digital image capture device, especially aspects of blood cells. Provided that the location of the high optical resolution imaging device 24 is adjusted to locate the position of the optical objective within the width of the ribbon-shaped sample stream, the view of the cell/particle in the ribbon-shaped sample stream is in focus. An autofocus pattern 44 can be located at an edge of a field of view of the high optical resolution imaging device or the digital image capture device, and does not interfere with viewing for that reason.

Figure 21:
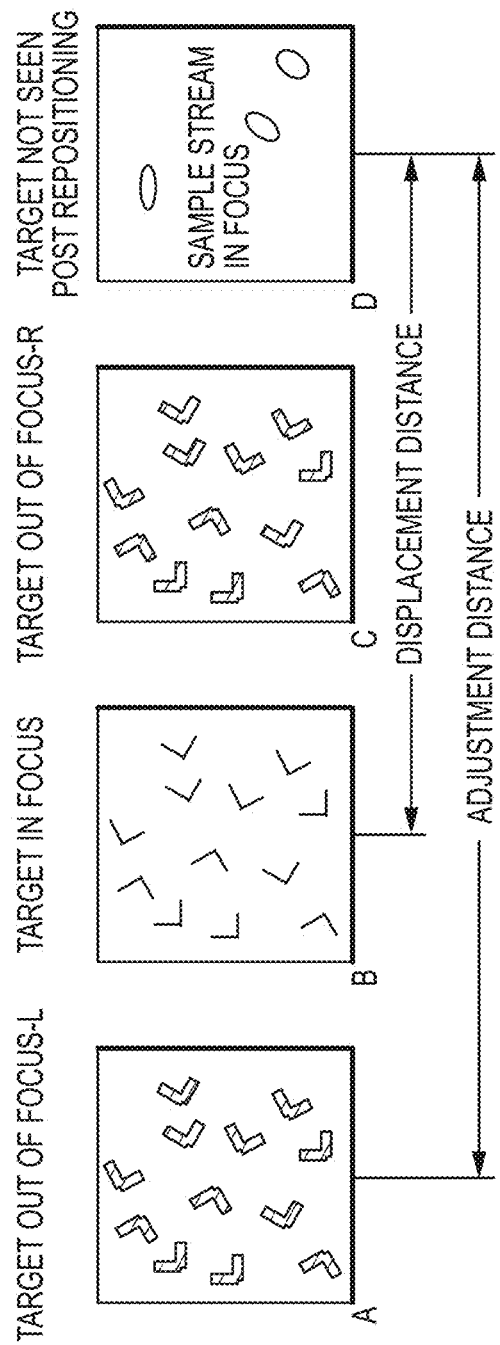
FIG. 21 depicts an elevation view showing embodiments of an autofocus pattern according to embodiments of the present invention.

Furthermore, when the high optical resolution imaging device is moved over the displacement distance and the autofocus pattern goes out of focus, the features that appear in focus are the blood cells as opposed to the autofocus pattern. In the embodiment of FIG. 21, for example, the autofocus pattern is defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 μm in a flowcell dimensioned for hematology (blood cell) imaging applications. In some embodiments, the autofocus feature maintains the high optical resolution imaging device within 1 μm of the optimal focus distance.

The flowcell internal contour and the PIOAL and sample flow rates can be adjusted such that the sample is formed into a ribbon shaped stream. The stream can be approximately as thin as or even thinner than the particles that are enveloped in the ribbon-shaped sample stream. White blood cells may have a diameter around 10 μm, for example. By providing a ribbon-shaped sample stream with a thickness less than 10 μm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. With returning reference to FIG. 1, the source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. In some cases the PIOAL viscosity can be up to 10 centipoise.

In the embodiment shown in FIG. 1C, the same digital processor 18 that is used to analyze the pixel digital image obtained from photosensor array is also used to control the autofocusing motor 54. However typically the high optical resolution imaging device 24 is not autofocused for every image captured. The autofocus process can be accomplished periodically (at the beginning of the day or at the beginning of a shift) or for example when temperature or other process changes are detected by appropriate sensors, or when image analysis detects a potential need for refocusing. In some cases, an automated autofocusing process may be performed within a time duration of about 10 seconds. In some cases, an autofocus procedure can be performed prior to processing a rack of samples (e.g. 10 samples per rack). It is also possible in other embodiments to have the hematology image analysis accomplished by one processor and to have a separate processor, optionally associated with its own photosensor array, arranged to handle the steps of autofocusing to a fixed target 44.

The digital processor 18 can be configured to autofocus at programmed times or in programmed conditions or on user demand, and also is configured to perform image based categorization and subcategorization of the particles. Exemplary particles include cells, white blood cells, red blood cells and the like.

In one embodiment, the digital processor 18 of FIG. 1 or FIG. 1C is configured to detect an autofocus re-initiation signal. The autofocus re-initiation signal can be triggered by a detected change in temperature, a decrease in focus quality as discerned by parameters of the pixel image date, passage of time, or user-input. Advantageously, it is not necessary to recalibrate in the sense of measuring the displacement distance 52 depicted in FIG. 1 to recalibrate. Optionally, the autofocus can be programmed to re-calibrate at certain frequencies/intervals between runs for quality control and or to maintain focus.

The displacement distance 52 varies slightly from one flowcell to another, but remains constant for a given flowcell. As a setup process when fitting out an image analyzer with a flowcell, the displacement distance is first estimated and then during calibration steps wherein the autofocus and imaging aspects are exercised, the exact displacement distance for the flowcell is determined and entered as a constant into the programming of processor 18.

Figure 1D:
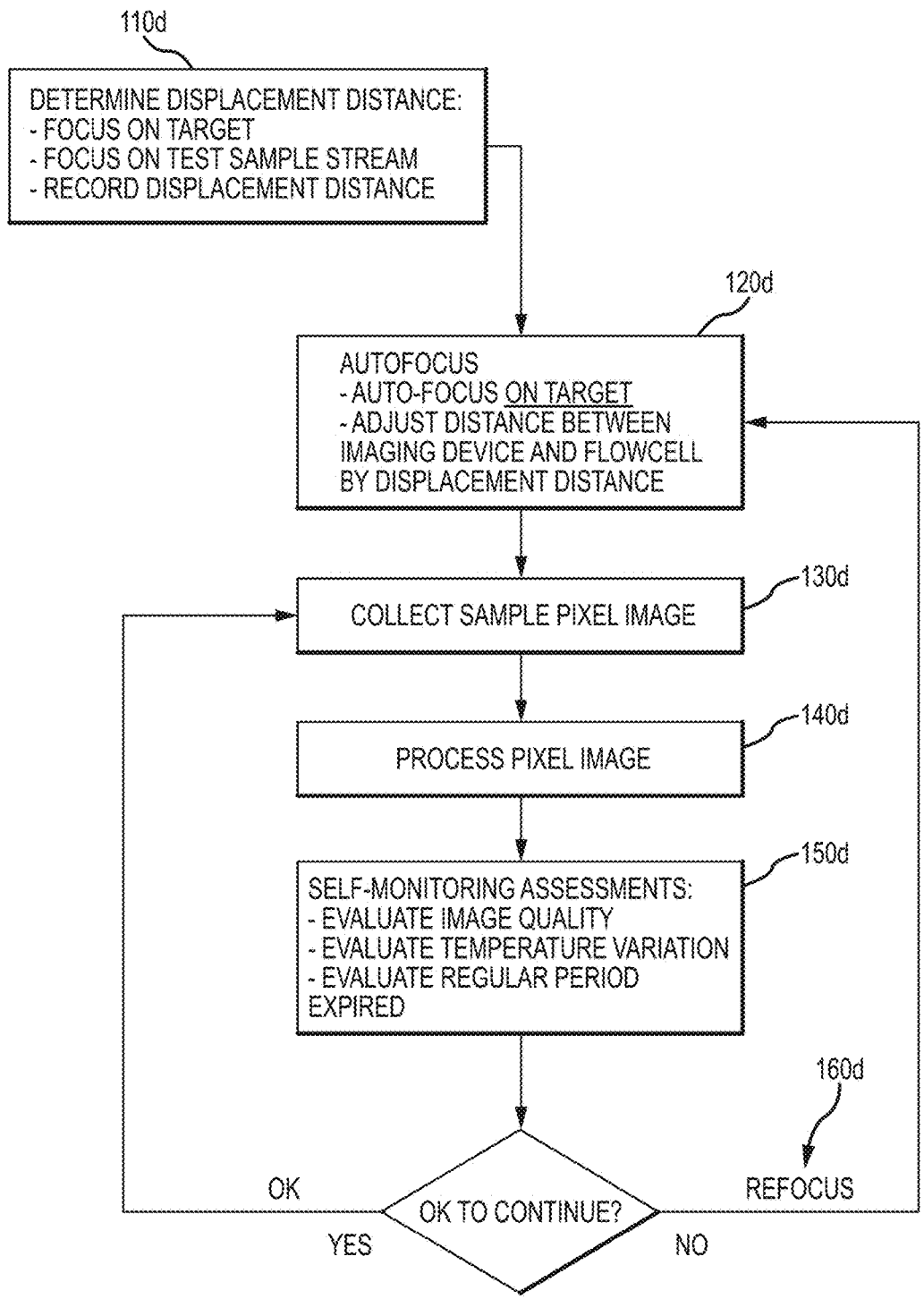
FIG. 1D shows a flowchart of a process according to embodiments of the present invention.

Accordingly, as shown in flowchart form in FIG. 1D, and with reference to hematology analyzer of FIG. 1 and/or FIG. 1C, the process undertaken according to the disclosed methods and apparatus may involve calibrating once or rarely. Calibration can include focusing on the contrast target 44, focusing on the ribbon-shaped sample stream 32, and noting the displacement along the optical axis between these two locations, as indicated in step 110d. That displacement can be noted as a constant. Thereafter by controlling motor 54 and analyzing image data from photosensor array, the processor 18 autofocuses on target 44 and displaces the high optical resolution imaging device 24 and/or flowcell 22 relative to one another by the noted displacement distance, as indicated in step 120d. The ribbon-shaped sample stream 32 is then in focus and its image can be collected (as indicated in step 130d) and processed (as indicated in step 140d) at regular intervals, especially at intervals sufficient to collect substantially non-overlapping adjacent views of portions of the ribbon-shaped sample stream passing through the viewing zone at viewing port 57. When self-monitoring (as indicated in step 150d) reveals a data anomaly or a temperature change that might have altered relative positions of the high optical resolution imaging device 24 and flowcell 22 due to differences in thermal expansion, then autofocus (at indicated in step 160d) is initiated, after which regular operation resumes. Hence, an autofocusing process may include detecting an autofocus re-initiation signal, and repeating autofocusing and image acquisition steps in response to the auto-focus re-initiation signal. In some embodiments the autofocus re-initiation signal can include or be based on change in temperature, a decrease in focus quality, a lapsed time interval, or a user-input.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

It is possible to use autofocusing on the target and displacement by the displacement distance to obtain a distance appropriate for focusing on the ribbon-shaped sample stream. Advantageously, however, autofocusing is not needed or repeated for each image capture. However autofocusing is commenced on certain conditions. An autofocus re-initiation signal can be detected or generated, leading to steps of refocusing on the autofocus pattern, operating the motor drive over the displacement distance, and refocusing the high optical resolution imaging device on the ribbon-shaped sample stream. The autofocus re-initiation signal can be cause by detection of a change for example in temperature, a decrease in focus quality, the passage of time, other process parameters or user-input.

Figure 1E:
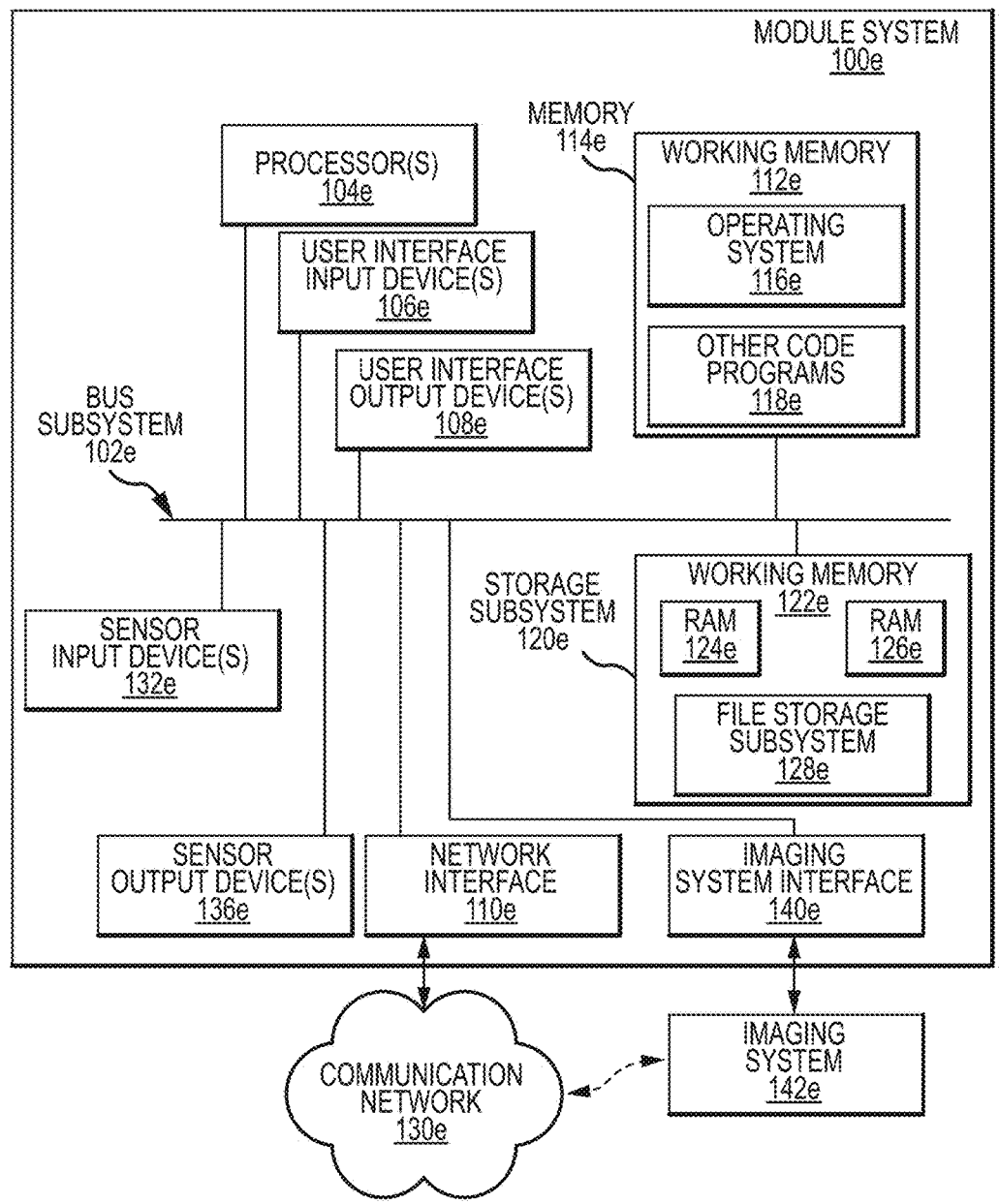
FIG. 1E is a simplified block diagram of an exemplary module system according to embodiments of the present invention.

FIG. 1E is a simplified block diagram of an exemplary module system that broadly illustrates how individual system elements for a module system 100e may be implemented in a separated or more integrated manner. Module system 100e may be part of or in connectivity with a particle analysis system for imaging particles in a blood sample fluid, according to embodiments of the present invention. Module system 100e is well suited for producing data or instructions related to focusing and imaging techniques, receiving input related to focusing and imaging techniques, and/or processing information or data related to focusing and imaging techniques, as described elsewhere herein. In some instances, module system 100e includes hardware elements that are electrically coupled via a bus subsystem 102e, including one or more processors 104e, one or more input devices 106e such as user interface input devices, and/or one or more output devices 108e such as user interface output devices. In some instances, system 100e includes a network interface 110e, and/or an imaging system interface 140e that can receive signals from and/or transmit signals to an imaging system 142e. In some instances, system 100e includes software elements, for example shown here as being currently located within a working memory 112e of a memory 114e, an operating system 116e, and/or other code 118e, such as a program configured to implement one or more aspects of the techniques disclosed herein.

In some embodiments, module system 100e may include a storage subsystem 120e that can store the basic programming and data constructs that provide the functionality of the various techniques disclosed herein. For example, software modules implementing the functionality of method aspects, as described herein, may be stored in storage subsystem 120e. These software modules may be executed by the one or more processors 104e. In a distributed environment, the software modules may be stored on a plurality of computer systems and executed by processors of the plurality of computer systems. Storage subsystem 120e can include memory subsystem 122e and file storage subsystem 128e. Memory subsystem 122e may include a number of memories including a main random access memory (RAM) 126e for storage of instructions and data during program execution and a read only memory (ROM) 124e in which fixed instructions are stored. File storage subsystem 128e can provide persistent (non-volatile) storage for program and data files, and may include tangible storage media which may optionally embody sample, patient, treatment, assessment, or other data. File storage subsystem 128e may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 100e. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 128e. In some embodiments, the software or code will provide protocol to allow the module system 100e to communicate with communication network 130e. Optionally, such communications may include dial-up or internet connection communications.

It is appreciated that system 100e can be configured to carry out various aspects of methods of the present invention. For example, processor component or module 104e can be a microprocessor control module configured to receive temperature parameter signals and/or flowcell operational parameters from a sensor input device or module 132e, from a user interface input device or module 106e, and/or from an imaging system 142e, optionally via an image system interface 140e and/or a network interface 110e and a communication network 130e. In some instances, sensor input device(s) may include or be part of a particle analysis system that is equipped to obtain images of blood fluid samples. In some instances, user interface input device(s) 106e and/or network interface 110e may be configured to receive image parameter signals generated by a particle analysis system that is equipped to obtain image parameters. In some instances, imaging system 142e may include or be part of a particle analysis system that is equipped to obtain image parameters related to blood fluid samples.

Processor component or module 104e can also be configured to transmit particle analysis parameter signals or image parameter signals, optionally processed according to any of the techniques disclosed herein, to sensor output device or module 136e, to user interface output device or module 108e, to network interface device or module 110e, to imaging system interface 140e, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present invention.

User interface input devices 106e may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 106e may also download a computer executable code from a tangible storage media or from communication network 130e, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 100e.

User interface output devices 106e may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 600 to a user.

Bus subsystem 102e provides a mechanism for letting the various components and subsystems of module system 100e communicate with each other as intended or desired. The various subsystems and components of module system 100e need not be at the same physical location but may be distributed at various locations within a distributed network. Although bus subsystem 102e is shown schematically as a single bus, alternate embodiments of the bus subsystem may utilize multiple busses.

Network interface 110e can provide an interface to an outside network 130e or other devices. Outside communication network 130e can be configured to effect communications as needed or desired with other parties. It can thus receive an electronic packet from module system 100e and transmit any information as needed or desired back to module system 100e. As depicted here, communication network 130e and/or imaging system interface 142e may transmit information to or receive information from an imaging system 142e that is equipped to obtain images or image parameters corresponding to blood fluid samples.

In addition to providing such infrastructure communications links internal to the system, the communications network system 130e may also provide a connection to other networks such as the interne and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 100e itself can be of varying types including a computer terminal, a personal computer, a portable computer, a workstation, a network computer, or any other data processing system. Due to the ever-changing nature of computers and networks, the description of module system 100e depicted in FIG. 1E is intended only as a specific example for purposes of illustrating one or more embodiments of the present invention. Many other configurations of module system 100e are possible having more or less components than the module system depicted in FIG. 1E. Any of the modules or components of module system 100e, or any combinations of such modules or components, can be coupled with, or integrated into, or otherwise configured to be in connectivity with, any of the particle analysis and/or imaging system embodiments disclosed herein. Relatedly, any of the hardware and software components discussed above can be integrated with or configured to interface with other medical assessment or treatment systems used at other locations.

In some embodiments, the module system 100e can be configured to receive one or more image parameters of a blood fluid sample at an input module. Image parameter data can be transmitted to an assessment module where diagnostic or other results can be predicted or determined based on analysis of the image data. Image or diagnostic data can be output to a system user via an output module. In some cases, the module system 100e can determine diagnostic results for a blood fluid sample, for example by using a diagnostic module. The diagnostic information can be output to a system user via an output module. Optionally, certain aspects of the diagnosis can be determined by an output device, and transmitted to a diagnosis system or a sub-device of a diagnosis system. Any of a variety of data related to the blood fluid samples or patients from whom samples are obtained can be input into the module system, including age, weight, sex, treatment history, medical history, and the like. Parameters of treatment regimens or diagnostic evaluations can be determined based on such data.

Relatedly, in some instances a system includes a processor configured to receive the image data as input. Optionally, a processor, storage medium, or both, may be incorporated within a hematology or particle analysis machine. In some instances, the hematology machine may generate image data or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

Flowcell

Figure 2:
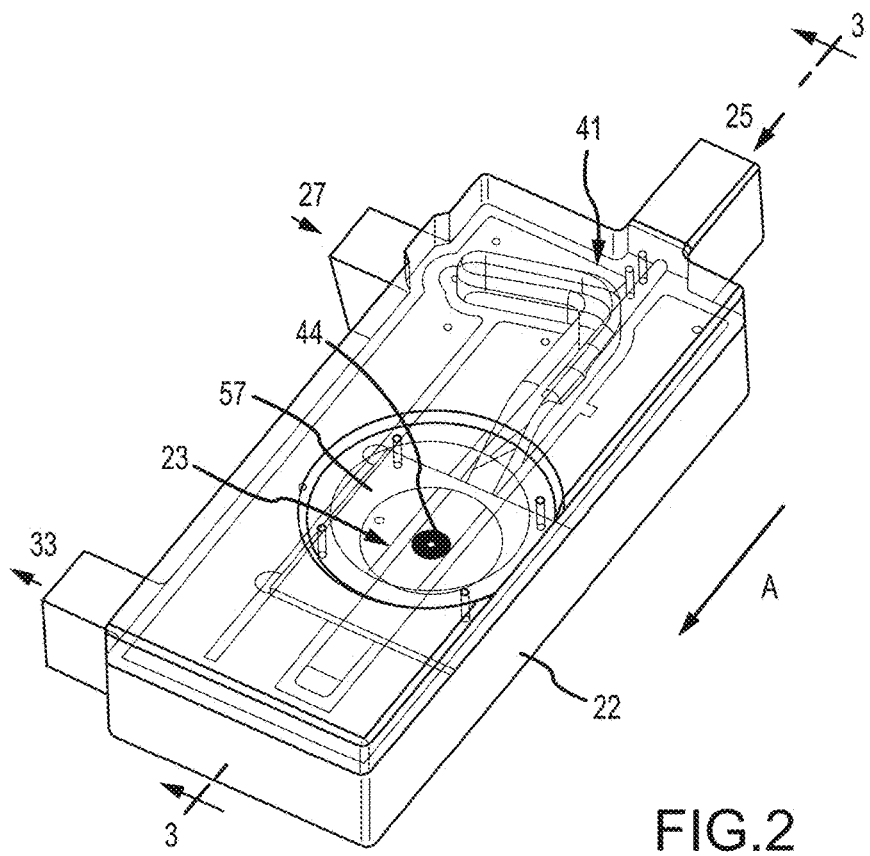
FIG. 2 shows parts of a flowcell according to embodiments of the present invention.
Figure 3:
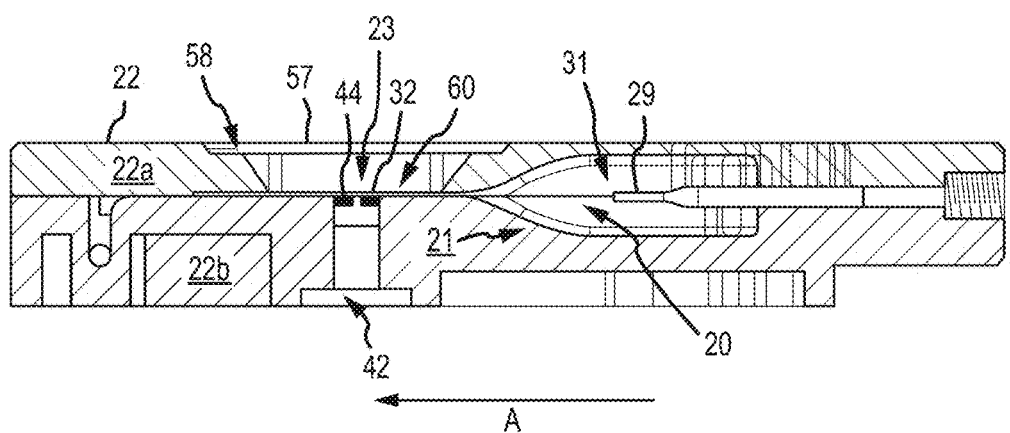
FIGS. 3, 3A, and 3B shows aspects of flowcells according to embodiments of the present invention.

A practical embodiment of flowcell 22 is further depicted in FIGS. 2 and 3. As shown here, flowcell 22 can be coupled with a sample source 25 and also to a source 27 of PIOAL material. The sample fluid is injected into the flowcell 22 via the cannula 29, for example through a distal exit port 31 of the cannula 29. Typically, the PIOAL sheath fluid is not in a laminar flow state as it travels through a curved channel section 41 in the flowcell from the source 27 toward the viewing zone 23. However, the flowcell 22 can be configured so that the PIOAL sheath fluid is or becomes laminar, or presents a flat velocity profile, as it flows past the distal exit port 31 where sample fluid is introduced into the flowing sheath fluid. The sample fluid and the PIOAL can flow along the flowcell 22 in a direction generally indicated by arrow A, and then out of the flowcell 22 via discharge 33. The flowcell 22 defines an internal flowpath 20 that narrows symmetrically (e.g. at transition zone 21) in the flow direction A. The symmetry of the flowpath contributes to a robust and centered flow of the sample stream. The flowcell 22 is configured to direct a flow 32 of the sample enveloped with the PIOAL through a viewing zone 23 in the flowcell, namely behind viewing port 57. Associated with the viewport 57 is an autofocus pattern 44. Flowcell 22 also has a rounded or recessed seat 58 which is configured to accept or receive a microscope objective (not shown).

According to some embodiments, the autofocus pattern 44 can have a position that is fixed relative to the flowcell 22, and that is located at a displacement distance from the plane of the ribbon-shaped sample stream 32. In the embodiment shown here, the autofocus pattern (target 44) is applied directly to the flowcell 22 at a location that is visible in an image collected through viewport 57 by a high optical resolution imaging device (not shown). Flowcell 22 can be constructed from a single piece of material. Alternatively, flowcell 22 can be constructed of a first or upper section or layer 22a and a second or lower section or layer 22b. As shown here, a glass or transparent window pane 60 is attached to or integral with the first section 22a. The pane 60 can define at least a portion of the sample flowpath within the flowcell. Light from light source 42 can travel through an aperture or passage of the autofocus pattern 44 so as to illuminate sample particles flowing within the flow stream 32.

In some cases, the thickness of pane 60 can have a value within a range from about 150 μm to about 170 μm. As noted above, the pane 60 can define or form part of the flowpath or sheath (e.g. PIOAL) channel. By using a thin pane 60, it is possible to place the microscope objective very close to the sample fluid ribbon, and hence obtain highly magnified images of particles flowing along the flowpath.

Figure 3A:
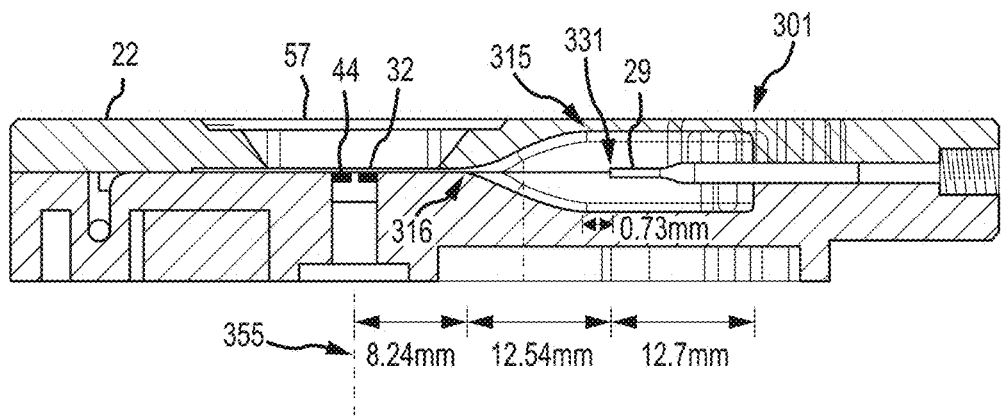
Figure 3B:
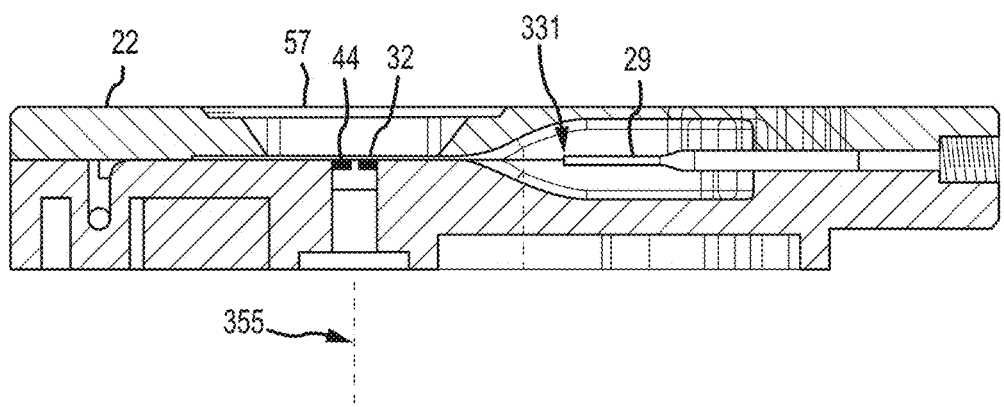

FIG. 3A depicts aspects of a flowcell embodiment, where a distance between the imaging axis 355 and the distal transition zone portion 316 is about 8.24 mm. A distance between the distal transition zone portion 316 and the cannula exit port 331 is about 12.54 mm. A distance between the cannula exit port 331 and the sheath fluid entrance 301 is about 12.7 mm. A distance between the cannula exit port 331 and a proximal transition zone portion 318 is about 0.73 mm. FIG. 3B depicts aspects of a flowcell embodiment where the cannula exit port has been moved to a more distal location relative transition zone, as compared to the FIG. 3A embodiment. As shown here, the cannula distal end is advanced into the narrowing transition zone of the flowcell, and a distance between the imaging axis 355 and the distal transition zone portion 316 is within a range from about 16 mm to about 26 mm. In some case, the distance between the imaging axis 355 and the distal transition zone portion 316 is about 21 mm.

With returning reference to FIG. 1, the flowcell internal contour (e.g. at transition zone 21) and the PIOAL and sample flow rates can be adjusted such that the sample is formed into a ribbon shaped stream 32. The stream can be approximately as thin as or even thinner than the particles that are enveloped in the ribbon-shaped sample stream. White blood cells may have a diameter around 10 μm, for example. By providing a ribbon-shaped sample stream with a thickness less than 10 μm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. The source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. The PIOAL viscosity can be up to 10 centipoise.

Referring also to FIGS. 2 and 3, the internal flowpath of the flowcell narrows downstream of the point of injection of the ribbon-shaped sample stream into the PIOAL, to produce a ribbon-shaped sample stream thickness, for example, up to 7 µm, and/or the internal flowpath produces a ribbon-shaped sample stream width of 500-3,000 µm. In exemplary embodiments, as depicted in FIG. 1, the internal flowpath of the flowcell begins a narrowing transition zone upstream of the point of injection of the sample stream into the PIOAL.

In another embodiment the internal flowpath narrows to produce a ribbon-shaped sample stream thickness of 2-4 µm in thickness, and/or the internal flowpath results in the ribbon-shaped sample stream of 2000 µm in width. These dimensions are particularly useful for hematology. The thickness of the stream in this case is less than the diameter of some particles, such as red blood cells in their relaxed state. Accordingly, those particles can become reoriented to face their wider a dimension to the imaging axis, which is helpful in revealing distinguishing characteristics.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

The method further can further include forming the ribbon-shaped sample stream into a ribbon-shape. The ribbon shape is presented such that the optical axis of the high optical resolution imaging device is substantially perpendicular to the ribbon-shaped sample stream, namely normal to the plane of the ribbon-shaped stream.

Figure 4:
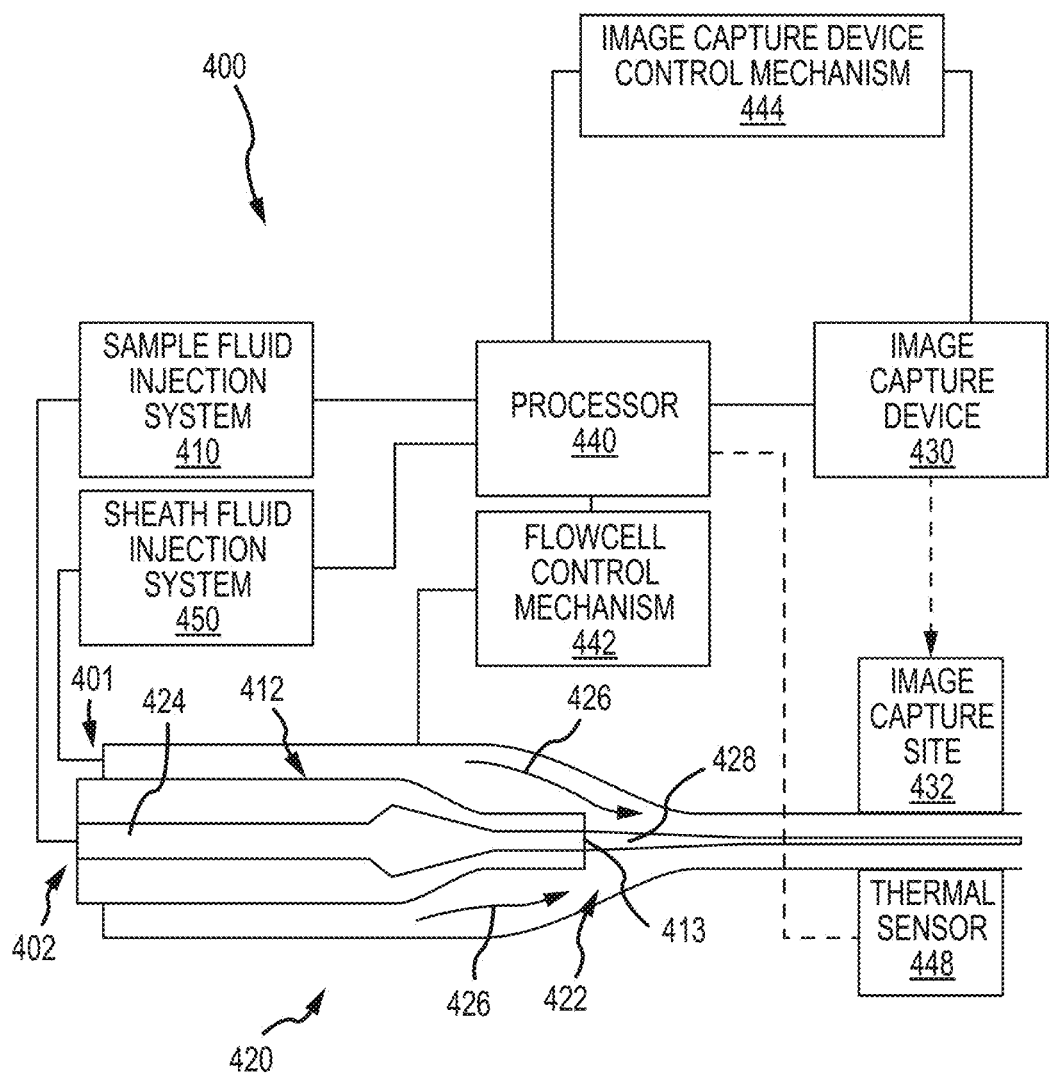
FIG. 4 illustrates aspects of an analyzer system according to embodiments of the present invention.

FIG. 4 depicts aspects of a system 400 for imaging particles in a blood fluid sample. As shown here, system 400 includes a sample fluid injection system 410, a flowcell 420, and image capture device 430, and a processor 440. The flowcell 420 provides a flowpath 422 that transmits a flow of the sheath fluid, optionally in combination with the sample fluid. According to some embodiments, the sample fluid injection system 410 can include or be coupled with a cannula or tube 412. The sample fluid injection system 410 can be in fluid communication with the flowpath 422 (e.g. via sample fluid entrance 402), and can operate to inject sample fluid 424 through a distal exit port 413 of the cannula 412 and into a flowing sheath fluid 426 within the flowcell 420 so as to provide a sample fluid stream 428. For example, the processor 440 may include or be in operative association with a storage medium having a computer application that, when executed by the processor, is configured to cause the sample fluid injection system 410 to inject sample fluid 424 into the flowing sheath fluid 426. As shown here, sheath fluid 426 can be introduced into the flowcell 420 by a sheath fluid injection system 450 (e.g. via sheath fluid entrance 401). For example, the processor 440 may include or be in operative association with a storage medium having a computer application that, when executed by the processor, is configured to cause the sheath fluid injection system 450 to inject sheath fluid 426 into the flowcell 420. As depicted in FIG. 4, the distal exit port 413 of cannula 412 can be positioned at a central location along the length of the narrowing transition zone 419. In some cases, the distal exit port can be positioned more closely to the beginning (proximal portion) of the transition zone 419. In some cases, the distal exit port can be positioned more closely to the end (distal portion) of the transition zone 419. In some cases, the distal exit port 413 can be positioned entirely outside of the transition zone 419, for example as depicted in FIG. 3A (where distal exit port 331 is disposed proximal to the narrowing transition zone).

The sample fluid stream 428 has a first thickness Ti adjacent the injection tube 412. The flowpath 422 of the flowcell having a decrease in flowpath size such that the thickness of the sample fluid stream 428 decreases from the initial thickness T1 to a second thickness T2 adjacent an image capture site 432. The image capture device 430 is aligned with the image capture site 432 so as to image a first plurality of the particles from the first sample fluid at the image capture site 432 of the flowcell 420.

The processor 440 is coupled with the sample fluid injector system 410, the image capture device 430, and optionally the sheath fluid injection system 450. The processor 440 is configured to terminate injection of the first sample fluid into the flowing sheath fluid 426 and begin injection of the second sample fluid into the flowing sheath fluid 426 such that sample fluid transients are initiated. For example, the processor 440 may include or be in operative association with a storage medium having a computer application that, when executed by the processor, is configured to cause the sample fluid injection system 410 to inject the second sample fluid into the flowing sheath fluid 426 such that sample fluid transients are initiated.

Further, the processor 440 is configured to initiate capture of an image a second plurality of the particles from the second sample fluid at the image capture site 432 of the flowcell 420 after the sample fluid transients and within 4 seconds of the imaging of the first plurality of the particles. For example, the processor 440 may include or be in operative association with a storage medium having a computer application that, when executed by the processor, is configured to cause the image capture device 430 to initiate capture of an image a second plurality of the particles from the second sample fluid at the image capture site 432 of the flowcell 420 after the sample fluid transients and within four seconds of the imaging of the first plurality of the particles.

In some embodiments, processor 440 may include or be in operative association with a storage medium having a computer application that, when executed by the processor, is configured to cause a flowcell movement control mechanism 442 to adjust the position of the flowcell 420, for example relative to the image capture device 430. In some embodiments, processor 440 may include or be in operative association with a storage medium having a computer application that, when executed by the processor, is configured to cause an image capture device movement control mechanism 444 to adjust the position of the image capture device 430, for example relative to the flowcell 420. The movement control mechanisms 442, 444 may include motors, gimbals, and other mechanical features that facilitate and produce movement in the flowcell and image capture device, respectively. In some cases, flowcell control mechanism 442 and/or image capture device control mechanism 444 may include a high precision stepper motor control that provides motorized and automated focusing of image capture device relative to the flowcell. As depicted in FIG. 1, a processor can control movement of the image capture device 24. Similarly, as depicted in FIG. 1B, a processor can control movement of a flowcell carrier 55.

Hence, embodiments of the present invention encompass particle analysis systems that perform combined viscosity and geometric hydrofocusing for imaging particles in a blood fluid sample. Exemplary systems can include a flowcell having a flowpath with an injection tube and an imaging window with an imaging axis therethrough. The flowpath of the flowcell can have a decrease in flowpath size. Further, analyzer systems can include a sheath fluid input in fluid communication with the flowpath, and a blood fluid input in fluid communication with the injection tube. The blood fluid input can be configured for injecting the blood fluid sample into the flowing sheath fluid within the flowcell so that the blood fluid sample flows in a sample flowstream with a flowstream width greater than a flowstream thickness. The sheath fluid can have a viscosity that is greater than a viscosity of the blood fluid sample. What is more, the anaylzer system can include an image capture device, and a focusing mechanism that sets a focal state of the image capture device relative to the flowcell. Further, the system can include an imaging target having a position fixed relative to the flowcell, where the imaging target and sample flowstream defining a displacement distance along the imaging axis. The system can also include a processor, and a focusing module having a tangible medium embodying machine-readable code executed on the processor for operating the focusing mechanism to set the focal state of the image capture device, suitable for particle characterization and counting, using the displacement distance. The the viscosity difference between the sheath fluid and blood fluid sample, in combination with the decrease in flowpath size, can be effective to hydrofocus the first and second sample fluids at the imaging axis while retaining viability of cells in the blood fluid sample. In some cases, the focusing mechanism can include a drive motor configured to adjust a distance between the image capture device and the flowcell.

In some cases, an analyzer system 400 may include a temperature or thermal sensor 448 that is thermally coupled with the flowcell 420, as depicted in FIG. 4. A focusing module, which may operationally associated with the processor, can include a tangible medium embodying machine-readable code that is executed on the processor for operating a focusing mechanism (e.g. flowcell control mechanism 442 or image capture device control mechanism 444) so as to set the focal state or focal plane of the image capture device, suitable for particle characterization and counting, in response to a change in temperature sensed by the temperature sensor and a known relationship between temperature and a desired focus.

Accordingly, embodiments of the present invention encompass a system 400 for imaging a plurality of particles in a blood fluid sample 424 having a sample fluid viscosity The system 400 can be used with a sheath fluid 426 having a sheath fluid viscosity that differs from the sample fluid viscosity by a viscosity difference in a predetermined viscocity difference range. The system 400 can include a flowcell 420 having a flowpath 422 and a sample fluid injection tube 412. The flowpath 422 can have a reduction in flowpath size or narrowing transition zone. Further, the system 400 can include a sheath fluid input 401 in fluid communication with the flowpath 422 of the flowcell 420 so as to transmit a flow of the sheath fluid along the flowpath 422 of the flowcell 420. The system 400 can also include a blood fluid sample input 402 in fluid communication with the injection tube 412 of the flowcell 420 so as to inject a flow or stream 428 of the blood fluid sample into the flowing sheath fluid 428 within the flowcell 420. For example, the sample fluid 424 can exit the distal exit port 423 of the cannula 412 and into an envelope of the flowing sheath fluid 426 to form a sample ribbon 428 therein.

As the sheath fluid 426, along with the sample fluid ribbon 428 formed from the sample fluid 424, flow through a reduction 419 in flowpath size and toward an imaging site 432, a viscosity hydrofocusing effect induced by an interaction between the sheath fluid 426 and the sample fluid 424 associated with the viscosity difference, in combination with a geometric hydrofocusing effect induced by an interaction between the sheath fluid 426 and the sample fluid 424 associated with the reduction in flowpath size, provides a target imaging state in at least some of the plurality of particles at the imaging site 432. As shown here, the system 400 also includes an imaging device 430 that images the plurality of particles at the imaging site 432.

Figure 4A:
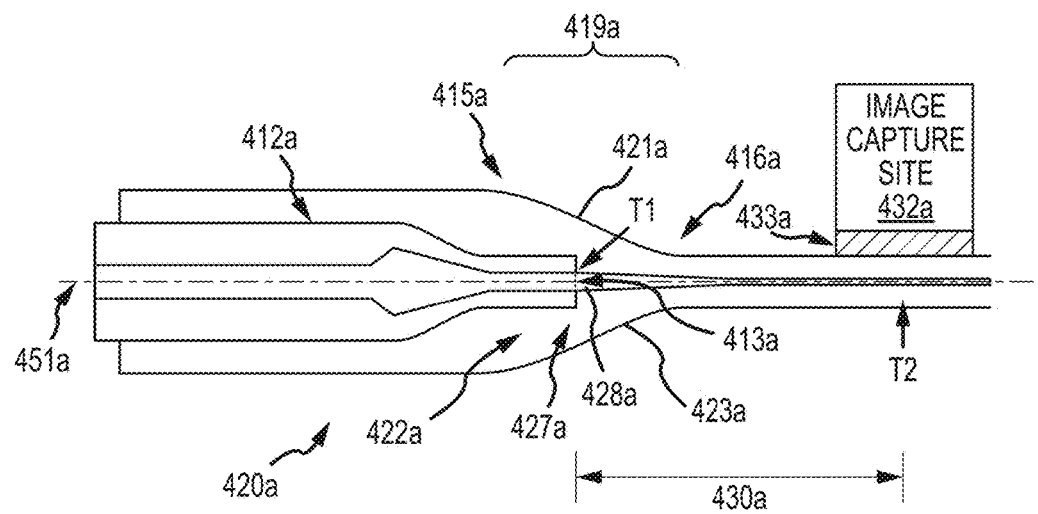
FIG. 4A shows a flowcell according to embodiments of the present invention.

As shown in the flowcell embodiment depicted in FIG. 4A, a decrease in flowpath size (e.g. at transition zone 419a) can be defined by opposed walls 421a, 423a of the flowpath 422a. The opposed walls 421a, 423a can angle radially inward along the flowpath 422a, generally symmetric about a transverse plane 451a that bisects the sample fluid stream 428a. The plane 451a can bisect the sample stream 428a where the sample stream has a first thickness T1, at a location where the sample stream 428a exits a distal portion 427a of the cannula or sample injection tube 412a. Similarly, the plane 451a can bisect the sample stream 428a where the sample stream has a second thickness T2, at a location where the sample stream 428a passes the image capture site 432a. According to some embodiments, the first thickness T1 has a value of about 150 µm and the second thickness T2 has a value of about 2 µm. In such cases, the compression ratio of the sample ribbon stream is 75:1. According to some embodiments, the first thickness T1 has a value within a range from about 50 µm to about 250 µm and the second thickness T2 has a value within a range from about 2 µm to about 10 µm. As the sample stream fluid flows through the flowcell, the ribbon thins out as it accelerates and is stretched. Two features of the flowcell can contribute to thinning of the sample fluid ribbon. First, a velocity difference between the sheath fluid envelope and the sample fluid ribbon can operate to reduce the thickness of the ribbon. Second, the tapered geometry of the transition zone can operate to reduce the thickness of the ribbon. As depicted in FIG. 4A, the distal exit port 413a of cannula 412a can be positioned at a central location along the length of the narrowing transition zone 419a. In some cases, the distal exit port can be positioned more closely to the beginning (proximal portion 415a) of the transition zone 419a. In some cases, the distal exit port can be positioned more closely to the end (distal portion 416a) of the transition zone 419a. In some cases, the distal exit port 413a can be positioned entirely outside of the transition zone 419a, for example as depicted in FIG. 3A (where distal exit port 331 is disposed proximal to the narrowing transition zone).

As depicted in FIG. 4A (as well as in FIGS. 4 and 4B-1), the transition zone 419a can be defined by an angular transitions at the proximal (415a) and distal (416a) portions. It is also understood that the transition zone 419a can instead present smooth or curved transitions at the proximal (415a) and distal (416a) portions, similar to the smooth or curved transitions as depicted in FIGS. 1, 3, 3A, 3B, and 4B-2).

Typically, the first thickness T1 is much larger than the size of the sample particles, and hence the particles are contained entirely within the sample ribbon stream. However, the second thickness T2 may be smaller than the size of certain sample particles, and hence those particles may extend out of the sample fluid and into surrounding sheath fluid. As shown in FIG. 4A, the sample ribbon stream can flow generally along the same plane as it exits the cannula and travels toward the image capture site.

The flowcell can also provide a separation distance 430a between the distal cannula portion 427a and the image capture site 432a. According to some embodiments, the distal portion 427a of the sample fluid injection tube 412a can be positioned at an axial separation distance 430a from the image capture site 432a, where the axial separation distance 432a has a value of about 21 mm. In some cases, the axial separation distance 430a has a value within a range from about 16 mm to about 26 mm.

The axial separation distance 430a between the cannula exit port and image capture site can impact the transition time for the sample fluid as the fluid travels from the exit port to the image capture site. For instance, a relatively shorter axial separation distance 430a can contribute to a shorter transition time, and a relatively longer axial separation distance 430a can contribute to a longer transition time.

The position of the exit port at the cannula distal portion 427a relative to the flowpath transition zone 419a, or relative to the proximal portion 415a of the flowpath transition zone 419a, can also inference the transition time for the sample fluid as the fluid travels from the exit port to the image capture site. For example, the sheath fluid may have a relatively slower speed at the proximal portion 415a, and a relatively faster speed at a location between the proximal portion 415a and the distal portion 416a. Hence, if the cannula exit port at distal portion 427a is positioned at the proximal portion 415a, it will take a longer amount of time for the sample fluid to reach the image capture site, not only because the travel distance is longer, but also because the initial speed of the sample fluid after it exits the cannula distal port is slower (due to the slower sheath fluid speed). Put another way, the longer the sample fluid is present in the thicker portion (e.g. near proximal portion 415a) of the flowcell, the longer it takes the sample to reach the image capture site. Conversely, if the cannula exit port at distal portion 427a is positioned distal to the proximal portion 415a (e.g. at a central location between proximal portion 415a and distal portion 416a, as depicted in FIG. 4A), it will take a shorter amount of time for the sample fluid to reach the image capture site, not only because the travel distance is shorter, but also because the initial speed of the sample fluid after it exits the cannula distal port is faster (due to the faster sheath fluid speed). As discussed elsewhere herein, the sheath fluid is accelerated as it flows through the transition zone 419a, due to the narrowing cross-sectional area of the zone 419a.

According to some embodiments, with a shorter transition time, more time is available for image collection at the image capture site. For example, as the duration of the transition time from the cannula distal tip to the imaging area decreases, it is possible to process more samples in a specific amount of time, and relatedly it is possible to obtain more images in a specific amoutn of time (e.g. images per minute).

Although there are advantages associated with positioning the exit port of the cannula distal portion 427a more closely to the image capture site 432a, it is also desirable to maintain a certain distance between the port and the capture site. For example, as depicted in FIG. 3, an optical objective or front lens of an imaging device can be positioned in the seat 58 of the flowcell 22. If the exit port 31 of the cannula is too close to the seat 58, then the sample fluid may not be sufficiently stabilized after it is injected into the sheath fluid so as to provide desired imaging properties at the image capture site. Similarly, it may be desirable to maintain the tapered transition region 21 at a distance from the viewing zone 23, so that the tapered region does not interfere with the positioning of the seat 58 which receives the image capture device objective.

With continuing reference to FIG. 4A, the downstream end 427a of the sample fluid injection tube 412a can be positioned distal to a proximal portion 415a of the flowpath transition zone 419a. Relatedly, the downstream end 427a of the sample fluid injection tube 412a can be positioned proximal to a distal portion 416a of the flowpath transition zone 419a. Hence, according to some embodiments, the sample fluid can be injected from the injection cannula 412a and into the flowcell at a location within the transition zone 419a.

According to some embodiments, symmetry in the decrease in flowpath size (e.g. at flowpath transition zone 419a) operates to limit particle misalignment in the blood fluid sample. For example, such symmetry can be effective to limit red blood cells imaging orientation misalignment in the blood fluid sample to less than about 20%.

According to some embodiments, methods disclosed herein are operable to the flagging rate during blood count analysis to below 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% of samples.

According to some embodiments, the image capture site 432a has a field of view 433a of between about 150 µm×150 µm and 400 µm×400 µm. In some cases, the image capture site 432a has a field of view 433a of about 275 µm×275 µm. In some cases, the field of view can be defined in terms of length times width. If expressed as surface area, a 275 µm×275 µm field of view has an area of 75,625 µm². According to some embodiments, the field of view can be determined by the imaging device objective and its magnification. In some cases, the field of view can correspond to the extent of the field (area) that is imaged by the collection optics (e.g. objective, tube lens, and camera). In some cases, the field of view is much smaller than the viewing port of transparent area at the image capture site.

FIGS. 4A-1 and 4A-2 illustrate the effects of hydrofocusing on the sample stream as it travels from the cannula exit port to the image capture site. As shown in FIG. 4A-1, the sample stream can have a height H(S) of about 150 µm and a width W(S) of about 1350 µm. Further, the PIOAL sheath stream can have a height H(P) of about 6000 µm and a width W(P) of about 4000 µm. Subsequent to the hydrofocusing, as shown in FIG. 4A-2, the sample stream can have a height H(S) of about 2 µm and a width W(S) of about 1350 µm. Further, the PIOAL sheath stream can have a height H(P) of about 150 µm and a width W(P) of about 4000 µm. In one embodiment, the cross sectional area of the PIOAL sheath stream at the cannula exit is 40 times larger than the cross sectional area near the image capture site.

According to some embodiments, it can be useful to determine the cross-section of the flowcell channel at the image capture site. This can correspond to the PIOAL sheath stream height H(P) of about 150 µm and a width W(P) of about 4000 µm as depicted in FIG. 4A-2. It can also be useful to determine the volumetric flow rate of the combined sample and sheath fluid streaming through the flowcell at the image capture site. When the cross-section area and the flow rate are known, it is possible to determine the velocity of the combined sample and sheath fluid at the image capture site.

According to some embodiments, the flow of the sample and sheath fluids through the flowcell can be approximated with a parallel plate profile model. Relatedly, the flow rate in the center of the sample fluid stream (e.g. as depicted in FIG. 4A-2), can be about 1.5 times the average flow rate of the combined sample and sheath fluid stream.

According to some embodiments, the cross-sectional area of the sample flow at the cannula exit (e.g. W(S)×H(S) in FIG. 4A-1) is 40 times larger than the cross-sectional area of the sample flow at the imaging site (e.g. W(S)×H(S) in FIG. 4A-2). The volumetric flow rate of sheath fluid at the imaging area can be about 45 µL/second. The volumetric flow rate of sample fluid at the imaging area can be about 0.232 µL/second. In some cases, the cross-sectional area of the combined sheath and sample streams at the imaging site is 600,000 µm². In some cases, the average flowstream velocity at the imaging site is 75 mm/second.

The flow rate or velocity can be determined as the rate that results in clear and focused cellular images. Exemplary flow rates and velocities were discovered based on flow rates of the two samples that were observed to achieve certain sample flowstream ribbon shapes or characteristics at the imaging site. For example, at flow rate of about 75 mm/sec (or within a range from 20-200 mm/sec), the cells do not flow too slow such that there are overlaps of cells in consecutive images, and the cells do not flow too fast such that ghosting effects are created (blurred image). Relatedly, by avoiding excessively high flow rates, it is possible to conserve more reagent and sample. According to some embodiments, an optimal or desired linear velocity can be achieved by either changing the volumetric flow (pump rate) or the shape of cannula.

The flow velocity of the sample stream through the image capture zone can also be related to the performance of the image capture device relative to the flowcell function. For example, if the sample stream if flowing too quickly, it may be difficult to obtain clear images of particles contained in the sample (e.g. the shutter speed of the image capture device may be too low, thus producing a blurred image). Similarly, if the sample stream is flowing too slowly, the image capture device may obtain consecutive images of the same particle (e.g. the same particle remains in the capture frame during two image captures). In some embodiments, the velocity of the sample ribbon can be modulated (e.g. by adjusting any of a variety of the flowcell operational parameters) relative to the image capture rate, so that there is minimal flow between frame captures, and hence a high percentage of the sample is imaged.

According to some embodiments, the particle analysis system and associated components can be configured so that as the sheath fluid and fluid sample flow through the flowcell, the sheath fluid can flow at a sheath fluid volumetric rate of 45 µL/s and the fluid sample can flow at a fluid sample volumetric flow rate of 0.232 µL/s (or within a range from 0.2 to 0.35 µL/s). In some cases, the ratio of the sheath fluid flow rate to the sample fluid flow rate is about 200. In some cases, the ratio of the sheath fluid flow rate to the sample fluid flow rate has a value within a range from about 70 to 200. In some cases, the ratio of the sheath fluid flow rate to the sample fluid flow rate is about 193. In some cases, the ratio of the sheath fluid flow rate to the sample fluid flow rate is about 70. In some instances, a ratio of sheath fluid volume to fluid sample volume flowing within the flowcell can be within a range from 25:1 to 250:1.

According to some embodiments, the system and associated components can be configured so that as sheath fluid and fluid sample flow through the flowcell 420, the sheath fluid can flow at a sheath fluid velocity of 75 mm/sec before the imaging area and the fluid sample can flow at a fluid sample velocity of 130 mm/sec before the imaging area. In some instances, a ratio of sheath fluid volume to fluid sample volume flowing within the flowcell can be within a range from 100:1 to 200:1.

In some instances, a flowcell can have a minimum compression ratio of about 50:1 and a maximum compression ratio of about 125:1. In some cases, the minimum compression ratio can be about 30:1 or 20:1. This compression ratio refers to the ratio of flow stream thicknesses H(S):H(S) when comparing FIG. 4A-1 to FIG. 4A-2. This compression ratio can be influenced by a combination of geometric compression (e.g. the ratio of the sheath fluid thicknesses H(P):H(P) when comparing FIG. 4A-1 to FIG. 4A-2, which can also correspond generally to the dimensions of the flowcell narrowing tapered transition zone 419a shown in FIG. 4A) and a hydrodynamic compression (e.g. also corresponding to a difference in velocity). According to some embodiments, the geometric compression ratio is about 40:1.

Figures 1, 2, 4B:
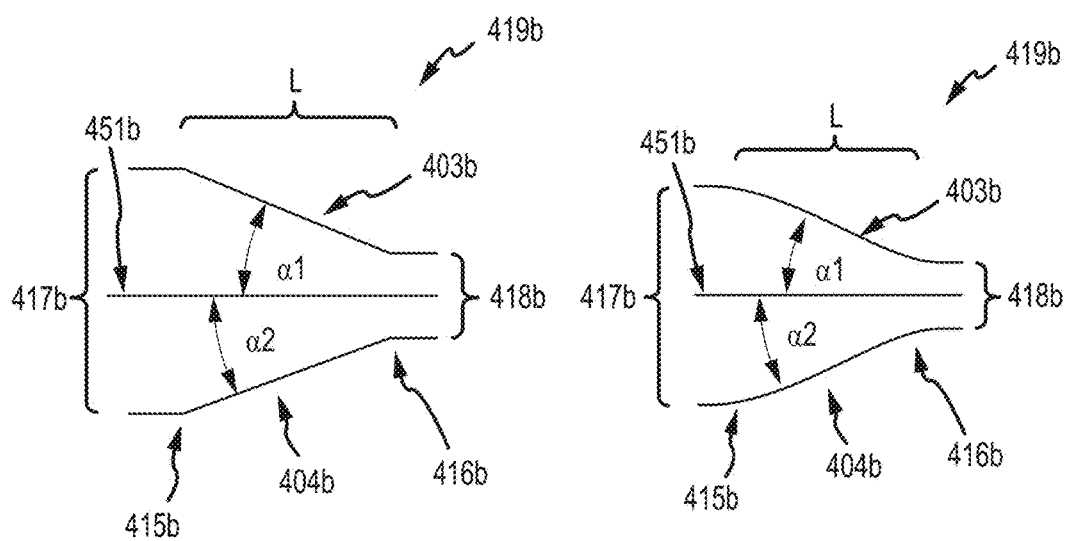
Figures 1, 4A:
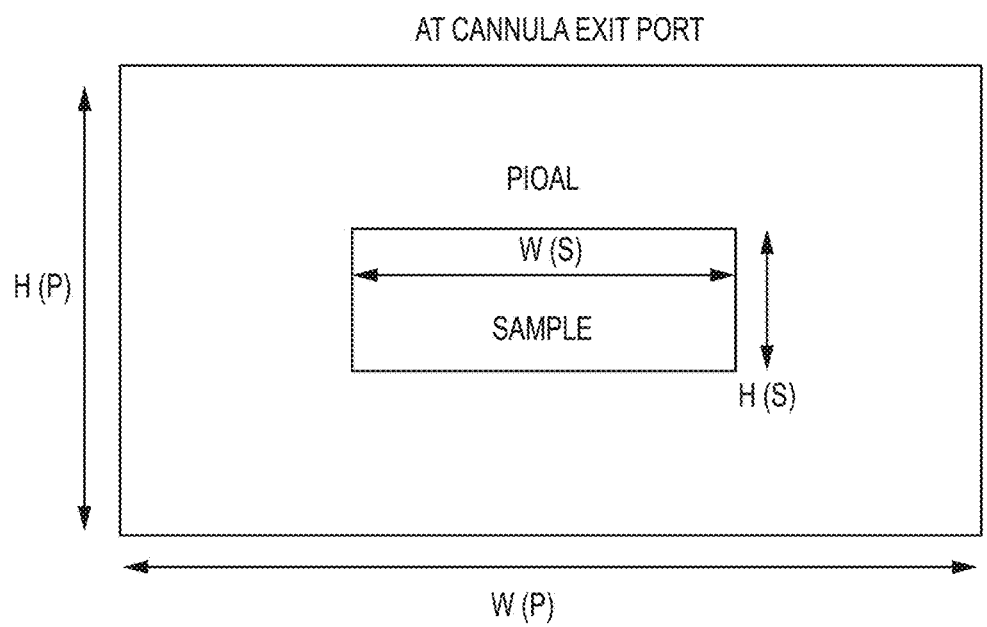
Figures 2, 4A:
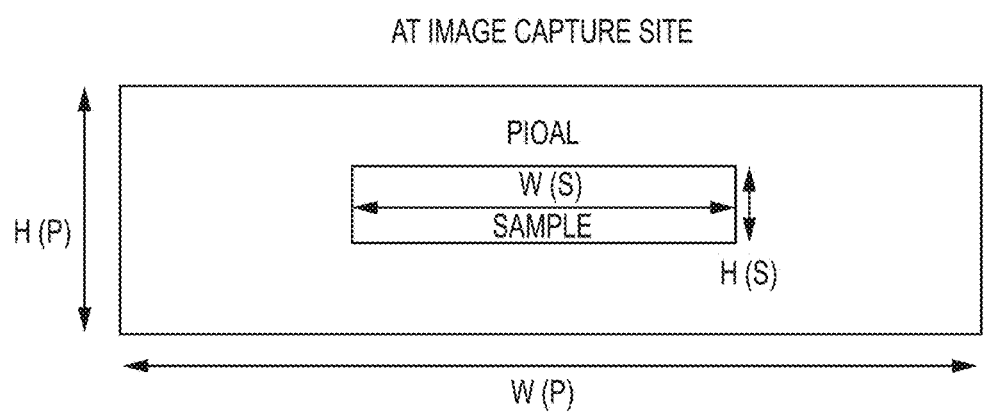

The decrease in flowpath size, corresponding to the transition zone, can be defined by a proximal flowpath portion having a proximal thickness or height, and a distal flowpath portion having a distal thickness or height that is less than the proximal thickness or height. For example, as shown in the partial views of FIGS. 4B-1 and 4B-2, the transition zone 419b of the flowpath can have a length L between a proximal portion 415b and a distal portion 416b, where the proximal portion 415b has a proximal height 417b, and the distal portion 416b has a distal height 418b. As depicted in FIG. 4B-2, and as noted elsewhere herein, the shape or contour of the transition zone can be curved or smooth, and for example can be provided in the shape of an S-curve, a sigmoidal curve, or a tangent curve. According to some embodiments, the proximal height 417b has a value of about 6000 µm. In some cases, the proximal height 417b has a value within a range from about 3000 µm to about 8000 µm. According to some embodiments, the distal height 418b has a value of about 150 µm. In some cases, the distal height 418b has a value within a range from about 50 µm to about 400 µm.

The geometry of the transition zone 419a can provide a first angle α1 between the first flowpath boundary 403b and the bisecting transverse plane 451b, and a second angle α2 between the second flowpath boundary 404b and the bisecting transverse plane 451b. In some cases, angle α1 is about 45 degrees and angle α2 is about 45 degrees. In some cases, angle α1 has a value within a range from about 10 degrees to about 60 degrees. In some cases, angle α2 has a value within a range from about 10 degrees to about 60 degrees. According to some embodiments, angles α1 and α2 have the same value. The angles α1 and α2 can be selected so as to maintain laminar flow or minimize turbulence of the sample fluid as it travels from proximal portion 415b to distal portion 416b, which in turn can enhance alignment of particles within the sample along the transverse plane 451b. As noted above with reference to FIG. 4A, the distal and proximal boundaries or portions of the transition zone may be curved or smooth, instead of angled.

Figure 4C:
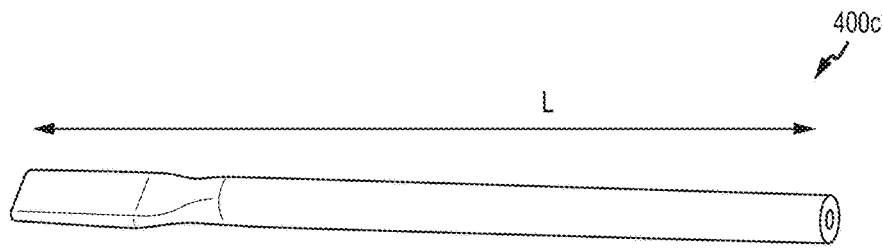
FIG. 4C depicts features of an exemplary cannula or sample feed tube according to embodiments of the present invention
Figure 4D:
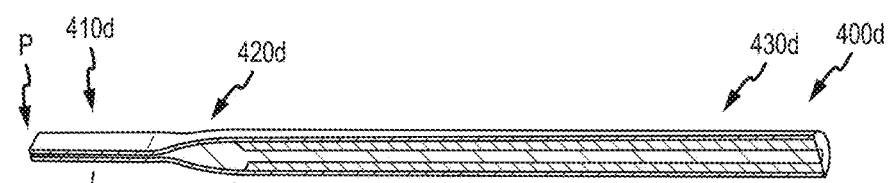
FIG. 4D depicts a longitudinal cross-section of cannula according to embodiments of the present invention.

FIG. 4C depicts features of an exemplary cannula or sample feed tube 400c according to embodiments of the present invention, where the cannula has a length L. FIG. 4D depicts a longitudinal cross-section of cannula 400d. As shown here, the cannula 400d includes a distal flattened section 410d, a central tapered section 420d, and a proximal tubular portion 430d. As depicted in FIG. 4C-1, an exemplary cannula or sample feed tube 400c-1 can have a distal portion 410c-1 and a proximal portion 430c-1. In some cases, the distal portion 410c-1 has a length of about 1.359 mm and a width of about 1.43 mm. In some cases, the exit port of the distal end has an exit width W(E) of about 1.359 mm. According to some embodiments, a cannula may have an internal flowpath geometry that is different from what is depicted in FIGS. 4C and 4D. For example, as illustrated in FIG. 4D-1, the cannula 400d-1 does not include a tapered central section having an expanded flow area cross-section. As depicted in FIG. 4D-1, cannula 400d-1 has a distal section 410d-1, a central tapered section 420d-1 having a tapering inner diameter, and a proximal section 430d-1. Corresponding to the tapering inner diameter of central section 420d-1, the cross-sectional inner area of 410d-1 is smaller than the cross-sectional inner area of 430d-1.

A hematology system according to embodiments of the present invention can process a blood sample having a volume of about 150 µL. The aspirated blood volume can be about 120-150 µL. In some cases, the minimum available blood volume in the sample tube is about 500 µL for an automatic sampling mode and about 250 µL for manual sampling mode. The cannula or injection tube 400d shown in FIG. 4D has an internal volume of about 13 uL. According to some embodiments, the cannula or injection tube has an internal volume of less than about 30 uL.

Figure 4E:
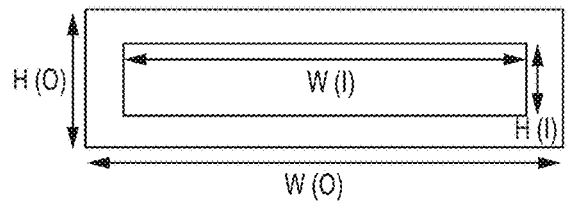
FIG. 4E illustrates a transverse cross-section of a distal flattened section according to embodiments of the present invention.

FIG. 4E illustrates a transverse cross-section of a distal flattened section 410e. As shown here, the distal section 410e has an inner width W(I) and an inner height H(I), through which a sample stream flows. Further, the distal section 410e has an outer width W(O) and an outer height H(O). As depicted in FIGS. 4D and 4E taken in combination, the distal portion 410e of the sample fluid injection tube has an outlet port P having a height H(I) and a width W(I), where the height H(I) is less than the width W(I). According to some embodiments, the height H(I) of the outlet port P of distal portion 410e (or the inner height of the distal portion 410d) can have a value of about 150 µm. In some cases, the height H(I) can be within a range from about 50 µm to about 250 µm. According to some embodiments, the width W(I) of the outlet port P of distal portion 410e (or the inner width of the distal portion 410d) can have a value of about 1350 µm. In some cases, the width is about 1194 µm. In some cases, the width W(I) can have a value within a range from about 500 µm to about 3000 µm. In some cases, distal flattened section 410d can be manufactured by applying a clamping force to a tube or conduit.

Figure 4F:
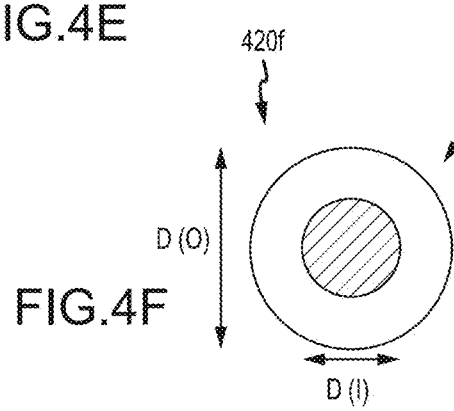
FIG. 4F illustrates a transverse cross-section of a central tapered section according to embodiments of the present invention.
Figure 4G:
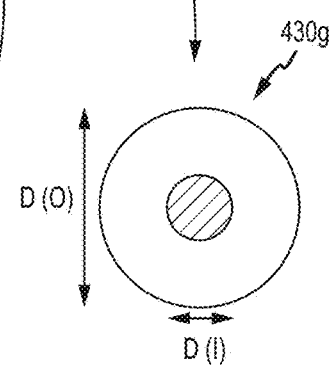
FIG. 4G illustrates a transverse cross-section of a proximal section according to embodiments of the present invention.
Figures 1, 4D:
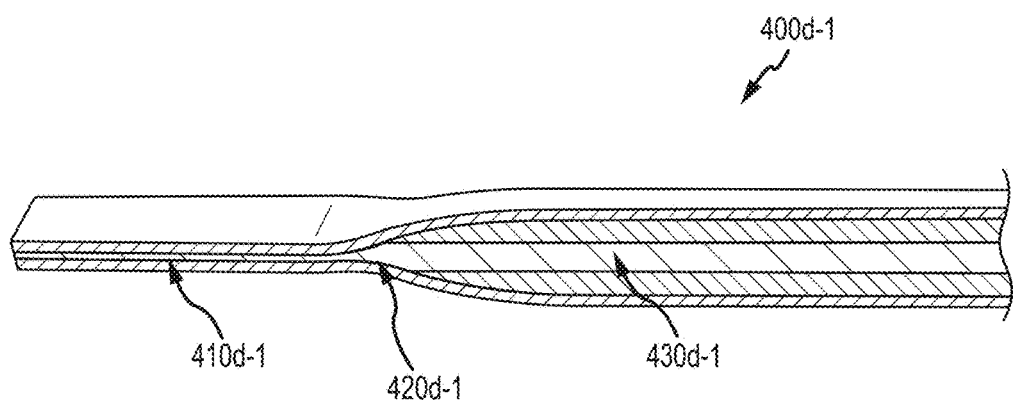
Figure 4H:
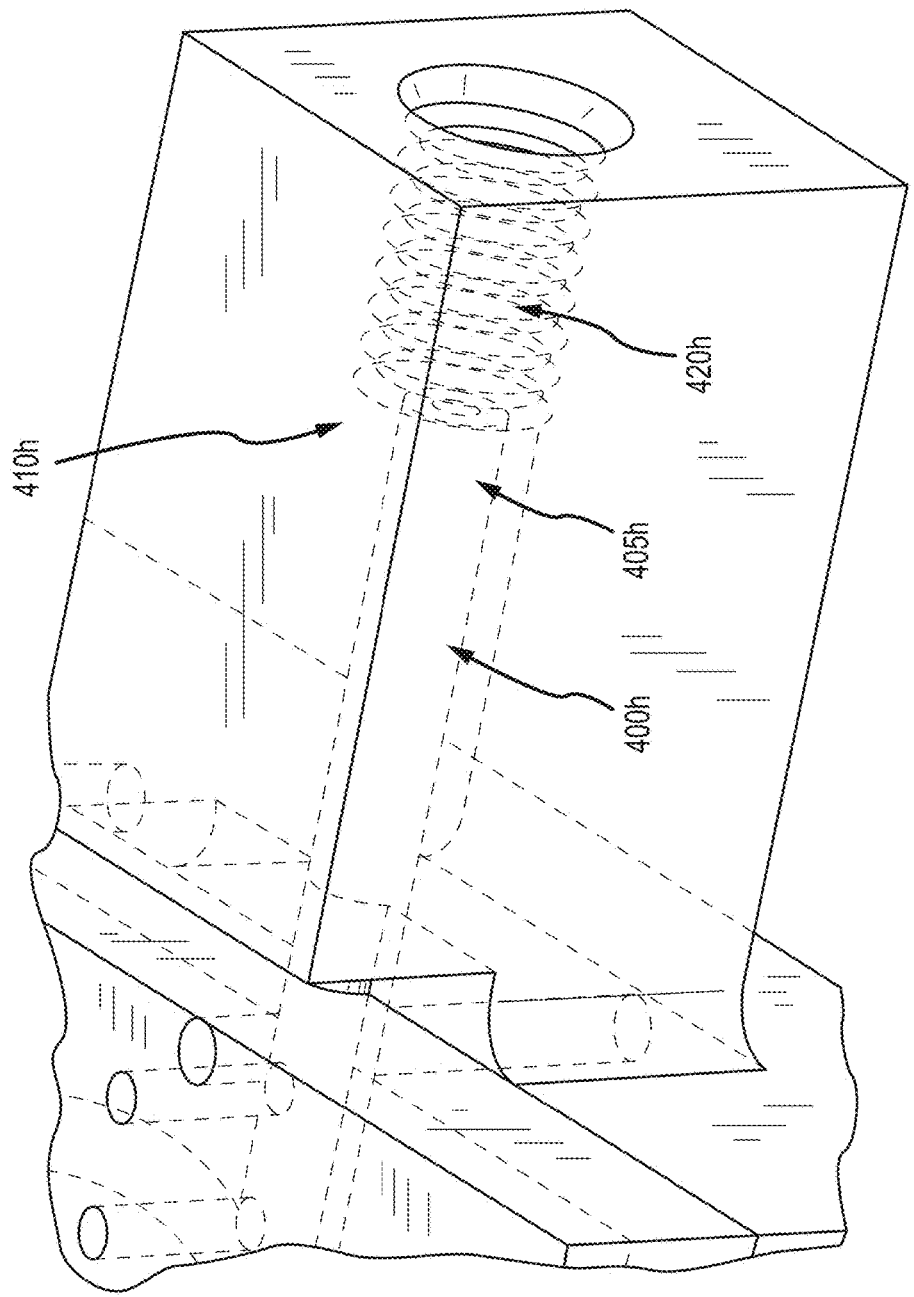
FIG. 4H shows a portion of a cannula according to embodiments of the present invention.

FIG. 4F illustrates a transverse cross-section of a central tapered section 420f. As shown here, the central tapered section 420f has an inner diameter D(I) through which a sample stream flows. Further, the central tapered section 420f has an outer diameter D(O). FIG. 4G illustrates a transverse cross-section of a proximal section 430g. As shown here, the proximal section 430g has an inner diameter D(I) through which a sample stream flows. Further, the distal section 430g has an outer diameter D(O).

As depicted in FIG. 4D, the injection tube or cannula 400d can have a proximal portion 430d having a first flow cross-section area (e.g. $\pi*(D/2)^2$ shown in FIG. 4G), a distal portion 410d having a second flow cross-section area (e.g. W(I)*H(I) shown in FIG. 4E) that is less than the first flow cross-section area, and a third portion 420d disposed between the proximal portion 430d and the distal portion 410d. The third portion 420d can have a third flow cross-section (e.g. $\pi*(D/2)^2$ shown in FIG. 4F) that is larger than the first and second flow cross-sections. In some instance, the outer diameter D(O) of proximal portion 430g is about 1067 µm and the inner diameter D(I) of proximal portion 430g is about 813 µm.

Figure 4I:
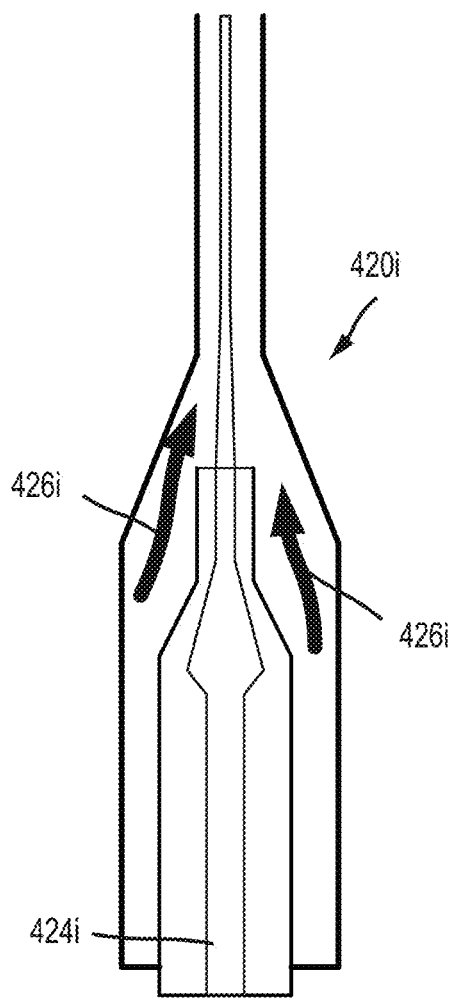
FIGS. 4I and 4J depict flowcells according to embodiments of the present invention.

According to some embodiments, a proximal portion of an injection tube can be coupled with a sample port of a sample inlet fitting. For example, as shown in FIG. 4I1, a proximal portion 405h of a cannula 400h can be coupled directly to a sample port 410h at an exit of a sample inlet fitting 420h.

Figure 4J:
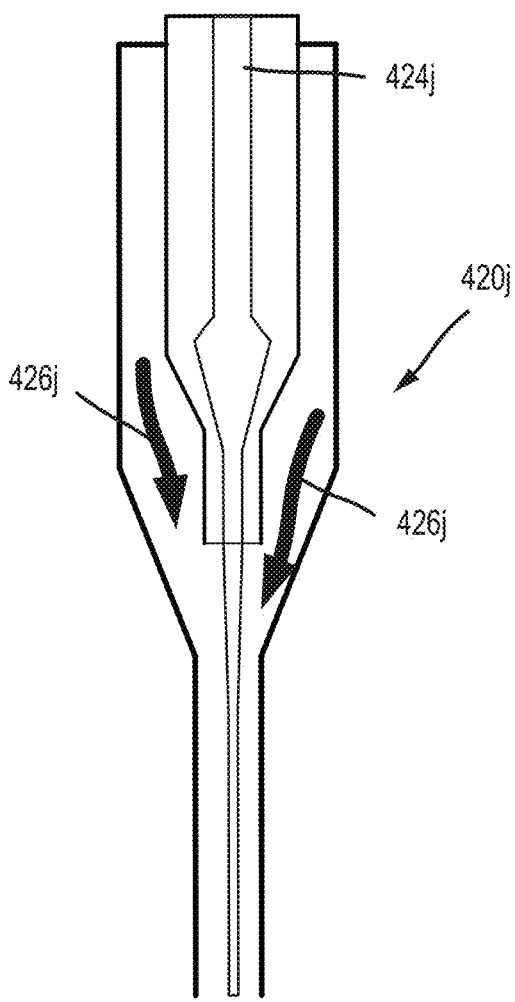

A flowcell of a system for imaging particles in a blood fluid sample can be oriented at any desired angle or direction relative to the direction of the force of gravity. For example, a flowcell can be oriented in an upward direction, so that fluid flowing within the flowcell (e.g. sheath fluid, optionally in combination with sample fluid) can travel in an upward direction, against the force of gravity. Likewise, a flowcell can be oriented in an downward direction, so that fluid flowing within the flowcell (e.g. sheath fluid, optionally in combination with sample fluid) can travel in a downward direction, with the force of gravity. FIG. 4I depicts a flowcell 420i oriented in an upward direction, so that sample fluid 424i and sheath fluid 426i flowing within the flowcell 420i flow against gravity G. FIG. 4J depicts a flowcell 420j oriented in a downward direction, so that sample fluid 424*j* and sheath fluid 426*j* flowing within the flowcell 420*j* do not flow against gravity G, but rather flow with gravity G.

Figure 4K:
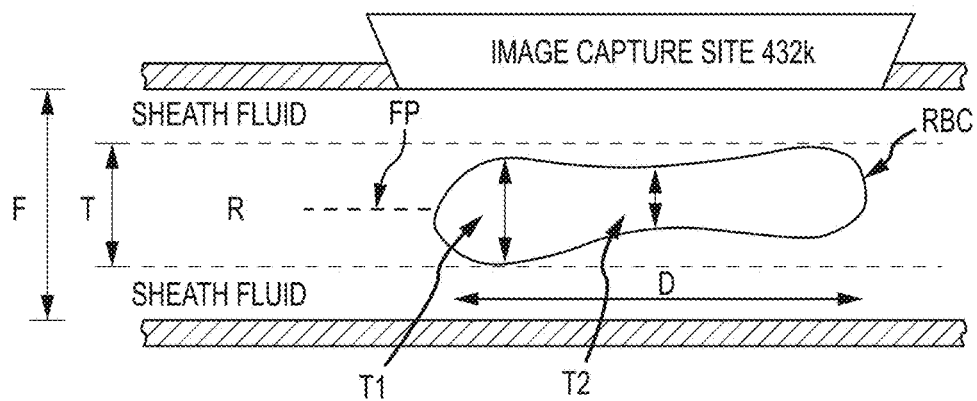
FIGS. 4K and 4L show a sample stream flowing through an image capture site of a flowcell according to embodiments of the present invention.

As shown in FIG. 4K, a sample stream ribbon R flowing through an image capture site 432*k* of a flowcell 420*k* can have a thickness T of about 2 µm. In some cases, thickness T of the sample stream ribbon can be up to about 3 µm. Typically, cells or particles that are smaller than the sample stream thickness will be contained within the ribbon. An exemplary red blood cell (RBC) can be present as a biconcave disk and can have a diameter D of between about 6.2 µm and about 8.2 µm. Further, an exemplary red blood cell can have a maximum thickness T1 of between about 2 µm and about 2.5 µm and a minimum thickness T2 of between about 0.8 µm and about 1 µm. In some cases, red blood cells can have a thickness of up to about 3 µm. Exemplary human platelets can vary in size, and can also have a thickness or diameter of about 2 µm. Although not shown to scale here, the flowcell can define a flow path thickness F having a value of about 150 µm, at the image capture site. In some cases, the flowpath thickness F has a value between 50 µm and 400 µm. This flowpath thickness F can also correspond to the distal height 418*b* of distal portion 461*b* depicted in FIGS. 4B-1 and 4B-2.

As shown in FIG. 4K, the ratio of the thickness T of the sample fluid stream to the thickness of the particle (red blood cell) is about 1:1. According so some embodiments, a ratio of the thickness T of the sample fluid stream at the image capture site to a size of one of the particles is within a range from 0.25 to 25. In some cases, the thickness T can have a value within a range from 0.5 µm to 5 µm. A viscosity differential between the sheath fluid and the sample fluid can be selected so as to achieve a desired positioning of the ribbon sample stream within the flowcell.

Viscosity differences between fluid of the sample ribbon R and the sheath fluid can operate to align or orient particles in the sample stream, for example red blood cells, along the direction of the flow. When so aligned, as shown in FIG. 4K, the imaging device or camera can obtain images of the red blood cells such they appear round, because the major surface of the blood cell is facing toward the camera. In this way, the red blood cell assumes an alignment that presents a low resistance relative to the flow. Hence, the relative viscosity characteristics of the sheath fluid and the sample fluid can contribute to a high percentage or number of red blood cells facing toward the camera, thus enhancing the evaluation capability of the particle analysis system.

According to some embodiments, the viscosity characteristics of the sheath fluid operate to limit particle misalignment in the blood fluid sample. For example, viscosity differentials can be effective to limit red blood cells imaging orientation misalignment in the blood fluid sample to less than about 10%. That is, 90 or more red blood cells out of 100 red blood cells in a sample can be aligned so that their major surfaces face toward the imaging device. A symmetrical narrowing transition zone can provide a value of 20%. As discussed elsewhere herein, for example with reference to FIG. 4R, it is possible to compare alignment results obtained from an analyzer configuration that involves a flowcell having a symmetrical narrowing flowcell transition zone and a viscous sheath fluid to alignment results obtained from an analyzer configuration that involves a flowcell having a symmetrical narrowing flowcell transition zone without the use of a viscous sheath fluid. Use of a viscous sheath fluid can reduce the percentage of misaligned cells. According to some embodiments, the sheath fluid has an index of refraction similar to that of water (i.e. n=1.3330). In some cases, the sheath fluid has a water content of about 89%. In addition to alignment effects observed as a result of the viscosity differential, alignment effects are also observed as a result of a bilateral tapered transition zone. In some cases, it is observed that a bilateral (i.e. symmetrical) tapered transition zone is twice as effective at aligning particles as compared to an asymmetric tapered transition zone design.

Efficient alignment of the red blood cells can contribute to improved diagnosis. In some cases, the shape of the imaged red blood cells can be used to determine whether a patient from whom the sample is obtained has a particular physiological condition or disease. For example, patients with sickle cell disease present with blood cells having an abnormal shape (i.e. in the shape of a sickle). Hence, by obtaining high quality images of aligned red blood cells, it is possible to ensure an accurate diagnosis. Other shape variations in red blood cells, for example red blood cells having thin peripheral area and a large flat central area, whereby the red blood cell appears to have the profile of a bicycle tire, can effectively be imaged using the instant alignment techniques. Similarly, red blood cells having a small central portion, and a thick peripheral area, whereby the red blood cell appears to have the profile of a truck tire, can be imaged for diagnostic purposes. The improved imaging techniques disclosed herein are also useful for evaluating other red blood cell characteristics, such as hemoglobin content, iron content, and the like.

Without being bound by any particular theory, it is believed that a viscosity differential between the viscosity of the sheath fluid and the viscosity of the sample fluid produces a modified parabolic profile, wherein the profile is generally parabolic and has a central bump corresponding to a center area of the flow where the acceleration is increased, and the central bump contributes to alignment of sample particles or intraparticle organelles. According to some embodiments, the velocity difference between the sheath and sample ribbon and the viscosity difference generate shear forces to increase alignment of the organelles or intracellular particles. Exemplary aspects of the sheath fluid parabolic profile are discussed in co-pending U.S. patent application Ser. No. 14/215,834, filed Mar. 17, 2014 (now U.S. Pat. No. 9,316,635, issued Apr. 19, 2016), the content of which is incorporated herein by reference.

Figure 4L:
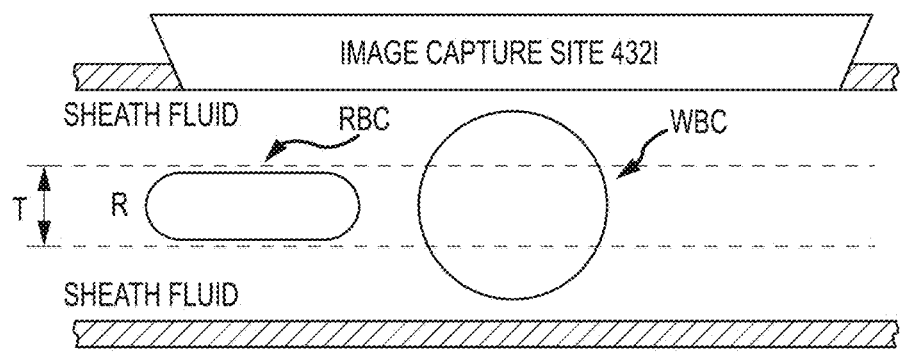
Figures 1, 4K:
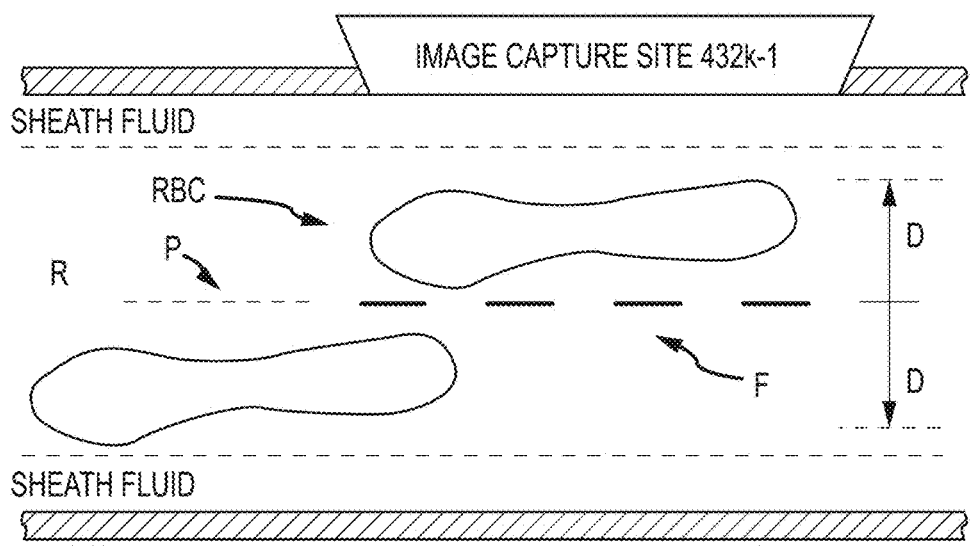
Figures 2, 4K:
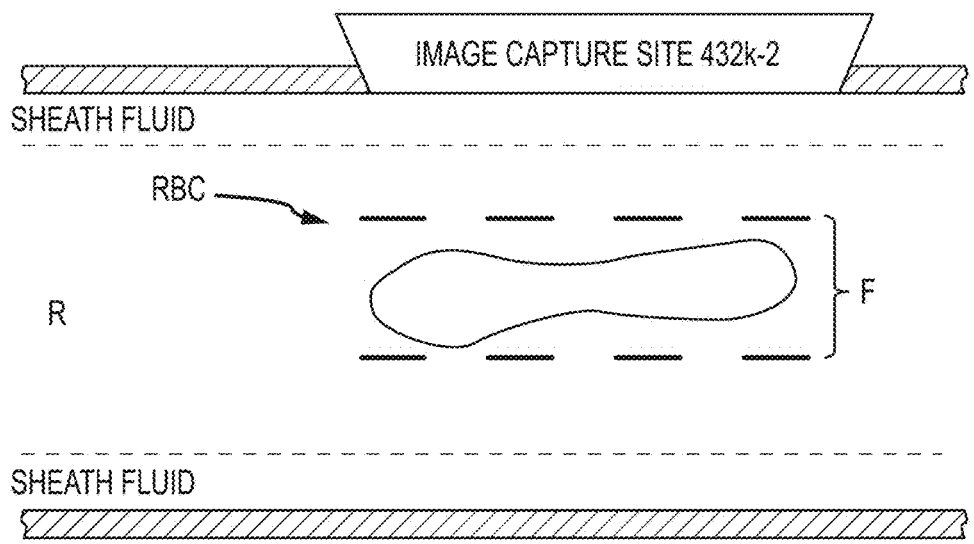
Figures 3, 4K:
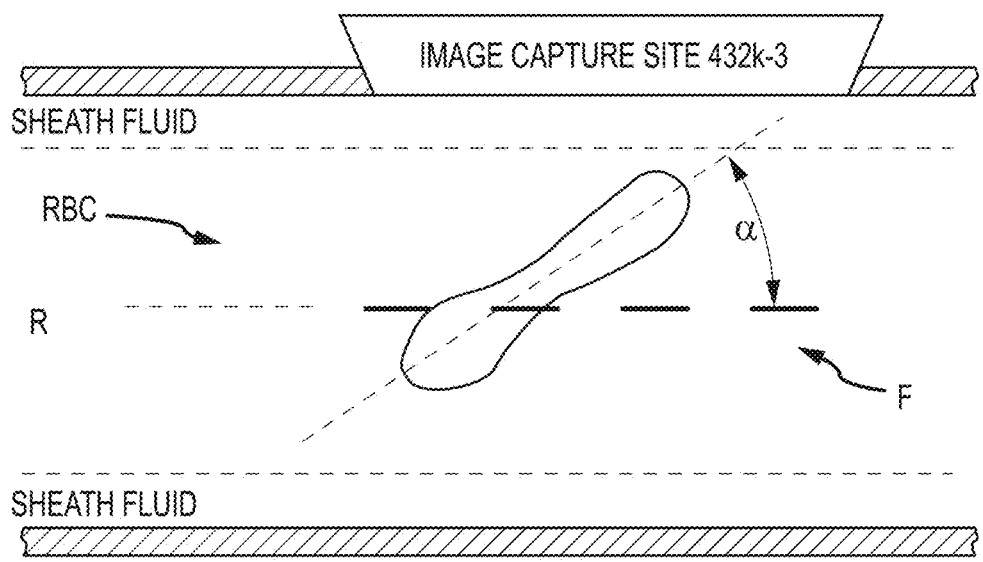
Figures 1, 4L:
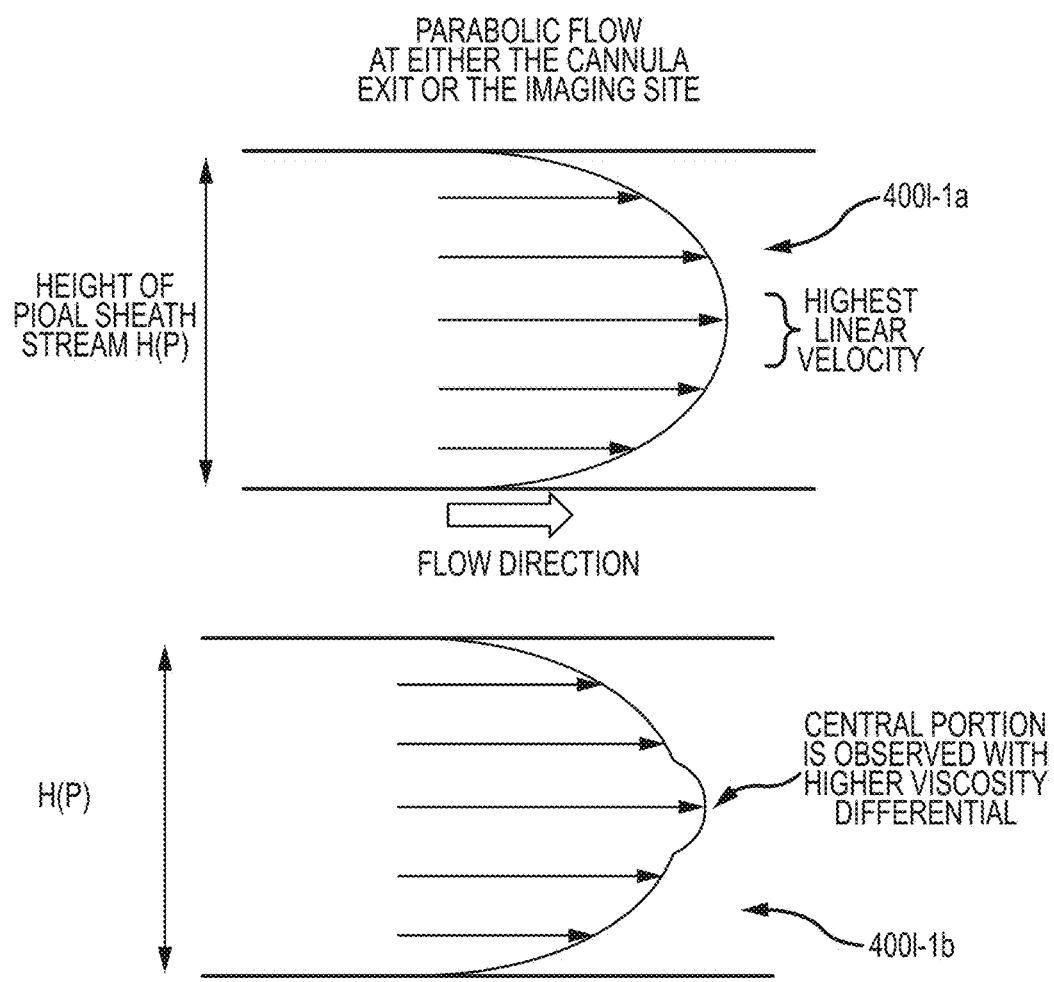

White blood cells are typically larger than red blood cells and platelets. For example, exemplary neutrophils and eosinophils can have a diameter of between about 10 µm and about 12 µm. Exemplary basophils can have a diameter of between about 12 µm and about 15 µm. Exemplary lymphocytes (small) can have a diameter of between about 7 µm and about 8 µm, and exemplary lymphocytes (large) can have a diameter of between about 12 µm and about 15 µm. Exemplary monocytes can have a diameter of between about 12 µm and about 20 µm. The configuration of the particle analysis system, including interaction between the sheath fluid and the fluid sample ribbon as they pass through the flowcell, can operate to compress white blood cells as they travel through the image capture site 432*l*, as indicated in FIG. 4L. Hence, for example, a central portion of the white blood cell (WBC) can be positioned within the sample fluid ribbon R, and peripheral portions of the white blood cell can be positioned within the sheath fluid. Hence, as the white blood cell is transported through the flowcell by the ribbon, the sides of the white blood cell can extend into the sheath fluid. The numerical values or ranges for the thickness T of sample stream ribbon R, and the thickness F of the flowpath as discussed above with regard to FIG. 4K are similarly applicable to FIG. 4L.

According to some embodiments, viscosity differences between the sheath fluid and the sample fluid can operate to align organelles or other intracellular features which are present within cells such as white blood cells. Without being bound by any particular theory, it is believed that shear forces associated with the viscosity differential between the sheath fluid and the sample fluid may act upon the white blood cells so as to align the intracellular features. In some cases, shear forces associated with velocity differentials between the sheath fluid and sample fluid may contribute to such alignment. These alignment effects may be impacted by a size differential between the particles and the sample fluid ribbon as well. For example, where portions of the particles extend out of the sample fluid ribbon and into the surrounding sheath fluid, shear forces associated with the difference in viscosity may have a pronounced effect on the intracellular feature alignment.

As depicted in FIG. 4L, portions of a cell such as a white blood cell can extend into the sheath fluid. Embodiments of the present invention encompass sheath fluid compositions that do not lyse or shred the cell, or otherwise compromise the integrity of the outer cell membrane, when the cell is exposed to the sheath fluid. A viscosity agent in the sheath fluid can operate to retain viability of cells in the sample fluid stream, so as to leave the structure (e.g. shape) and the content (e.g. nucleus) of the cells intact when the cell membrane or wall traverses an interface between the sample fluid ribbon and the sheath fluid envelope or otherwise extends from the sample fluid stream into the flowing sheath fluid.

Often, there are compressive forces acting upon the cells or particles as they flow within the sample fluid ribbon along the flowcell. Hence, the cells may come into contact with the sheath fluid while the cells are in a compressed state or are otherwise subject to compressive forces as a result of a narrowing transition zone. The viscosity agent of the sheath fluid can operate to protect the compressed cells from being shredded or destroyed when they emerge from the thin sample fluid ribbon and become exposed to the viscous sheath fluid, at least until the cells reach the image capture site. Hence, the viscosity agent composition of the sheath fluid can operate as a cellular protectorant, while also enhancing alignment of the particles or intraparticle content.

With reference to FIGS. 4K and 4L, in some instances portions of the cell or particle may extend out of the thin sample fluid ribbon R and into the surrounding sheath fluid. As discussed in co-pending U.S. patent application Ser. No. 14/215,834, filed Mar. 17, 2014 (now U.S. Pat. No. 9,316,635, issued Apr. 19, 2016), the sheath fluid may contain cellular protectants that inhibit or prevent the sheath fluid from disrupting or lysing the cells or particles. For example, the sheath fluid may contain cellular protectants that preserve the structural integrity of the cells walls as the cells are exposed to the chemical environment of the sheath fluid. Similarly, the cellular protectants may also operate to preserve the structural integrity of the cells walls as the cells experience any shear forces induced by flowcell geometry, and a difference in velocity and/or viscosity between the sample fluid and the sheath fluid. Relatedly, the protectorants can protect the cells or particles from forces resulting from the difference in velocity between the sample fluid and sheath fluid. In this way, the cells retain their viability as they reach the image capture site.

The shear forces can be significant at the interface between the sample fluid ribbon and the sheath fluid envelope. According to some embodiments, flow within the flowcell flowpath can be characterized by a parabolic flow profile. FIG. 4L-1 depicts exemplary aspects of parabolic flow profiles 400/-1a and 400/-1b. The parabolic profile 400/-1a in the upper panel is a typical velocity profile found in flows within certain flowcell embodiments of the present invention (e.g. where there is little or no viscosity differential between a sample fluid flowstream that is enveloped within a sheath fluid flowstream). As can be seen, a highest linear velocity is observed in the middle of the fluid stream and slower linear velocities are observed near the flowcell wall. Profile 400/-1a can also be observed in fluid stream with a slight viscosity difference between the sheath and sample fluids. In a case where there is a high viscosity differential between the sheath and fluid streams, a central bump is observed as shown in profile 400/-1b, where there is a localized central area with amplified linear velocities. According to some embodiments, particles that are sufficiently large in size will be subjected to some amount of shear force, even where such particles are fully contained within a single fluid phase (i.e. either within the sheath fluid envelope, or alternatively within the sample fluid ribbon).

In some instances, the velocity of the sheath fluid may be different from the velocity of the sample fluid. For example, the sheath fluid may be traveling at 80 mm/second and the sample fluid may be traveling at 60 mm/second. Hence, in some instances, the sample fluid exits the distal cannula port at a sample fluid speed that is slower than the sheath fluid speed of the surrounding envelope. Hence, the sheath fluid can operate to drag the sample fluid along the flowpath of the cannula, thus accelerating the sample fluid and reducing the thickness of the sample fluid ribbon. The sample fluid ribbon maintains the overall volume and mass, so as it travels faster it becomes thinner. According to some embodiments, both the sheath fluid and the sample fluid have a velocity of between about 20 and 200 mm/second at the image capture site.

Typically, the velocity of the sample fluid increases as the sample fluid travels from the cannula exit port to the image capture site. In some instances, the velocity of the sample fluid at the image capture site is 40 times the velocity of the sample fluid as it exits the cannula port at the cannula distal portion. According to some embodiments, the decrease in cross sectional area of the sample ribbon is linear to the increase in velocity. According to some embodiments, if the sheath velocity at the cannula exit is higher than the sample ribbon velocity this will also increase the final sample ribbon velocity at the imaging area.

The sheath fluid can operate to apply significant shear forces on the sample fluid ribbon and on particles within the sample fluid ribbon. Some forces are parallel to the direction of flow, and particles may also encounter forces which are perpendicular to the direction of flow. Often, as the sheath fluid and sample fluid approach the image capture site or zone, the sheath and sample fluids are traveling at or near the same velocity. Hence, the boundary or interface between the sheath and sample fluids as they pass the image capture site may present lower shear forces, as compared to the boundary or interface at the distal cannula exit port or at the tapered transition zone. For example, at the tapered transition zone, the boundary or interface between the sheath fluid envelope and sample fluid ribbon can be in transition, such that the sample ribbon which is initially slower and thicker becomes faster and thinner, and particles in the sampel fluid become more aligned. Put another way, the shear forces may be prominent at the tapered transition zone, and can dissipate toward the image capture site. The shear forces at the image capture site can be represented by a parabolic profile, and can be much lower than the shear forces at the tapered transition zone. Hence, cells or particles can experience higher shear forces as they pass through the transition zone, and lower shear forces as they pass through the image capture site. According to some embodiments, the viscosity difference between the sheath and sample fluids can bring the red blood cells into alignment and thereby into focus. According to some embodiments, the viscosity difference between the sheath and sample fluids can bring white blood cell organelles into alignment and thereby into focus. Relatedly, enhanced imaging results can be obtained for cellular and organelle components that are aligned and brought into focus, resulting from the geometric narrowing of the stream and the velocity difference between the sheath and sample fluids.

As noted elsewhere herein, and with reference to FIGS. 4K and 4L, as the sheath fluid and the sample fluid R flow through a reduction in flowpath size or transition zone of a flowcell, and toward an imaging site 432$k$ or 432$l$, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site 432$k$ or 432$l$.

In some cases, the target imaging state is a target orientation relative to a focal plane F at the imaging site. For example, as depicted in FIG. 4K-1, the particle (RBC) can be displaced at a distance from the focal plane F. In some cases, the target orientation involves a target particle orientation relative to the focal plane F at the imaging site 432$k$-1. The particle can be a blood cell, such as a red blood cell, a white blood cell, or a platelet. As shown here, the flowpath at the imaging site 432$k$-1 can define a P plane that is substantially parallel to or coplanar with the focal plane F. In some cases, a portion of the particle may be positioned along the focal plane F, yet the central portion of the particle may otherwise be offset from the focal plane F. In some cases, the target orientation involves a target position relative to the focal plane F at the imaging site 432$k$-1. For example, the target position may involve positioning of the particle so that at least a portion of the particle is disposed along the focal plane F. In some cases, the target position may involve positioning of the particle so that a distance between the particle and the focal plane F does not exceed a certain threshold. In some cases, the target position involves a target particle position that is relative to the focal plane F at the imaging site 432$k$-1. In some cases, the target position is at or less than a distance D from the focal plane F, where distance D corresponds to a positional tolerance. A viscosity differential between the sheath fluid and the sample fluid can be selected so as to achieve a desired positioning of the ribbon sample stream within the flowcell (e.g. relative to flowpath plane P and/or focal plane F). In some cases, the viscosity differential can be selected so as to achieve a target particle position that is at or less than the positional tolerance D.

In some cases, the focal plane F has a thickness or depth of field as indicated in FIG. 4K-2, and the particle (RBC) has a target imaging state relative to the focal plane thickness. For example, the target position for the particle can be within the focal plane F or at least partially within the focal plane F. In some cases a high optical resolution imaging device or camera can have a depth of field or focal plane thickness of about 7 μm. In some cases, the depth of field or focal plane thickness has a value with a range from about 2 μm to about 10 μm. In some cases, the depth of the field of the camera is similar or equal to the sample ribbon thickness at the image capture site.

In some cases, the target orientation can involve a target alignment relative to the focal plane F at the imaging site. For example, the target alignment can indicate that a plane defined by the particle is aligned with the focal plane F, not to exceed a certain angle a relative to the focal plane F at the image capture site 432$k$-3 as shown in FIG. 4K-3. In some cases, the target imaging state can involve a limitation on the number or percentage of misaligned particles in a sample. For example, a difference in viscosity between the sheath fluid and the sample fluid R can be effective to limit red blood cells imaging orientation misalignment in the blood fluid sample to less than about 10%. That is, 90 or more red blood cells out of 100 red blood cells in a sample can be aligned so that their major surfaces face toward the imaging device (as depicted in FIGS. 4K-1 and 4K-2) or so that the alignment of those 90 or more RBCs is within 20 degrees from a plane substantially parallel to the direction of flow (e.g. RBC alignment angle α is 20 degrees or less). As discussed elsewhere herein, in some cases at least 92% of non-spherical particles such as RBCs can be aligned in a plane substantially parallel to the direction of flow. In some cases, at least between 75% and 95% of non-spherical particles such as RBCs can be substantially aligned, namely within 20 degrees from a plane substantially parallel to the direction of flow (e.g. alignment angle α is 20 degrees or less). According to some embodiments, 90% or more of certain particles (e.g. red blood cells and/or platelets) can be oriented transverse to the imaging axis of the imaging device.

In some cases, embodiments of the present invention include compositions for use with a hematology system as described herein, such as a sheath fluid or particle and intracellular organelle alignment liquid (PIOAL). Such sheath fluids or PIOALs are suitable for use in a combined viscosity and geometric hydrofocusing visual analyzer. The PIOAL can operate to direct or facilitate flow of a blood sample fluid of a given viscosity through a narrowing flowcell transition zone of the visual analyzer. The PIOAL can include a fluid having a higher viscosity than the viscosity of the sample. A viscosity hydrofocusing effect induced by an interaction between the PIOAL fluid and the sample fluid associated with the viscosity difference, in combination with a geometric hydrofocusing effect induced by an interaction between the PIOAL fluid and the sample fluid associated with the narrowing flowcell transition zone, can be effective to provide a target imaging state in at least some of the plurality of particles at an imaging site of the visual analyzer while retaining viability of cells in the blood sample fluid.

Figure 4M:
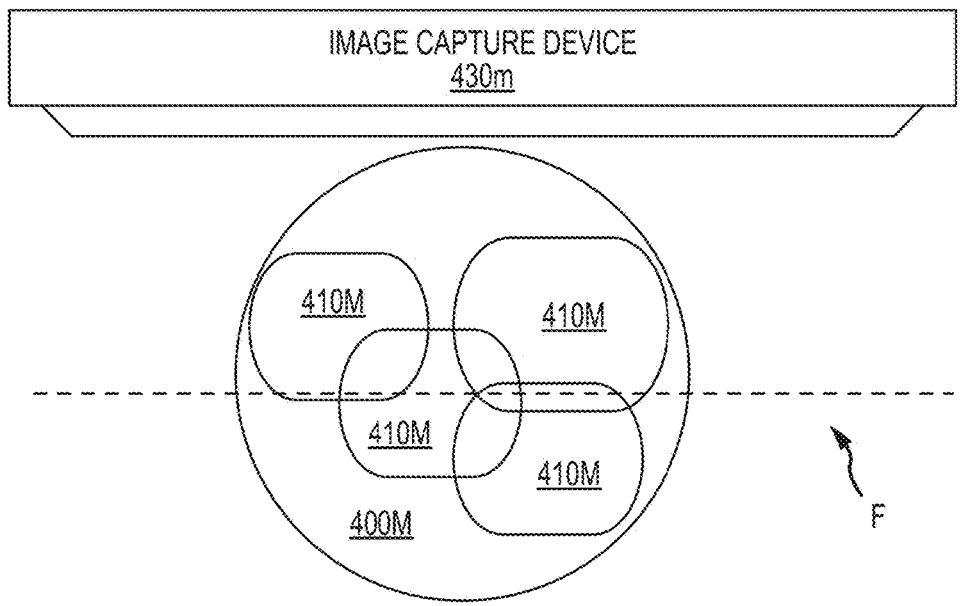
FIGS. 4M and 4N show aspects of intracellular particle alignment according to embodiments of the present invention.
Figure 4N:
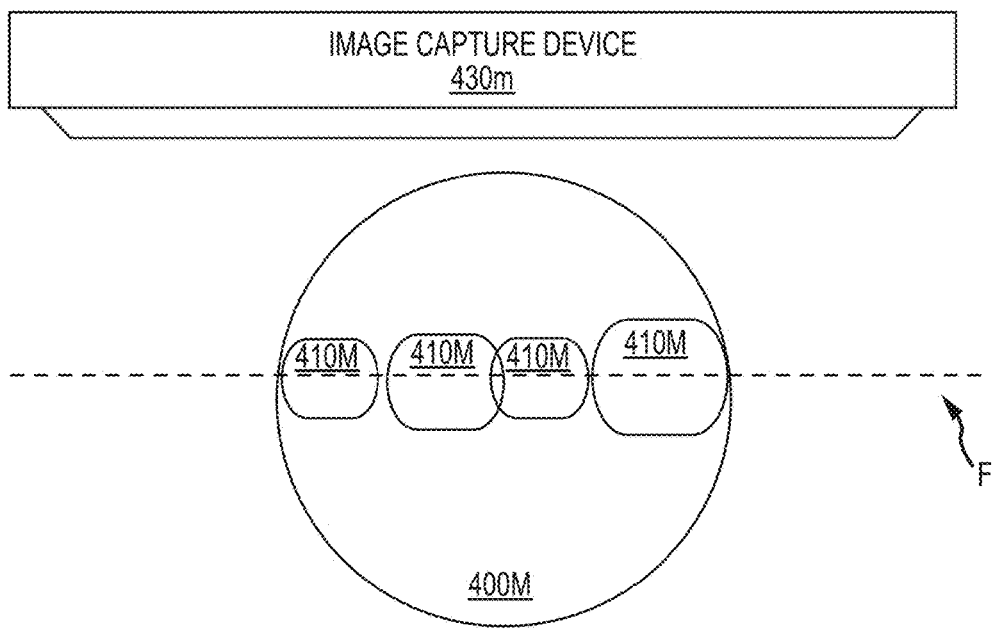

FIG. 4M depicts an exemplary neutrophil 400$m$ (a type of white blood cell) having internal organelles such as lobes 410$m$. As a result of the viscosity differential between the sample fluid and the sheath fluid, the internal organelles can align within the cell, as indicated by FIG. 4N. Hence, the intracellular organelles can be effectively imaged with an image capture device 430$m$, without the organelles overlapping one another. That is, instead of the lobes being stacked upon one another as depicted in FIG. 4M, when viewed from the imaging or optical axis of the image capture device the lobes are aligned and sitting side by side as depicted in FIG. 4N. Hence, the lobes can be visualized in the captured imaged more effectively. The internal organelle alignment is a surprising and unexpected result of the viscosity differential between the sample and sheath fluids. Accordingly, enhanced imaging results corresponding to cell alignment and in-focus are achieved using the viscosity differential, hydrodynamic flow, and geometric compression features.

As noted elsewhere herein, and with reference to FIGS. 4M and 4N, as the sheath fluid and the sample fluid R flow through a reduction in flowpath size or transition zone of a flowcell, and toward an imaging site of an image capture device 430*m* or 430*n*, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site. According to some embodiments, the target imaging state may correspond to a distribution of imaging states.

In some cases, the target imaging state can involve a target intraparticle structure orientation (e.g. alignment and/or position) relative to a focal plane at the imaging site. For example, as depicted in FIG. 4N, the internal structures 410*m* (e.g. intracellular structure, organelle, lobe, or the like) can be oriented relative to the focal plane F. In some cases, the target alignment involves a target intraparticle structure alignment relative to a focal plane F at the imaging site, similar to the particle alignment relationship depicted in FIG. 4K-3. In some cases, the target position involves a target intraparticle structure position relative to a focal plane at the imaging site, similar to the particle position relationship depicted in FIG. 4K-1. In some cases, the target orientation of the intraparticle structure can include both a target alignment relative to the focal plane and also a target position relative to the focal plane. In some cases, the target imaging state can involve a target deformation at the imaging site. For example, as depicted in FIG. 4N, the particle 400*m* has a compressed shape as compared to the particle shape depicted in FIG. 4M. Hence, it can be seen that operation of the flowcell can produce a lateral compression effect on the particle shapes. Relatedly, the intraparticle features can be positionally or directionally oriented (e.g. aligned with respect to the focal plane F and/or ribbon flow plane) as the particle itself is compressed in shape. According to some embodiments, a velocity difference between the sheath and and sample fluids can produce friction within the flowstream, and a viscosity difference between the sheath and sample fluids can amplify that hydrodynamic friction.

EXAMPLES

Any of a variety of hematology or blood particle analysis techniques can be performed using images of sample fluid flowing through the flowcell. Often, image analysis can involve determining certain cell or particle parameters, or measuring, detecting, or evaluating certain cell or particle features. For example, image analysis can involve evaluating cell or particle size, cell nucleus features, cell cytoplasm features, intracellular organelle features, and the like. Relatedly, analysis techniques can encompass certain counting or classification methods or diagnostic tests, including white blood cell (WBC) differentials. In some cases, images obtained using the flowcell can support a 5-part WBC differential test. In some cases, images obtained using the flowcell can support a 9-part WBC differential test. Relatedly, with reference to FIG. 4, the processor 440 can include or be in operative association with a storage medium having a computer application that, when executed by the processor, is configured to cause the system 400 to differentiate different types of cells based on images obtained from the image capture device. For example, diagnostic or testing techniques can be used to differentiate various cells (e.g. neutrophils, lymphocytes, monocytes, eosinophils, basophils, metamyelocytes, myelocytes, promyelocytes, and blasts).

The Examples provided herein are for the purpose of illustration only, and the invention is not limited to these Examples, but rather encompasses all variations that are evident as a result of the teaching provided herein.

Prior to the experiments described herein, there was no published protocol that allows for the development and the methods of use comprising PIOAL for aligning particles and repositioning intracellular content as disclosed herein. This is useful for image-based analysis and differential categorization and subcategorization of particles in body fluid (e.g. blood) samples. The methods and compositions disclosed herein can optionally stain and/or lyse particles in a suitable manner to achieve white cell staining, reticulocyte staining and platelet staining, that mimic's Wright stained cells seen on a whole blood smear.

The exemplary compositions described herein allow staining to occurs at a relatively low blood to reagent dilution and the staining can occurs rapidly (e.g. within 30 sec). If desired, the exemplary method can employ the use of a surfactant in combination with heat to achieve red cell lysis. The exemplary formulations can be modified to retain RBC integrity and still achieve WBC, retic and platelet staining efficacy.

Aspects and embodiments of the present disclosure are based on the surprising and unexpected discovery that certain PIOAL compositions have unexpected properties aligning cells and re-positioning intracellular structures when used to perform image-based particle/cell analysis.

By way of example, several exemplary PIOAL formulations and methods of use thereof were developed. The following are some exemplars of PIOAL formulations with the desired properties.

Figure 4O:
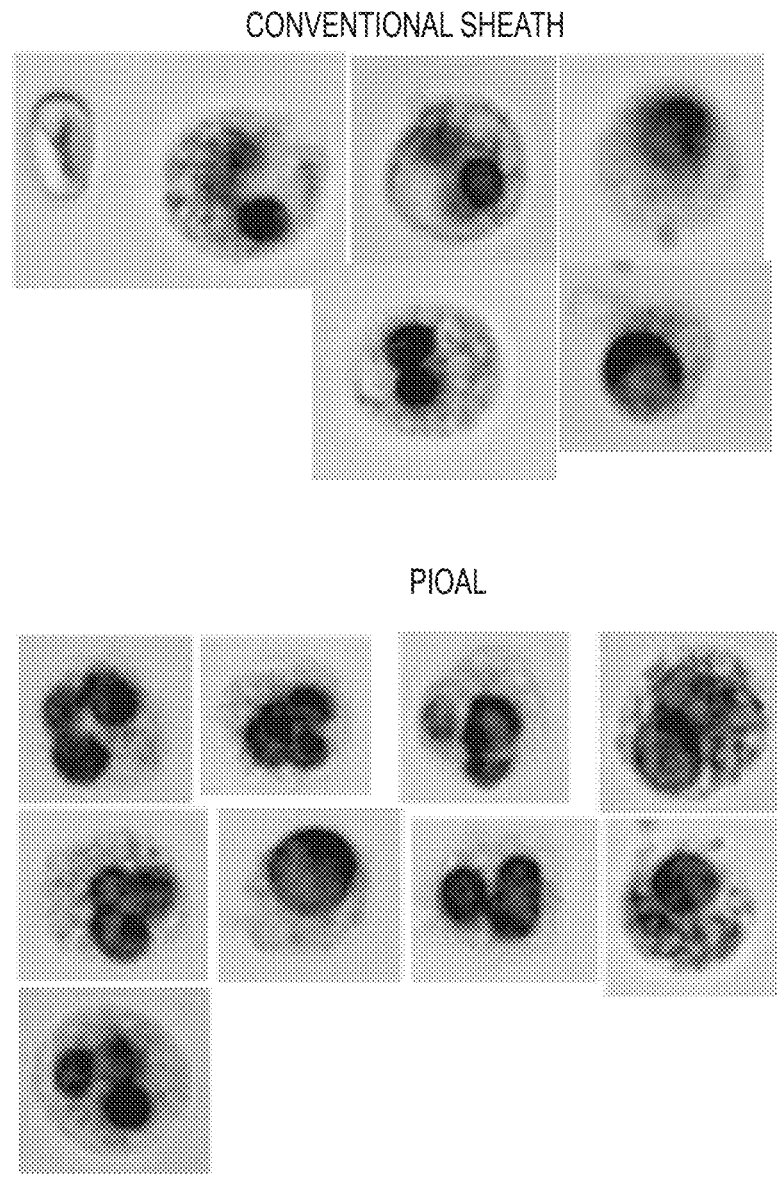
FIG. 4O shows a comparison of images obtained using PIOAL versus images obtained using a non PIOAL sheath fluid according to embodiments of the present invention.

FIG. 4O shows a comparison of images obtained using PIOAL versus images obtained using a non PIOAL sheath fluid. Use of the PIOAL resulted in more in-focus cellular contents such as lobes, cytoplasm, and/or granule. In this example, a PIOAL comprising a viscosity agent (about 30% glycerol) was used to process the sample. The pH was adjusted to a pH of about 6.8 to 7.2 and the sample mixture was made isotonic by (0.9% sodium chloride). The results shown here demonstrate the efficacy of an exemplary PIOAL used on an image analyzer to align cells and intracellular organalles.

Figure 4P:
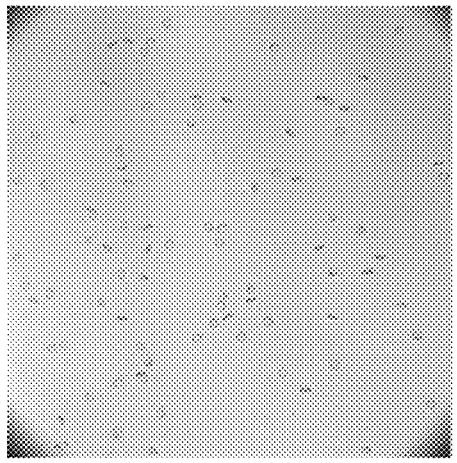
FIGS. 4P and 4Q show a comparison of images obtained using a standard sheath fluid and exemplary PIOAL fluid according to embodiments of the present invention.
Figure 4P:
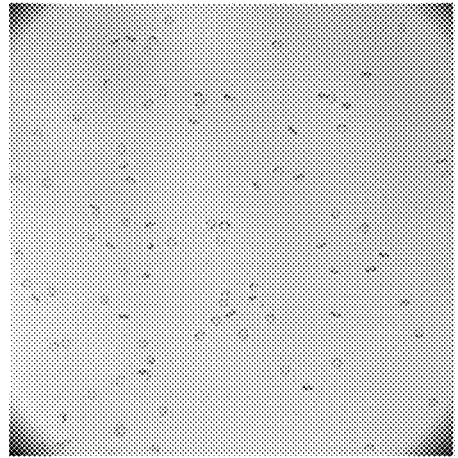
Figure 4P:
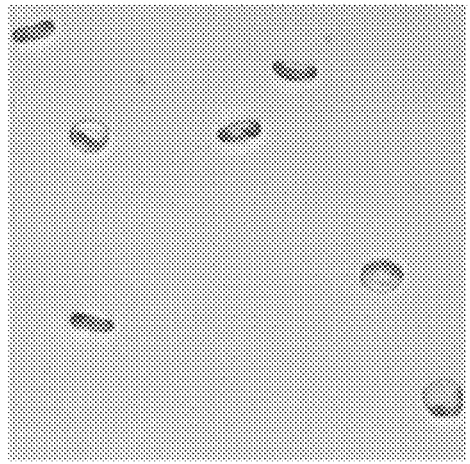
Figure 4Q:
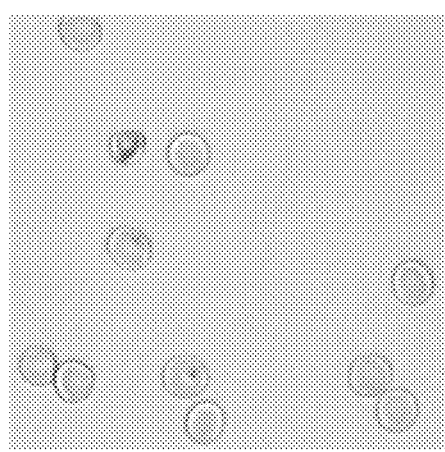

FIGS. 4P and 4Q show a comparison of images obtained using a standard sheath fluid (FIG. P upper and lower panels) versus images obtained using an exemplary PIOAL fluid (FIG. 4Q upper and lower panels). As shown here, the use of PIOAL resulted in an improved RBC alignment, for example by orienting the major surfaces of the red blood cells to face toward the camera or imaging device. The sample was analyzed using an instrument focusing protocol (on an exemplary target 44 as depicted in FIG. 1) and the target was brought into focus by a visual analyzer. The focusing system was then offset by displacement distance 52, resulting in the particles in the ribbon-shaped sample stream being in focus. The blood sample was previously diluted using a sample diluent. The sample flowed through a cannula and along a flowpath of a flowcell, thereby generating a ribbon-shaped sample stream (e.g. 2 microns in thickness) which was between two layers of PIOAL or standard sheath (in controls). The visual analyzer then generates focused images of the particles in the ribbon-shaped sample stream (e.g. at about 60 frames per second) to be used for analysis. The blood sample is obtained from a subject and processed for analysis by the blood analyzer. Images of RBCs in a flowcell are captured while the sample is processed using a standard sheath fluid or a PIOAL. Relative percentages demonstrate significant improvement in the number of aligned RBCs based on imaging data (e.g. 4P and 4Q). The result demonstrated that PIOAL was efficacious at increasing the percentage of RBC alignment while in flow in the ribbon-shaped sample stream using the focusing instrument/protocols as described herein.

It was also observed that the implementation of PIOAL results in improved alignment based on using increasing levels of glycerol (gly) in symmetric and asymmetric flow-cells.

Figure 4R:
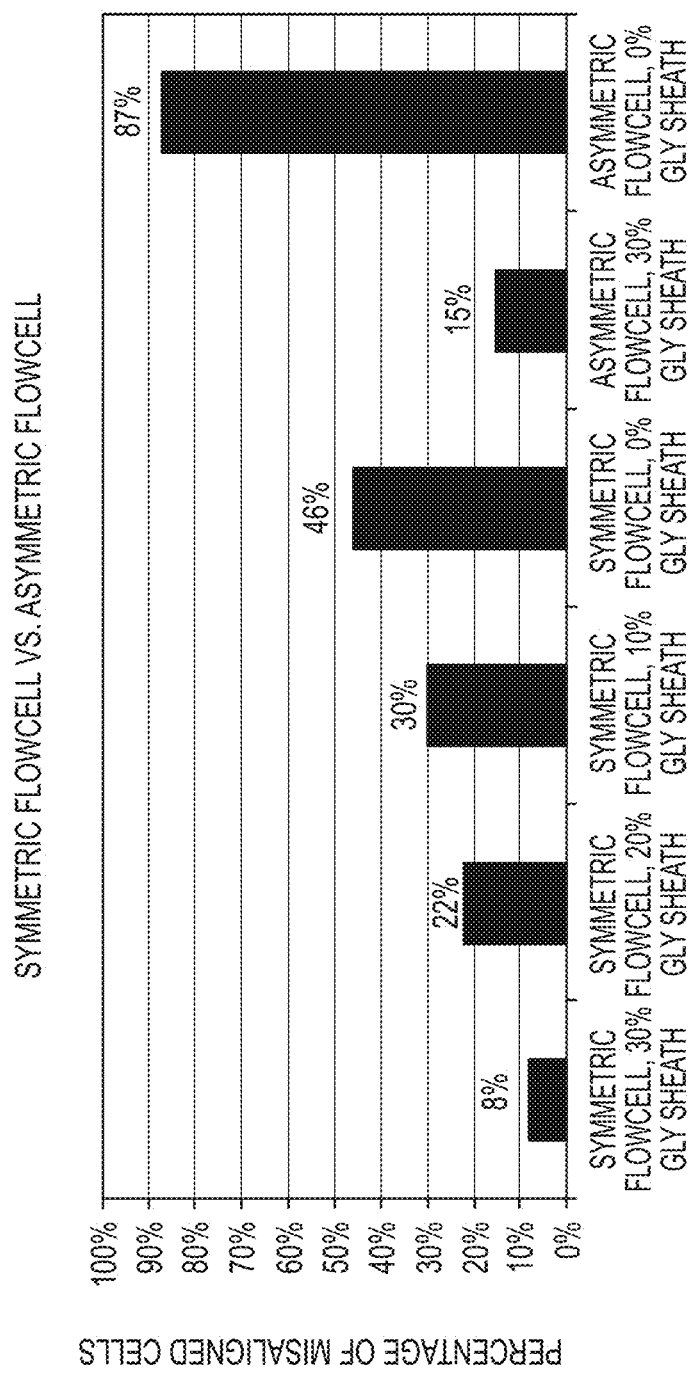
FIG. 4R shows a chart of the percentage of non-aligned cells obtained using 0%-30% glycerol in the PIOAL with symmetric vs. asymmetric flow cells according to embodiments of the present invention.

The chart in FIG. 4R shows the percentage of non-aligned cells obtained using 0%-30% glycerol in the PIOAL with symmetric vs. asymmetric flow cells. Using 30% glycerol in the PIOAL and a symmetric flowcell results in reducing the percentage of misaligned cells to only 8%. Note without glycerol in the PIOAL, and with an asymmetric cell, the percentage of misaligned cells increased to 87%. Hence, this chart demonstrates the effect of glycerol percentage and flowcell geometry on particle (e.g. RBC) alignment. The addition of glycerol decreases the percentage of misaligned RBC cells using either symmetric or asymmetric flowcell geometry. The % non-aligned RBCs was reduced from 87% down to 15% in the asymmetric and 46% to 8% in symmetrical cells. Thus, the chart provides a comparison between misalignment results (8%) obtained from an analyzer configuration that involves a flowcell having a symmetrical narrowing flowcell transition zone and a viscous sheath fluid and misalignment results (46%) obtained from an analyzer configuration that involves a flowcell having a symmetrical narrowing flowcell transition zone without the use of a viscous sheath fluid.

These results provide evidence for the surprising and unexpected discovery that certain PIOAL compositions have unexpected properties aligning cells and re-positioning intracellular structures when used to perform image-based particle/cell analysis.

By way of example, several exemplary PIOAL formulations and methods of use thereof were developed. The following are some exemplars of PIOAL formulations with the desired properties. The PIOAL comprises a diluent and at least one viscosity modifying agent.

Exemplary PIOAL formulation A includes a 30% (v/v) glycerol solution having 300 mL glycerol and QS (quantity sufficient or to bring the final volume up to) to 1 L with diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation B includes a 6.5% (v/v) glycerol solution having 65 mL glycerol and QS to 1 L with suitable exemplary diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation C includes a 5% glycerol (v/v) solution with 1% PVP(w/v) in buffer having 50 mL glycerol, 10 g PVP (MW: 360,000), 1 packet of Sigma PBS powder, at pH 7.4 (0.01M phosphate buffered saline; 0.138M sodium chloride; 0.0027M potassium chloride), and QS to 1 L with deionized water.

Exemplary PIOAL formulation D includes a 1.6% PVP (w/v) solution having 16 g PVP (MW: 360,000) and 1 packet of Sigma PBS powder, at pH 7.4 (0.01M phosphate buffered saline; 0.138M sodium chloride; 0.0027M potassium chloride), and QS to 1 L with deionized water.

Throughput

Figure 5:
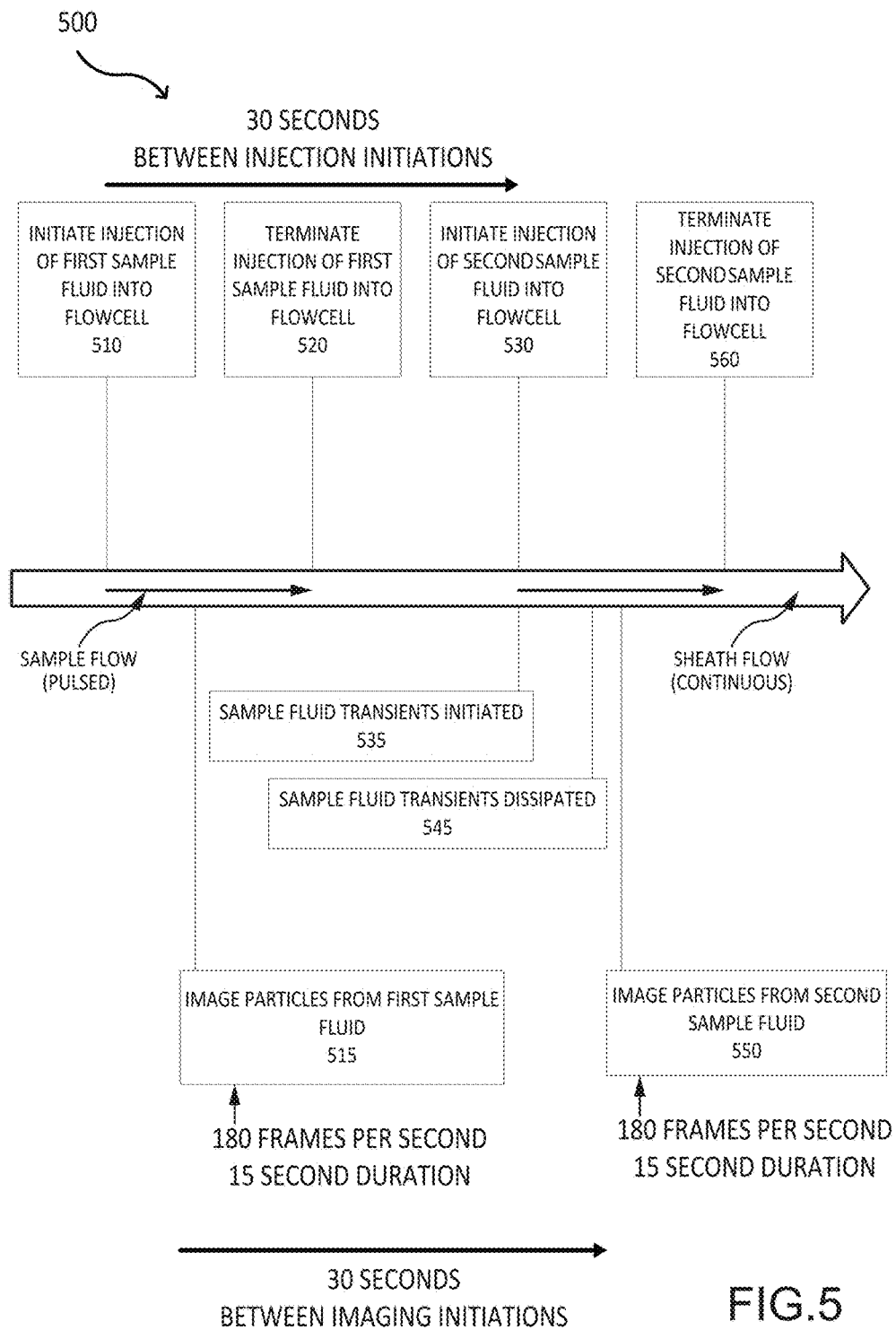
FIG. 5 depicts a timeline corresponding to the injection of one or more sample fluids in a flowcell according to embodiments of the present invention.

FIG. 5 depicts a timeline 500 corresponding to the injection of one or more sample fluids in a flowcell. As shown here, injection of a first sample fluid can be initiated into a flowcell, as indicated by step 510. Thereafter, particles from the first sample fluid can be imaged in the flowcell, as indicated by step 515. According to some embodiments, the first sample fluid can have a volume in a range from about 5 µL to about 150 µL. In some cases, the flow is 0.232 µL/sec (or within a range from 0.2 µL/sec to 0.35 µL/sec) at the imaging area. For 20 seconds of imaging, the flow value can be within a range from 5 µL to 15 µL. The injection of the first sample fluid can be terminated, as indicated by step 520, and injection of a second sample fluid can be initiated into the flowcell, as indicated by step 530. Sample fluid transients can be initiated, as indicated by step 535, as a result of termination of the first sample fluid injection and initiation of the second sample fluid injection. Subsequently, sample fluid transients in the flowcell can dissipate, as indicated by step 445. Particles from the second sample fluid can be imaged in the flowcell, as indicated by step 550. The injection of the second sample fluid can be terminated, as indicated by step 560. In some instances, the injection and flow procedures are performed at temperatures within a range from about 18° C. to about 40° C.

Typically, the stream of the sheath fluid remains flowing within the flowcell as the sample is injected, and as the injection is terminated. Hence, according to some embodiments, a continuous flow of sheath fluid is maintained while injections of sample fluid are pulsed into the flowing sheath. The continuous flow of the sheath fluid can contibute to preservation of a ribbon shape in the sample fluid as the sample fluid flows along the flowcell.

According to some embodiments, the image capture associated with step 550 can be performed within four seconds of the image capture associated with step 515. According to some embodiments, the time between first and second sample fluid injections (e.g. between steps 510 and 530) is about 30 seconds. Relatedly, according to some embodiments, the time between initiation of imaging of the first and second sample fluids (e.g. between initiation of step 515 and initiation of step 550) is about 30 seconds. In this way, it is possible to process 120 sample fluids per hour. In some cases, an image capture device operates at a frame rate of 180 frames per second (FPS), thus producing multiple unique consecutive images or frames at a high frequency or rate. As shown here, the duration of an imaging step (e.g. 515 or 550) can be 15 seconds, thus producing 2,700 images per sample fluid.

In some instances, the first sample fluid reaches a stabilized state within about 1 to 3 seconds following injection (e.g. step 510) of the first sample fluid from the sample fluid injection tube into the flowing sheath fluid. In some instances, the first sample fluid reaches a stabilized state within less than 1 second following injection (e.g. step 510) of the first sample fluid from the sample fluid injection tube into the flowing sheath fluid. The injection of the sample into the flowcell can be a two step process. According to this embodiment, the first step is a high speed push that clears all the diluent out of the cannula, and after the intial push the flow rate of the sample is reduced significantly. The transition time can be defined as the time it takes the sample (e.g. a cell) to travel from the cannula exit to the imaging area under the imaging flow conditions (slower sample flow rate). In some instances, the first sample fluid reaches a stabilized state within about 1.8 seconds from injection (e.g. step 510) of the first sample fluid from the sample fluid injection tube into the flowing sheath fluid. In some instances, the sample fluid has a transit time through the flowcell (e.g. from an cannula exit port to an image capture site) within a range from about 2 to 4 seconds.

According to some embodiments, it takes about 5 seconds for the flow to stabilize, or to travel from a distal exit port of the cannula to the imaging area. In some cases, an image capture duration period can be about 20 seconds.

A hematology system according to embodiments of the present invention can process a blood sample having a volume of about 150 μL. The aspirated blood volume can be about 120-150 μL. In some cases, the minimum available blood volume in the sample tube is about 500 μL for an automatic sampling mode and about 250 μL for manual sampling mode. The cannula or injection tube 400d shown in FIG. 4D has an internal volume of about 13 uL. According to some embodiments, the cannula or injection tube has an internal volume of less than about 30 uL. The volume of blood sample is effective to flush the cannula before starting image collection, and thus can avoid extended periods of time where the sample flow is not stable. For example, use of a cannula having a internal volume of about 13 uL can correspond to a sample flow instability period of about 2 to 3 seconds. According to some embodiments, the cannula internal volume may not impact sample flow stability. According to some embodimetns, the cannula internal volume may impact the cell concentration stability in the sample ribbon itself if the initial high speed sample push is insufficient to replace all diluent inside the cannula. Relatedly, the cannula can be cleaned in between samples in a short amount of time using a small amount of dilent. In this way, it is possible to achieve a stable sample flow which facilitates the capture of a high quality image, and at the same time achieve a high throughput, with a low carry-over. According to some embodiments, a cannula with a high internal volume may require a high volume initial high speed push of sample to clear out all diluent in the lines and cannula. Embodiments of the present invention encompass the implementation of lower internal cannula volumes, which are suitable for hematological applications where the available sample volumes are low, and where a lower volume push can be accomplished in a shorter amount of time.

According to some embodiments, hematology systems can be configured to limit transients and sequential sample cross-contamination so as to speed image acquisition from blood fluid samples.

Cellular Structure, Content, and Alignment

According to some embodiments, to accomplish staining and visualization of white blood cells, it is helpful to lyse red blood cells in the sample and permeabilize the white blood cells so as to allow the stain to incorporate with the white blood cells. It is often desirable to obtain a stain of the white blood cells with little to no change in morphology to the cells. Further, it is often desirable to obtain staining properties which resemble a Wright stain. What is more, it is often desirable to obtain a high red cell alignment (e.g. target >90%).

Figure 5A:
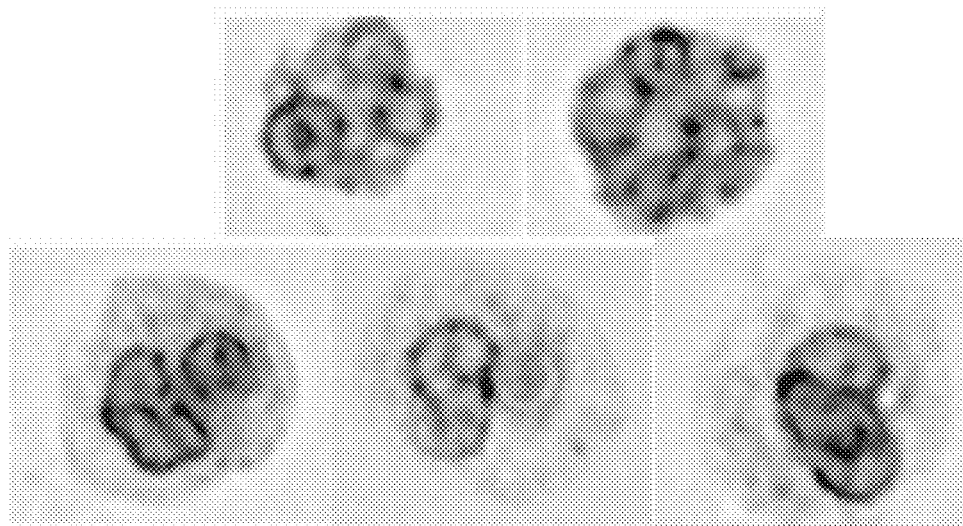
FIGS. 5A, 5B, 5C, and 5D depict results obtained using certain processing techniques according to embodiments of the present invention.

FIG. 5A depicts results obtained using a stain formulation that does not include glutaraldehyde. It was observed that the cells fell apart as a result of shear forces encountered in the flowcell. Although a good stain of the nucleus was achieved, the nucleus itself appeared deformed, and the cell membrane appeared damaged. In sum, when imaged the cell appeared to be destroyed due to disruption to the cellular content and structure.

Figure 5B:
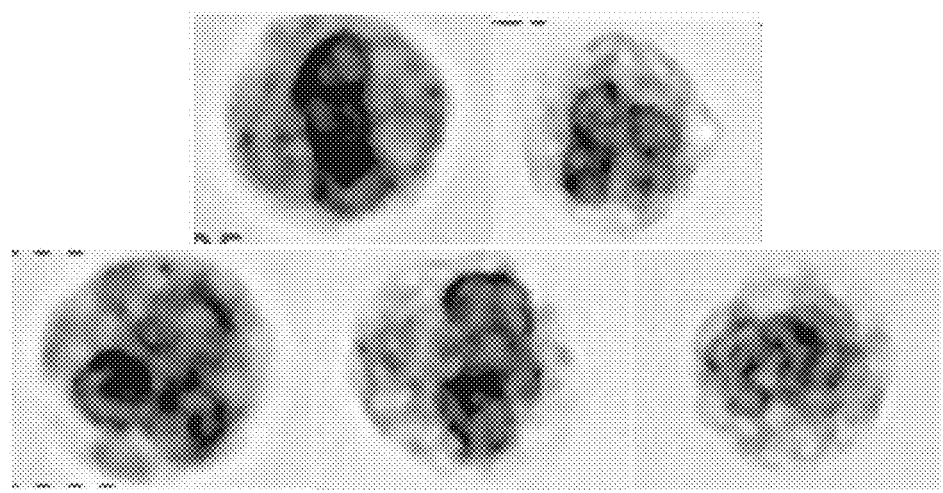

FIG. 5B depicts WBC results obtained using a stain formulation that includes glutaraldehyde. As shown here, the cell membranes are intact and the cells are round. Hence, it was observed that the version of the stain which did not use gluteraldehyde (e.g. shown in FIG. 5A) resulted in resulting in weakened WBC's. Although the WBC's are more intact in FIG. 5B, the nucleus portions are damaged.

Figure 5C:
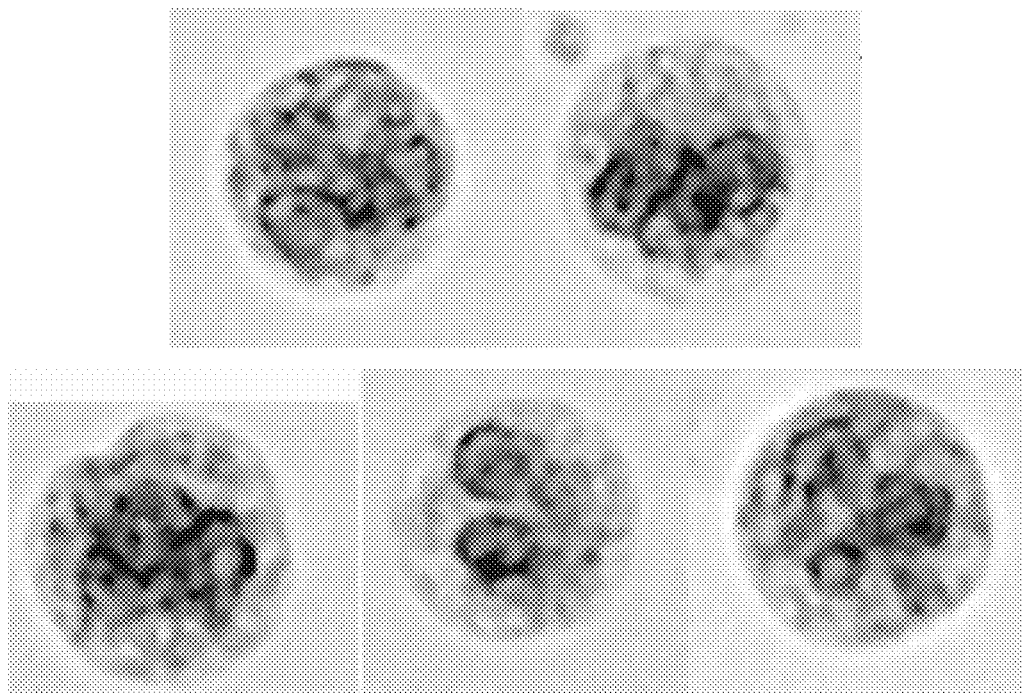

The sheath fluid (PIOAL) used to obtain the FIG. 5B images included 30% glycerol. In contrast, the sheath fluid (PIOAL) used to obtain the FIG. 5C images included 6.5% glycerol. The lower concentration of glycerol resulted in a better morphology, with the nucleus mostly unchanged. Hence, it was observed that the cell membrane in FIG. 5C is even more intact that than the cell membrane in FIG. 5B. The lower glycerol concentration in FIG. 5C can operate to reduce the viscosity difference, thereby reducing the shear force. If excessive shear force is present, the force can destroy the cell membranes. The glycerol may have some properties that are incompatible with the cells and thus a higher concentraton of glycerol may also destroy the cell membranes. Hence, it is possible to conclude that the damage to the nucleus depicted in FIG. 5A can be the result of the 30% glycerol in the sheath fluid.

When the glycerol concentration was lowered to 6.5% as depicted in FIG. 5C, however, the alignment of the red blood cells in the sample fluid was observed to diminish.

Various alternative PIOAL formulations were used in an attempt to obtain improved alignment in red blood cells, but these alternative formulations did not provide satisfactory results. For example, several different viscosity enhancers were tried, but many of them exhibited behavior similar to that of the higher 30% glycerol formulation, such that the cell contents were damaged.

Figure 5D:
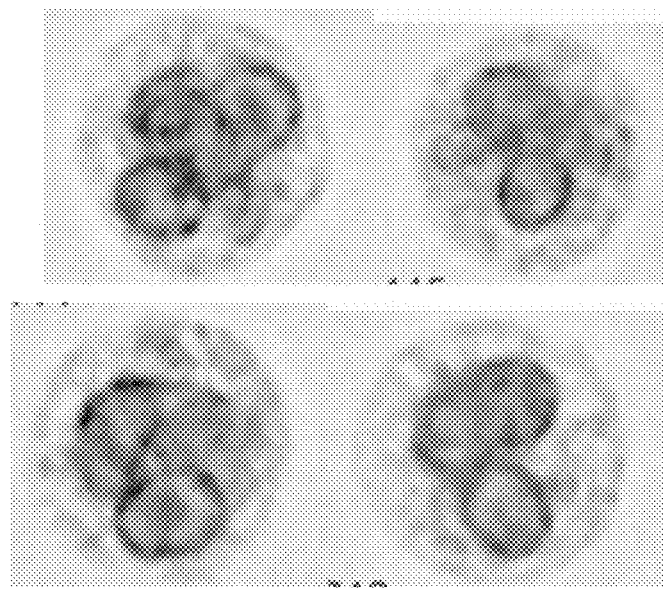

It was discovered that by using polyvinylpyrrolidone (PVP) and 5% glycerol as a viscosity agent component, it was possible to obtain a sheath fluid having a viscosity that matched the viscosity of the 30% glycerol formulation (and hence improved alignment results were achieved) without the negative effects of destroying the nucleus. FIG. 5D depicts results obtained using a PIOAL with 5% glycerol and 1% PVP. Hence, it can be seen that the viscosity agent in the sheath fluid retains viability of cells in the sample fluid stream, leaving structure and content of the cells intact, for example when cells flow through the flowcell and are exposed to the flowing sheath fluid. According to some embodiments, the concentration percentage of glycerol is expressed in terms of (v/v) and the concentration percentage of PVP is expressed in terms of (w/v).

Figure 5E:
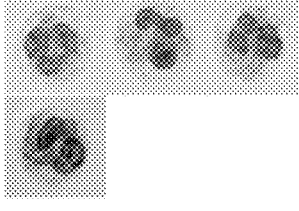
FIG. 5E depicts image capture results based on a traditional microscope wet mount technique as compared to a flowcell technique according to embodiments of the present invention.

FIG. 5E depicts image capture results based on a traditional microscope wet mount technique (left column) as compared to a flowcell technique according to embodiments of the present invention (right column). The wet mount procedure can be considered as a target standard for image clarity and quality. It was observed that techniques involving sheath fluids and flow cell designed as disclosed herein were effective in achieving image clarity and quality equivalent to that of the wet mount procedure.

According to some embodiments, a flowstream ribbon can split when the viscosity differential between the sample fluid and the sheath fluid exceeds a certain threshold. According to some embodiments, a flowstream ribbon split was observed when using a sheath fluid containing glycerol at 60%.

Methods

Figure 6:
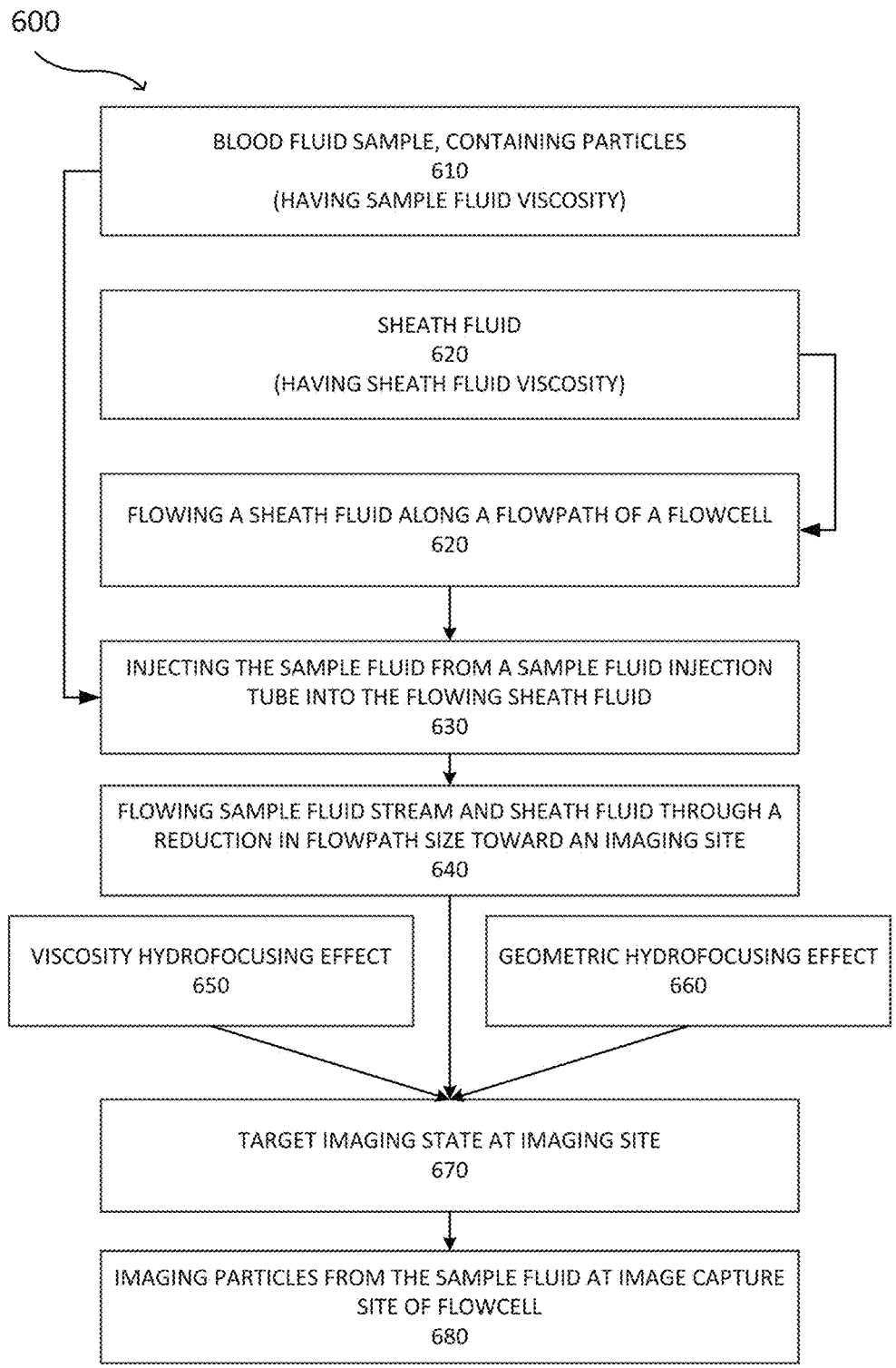
FIG. 6 depicts aspects of an exemplary method for imaging a plurality of particles using a particle analysis system configured for combined viscosity and geometric hydrofocusing according to embodiments of the present invention.

FIG. 6 depicts aspects of an exemplary method 600 for imaging a plurality of particles using a particle analysis system configured for combined viscosity and geometric hydrofocusing according to embodiments of the present invention. The particles can be included in a blood fluid sample 610 having a sample fluid viscosity. As shown here, the method can include flowing a sheath fluid 620 along a flowpath of a flowcell as indicated by step 630. The sheath fluid 620 can have a sheath fluid viscosity that differs from the sample fluid viscosity by a viscosity difference in a predetermined viscosity difference range. The method can also include injecting the blood fluid sample 610 into the flowing sheath fluid within the flowcell, as indicated by step 630, so as to provide a sample fluid stream enveloped by the sheath fluid. Further, the methods can include flowing the sample fluid stream and the sheath fluid through a reduction in flowpath size toward an imaging site as indicated by step 640. As the sample stream and sheath fluids pass through the reduction in flowpath size or narrowing transition zone, a viscosity hydrofocusing effect induced by an interaction between the sheath fluid and the sample fluid stream associated with the viscosity difference (as depicted in step 650), in combination with a geometric hydrofocusing effect induced by an interaction between the sheath fluid and the sample fluid stream associated with the reduction in flowpath size (as depicted in step 660), is effective to provide a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid as depicted by step 670. Methods may also include imaging the plurality of particles at the imaging site, as depicted by step 680.

Figure 6A:
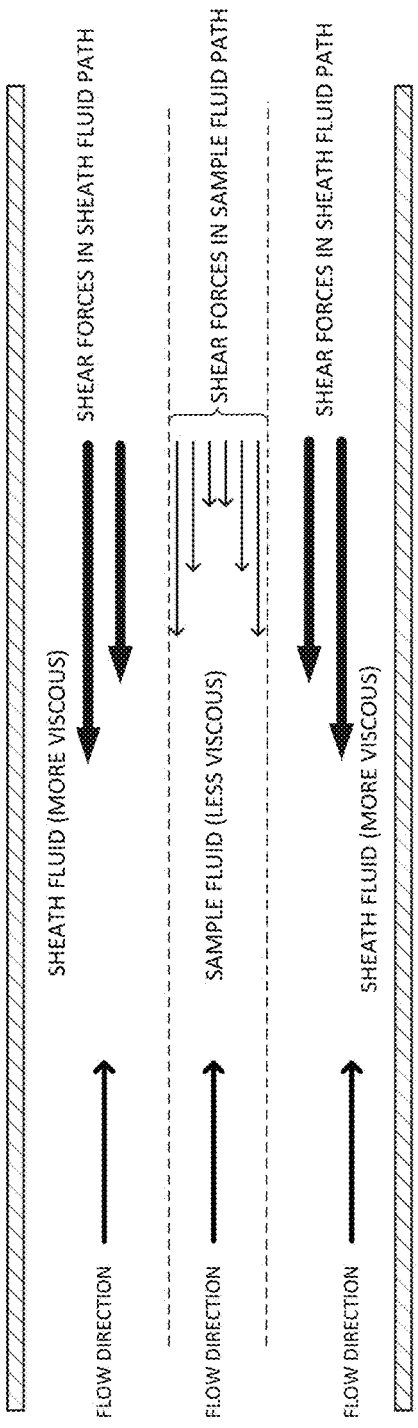
FIGS. 6A and 6B depict exemplary flowstream characteristics according to embodiments of the present invention.
Figure 6B:
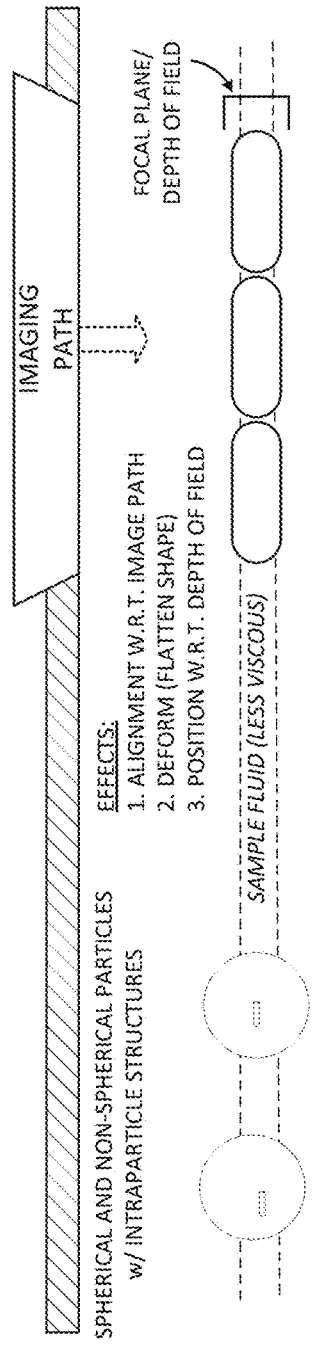

FIGS. 6A and 6B depict exemplary flowstream characteristics related to shear force, lateral compression, orientation, differential viscosity, relative movement between sheath and sample fluids, and the like.

Figure 6C:
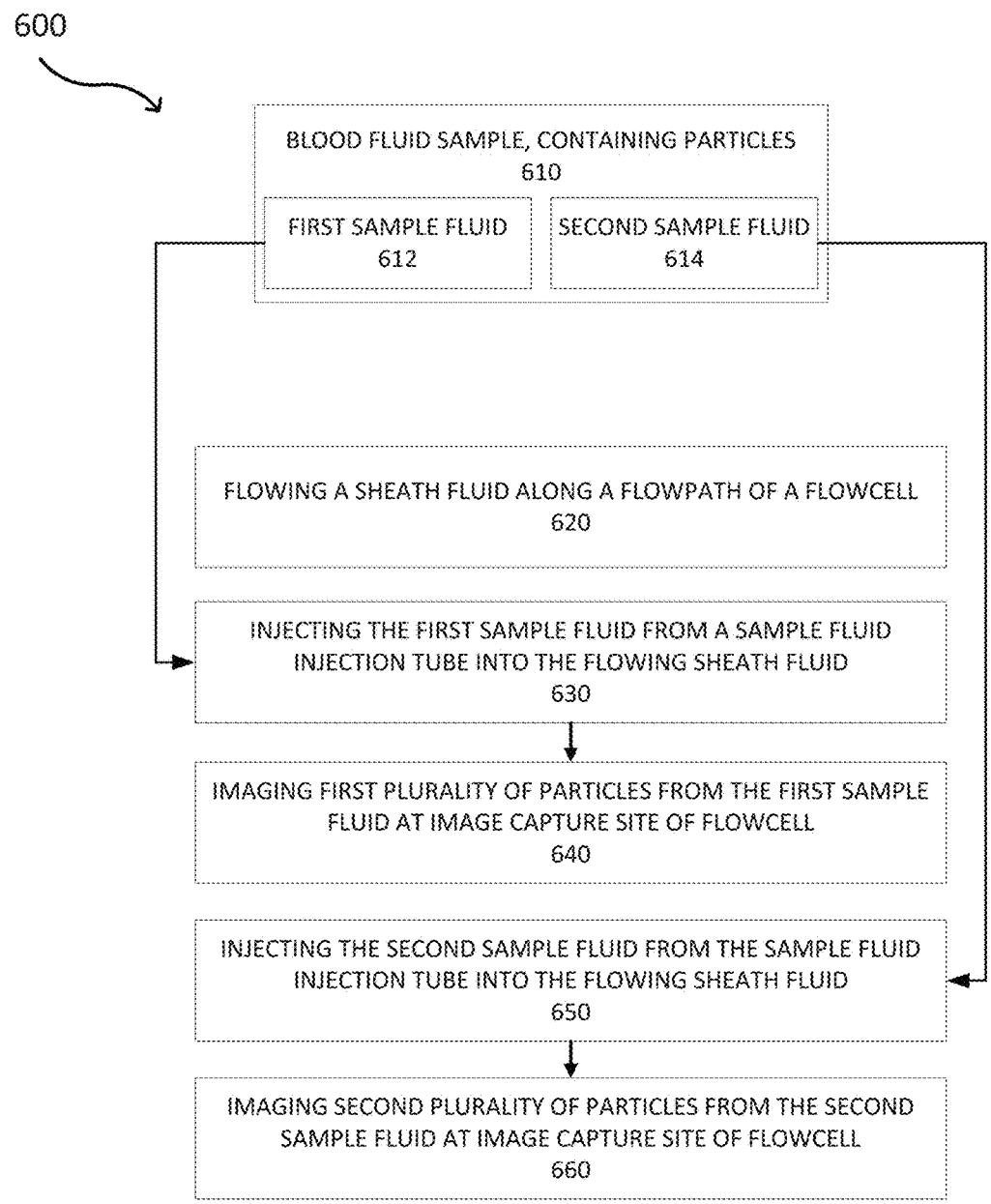
FIG. 6C depicts aspects of an exemplary method for imaging particles in a blood fluid sample, according to embodiments of the present invention.

FIG. 6C depicts aspects of an exemplary method 6000 for imaging particles in a blood fluid sample, according to embodiments of the present invention. As shown here, the blood sample 6010 includes particles, and can be portioned into one or more sample fluids, such as a first sample fluid 6012 containing particles and a second sample fluid 6014 containing particles. The method can include flowing a sheath fluid along a flowpath of a flowcell, as indicated by step 6020. Further, the method can include injecting the first sample fluid 6012 from a sample fluid injection tube into the flowing sheath fluid within the flowcell, as indicated by step 6030, so as to provide a sample fluid stream having a first thickness adjacent the injection tube. The flowpath of the flowcell can have a decrease in flowpath size, such that a thickness of the sample fluid stream decreases from the initial thickness to a second thickness adjacent an image capture site. The method 6000 may further include imaging a first plurality of the particles from the first sample fluid at the image capture site of the flowcell, as indicated by step 6040.

The method 6000 can also include initiating sample fluid transients. For example, sample fluid transients can be initiated by terminating injection of the first sample fluid into the flowing sheath fluid, and injecting the second sample fluid into the flowing sheath fluid as indicated by step 6050. Further, the method 6000 can include imaging a second plurality of the particles from the second sample fluid at the image capture site of the flowcell, as indicated by step 6060. According to some embodiments, the imaging of the second plurality of particles can be performed substantially after the sample fluid transients and within 4 seconds of the imaging of the first plurality of the particles.

Shear Strain Rate

Figure 7:
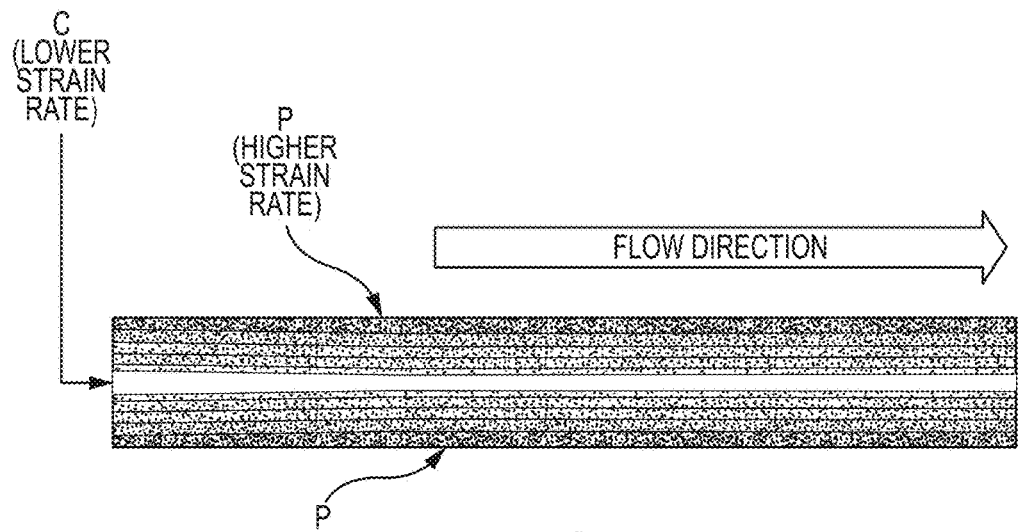
FIGS. 7 and 8 depict aspects of flowstream strain rate according to embodiments of the present invention.
Figure 8:
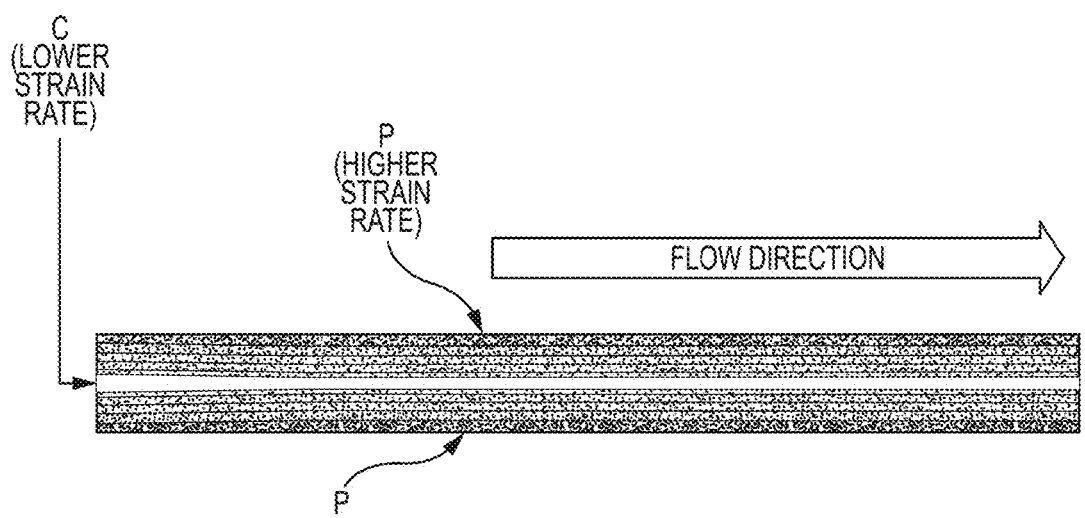

FIGS. 7 and 8 depict aspects of shear strain rate values for certain flow conditions in a flowcell according to embodiments of the present invention. In each of these drawings, a 30% glycerol sheath fluid is used. In some cases, the viscosity can have a value of $2.45 \times 10^{-3}$. A shear stress value can be equal to the product obtained by multiplying a viscosity value with a strain rate value. With regard to FIG. 7, the sample can have a flow rate of 0.3 µL/sec and the sheath fluid can have a flow rate of 21 µL/sec. With regard to FIG. 8, the sample can have a flow rate of 1 µL/sec and the sheath fluid can have a flow rate of 70 µL/sec. In each of these figures, it can be seen that the flow presents a lower strain value toward the center (C) and a higher strain value toward the periphery (P). Such strain values can correspond to an asymmetric flowcell configuration, in some embodiments.

As depicted in FIG. 7, according to some embodiments, the lower strain rate toward the center (C) portion of the flowstream can have a value of about 500 (1/s) or lower and the higher strain rate toward the periphery (P) of the flowstream can have a value of about 3000 (1/s) or higher. As depicted in FIG. 8, according to some embodiments, the lower strain rate toward the center (C) portion of the flowstream can have a value of about 1000 (1/s) or lower and the higher strain rate toward the periphery (P) of the flowstream can have a value of about 9000 (1/s) or higher.

Hence, it can be seen that lower sample and sheath fluid rates (e.g. FIG. 7) correspond to lower strain rates, and higher sample and sheath fluid rates (e.g. FIG. 8) correspond to higher strain rates. It is understood that embodiments of the present invention encompass the use of sample and/or sheath fluids corresponding to various viscosity values, various strain rate values, and/or various shear stress values.

Autofocus Target

The PIOAL can be introduced into a flowcell and carries the sample through the imaging area, then along toward the discharge. The stream of sample fluid can be injected through a cannula with a flattened opening to establish a flowpath with a considerable width. For example, the PIOAL can have a relatively higher viscosity than the sample fluid, suitable density, and flow rates at the point of injection of the sample are such that the sample fluid flattens into a thin ribbon shape. The ribbon of sample fluid is carried along with the PIOAL, to pass in front of a viewing port where a high optical resolution imaging device and a light source are arranged to view the ribbon-shaped sample stream.

The ribbon-shaped sample stream is carried along with the PIOAL, to pass in front of a viewing port where a high optical resolution imaging device and a light source (e.g., UV, visible, or IR) are arranged to view the ribbon-shaped sample stream. The high optical resolution imaging device and light source can be placed on opposite sides of the flowcell, for obtaining backlit images of the particles such as blood cells. The high optical resolution imaging device captures pixel data images of the sample through a viewing port in the flowcell. For example, the high optical resolution imaging device captures images at a repetition rate consistent with the sample flow velocity such that sections of the ribbon-shaped sample stream are imaged without substantial gaps or overlap.

Embodiments of the present invention provide a number of unique structural and functional features implemented in the design and operation of a system for collecting images of a ribbon-shaped sample stream flowing through a flowcell. Exemplary embodiments are configured to obtain sufficiently focused images of the particles, with sufficient clarity and resolution to reveal the different features of the various particles such as blood cells, that allow the particle and/or cell types to be distinguished from one another.

In order to bring the ribbon-shaped sample stream into focus, the distance between the high optical resolution imaging device and the ribbon-shaped sample stream can be set such that the ribbon-shaped sample stream is at a desired distance (e.g., the focusing distance) from the high optical resolution imaging device along the optical axis.

A focusing distance is a characteristic of the lenses of the high optical resolution imaging device used to resolve the image on a photosensor array, namely defined by the material, shape and dimensions of the lens elements and their configuration and placement along the optical axis. The dimensions of the area of the sample that is imaged, and the depth of field that is in focus in the sample, are determined by the lens configuration.

Aperture adjustments and zoom adjustments are possible, but for purposes of simplicity, certain examples in this disclosure are such that focusing the high optical resolution imaging device on the particles in the ribbon-shaped sample stream simply requires relatively positioning the high optical resolution imaging device and the ribbon-shaped sample stream in the flowcell at a correct distance, namely the distance that resolves a focused image on the photosensor array (e.g., a charge-coupled device array) of particles in the ribbon-shaped sample stream. The high optical resolution imaging device may include a camera that records or transmits still images or video images for display and/or processing and/or transmission.

In one aspect, the symmetrical nature of the flowcell and the manner of injection of the sample fluid and PIOAL provide a repeatable position within the flowcell for the ribbon-shaped sample stream in the PIOAL. However, the relative positions of the flowcell and the high optical resolution imaging device are subject to change and require occasional position adjustments to maintain the optimal distance between the high optical resolution imaging device and the ribbon-shaped sample stream, thus providing a quality focus image.

Embodiments of the present invention encompass automated visual analyzer systems and methods for blood and/or other biological fluids that incorporate an autofocus device/apparatus to provide reliably focused images of the sample by very accurately setting the distance between the ribbon-shaped sample stream and the high optical resolution imaging device. In one aspect, autofocus system embodiments disclosed herein can very accurately set the distance between the ribbon-shaped sample stream and the high optical resolution imaging device and capture reliably focused images of the sample. In some embodiments, algorithms are used to establish the distance that achieves good focus results.

It is an object to employ a flowcell, that provides a stable and highly repeatable position for a ribbon-shaped sample stream enveloped in a flow of PIOAL, in combination with a high optical resolution imaging device and autofocus device/apparatus that maintains the optimal distance between the high optical resolution imaging device and the ribbon-shaped sample stream, thus providing a quality focused image.

Such apparatus and methods are disclosed and claimed herein. A symmetrical flowcell is provided, which has been found to produce a repeatable ribbon-shaped sample stream position within the flowcell. Focusing involves setting a precisely correct relative position of the high optical resolution image device relative to the ribbon-shaped sample stream, so as to maintain focus on the ribbon-shaped sample stream.

Advantageously, the flowcell and/or the high optical resolution image device can be moved relative to one another in an autofocusing process using an autofocus pattern such as a high contrast pattern or similar focusing target, preferably a planar target with sharply contrasting features such as edges, the autofocus pattern being fixed in position relative to the flowcell and used as a focusing subject in lieu of the sample itself. The ribbon-shaped sample stream is a thin ribbon at a fixed distance from the autofocus pattern along the line parallel to the optical axis of the high optical resolution imaging device. The displacement distance between the autofocus pattern and the ribbon-shaped sample stream position is a constant distance, which is determined initially and programmed into the autofocus procedure. The exemplary technique thereafter is to autofocus on the autofocus pattern, then to displace the high optical resolution image device and/or flowcell relative to one another by the known and constant predetermined distance, whereupon the distance between the high optical resolution image device and the location of the ribbon-shaped sample stream is the optimal distance to provide a quality focused image of the ribbon-shaped sample stream. For example, at first, an autofocus algorithm focuses the position of the high optical resolution imaging device on the autofocus pattern located at a fixed distance from the ribbon-shaped sample stream. Having focused on the autofocus pattern, the processor operates the motor drive over the fixed distance, thereby bringing the ribbon-shaped sample stream into focus of the high optical resolution imaging device.

An exemplary high optical resolution image device comprises an objective lens and associated pixel image sensor, capable of capturing an image that reveals the particles at sufficient magnification and resolution to provide sufficient detail to resolve visual features of the particles. In certain embodiments, the magnification is higher by a factor of at least 2× (thus providing a 2× image area per each image taken), thereby generating more detailed information for each particle as compared to traditional hematology analyzers.

The PIOAL flowpath can be arranged symmetrically such that equal amounts of PIOAL flow above and below the ribbon-shaped sample stream which stretches and locates the ribbon-shaped sample stream as a thin ribbon at a fixed distance from the autofocus pattern along the line parallel to the optical axis of the high optical resolution imaging device. In one embodiment the autofocus pattern comprises an opaque border around an opening admitting light from a source of rear illumination and the distance of the autofocus pattern is readily and unambiguously homed in upon by the autofocus controls. Then, the ribbon-shaped sample stream is brought into focus by displacing the high optical resolution imaging device relatively to the flow cell over the predetermined and constant displacement distance. There is no need for autofocusing directly on the image content of the sample, although further autofocusing is conceivable.

An automated focusing configuration includes a motor drive that adjusts the relative position of the flowcell and a high optical resolution imaging device along the optical axis, responsive to control signals from a processor that assesses one or more measures of focus quality over a range of distances and seeks an optimal distance. For example, the processor may assess a measure of contrast and operate the motor drive for autofocusing. In normal operation the processor operates the motor drive to autofocus on the target and then adjusts the distance between the high optical resolution imaging device and the flowcell by the recorded displacement from the target to bring the ribbon-shaped sample stream into focus. So long as the device continues to move the ribbon-shaped sample stream in the same way, and thermal expansion or similar confounding factors do not arise, the image of the ribbon-shaped sample stream will remain in focus.

A preliminary set-up or calibration process can be used to determine and record the displacement distance between the target and the ribbon-shaped sample stream position in the flowcell. The exact displacement distance, which may differ slightly for different flowcells, is established by preliminary testing, such as by autofocusing alternatively on the target and on a test ribbon-shaped sample stream several times, and recording the mean result as a constant associated with the flowcell.

Accordingly, a sample to be imaged, such as a prepared blood sample or another type of sample, is directed along a defined flowpath through a viewing zone in a flowcell. The PIOAL flowpath preferably is symmetrical and the sample is injected in the center of the PIOAL flow, with which the sample is enveloped. The flow rates and viscosity and density characteristics of the sample and the sheath material such as a PIOAL, together with the contour of the flowcell, cooperate so as to form the ribbon-shaped sample stream into a flat ribbon flowing consistently through the viewing zone at a repeatable position.

The sample may be imaged by a camera component of the high optical resolution imaging device and digital images collected to be analyzed by at least partly automated image analysis processes, including an autofocus process as described herein.

One object is to distinguish, categorize, subcategorize and/or count particles such as blood cells in blood samples as well as other biological samples described herein, which may be associated with particular conditions. In one aspect, the particle contrast agent compositions of this disclosure can be combined with a visual analyzer such as the analyzer described herein in a method to provide surprisingly high quality focused images of cells in flow. The cells may be automatically captured and processed.

The images allow for automated image based WBC differential counting, as well as automated identification of morphological abnormalities useful in determining, diagnosing, prognosing, predicting, and/or supporting a diagnosis of whether a subject is healthy or has a disease, condition, abnormality and/or infection and/or for determining or monitoring whether the subject is responsive or non-responsive to treatment. Cell category and/or subcategory counts in blood samples are used in this disclosure as nonlimiting examples of the sort of fluids that may be analyzed.

In one aspect, the image analyzers for use with the compositions of this invention can capture reliably focused images of the sample by very accurately setting the distance between the ribbon-shaped sample stream and the high optical resolution imaging device of the optical system. In some embodiments, the visual analyzers can be used in combination with the compositions of this invention and algorithms to establish said distance that can achieve good focus results. The sample is arranged in the flowcell and illuminated to enable viewing through a viewing port. The individual cells or particles appear clearly in the captured pixel data image, with sufficient feature detail to reveal attributes that are then compared and contrasted with parameters known to distinguish categories and subcategories of cells from one another.

It is an object to employ a flowcell in combination with the exemplary particle contrast agent compositions described herein, and an exemplary PIOAL, that provides images of optimal quality and detail for particle recognition. In addition, the PIOAL and apparatus provides a stable and highly repeatable position for a ribbon-shaped sample stream enveloped in a flow of PIOAL This, in combination with a high optical resolution imaging device and the autofocus device/apparatus that maintains the optimal distance of the high optical resolution imaging device to the ribbon-shaped sample stream, provides a quality focused image.

Autofocus Target

With returning reference to FIG. 1, particle imaging systems can include an autofocus pattern or target 44 that is fixed relative to the flowcell 22. The autofocus target 44 can be used to achieve focused images of blood fluid particles that flow through the flowcell.

Figure 9A:
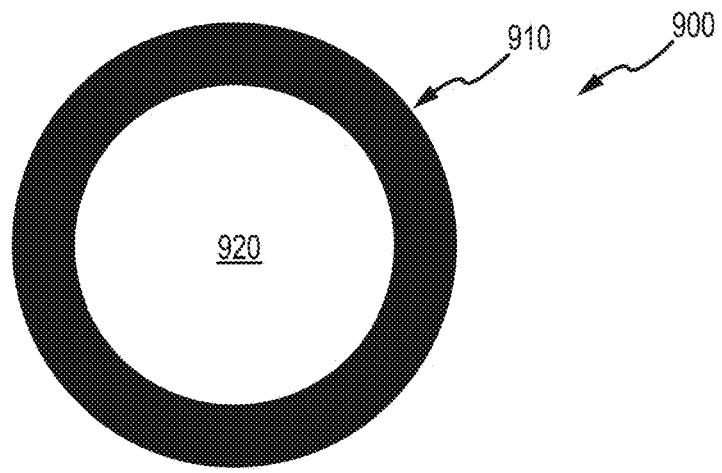
FIG. 9A depicts an exemplary autofocus target according to embodiments of the present invention.
Figure 9B:
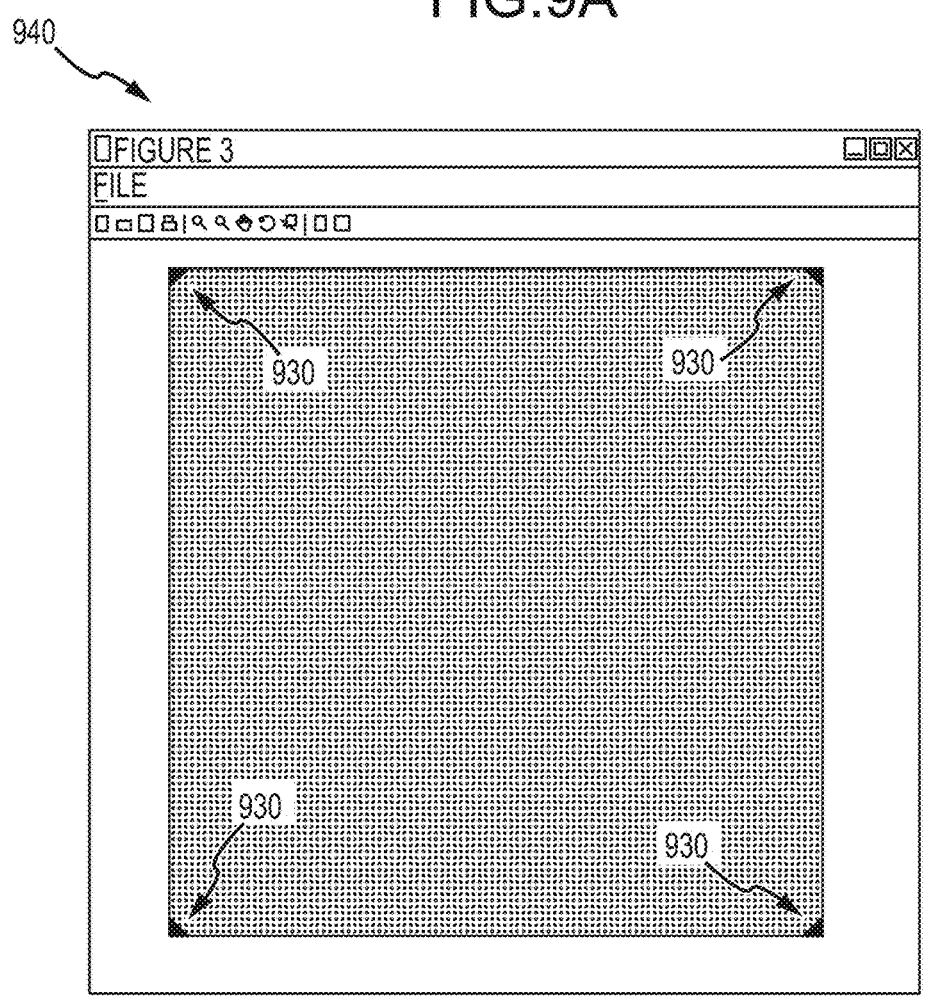
FIG. 9B shows a captured image including portions of an autofocus target according to embodiments of the present invention.

FIG. 9A depicts an exemplary autofocus target 900 according to embodiments of the present invention. As shown here, the target 900 includes an opaque annular band 910 and a transparent center or aperture 920. In operation, the imaging device focuses on the band 910, and captures the image through the aperture. As discussed elsewhere herein, and in co-pending U.S. patent application Ser. No. 14/216,811, filed Mar. 17, 2014, an image capture process can involve first focusing (or auto-focusing) on the band 910, and then adjusting a distance between the image capture device and the sample fluid stream prior to obtaining the image through the aperture 920. Accordingly, the band 910 can present a target upon which an auto-focus system of the image capture device can detect and focus upon, and certain portions of the target (e.g. edges or segments) can be included in the image. In some cases, the target can be provided as a chrome disc having a central aperture. An exemplary target can be be provided with a central pinhole, having a diameter of about 0.5 mm, that is glued or fixed to the flowcell. The size of the central pinhole or aperture 920 can be selected so that only four edge portions 930 of the opaque annular band 910 are visible in the captured image 940, as illustrated in FIG. 9B. Hence, the annular band 910 does not interfere with the capturing of cell images (e.g. light can pass through the aperture 920 so as to illuminate the sample particles, and the field of view is substantially unimpeded by the annular band). In this way, the band 910 shows up only in the corners of the image.

Figure 11:
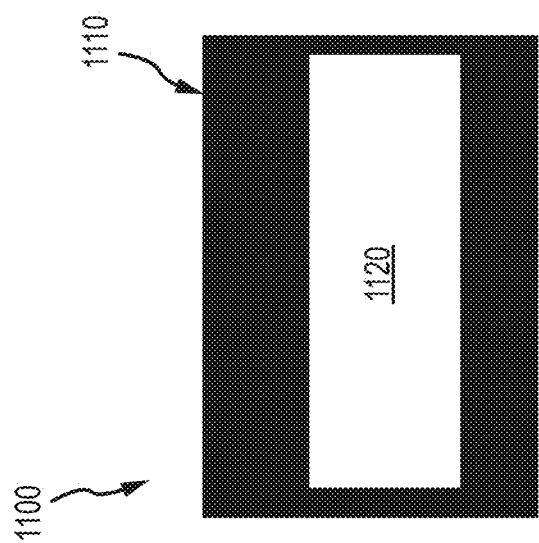
FIGS. 10 and 11 depict exemplary autofocus targets according to embodiments of the present invention.
Figure 10:
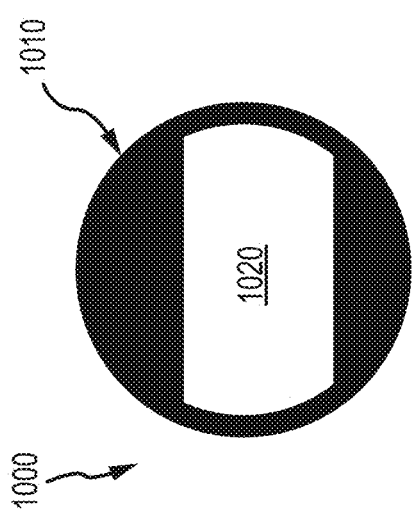

FIG. 10 depicts an exemplary autofocus target 1000 according to embodiments of the present invention. The target 1000 includes a band or border 1010 and a central aperture 1020. FIG. 11 shows another exemplary autofocus target 1100 according to embodiments of the present invention. The target 1100 includes a band or border 1110 and a central aperture 1120. According to some embodiments, the autofocus target 1100 provides an image having 50 pixels of black on the top and the bottom. In some cases, the autofocus target 1100 provides a flowcell focus offset (FCFO) of about 65.3 µm. Aspects of the FCFO are further discussed in co-pending U.S. patent application Ser. No. 14/216,811, filed Mar. 17, 2014, the content of which is incorporated herein by reference.

Figure 12A:
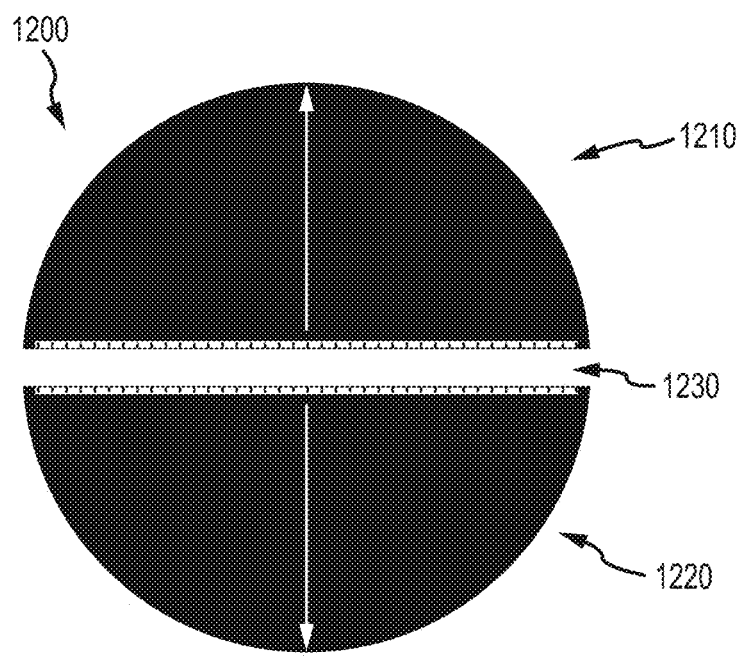
FIG. 12A depicts an exemplary autofocus target according to embodiments of the present invention.

FIG. 12A depicts an exemplary autofocus target 1200 according to embodiments of the present invention. The target 1200 is presented as a letterbox design, and includes a first or upper border 1210 and a second or lower border 1220. The target 1200 also includes an aperture or transparent passage 1230 between the first and second borders. According to some embodiments, the target has a diameter of about 4 mm, and the height of the letterbox is 265 µm. In some cases, the upper and lower borders can be present as half circles, and can be produced with a deposited metal such as chromium oxide or some other opaque material.

Figure 12B:
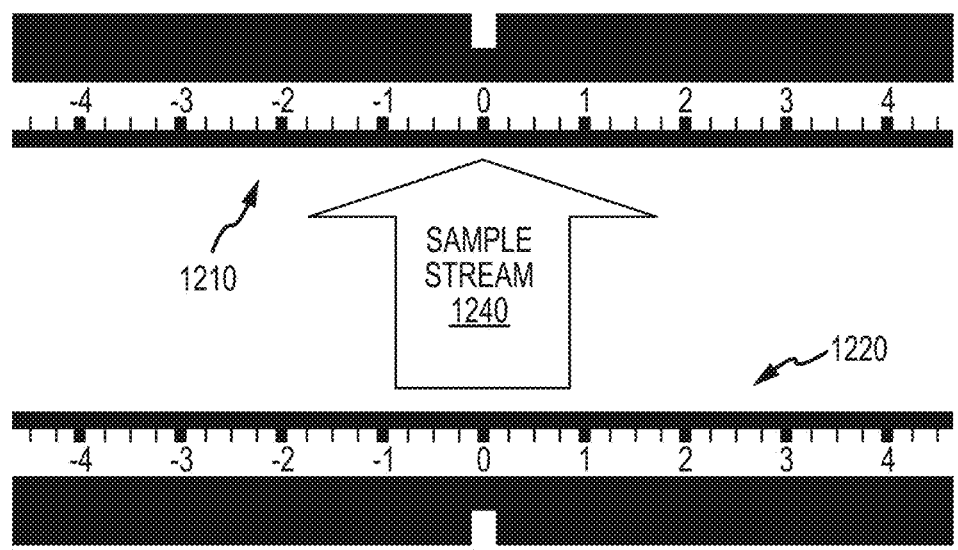
FIG. 12B shows a close-up view of the central portion of the autofocus target according to embodiments of the present invention.

FIG. 12B shows a close-up view of the central portion of the autofocus target 1200. As shown here, the first border 1210 includes a negative/positive numerical scale, with a centered zero value. The second border 1220 includes a similar scale. In some cases, the scale increments are 100 µm. According to some embodiments, the scales can be used to facilite positioning of the flow cell so that the field of view of the imaging device or camera can be centered on the sample stream. As shown here, the sample stream 1240 flows in a direction perpendicular to the scales of the first and second borders. As part of a focusing protocol, the image capture device can operate to focus on the numbers or other characters or imageable objects present on the borders 1210, 1220.

Figure 13A:
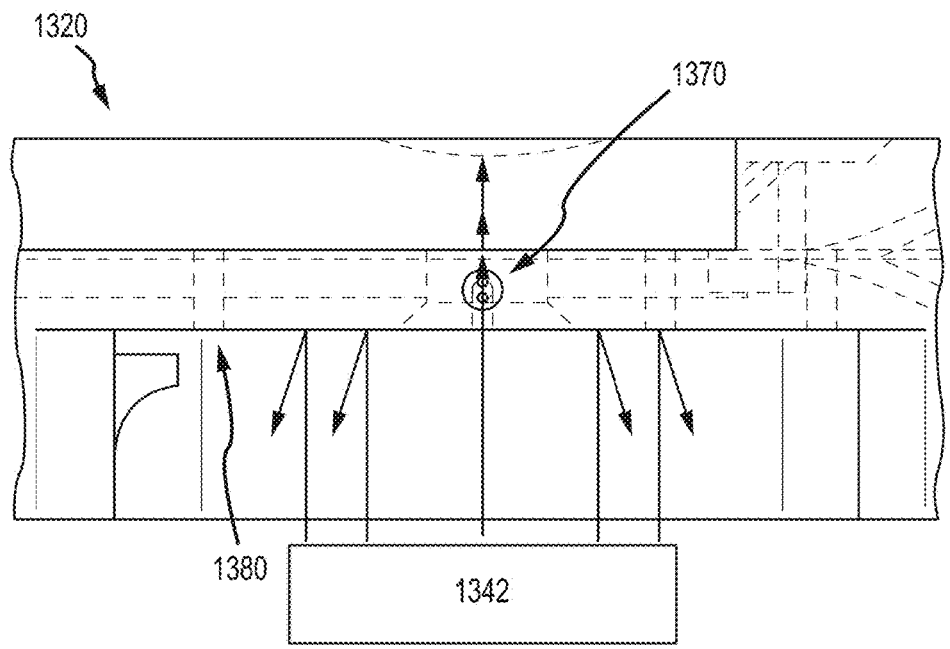
Figure 13B:
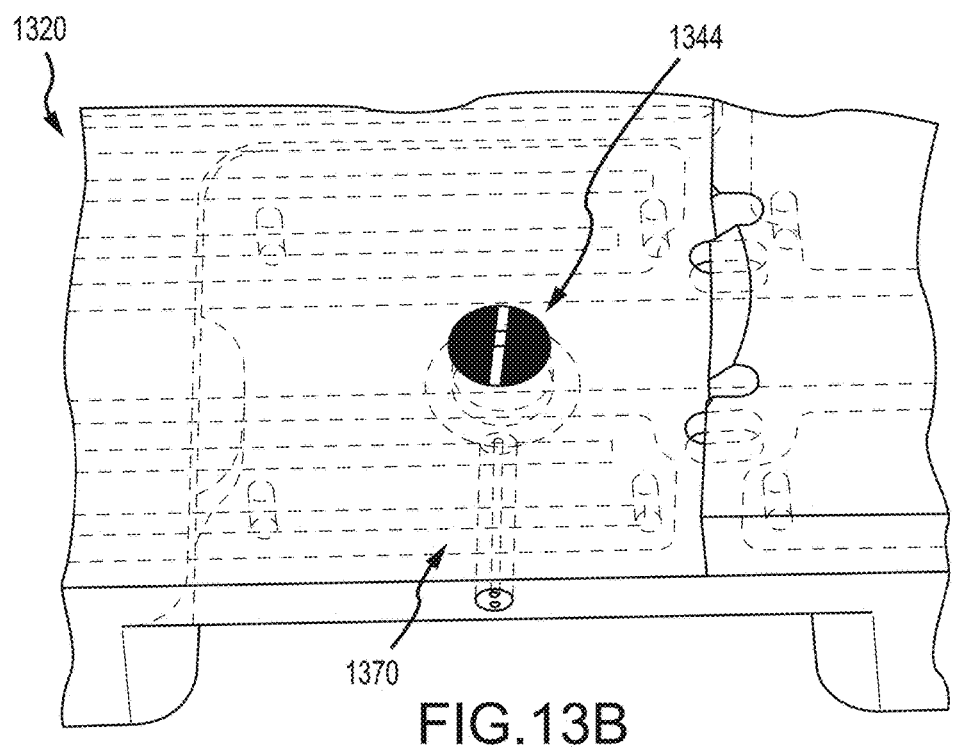

Embodiments of the present invention encompass techniques for addressing thermal drift associated with use of the particle analysis system, whereby such thermal effects may otherwise compromise the quality of images obtained with the imaging device. FIG. 13A depicts a partial side view of a flowcell 1320 having a thermal sensor 1370, a reflector 1380, and an autofocus target 1344. During operation of a particle analysis system, thermal effects may cause the sample stream to slowly drift out of focus of the imaging device. For example, thermal effects can be caused by thermal expansion of the flow cell through radiated heat coming from the lamp. Further, thermal effects can be caused by thermal expansion of the flowcell and optical bench assembly (OBA) assembly through conductive and radiative heating. In some embodiments, certain components of the OBA can expand, which may contribute to focusing errors. For example, such components may include metal plates that hold camera 24 together, a metal plate that holds or is connected to the flow cell, or a metal plate that holds both the flowcell and camera 24 together. FIG. 13B depicts a partial perspective view of flowcell 1320 having thermal sensor 1370 and autofocus target 1344. Further, FIG. 13C depicts another perspective view of flowcell 1320 having a thermal sensor 1370, reflector 1380, and autofocus target 1344.

FIG. 13B depicts a partial perspective view of flowcell 1320 having thermal sensor 1370 and autofocus or imaging target 1344. According to some embodiments of the present invention, an image capture device can be focused on the sample flowstream using a temperature that is sensed by a thermal sensor associated with the analyzer. For example, the temperature can correspond to a sample fluid temperature, a sheath fluid temperature, a flowcell temperature, or an image capture device temperature. In some cases, the temperature is a temperature at the imaging site of a flowcell. In some cases, the temperature is a temperature at a location downstream of the imaging site. In some cases, the temperature is a temperature at a location upstream of the imaging site. According to some embodiments of the present invention, an image capture device can be focused on the sample flowstream using a temperature rate of change associated with the analyzer. For example, the temperature rate of change correspond to a sample fluid temperature rate of change, a sheath fluid temperature rate of change, a flowcell temperature rate of change, or an image capture device temperature rate of change.

FIG. 13C depicts another perspective view of flowcell 1320 having a thermal sensor 1370, reflector 1380, and autofocus or imaging target 1344. Reflector 1380 can operate to reduce or limit the amount of heat absorbed by flowcell 1320. For example, reflector 1380 can block heat radiated by a flash lamp 1342 as indicated in FIG. 13A. Hence, reflector 1380 can minimize the thermal impact of the lamp. Reflector 1342 can also reduce glare and light scatter generated by the lamp, thus resulting in improved image quality. Thermal sensor 1370 is positioned near the fluid flow channel and adjacent to the image capture site, so that accurate temperature readings can be obtained. Information from the temperature sensor can be used to focus the image capture device on the sample fluid ribbon stream. Exemplary autofocusing techniques disclosed herein can be based on temperature fluctuations occuring within certain elements of the analyzer.

Figure 13D:
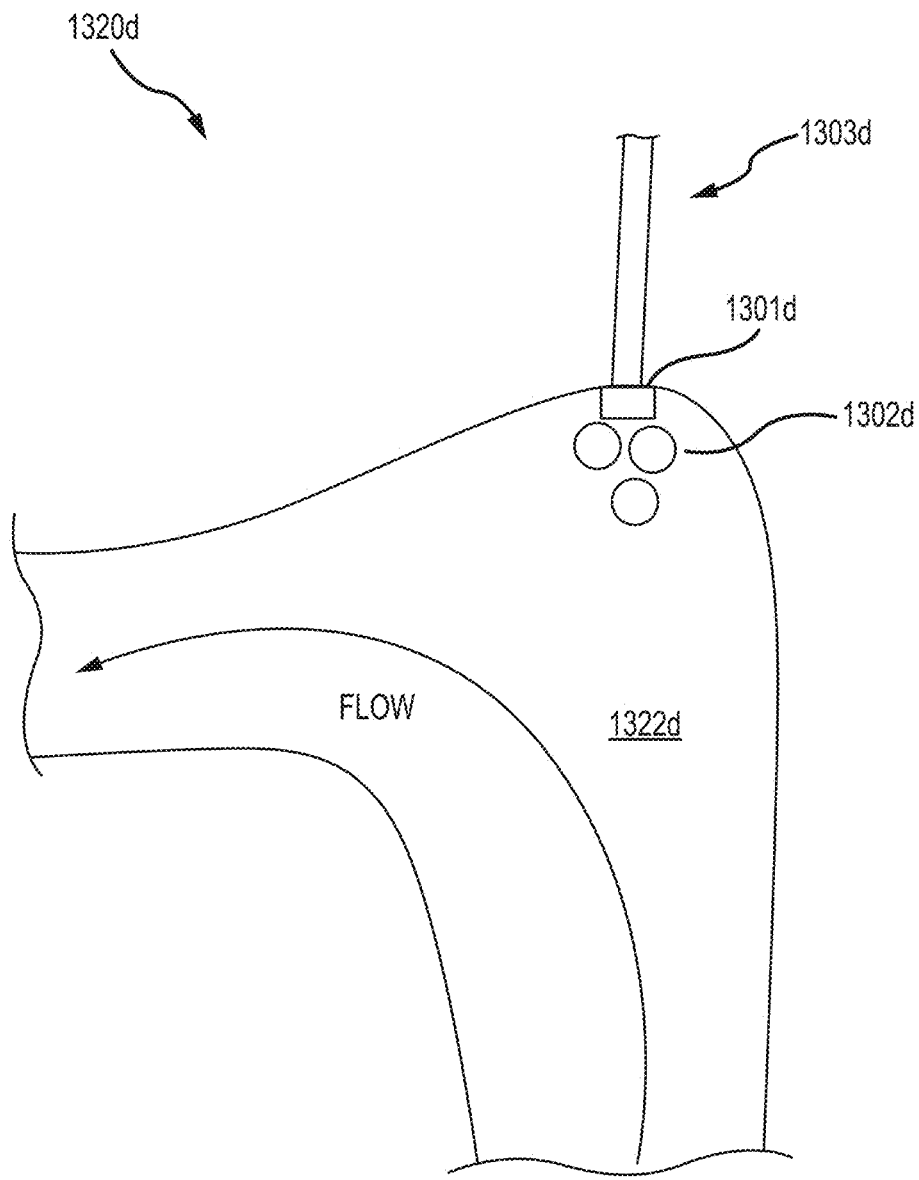
FIG. 13D depicts aspects of flowcell bubble removal techniques according to embodiments of the present invention.

As depicted in FIG. 13D, a flowcell 1320*d* can include a flowpath 1322*d* having a port or vent 1301*d* through which bubbles 1302*d* may be released or removed. As depicted here, a tube 1303*d*, through which vacuum can be applied, can be contacted with the port 1301*d* so as to withdraw bubbles 1302*d* from the flowstream. Such a bubble removal mechanism is suitable for removing bubbles from the flowing fluid within the flowcell, and can operate to prevent bubbles or microbubbles from becoming lodged or stuck inside of the flowcell.

According to some embodiments, a method for imaging particles in a blood fluid sample may include flowing a sheath fluid along a flowpath of a flowcell, and injecting the blood fluid sample into the flowing sheath fluid within the flowcell so that the blood fluid sample flows in a sample flowstream with a flowstream width greater than a flowstream thickness, such that the flowcell has an associated temperature. Further, the method may include focusing an image capture device, along an imaging axis, on the flowstream to a first focal state while the temperature associated with the flowcell is at a first temperature, and acquiring a first focused image of a first subset of the particles within the flowstream with the image capture device at the first focal state. What is more, the method may include determining that the temperature associated with the flowcell has undergone a change from the first temperature to a second temperature, and automatically adjusting focus of the image capture device from the first focal state to a second focal state in response to the change in temperature and a known relationship between flowcell temperature and desired focus. Still further, the method may include acquiring a second focused image of a second subset of the particles within the flowstream with the image capture device at the second focal state.

In some cases, the process of adjusting focus of the image capture device includes adjusting a distance between the image capture device and the flowcell using the change in temperature and the known relationship between flowcell temperature and desired focus. In some cases, the process of adjusting focus of the image capture device includes adjusting a focal distance of the image capture device using the change in temperature and the known relationship between flowcell temperature and desired focus.

Dynamic Range Extension

Figure 14:
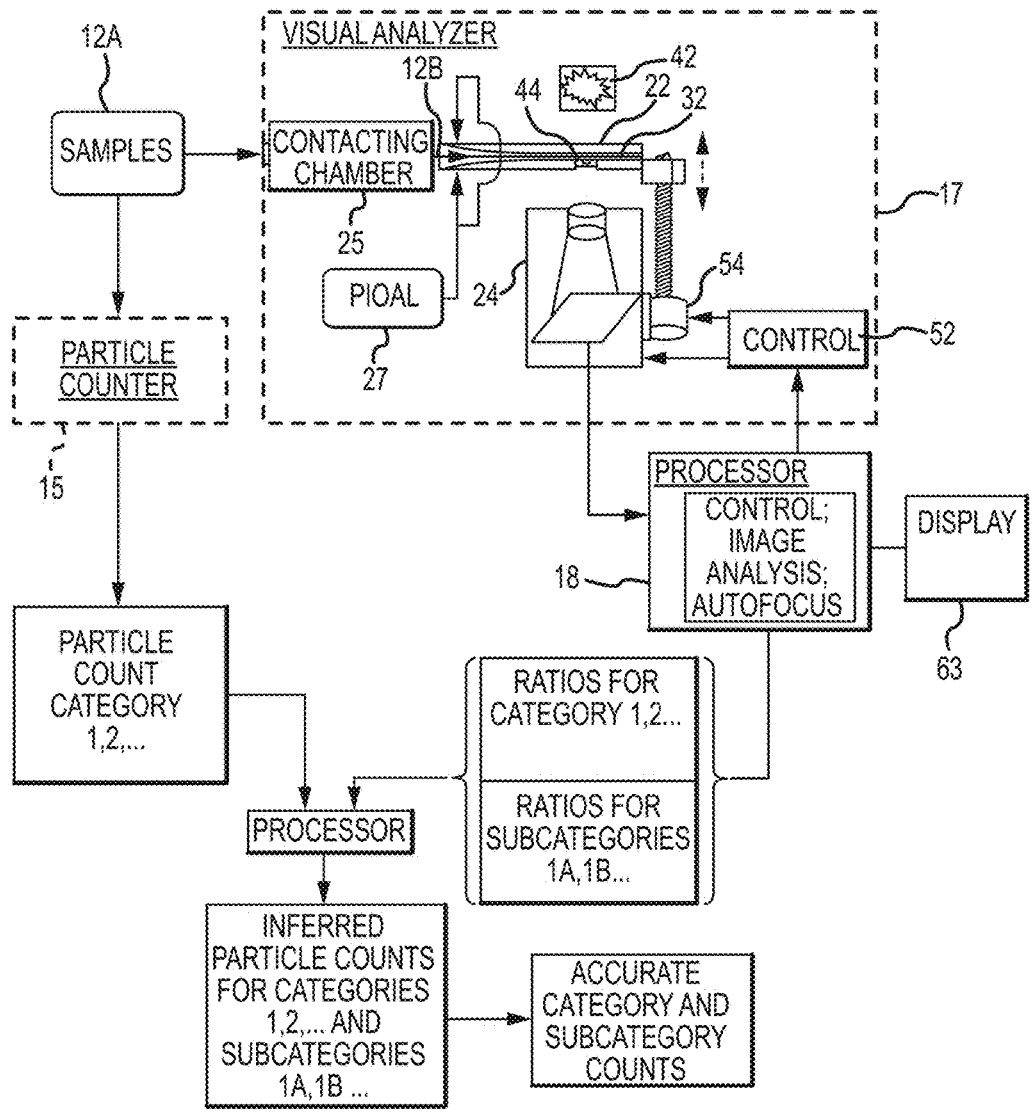
FIG. 14 is a block diagram showing additional aspects of systems and methods for achieving dynamic or detection range extension for particle analysis in blood samples, according to embodiments of the present invention.

FIG. 14 is a block diagram showing additional aspects of systems and methods for achieving dynamic or detection range extension for particle analysis in blood samples, according to embodiments of the present invention. As depicted here, at least one digital processor 18 is coupled to operate the motor drive 54 and to analyze the digitized image from the photosensor array as collected at different focus positions relative to the target autofocus pattern 44. The processor 18 is configured to determine a focus position of the autofocus pattern 44, i.e., to autofocus on the target autofocus pattern 44 and thus establish an optimal distance between the high optical resolution imaging device 24 and the autofocus pattern 44. This can be accomplished by image processing steps such as applying an algorithm to assess the level of contrast in the image at a first distance, which can apply to the entire image or at least at an edge of the autofocus pattern 44. The processor moves the motor 54 to another position and assesses the contrast at that position or edge, and after two or more iterations determines an optimal distance that maximizes the accuracy of focus on the autofocus pattern 44 (or would optimize the accuracy of focus if moved to that position). The processor relies on the fixed spacing between the autofocus target autofocus pattern 44 and the ribbon-shaped sample stream, the processor 18 then controls the motor 54 to move the high optical resolution imaging device 24 to the correct distance to focus on the ribbon-shaped sample stream 32. More particularly, the processor operates the motor to displace the distance between the high optical resolution imaging device and the ribbon-shaped sample stream 32 by the displacement distance 52 (see FIG. 1) by which the ribbon-shaped sample stream is displaced from the target autofocus pattern 44. In this way, the high optical resolution imaging device is focused on the ribbon-shaped sample stream.

According to some embodiments, visual analyzer 17 is an exemplary analyzer 17 of FIG. 1. Visual analyzer 17 can comprise at least one flowcell 22 and at least one imaging device 24 such as a high optical resolution imaging device having an imaging sensor such as a digital camera. Visual analyzer 17 can also comprise a sample injector 29. Sample injector 29 is configured to provide sample 12 into the at least one flowcell 22. Flowcell 22 defines an internal PIOAL flow path that narrows, for example, symmetrically in the flow direction. Flowcell 22 is configured to direct a flow 32 of the sample through a viewing zone in the flowcell 22.

FIG. 14 illustrates the autofocus and other aspect of digital imaging as described. Such techniques can be employed in conjunction with blood cell apparatus that are not based on imaging or perhaps are less image related than the embodiments described, such as Coulter blood cell counters, also known as flow cytometers. Such counters are known for detecting and counting blood cells and particles in fluids, but usually not by imaging. In a counter of that type, a flowcell is arranged to carry a flow of particles enveloped in a fluid. The flowcell narrows to force particles in the flow path into single file. A pair of electrodes or other detectors spanning the flow path produce a count by detection of a pulsed change in electrical impedance, or obstruction of a light path between a light source and photo-detector when cells pass.

Flow cytometers are advantageous because a large number of cells or other particles can be counted, much larger than the number of cells that can be imaged practically in a visual counter. But flow cytometers are not as effective in distinguishing between cells by type, or enabling distinctions between normal and abnormal cells, or distinguishing grouped cells such as platelet clumps, from discrete blood cells. By operating an analyzer, for example, the visual analyzer, as described, through a statistically significant number of image frames of a ribbon-shaped sample stream, a distribution or proportionate ratio of blood cell types can be measured. The proportionate ratios determined from a visual analyzer, or a function thereof, are applied to blood cell counts, and the larger numbers of blood cells counted by the cytometer, albeit with less discrimination or no discrimination as to cell type, to provide an accurate total blood count that exploits the peculiar advantages of both types of analyzers.

According to some embodiments, particle counts can be inferred by applying an algorithm, for example, an algorithm based on a proportionate ratio of particle counts. FIG. 14 illustrates an exemplary apparatus adapted to blood analysis. In some embodiments the particle counter 15 and the visual analyzer 17 may be connected in series other than in parallel. The particle counter 15, may be, for example, a Coulter blood cell counter, which detects and counts blood cells and particles in fluids. In a counter of that type, a flow path (not shown) is arranged to carry a flow of particles enveloped in a fluid. The flow path narrows to force particles in the flow path into single file. A pair of electrodes or other detectors spanning the flow path produce a count by detection of a pulsed change in electrical impedance, or obstruction of a light path between a light source and photo-detector when cells pass. Particle counter 15 is configured to count a large number of cells or other particles. But particle counter 15 might not be able to distinguish between members in sub-categories of cells, and/or to distinguish between normal and abnormal cells, or to distinguish grouped cells such as platelet clumps, from discrete blood cells.

Visual analyzer 17 can also comprise at least one contacting chamber 25 configured to provide at least one chemical comprising at least one of a diluent, a permeabilizing agent, a contrast agent effective to generate visual distinctions for particle categorization and/or subcategorization. For example, as shown with reference to FIGS. 1 and 14, the contacted sample is introduced into the flowcell through sample injector 29, and a sheath or intracellular organelle alignment reagent is introduced from injector 27. A diluent can be used for diluting the sample to a suitable concentration. A contrast agent and/or permeabilizing agent is used to generate visual distinctions for categorizing and/or subcategorizing particles. PIOAL is used to align certain type of cells or cellular structures in a direction for better imaging. In some embodiments, the at least one chemical can be applied to contact a sample first and then the treated sample is provided onto visual analyzer 17. Treatment of the sample with the at least addition of at least one chemical can be performed at room temperature. In some embodiments, such a treatment can be performed at a temperature such as 10, 15, 20, 25, 30, 35, 36, 37, 38, 38, 39, 40, 45, 46, 47, 48, 49 or 50° C. The treatment at a selected temperature can be conducted in an incubator which is separate from visual analyzer 17, or on a visual analyzer 17 which is temperature controlled.

In some embodiments, the visual analyzer may have a contrast agent injector for bringing the sample in contact with a contrast agent and/or permeabilizing agent or surfactant. In other embodiments, the sample may be contacted with contrast agent, permeabilizing agent prior to injection into the visual analyzer. In other embodiments, the visual analyzer containing a heating element for heating the sample while in contact with the contrast agent and/or permeabilizing agent, at a controlled temperature for a controlled time. The visual analyzer may also have a cooling element for cooling the sample mixture after the heating step. Exemplarly contrast agent compositions and methods which can be used for processing blood fluid samples are disclosed in copending U.S. patent application Ser. No. 14/216,339, filed Mar. 17, 2014 (now U.S. Pat. No. 9,279,750, issued Mar. 8, 2016), the content of which is incorporated herein by reference.

By operating the visual analyzer 17 as described, through a statistically significant number of image frames of a ribbon-shaped sample stream, a proportionate ratio of cells in cell categories and/or subcategories can be determined by processor 18. The proportionate ratios determined from visual analyzer 17 are applied to blood cell counts, and the larger numbers of blood cells counted by particle counter 15, albeit with less discrimination or no discrimination as to members within a cell category and/or subcategory, to provide an accurate total blood count that exploits the peculiar advantages of both particle counter 15 and visual analyzer 17.

In addition to providing accurate results, the apparatus comprising a particle counter 15 and a visual analyzer 17 offers significant advantages in improving speed of analysis. In FIG. 14, accurate results of counting different blood cells can be output through display 63. During an analysis process, an operator may interact with processor 18 through a terminal 65. Previously, up to about 25% to 30% of results were reviewed manually by making slides with contrast agent which were examined under a microscope by an operator. In comparison, an exemplary method using the apparatuses of this invention comprises a CBC on a particle counter, and categorizing and/or subcategorizing blood cells in accordance with some embodiments. By operating the apparatus as described in this disclosure, images can be reviewed on the visual analyzer and the samples will require less frequent manual review.

The motor 54 can comprise a geared stepping motor with precision somewhat smaller than the distinguishing features imaged by the high optical resolution imaging device or the digital image capture device, especially aspects of blood cells. Provided that the location of the high optical resolution imaging device 24 is adjusted to locate the position of the optical objective within the width of the ribbon-shaped sample stream, the view of the cell/particle in the ribbon-shaped sample stream is in focus. The autofocus pattern can be located at an edge of a field of view of the high optical resolution imaging device or the digital image capture device, and does not interfere with viewing for that reason.

Furthermore, when the high optical resolution imaging device is moved over the displacement distance and the autofocus pattern goes out of focus, the features that appear in focus are the blood cells as opposed to the autofocus pattern. According to some embodiments, the autofocus pattern can be defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 µm in a flowcell dimensioned for hematology (blood cell) imaging applications. In some embodiments, the autofocus feature maintains the high optical resolution imaging device within 1 µm of the optimal focus distance.

The flowcell internal contour and the PIOAL and sample flow rates can be adjusted such that the sample is formed into a ribbon shaped stream. The stream can be approximately as thin as or even thinner than the particles that are enveloped in the ribbon-shaped sample stream. White blood cells may have a diameter around 10 µm, for example. By providing a ribbon-shaped sample stream with a thickness less than 10 µm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

The ribbon-shaped sample stream thickness can be affected by the relative viscosities and flow rates of the sample fluid and the PIOAL. The source 25 of the sample and/or the source 27 of the PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. The PIOAL viscosity can be up to 10 centipoise.

In the embodiment depicted in FIG. 14, the same digital processor 18 that is used to analyze the pixel digital image obtained from photosensor array is also used to control the autofocusing motor 54. However the high optical resolution imaging device 24 is not autofocused for every image captured. The autofocus process can be accomplished periodically or for example when temperature or other process changes are detected by appropriate sensors, or when image analysis detects a potential need for refocusing. It is also possible in other embodiments to have the hematology image analysis accomplished by one processor and to have a separate processor, optionally associated with its own photosensor array, arranged to handle the steps of autofocusing to a fixed target 44.

In FIG. 14, the at least one said digital processor 18 is configured to autofocus at programmed times or in programmed conditions or on user demand, and also is configured to perform image based categorization and subcategorization of the particles. Exemplary particles include cells, white blood cells, red blood cells and the like.

In one embodiment, the at least one said digital processor 18 is configured to detect an autofocus re-initiation signal. The autofocus re-initiation signal can be triggered by a detected change in temperature, a decrease in focus quality as discerned by parameters of the pixel image date, passage of time, or user-input. Advantageously, it is not necessary to recalibrate in the sense of measuring the displacement distance 52 to recalibrate. Optionally, the autofocus can be programmed to re-calibrate at certain frequencies/intervals between runs for quality control and or to maintain focus.

The displacement distance 52 varies slightly from one flowcell to another, but remains constant for a given flowcell. As a setup process when fitting out an image analyzer with a flowcell, the displacement distance is first estimated and then during calibration steps wherein the autofocus and imaging aspects are exercised, the exact displacement distance for the flowcell is determined and entered as a constant into the programming of processor 18.

Figure 15:
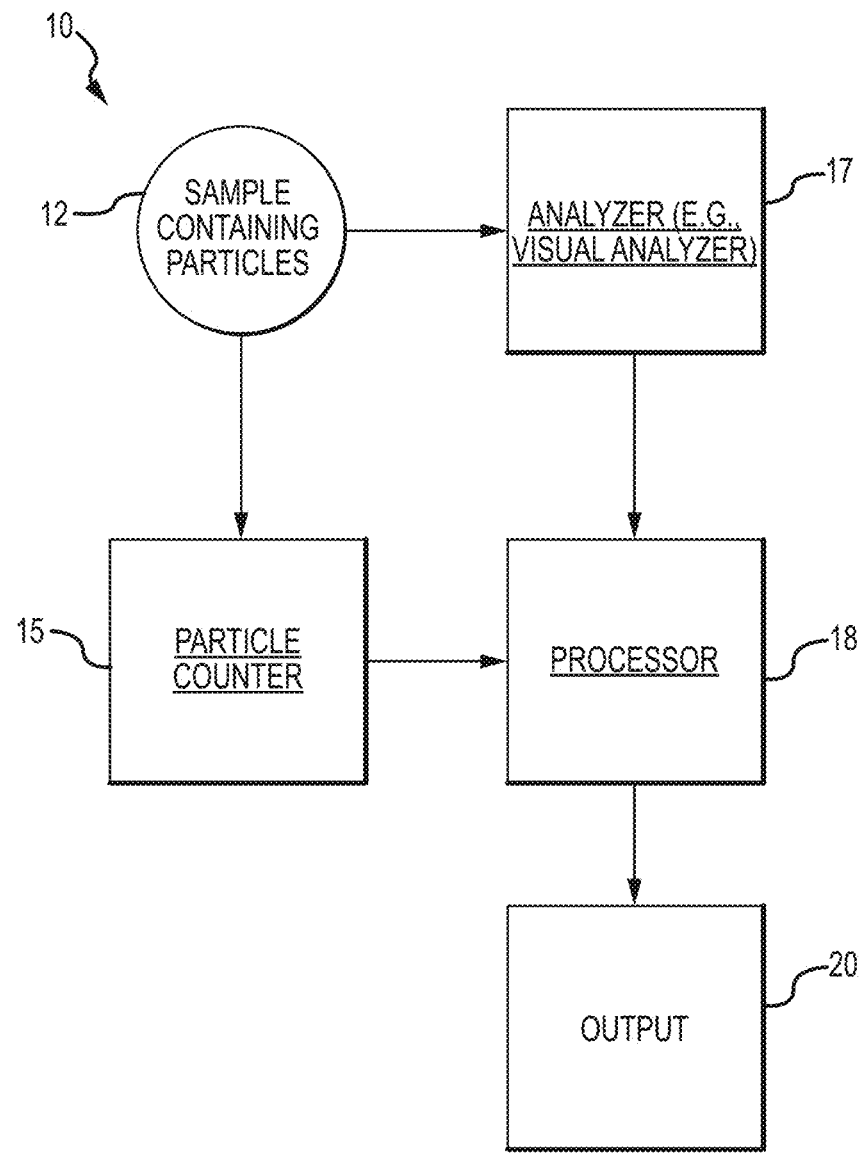
FIG. 15 shows an exemplary apparatus for analyzing a sample according to embodiments of the present invention.

Referring to FIG. 15, an exemplary apparatus 10 for analyzing a sample 12 containing particles includes a particle counter 15 having at least one detection range, an analyzer 17, and a processor 18 in accordance with some embodiments. The block diagram of FIG. 15 is for the purpose of illustration. Particle counter 15, analyzer 17, and processor 18 may or may not be connected to each other. In some embodiments the processor may be coupled to the analyzer and/or particle counter. In other embodiments the processor may be a component of the analyzer and/or particle counter.

Particle counter 15 comprises at least one channel, and is configured to provide a particle count for at least one category and/or subcategory of particles. In some embodiments, a particle counter 15 comprises at least two channels for different categories and/or subcategories of particles. In some embodiments, particles are counted through sensing electrical impedance or light scatter of the sample. An example of a suitable particle counter 15 includes but is not limited to a flow cytometer. In some embodiments, detection may take place in each of a plurality of channels responsive to different physical properties, either simultaneously or sequentially.

Analyzer 17 is configured to differentiate different categories and/or subcategories and corresponding members of each category and/or subcategory of particles. Examples of a suitable analyzer 17 include but are not limited to a visual analyzer, a digital camera, or any other pixel data analyzer which can capture pixel data, and is programmed to discriminate for attributes represented in a pixel file. Processor 18 and analyzer 17 are configured to apply an algorithm, such as determining a proportionate ratio of the counts of two categories or two corresponding subcategories of particles, and apply such a proportionate ratio to the particle count of at least one category and/or subcategory of particles obtained in at least one channel of particle counter 15. After data analysis, processor 18 provides, at output 20, an accurate measure of concentration of each category and each corresponding subcategory of particles in sample 12.

In some embodiments, in sample 12, at least a first category and/or subcategory of particles can be present at a concentration outside a detection range applicable to the first category and/or subcategory of particles while at least a second category and/or subcategory of particles is present at a concentration within a detection range applicable to the second category and/or subcategory of the particles. The concentration of the second category and/or subcategory of particles is determined on particle counter 15. A proportionate ratio of the first category and/or subcategory to the second category and/or subcategory of particles is determined on analyzer 17. The concentration of particles in the first category and/or subcategory is calculated on processor 18 at least in part by applying such a proportionate ratio to the concentration of the second category and/or subcategory of particles.

In some embodiments, a category and/or subcategory of particles detected in the at least one channel of particle counter 15 can comprise at least two classes of particles. And each class of particles may comprise a plurality of subclasses. Particle counter 15 is configured to detect a plurality of particles that meet one or more selection criteria, for example, based on a predetermined size range, and to provide a particle count thereof. The selection criteria encompass members of at least two classes of particles. Analyzer 17 and processor 18 are programmed to distinguish the members of the at least two categories and/or subcategories of particles. A distribution of each the members over at least two categories and/or subcategories are determined on processor 18. Processor 18 uses such a distribution to correct the particle count for the members of at least one of the at least two categories and/or subcategories obtained on particle counter 15.

More particularly, apparatus 10 can be used for identifying and quantifying different blood cells including RBCs, WBCs, PLTs, and other blood cells, fetal cells, or bacterial cells, viral particles, parasites, cysts, including parasitic cysts, crystals, or fragments thereof or other cell fragments in a sample.

Figure 15A:
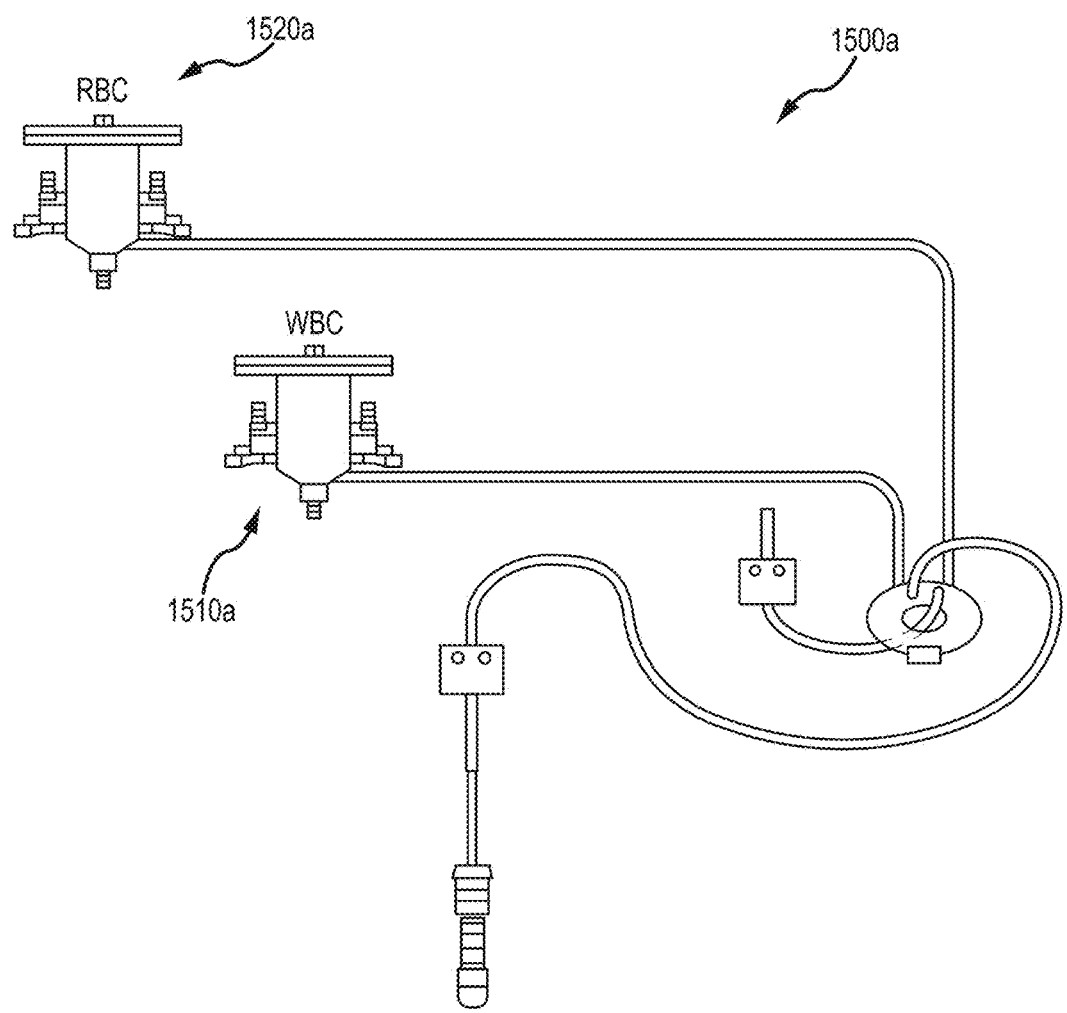
FIG. 15A depicts aspects of an exemplary counter or counting module according to embodiments of the present invention

FIG. 15A depicts aspects of an exemplary counter or counting module 1500a, according to embodiments of the present invention. Such counters can operate to control or carry out various mechanical functions as well as electronic and photometric measurement functions for WBC, RBC and PLT cell counting and hemoglobin measurements. Exemplary counters can be used to prepare the samples for CBC analysis, and to generate CBC parameter measurements via aperture bath assemblies (e.g. WBC bath 1510a and RBC bath 1520a). According to some embodiments, the counter 15 of FIG. 15 can be represented by counter 1500a of FIG. 15A. Similarly, according to some embodiments, the counter 15 of FIG. 14 can be represented by counter 1500a of FIG. 15A. According to some embodiments, the counter 722 of FIG. 16 can be represented by counter 1500a of FIG. 15A.

Cellular elements of the blood (e.g. erythrocytes, leukocytes, and platelets) can be counted using electrical impedance methods. For example, an aspirated whole blood sample can be divided into two aliquots and mixed with an isotonic diluent. The first dilution can be delivered to the RBC aperture bath 1520a, and the second can be delivered to the WBC aperture bath 1510a. In the RBC chamber, both RBCs and platelets can be counted and discriminated by electrical impedance as the cells pass through sensing apertures. For example, particles between 2 and 20 fL can be counted as platelets, and those greater than 36 fL can be counted as RBCs. For the WBC chamber processing, an RBC-lysing reagent can be added to the WBC dilution aliquot to lyse RBCs and release hemoglobin, and then WBCs can be counted by impedance in sensing apertures of the WBC bath. In some instances, the baths may include multiple apertures. Hence, for example, a blood cell count used in a blood cell enumeration technique may be obtained using an RBC triple aperture bath.

An exemplary CBC sample preparation technique may include two processes, sample acquisition and sample delivery. Sample acquisition may occur when 165 uL of patient sample is aspirated and directed to a Blood Sampling Valve (BSV). The BSV can operate to direct specific volumes of the patient sample with the processing reagents for delivery to the two triple-aperture baths. The patient sample and the processing reagents can be delivered to the bottom of aperture baths at an angle that, with a round design, allow the sample and reagents to thoroughly mix without mixing bubbles. The sample can then be prepared for measurement and analysis. According to some embodiments, in the WBC bath, 6.0 mL (±1.0%) of diluent and 28 uL of sample can be combined with 1.08 mL (±1.0%) of D×H cell lyse for a final dilution of 1:251. According to some embodiments, in the RBC bath, 10 mL (±1.0%) of diluent and 1.6 uL of sample can be combined for a final dilution of 1:6250. After the patient sample and reagents are mixed, vacuum and aperture current can be applied to the apertures for the measurements of cell count and cell volume. The RBC and PLT counts can also include the application of sweep flow to prevent recirculation of cells near the aperture. In certain embodiments, data acquisition for the RBC and PLT can be up to a maximum of 20 seconds and for the WBC a maximum of 10 seconds. In certain embodiments, all analog pulses generated by the aperture assemblies can be amplified by a preamp card and then sent to a CBC signal conditioner analyzer card for analog-to-digital conversion and parameter extraction. According to some embodiments, a system can be used to measure multiple parameters for each cellular event, and a digital parameter extraction process can be used to provide digital measurements such as time, volume (pulse attributes including amplitude and pulse width), count and count rate, and wait time. Such measurements can be used for pulse editing, coincidence correction, count voting, generation of histograms for WBC, RBC and PLT, histogram voting, pattern analysis, and interference correction, and the like.

Figure 16:
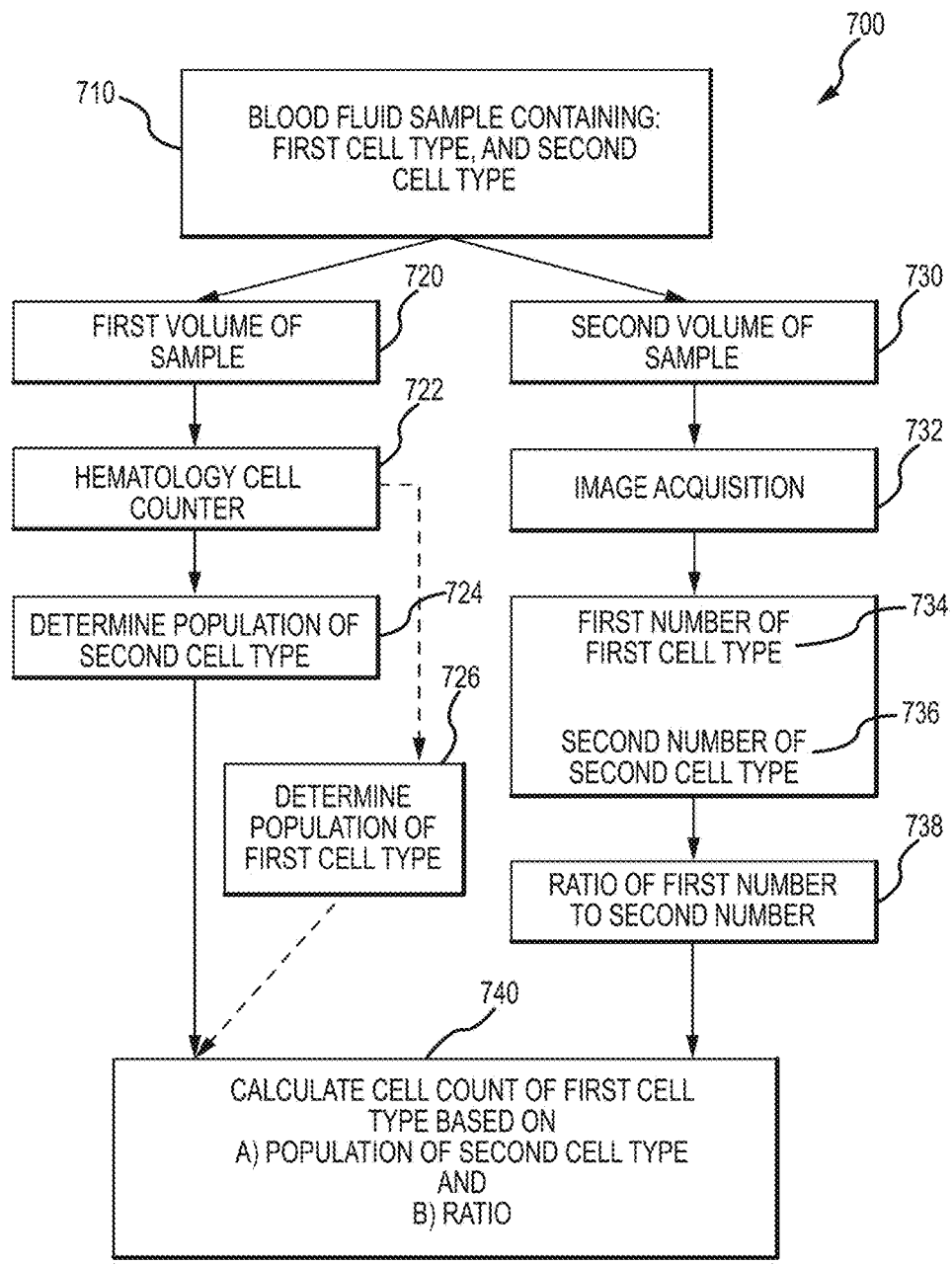
FIG. 16 depicts aspects of systems and methods for measuring a quantity of a first cell type in a blood fluid sample according to embodiments of the present invention.

FIG. 16 depicts aspects of systems and methods for measuring a quantity of a first cell type in a blood fluid sample, where the sample also includes a second cell type, according to embodiments of the present invention. As shown here, the method 700 can include obtaining a first volume of sample 720 and a second volume of sample 730 from the blood fluid sample 710. As indicated at step 724, the method may include determining a population of the second cell type in the first volume 720 of the sample by flowing the first volume through a hematology cell counter 722. Often, cell counter 722 is suitable for accurately counting cells when there is a sufficient amount of an electrically distinguishable type of cell in the sample, and not when the cell type amount exceeds a certain limit or threshold. Cell counters may be used to count red blood cells or the total number of other components (e.g. large components) in a blood sample in a short amount of time. In some cases, cell counters may encounter challenges when discriminating between white blood cells and other components (e.g. large components) in blood, or which there may be several different species, but with a relatively small number each.

Further, method 700 may include acquiring images of a first number of the first type cells and a second number of the second cell types, as indicated by step 732, by injecting the second volume 730 of the sample into a sheath fluid flowing within a flowcell so as to provide a sample stream having a thickness and a width greater than the thickness, the acquired images being acquired along an image path traversing the thickness of the sample stream. In some cases, the image acquisition 732 can be performed using an analyzer 17 as depicted in FIG. 14 and/or FIG. 15. In some cases, analyzers can efficiently discriminate between white blood cells, giant platelets, and other large components in blood fluid sample. However, there may be challenges when using such analyzers to obtain a complete particle count in a sample. Further, in some instances it may not be desirable to use the analyzer to obtain certain counts (e.g. a count of all red blood cells) because such counting procedures may also involve performing a characterization of the particles as well, in addition to obtaining the count. According to some embodiments, the analyzer is used to obtain images for only a percentage or portion of the sample which is processed through the analyzer.

As depicted in FIG. 16, the method 700 may include determining a ratio of the first number of the first cell type 734 to the second number of the second cell type 736 using the acquired images, as indicated at step 738. Methods also include calculating a cell quantity measure of the first cell type in the sample using the ratio 738 and the population of the second cell type 724, as indicated at step 740.

According to some embodiments, the cell quantity measure calculated at step 740 is a cell concentration for the first cell type in the blood fluid sample 710. In some cases, the cell quantity measure calculated at step 740 is a cell count for the first cell type in the blood fluid sample 710. In some cases, the cell counter 722 has a first accuracy associated with counting of the first cell type and a second accuracy associated with counting the second cell type, where the second accuracy is superior to or higher than the first accuracy. In some cases, (see, e.g. FIGS. 19A and 19B) the hematology cell counter 722 has a desired accuracy range, and the desired accuracy range extends between a minimum population of cells in the first volume 720 and a maximum population of cells in the first volume 720, where the population of the second cell type in the volume determined at step 724 is within the desired accuracy range, and where the cell quantity measure of the first cell type of the sample calculated at step 740 is outside the desired accuracy range.

As further depicted in FIG. 16, (and with continued reference to FIGS. 19A and 19B) methods may optionally include determining a population of the first cell type 726 in the first volume of the sample as a result of flowing the first volume through the hematology cell counter 722. The determined population of the first cell type 726 in the first volume may be above or below a desired accuracy range for the first cell type, and may also be different from the cell quantity measure of the first cell type as calculated in step 740. In some cases, (e.g. FIG. 19A), the determined population of the first cell type 726 is zero. In some cases, (e.g. FIG. 19B), the determined population of the first cell type 726 is greater than zero.

According to some embodiments of the present invention, the hematology cell counter 722 can include a sensor mechanism that detects a change in electrical impedance in response to a second type cell flowing through the cell counter. According to some embodiments, the hematology cell counter 722 includes a sensor mechanism that detects an obstruction of a light path in response to a second type cell flowing through the cell counter.

In some cases, the hematology cell counter 722 has a minimum detectable concentration limit and a maximum detectable concentration limit for the first cell type, and a minimum detectable concentration limit and a maximum detectable concentration limit for the second cell type. The determined population of the second cell type 724 can be based on a detected concentration parameter for the second cell type that is above the minimum limit and below the maximum limit for the second cell type. The first cell type can be present at a concentration that is either below the minimum limit or above the maximum limit for the first cell type.

In some cases, the hematology cell counter 722 has a minimum detectable volume limit and a maximum detectable volume limit for the first cell type, and a minimum detectable volume limit and a maximum detectable volume limit for the second cell type. The determined population of the second cell type 724 can be based on a detected volume parameter for the second cell type that is above the minimum limit and below the maximum limit for the second cell type. The first cell type can be present at a volume parameter that is either below the minimum limit or above the maximum limit for the first cell type.

In some cases, the hematology cell counter 722 has a minimum detectable size limit and a maximum detectable size limit for the first cell type, and a minimum detectable size limit and a maximum detectable volume size for the second cell type. The determined population of the second cell type 724 can be based on a detected size parameter for the second cell type that is above the minimum limit and below the maximum limit for the second cell type. The first cell type can be present at a size parameter that is either below the minimum limit or above the maximum limit for the first cell type.

According to some embodiments of the present invention, (refer FIGS. 13*b*, *c*), the determination of the population of the second cell type 724 in the first volume of the sample includes grouping together cells of the first cell type and cells of the second cell type. In some cases, methods may also include calculating a cell quantity measure of the second cell type in the sample using the ratio and the population of the second cell type. In some cases (e.g. as depicted in FIG. 19D), the determination of the population of the second cell type 724 in the first volume of the sample includes grouping together cells of the first cell type and cells of the second cell type, and determining a population of the first cell type 726 in the first volume of the sample as a result of flowing the first volume through the hematology cell counter 722. The cell quantity measure of the first cell type in the sample as calculated in step 740 can use the ratio 738, the population of the second cell type 724, and the population of the first cell type 726.

Figure 17:
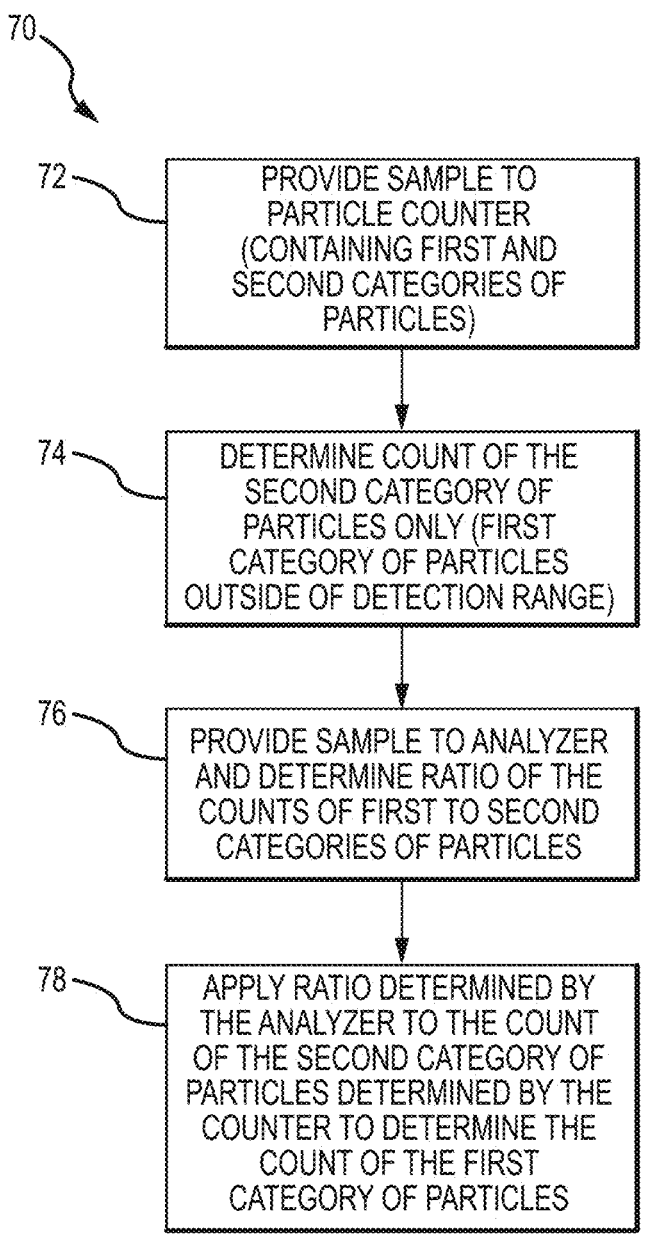
FIG. 17 shows a method for analyzing a sample containing particles according to embodiments of the present invention.
Figure 19A:
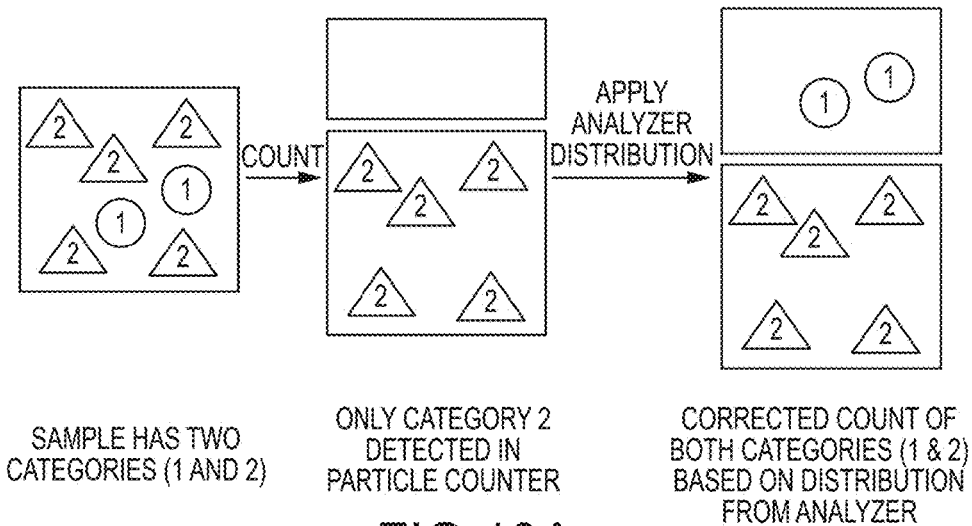
FIGS. 19A, 19B, 19C, and 19D show detection of categories of particles according to embodiments of the present invention.
Figure 19B:
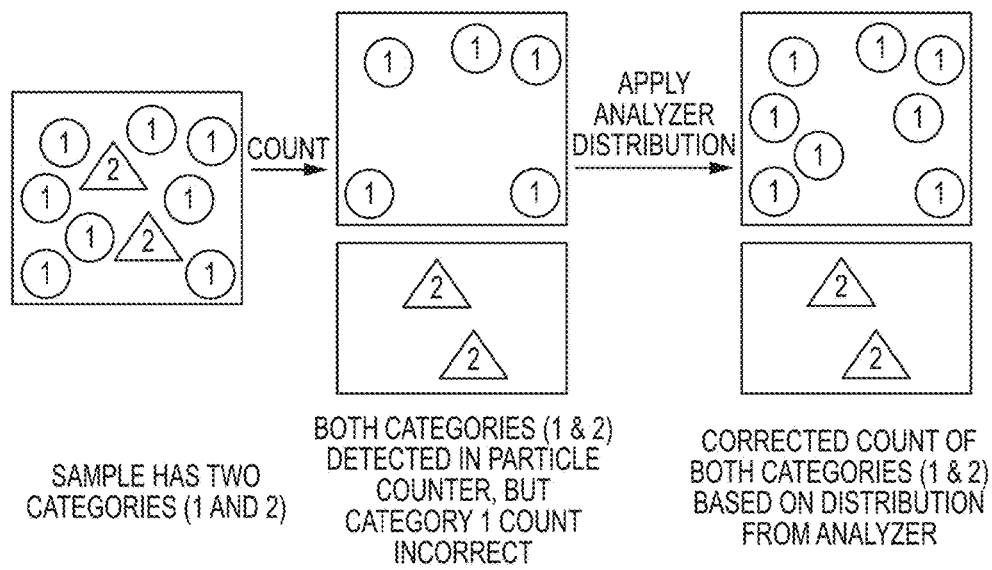

In other aspects, for example as depicted in FIG. 17 and/or FIGS. 19A and 19B, a method is provided for analyzing a sample containing particles. In such a method, a sample is provided onto a particle counter having detection limits, as indicated at step 72 in the method 70 of FIG. 17. At least a first category and/or subcategory of particles can be present in the sample at a concentration outside a detection range applicable to the first category and/or subcategory of particles, and at least a second category and/or subcategory of particles is present in the sample within a detection range applicable to the second category and/or subcategory of particles. The concentration of the second category and/or subcategory of particles in the sample is determined on the particle counter, as indicated at step 74. The sample is also provided onto an analyzer to determine a proportionate ratio of the first category and/or subcategory of particles to the second category and/or subcategory of particles, as indicated at step 76. The concentration of particles in the first category and/or subcategory can be then calculated at least in part by applying the proportionate ratio to the concentration of the second category and/or subcategory of particles, as indicated step 78. FIG. 19A shows detection of particles in a sample below the detection range, and FIG. 19B shows detection of particles present in a sample above the detection range.

FIG. 17 therefore illustrates an exemplary method 70 of determining the concentration of the first category of particles, which is present in a sample at a concentration outside a detection range on a particle counter, in accordance with some embodiments. In step 72, referring also to FIGS. 15 and 17, a sample 12 is provided onto a particle counter 15, which has at least one detection range. Sample 12 includes particles, which may be dispersed in a fluid. In some embodiments, the first category of particles is present in the sample at a concentration above an upper limit of a detection range applicable to the first category of particles. The second category of particles is present in the sample within a detection range applicable to the second category of particles. For example, the first category and/or subcategory of particles can include WBCs. The second category of particles can include platelets.

In some embodiments, the first category of particles is present in the sample at a concentration below a lower limit of a detectable range applicable to the first category of particles. The second category of particles is present in the sample within a detection range applicable to the second category of particles. For example, the first category of particles comprises platelets. The second category of particles comprises white blood cells.

In step 74 of FIG. 17, the concentration of the second category of particles in sample 12 is determined on particle counter 15. The particle counter can comprise at least one channel. The second category of particles is measured in one of the channels in some embodiments. The particle counter can comprise at least two channels in some embodiments. The first category of particles, if the concentration is within a detection range applicable to the first category of particles, can be counted in another channel.

In step 76 of FIG. 17, sample 12 is provided onto an analyzer, such as a visual analyzer 17 (e.g. as depicted in FIG. 14 or 15), to determine a proportionate ratio of the first category of particles to the second category of particles. In some embodiments, visual analyzer 17 comprises a flowcell 22 connected to an imaging device as described above. The proportionate ratio of the first category of particles to the second category of particles can be determined according to method described herein. For example, at least one chemical including at least one of a diluent, a permeabilizing agent, and a contrast agent may be introduced to the sample. Exemplary chemicals, compositions, contrast agents, and related compositions which can be used for processing blood fluid samples are discussed in copending U.S. patent application Ser. No. 14/216,339, filed Mar. 17, 2014 (now U.S. Pat. No. 9,279,750, issued Mar. 8, 2016), the content of which is incorporated herein by reference. The contrast agent can be effective to generate visual distinctions that differentiate the first categories and/or subcategories and the second categories and/or subcategories of particles. The prepared sample 12B depicted in FIG. 14 can be applied to the at least one flowcell 22 in some embodiments. Images of particles of prepared sample 12B are captured. An image analysis is performed by the analyzer which can be a visual analyzer 17 and/or processor 18. A proportionate ratio of the first category of particles to the second category of particles is then determined by analyzing the plurality of images of the ribbon-shaped sample stream.

In step 78 of FIG. 17, the concentration of particles in the first category can be then calculated by processor 18 (e.g. as depicted in FIG. 15), at least in part by applying the proportionate ratio to the concentration of the second category of particles.

Figure 18:
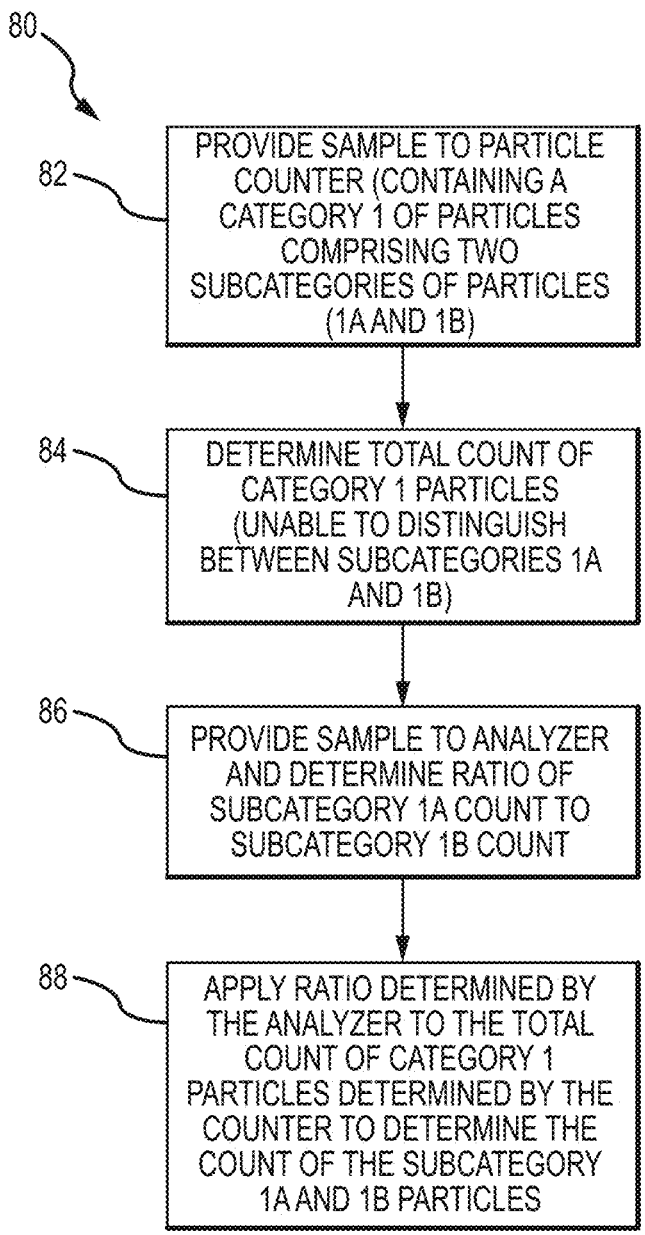
FIG. 18 illustrates an exemplary method of determining the concentration of two subcategories of particles according to embodiments of the present invention.

The present disclosure also provides methods for analyzing a sample containing particles. FIG. 18 illustrates an exemplary method 80 of determining the concentration of two subcategories of particles, which particles cannot be distinguished by the particle counter, in accordance with some embodiments. In step 82, a sample (e.g. sample 12 of FIG. 15) is provided onto a particle counter (e.g. particle counter 15 of FIG. 15), which has a detection criteria which are met by at least two categories or subcategories of particles which are desired to be distinguished. The results from the particle counter encompass these categories or subcategories within a single count in step 84 of FIG. 18.

In step 86, the sample is provided onto the analyzer (such as a visual analyzer) to determine a proportionate ratio of the first category or subcategory of particles to the second category or subcategory of particles. In some embodiments, for example as depicted in FIGS. 14 and/or 15, a visual analyzer 17 includes a flowcell 22 connected to an imaging device.

The proportionate ratio of the first category or subcategory of particles to the second category or subcategory of particles can be determined according to methods described herein. At least one chemical comprising at least one of a diluent, a permeabilizing agent, and a contrast agent is introduced to sample. The contrast agent is effective to generate visual distinctions for particle categorization and subcategorization that differentiate the first category or subcategory from the second category or subcategory of particles. As depicted in FIG. 14, the prepared sample 12B can be applied to the at least one flowcell 22 in some embodiments. Images of particles of prepared sample 12B are captured. An image analysis is performed by the visual analyzer and/or processor 18. A proportionate ratio of the at least first subcategory of particles to the second subcategory of particles is then determined by analyzing the plurality of images.

In step 88 of FIG. 18, the concentration of particles in the first category or subcategory can be then calculated by processor 18, as depicted in FIG. 14 or 15, at least in part by applying the proportionate ratio to the single count (e.g. step 84 of FIG. 18) obtained from the particle counter.

In some embodiments, the first category and/or subcategory of particles is present in the sample at a concentration above an upper limit of a detection range applicable to the first category and/or subcategory of particles. The second category and/or subcategory of particles is present in the sample within the detection range applicable to the second category and/or subcategory of particles. For example, the first category of particles comprises white blood cells. The second category of particles comprises platelets. As illustrated in FIG. 19B, the particle count from the analyzer of this disclosure can be used to correct inaccurate particle counts associated with at least one detection range used by the particle counter, such as particle concentration, volume and/or size. By operating the apparatus as described in the present disclosure, particles present in amounts above the upper limit of the detection range can be detected and measured accurately.

In some embodiments, the first category and/or subcategory of particles is present in the sample below a lower limit of a detectable range of some parameter, for example concentration, applicable to the first category and/or subcategory of particles, as illustrated in FIG. 19A. The second category and/or subcategory of particles is present in the sample within the detection range applicable to the second category and/or subcategory of particles. As illustrated in FIG. 19A, the proportionate ratio of particle counts in the two categories and/or subcategories from the analyzer of this disclosure can be used to correct inaccurate counts from the particle counter for at least one category and/or subcategory. By operating the apparatus as described in the present disclosure, particles present below the detection range limit, which are not detected by the particle counter, can be measured accurately.

As shown in FIG. 19A, the particle counter provides a particle count for category 2. The analyzer provides a proportionate ratio of particle counts for categories 1 and 2. By multiplying the proportionate ratio times the particle count for category 2, the process arrives at the particle count for category 1. The first category and/or subcategory of particles may comprise, for example, platelets. The second category and/or subcategory of particles comprise white blood cells. According to some embodiments, the dynamic or detection range extensions systems and method disclosed herein can be used to obtain accurate platelet counts when the number of platelets contained in the sample is low.

In some embodiments, the analyzer includes an imaging device and a flowcell connected to the imaging device to determine a proportionate ratio of the first category and/or subcategory of particles to the second category and/or subcategory of particles. At least one of a diluent, a permeabilizing agent, a contrast agent is introduced to the sample. The at least one chemical is effective to generate visual distinctions that differentiate the first and the second categories and/or subcategories of particles. In a step of determining such a proportionate ratio, the sample is applied to the at least one flowcell present in some embodiments. A plurality of images of particles of the sample are captured to provide a statistically significant estimation of a count or proportionate ratio. A proportionate ratio of the at least first category and/or subcategory of particles to the second category and/or subcategory of particles is then determined by counting the particles in each of the first and second categories and/or subcategories of particles.

In another aspect, as depicted in FIG. 18 and/or FIG. 19D, a method 80 for analyzing a sample containing particles is provided to correct the particle count obtained on a particle counter. For example, the results from the analyzer, for example, the relative count, of this disclosure can be used to obtain accurate particle counts of categories and/or subcategories of particles which cannot be differentiated by the detection criterion or criteria used by the particle counter alone.

Figure 19C:
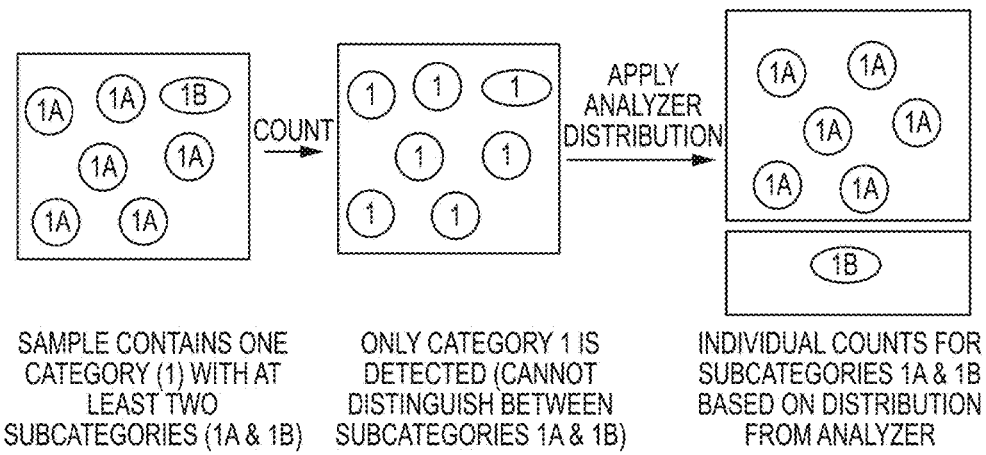
Figure 19D:
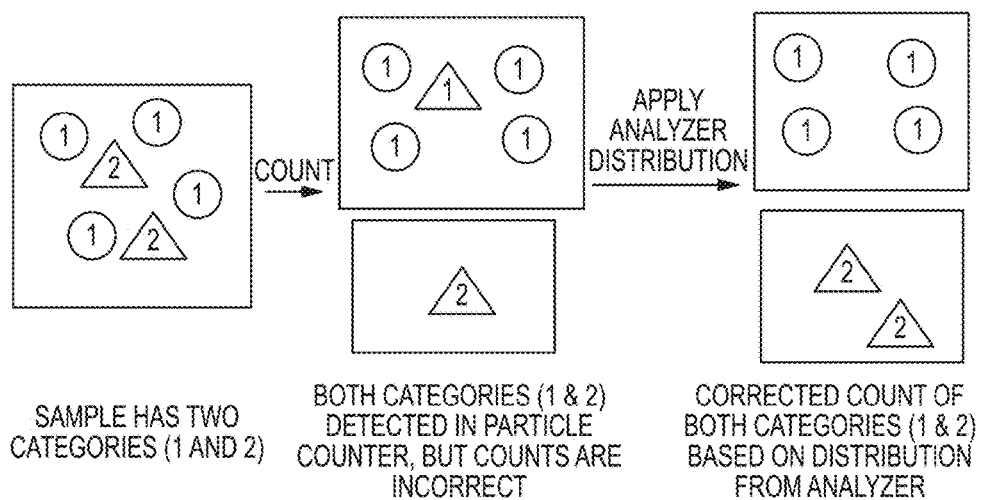

In another embodiment shown in FIG. 19C, the counter may provide a substantially accurate count for a plurality of particles. The plurality of particles encompasses members of at least two subcategories but the count does not distinguish between the subcategories. A distribution of each of the members of the at least two subcategories can be determined on an analyzer. The distribution of the subcategories is the proportionate ratio of the counts of the respective subcategories to the total. A processor is programmed to distinguish the members of the at least two subcategories. By using the distribution from the analyzer and the total particle count from the particle counter, for example as depicted in FIG. 19C, the particle count for the members of at least one of the at least two subcategories can then be determined by the processor by using the distribution of each of the members.

According to some embodiments, as depicted in FIG. 19D, the sample may have two categories of particles present. In this context, categories may be construed to include the possibility of multiple categories and/or multiple subcategories. By operating the apparatus as described in this disclosure, correction can be made to the count of particles where at least some members from at least one additional category of particles are incorrectly categorized or subcategorized, by the particle counter, as members of a first category of particles. In such a method, the count for a plurality of particles can be determined using a predetermined range, for example, size and/or volume range, to provide particle counts thereof on a particle counter. The predetermined range groups together the members of a first category of particles and at least some members of at least a second category of particles in the particle count. Those particles in the one or more categories or subcategories which are incorrectly counted as another category of particle in one channel of the apparatus can be measured separately and accurately using the analyzer configured to distinguish a distribution of the particles over the first category of particles and the at least a second category of particles in the sample. The distribution of the categories and/or subcategories is the proportionate ratio of the counts of the respective categories and/or subcategoires to the total. The processor then uses the distribution to calculate the particle count for the members of the first category and the at least a second category and/or subcategory of particles. In this embodiments, as illustrated in FIG. 19D, the apparatus and methods of this disclosure and the count of particles in each category and/or subcategory can be corrected.

As shown in FIG. 19D, the particle counter may provide a substantially accurate total count comprising two categories. This count may include presumed counts for categories 1 and 2. However, the presumed count is inaccurate in that the particle counter has misclassified at least one member of category 2 with category 1. The analyzer provides a distribution of particle counts based on a smaller sample than used in the particle counter, for categories 1 and 2, but the analyzer produces an accurate distribution. The processor uses this information to arrive at an accurate count for both categories. This same process can be used for samples containing more than two categories and/or subcategories of particles.

For example, members of different particle categories or subcategories with similar size or morphology may not be accurately categorized or subcategorized by the particle counter. For example, "giant" PLTs, PLT aggregates, clumps, multiple platelets and nucleated RBCs may be mistakenly counted as WBCs, resulting in a WBC count higher than that actually exists in the sample. As another example, microcytic red cells, cell fragments, artifacts, and even electronic noise may be mistakenly counted as platelets, resulting in an inaccurately high count of PLTs.

In some embodiments, the analyzer is a visual analyzer comprising an imaging device and a flowcell. As an example, at least one chemical comprising at least one of a diluent, a permeabilizing agent, a contrast agent is introduced to the sample. The at least one chemical is effective to generate visual distinctions that differentiate the first category and/or subcategory and the second category and/or subcategory of particles. In a step of determining such a distribution, the sample is applied to the at least one flowcell present in some embodiments.

In a step of determining a distribution of each of the members of at least two categories and/or subcategories of particles, at least a part of the sample is applied into the at least one flowcell. The at least one chemical is effective to generate visual distinctions that differentiate the members of the categories and/or subcategories of particles. A plurality of imaging of particles of the sample is captured. A plurality of images of particles of the sample is captured to provide a statistically significant estimation of a count or proportionate ratio. A proportionate ratio of the at least first category and/or subcategory of particles to the second category and/or subcategory of particles is then determined by counting the particles in each of the first and second categories and/or subcategories of particles.

A proportionate ratio of the members of each of two or more subcategories of particles within a category and/or subcategory of particles, and/or a proportionate ratio of the members of a first category and/or subcategory of particles to the members of at least one other category and/or subcategory of particles can be determined, based on the plurality of images of particles of the sample. A count or concentration value for each category and/or subcategory of particles can then be calculated, estimated, inferred and/or derived. As an example, the concentration of subcategories of particles can be determined based on the proportionate ratio of each subcategory of particles from the analyzer, and the count of the total number of particles in the category from the particle counter. In some embodiments, the members of the at least two subcategories comprises at least one type of particles selected from a group consisting of subcategories of white blood cells, platelets, and red blood cells.

Accordingly, in some embodiments, the method further comprises determining a proportionate ratio of the count of particles in one category and/or subcategory of particles present at a concentration outside a detection range applicable to the one category of particles of the particle counter versus the count of particles in a second category and/or subcategory of particles that is within a detection range applicable to the second category and/or subcategory of particles, based on the plurality of images of particles of the sample from the analyzer and/or processor. The concentration in the sample of the category and/or subcategory of particles outside the detection range of the particle counter can be then determined, by applying the proportionate ratio to the particle count obtained on the particle counter. For example, in some embodiments, the first category and/or subcategory of particles is present in the sample at a concentration above an upper limit of the detection range limit applicable to the first category and/or subcategory of particles. The second category and/or subcategory of particles is present in the sample within the detection range of the particle counter (below an upper limit and above the lower limit of the detection range) applicable to the second category and/or subcategory of particles. As another example, where the detection criterion or criteria used by the particle counter miscategorizes particles by grouping particles of a first category and/or subcategory with particles of at least a second category and/or subcategory, the particle count for the first and second categories and/or subcategories can be corrected from proportionate ratios of the particles determined from the plurality of images of the particles of the sample from the visual analyzer and/or processor.

The detection range of measurement may be limited on a particle counter 15 alone in FIG. 15. For example, the upper detection limit for WBCs might be less than 100,000 to 200,000 per μL on a particle counter 15. The lower detection limit for PLTs might be higher than 10,000 per μL. By using the apparatus described herein, the effective detection range of measurement can be extended, for example, the upper detection limit for WBCs can be extended up to about 300,000, 350,000, 400,000, 410,000, 420,000, 430,000, 440, 000, 450,000, 460,000, 470,000, 480,000, 490,000, 500,000, 510,000, 520,000, 530,000, 540,000, 550,000, 560,000, 570,000, 580,000, 590,000, 600,000, 610,000, 620,000, 630,000, 640,000, 650,000, 660,000, 670,000, 680,000, 690,000, 700,000, 710,000, 720,000, 730,000, 740,000, 750,000, 760,000, 770,000, 780,000, 790,000, 800,000, 810,000, 820,000, 830,000, 840,000, 850,000, 860,000, 870,000, 880,000, 890,000, 900,000, 910,000, 920,000, 930,000, 940,000, 950,000, 960,000, 970,000, 980,000, 990,000, or 1,000,000, 1,000,000, 1,010,000, 1,020,000, 1,030,000, 1,040,000, 1,050,000, 1,060,000, 1,070,000, 1,080,000, 1,090,000, 1,100,000, 1,110,000, 1,120,000, 1,130,000, 1,140,000, 1,150,000, 1,160,000, 1,170,000, 1,180,000, or about 1,190,000, cells per µL, or any range between any two of those values, in some embodiments. The lower detection limit for PLTs can be extended down to 10,000, 9,500, 9,000, 8,500, 8,000, 7,500, 7,000, 6,500, 6,000, 5,500, 5,000, 4,500, 4,000, 3,500, 3,000, 2,500, 2,000, 1,500 or 1,000, or 500, 400, 300, 200, or 100 cells per µL in some embodiments.

The analyzer preferably comprises a visual analyzer 17 operable to determine a proportionate ratio of the first category and/or subcategory of particles to the second category and/or subcategory of particles. In this embodiment, the proportionate ratio as described above can be determined by analyzing the plurality of images of particles in the sample taken on visual analyzer 17.

Visual analyzer 17 can be configured to introduce to the sample at least one chemical comprising at least one of a diluent, a permeabilizing agent, and/or a contrast agent to generate visual distinctions for particle categorization and subcategorization. Such visual distinctions differentiate the members of the at least two categories. Images of particles of the sample are captured. Visual analyzer 17 and the processor 18 are configured to determine a proportionate ratio of each category or subcategory of particles, by discriminating among the images of particles of the sample. The concentration of each category or sub-category of particles is then calculated. For example, accurate results of WBCs, giant PLTs and NRBCs can be determined. On a particle counter, due to similar size or morphology, giant PLTs and NRBc are counted as WBCs. By operating the apparatus as described, particle count or concentration of giant PLTs and nRBCs can be reported accurately.

In some embodiments, the sample can comprise particles whose size is outside a detection size range of particle counter 15. Visual analyzer 17 and processor 18 are configured to detect the particles and determine a proportionate ratio of the particles outside a detection size range to particles within the detection size range of the particle counter 15, based on the images of particles of the sample. The concentration of the category and sub-category of particles outside the detection size range of the particle counter 15 can be then calculated.

Generally, methods for analyzing a sample containing particles are provided to correct the particle count obtained on a particle counter. An exemplary method can be used for differentiating different categories of particles, including the corresponding subcategories, falling into the same category and/or subcategory of particles on the particle counter 15, for example as depicted in FIGS. 14 and 15. The method can be used to correct particle counts obtained in particle counter 15. In some embodiments, for example, the first category and/or subcategory of particles comprises one or more types of abnormal blood cells, immature blood cells, clumped blood cells, or abnormally sized blood cells. The second category and/or subcategory of particles comprise white blood cells. By operating the apparatus as described herein, the particles in subcategories can be distinguished by the analyzer, and counts of categories and/or subcategories of particles obtained from the particle counter can be corrected.

A sample or portion thereof is provided onto particle counter 15 to detect particles and provide particle counts based on one or more selection criteria that may encompass sub-categories of at least two categories of particles. For example, the purported WBC category from the particle counter may also contain a small amount of giant PLTs and NRBCs. That category from the particle counter can further comprise subcategories of white blood cells that cannot be distinguished by the particle counter. Another portion of the sample may also be analyzed on the visual analyzer, as described below, to resolve these miscategorizations and/or subcategorize the undistinguished WBC subcategories.

A distribution of each of the at least two subcategories or categories can be determined on analyzer 17 as depicted in FIG. 14. Such a distribution can be presented in a numerical ratio, proportionate ratio and/or other function of the relative counts. In some embodiments, such a distribution can be determined according to methods disclosed herein on a visual analyzer 17 comprising a flowcell 22 and an imaging device 24. As described, sample 12A, which may be a portion of a sample, is applied to the at least one flowcell 22. At least one chemical comprising at least one of a diluent, a permeabilizing agent, a contrast agent is introduced to sample 12A. The at least one chemical comprising at least one of a diluent, a permeabilizing agent, and/or a contrast agent is effective to generate visual distinctions that differentiate the at least two categories of particles, and differentiate the at least two subcategories of the at least one category of particles. A plurality of images of particles of sample 12B is captured. An image analysis is performed on visual analyzer 17 and/or processor 18.

In some embodiments, processor 18 is programmed to distinguish the members of the at least two categories and/or subcategories. A proportionate ratio of the count of particles in each of the at least two subcategories or categories of particles can be determined, based on the plurality of images of particles of the sample. The particle count for the sub-categories of at least one of the at least two categories obtained from the particle counter 15 can then be corrected on processor 18 by using the distribution of each of the sub-categories. The concentration of each subcategory of particles can be calculated on processor 18, based on the proportionate ratio of each subcategory of particles and the particle count of the category of particles obtained from the particle counter.

Methods disclosed herein also can be used for differentiating one or more types of particles outside a detection range on particle counter 15, in accordance with some embodiments. For example, these particles can be blood cells or other fragments, which are too large or too small to be detected on particle counter 15. On visual analyzer 17 a proportionate ratio of the counts of one type of particle outside a detection range on the particle counter to another type of particle within the detection range of the particle counter can be determined based on the plurality of images of particles of the sample. The concentration of the type of particles outside the detection range in the sample then can be determined, by applying at least in part the proportionate ratio to the particle count obtained on the particle counter 15.

Focused Images

Figures 20A, 20B:
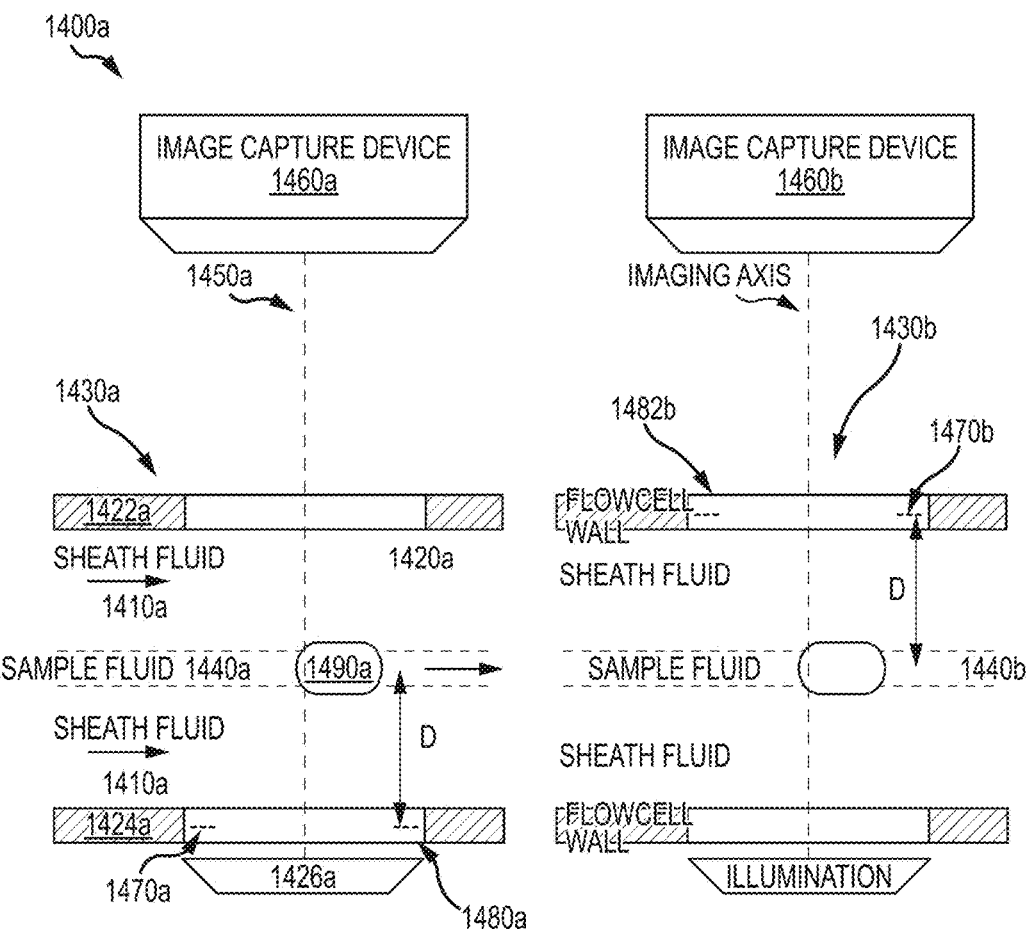
FIGS. 20A and 20B provide cross-section side views that illustrate aspects of imaging systems and methods, according to embodiments of the present invention.

FIGS. 20A and 20B provide cross-section side views that illustrate aspects of imaging systems and methods, according to embodiments of the present invention. With reference to FIG. 20A, a particle analysis system 1400a such as a hematology analyzer can be configured for combined viscosity and geometric hydrofocusing, for example using flowcell and viscous sheath fluid techniques such as those described in co-pending U.S. patent application Ser. No. 14/215,834, filed Mar. 17, 2014 (now U.S. Pat. No. 9,316,635 issued Apr. 19, 2016) and Ser. No. 14/216,533 filed Mar. 17, 2014 (now U.S. Pat. No. 9,322,752 issued Apr. 26, 2016), the contents of which are incorporated herein by reference. An exemplary method for imaging particles in a blood fluid sample using the particle analysis system can include flowing a sheath fluid 1410a along a flowpath 1420a of a flowcell 1430a of the particle analysis system. The flowpath 1420a can be defined at least in part by opposing flowcell walls 1422a, 1424a of the flowcell. The sheath fluid 1410a can have a viscosity that is different from a viscosity of the blood fluid sample. The imaging method can further include injecting the blood fluid sample into the flowing sheath fluid 1410a within the flowcell 1430a so that the blood fluid sample fluid flows in a sample flowstream 1440a. The sample flowstream 1440a can have a flowstream width greater than a flowstream thickness. The sample flowstream 1440a can also flow through a decrease in flowpath size and traverse an imaging axis 1450a. In the FIG. 20A illustration, the direction of flow is from the left to the right.

Additionally, the imaging method can include focusing an image capture device 1460a by imaging an imaging target 1470a having a position fixed relative to the flowcell 1430a. For example, as depicted here, the imaging target 1470a can have a position fixed relative to an illumination window 1480a of the flowcell. In some cases, the imaging target 1470a can be embedded within or fixed upon the window 1480a. Methods can also include acquiring a focused image of the particles of the sample fluid (e.g. particle 1490a, disposed at least partially within the flowstream 1440a) with the image capture device 1460a. The focused image is suitable for particle characterization and counting.

The image capture device 1460a can be focused on the sample flowstream 1440a using a displacement distance. For example, the displacement distance can correspond to a distance D between the sample flowstream 1440a and the imaging target 1470a. The viscosity difference between the sheath fluid 1410a and blood fluid sample, in combination with the decrease in flowpath size, is effective to hydrofocus the sample fluid in the sample flowstream 1440a at the imaging axis 1450a while retaining viability of cells in the blood fluid sample. For example, a viscosity hydrofocusing effect induced by an interaction between the sheath fluid 1410a and the sample fluid stream 1440a associated with the viscosity difference, in combination with a geometric hydrofocusing effect induced by an interaction between the sheath fluid 1410a and the sample fluid stream 1440a associated with the reduction in flowpath size, can be effective to provide a target imaging state in at least some of the fluid sample particles at the imaging axis 1450a while a viscosity agent in the sheath fluid 1410a retains viability of cells in the sample fluid stream 1440a leaving structure and content of the cells intact when the cells extend from the sample fluid stream 1440a into the flowing sheath fluid 1410a.

As the image capture device 1460a is focused on the sample flowstream 1440a using the displacement distance, the image capture device 1460a can obtain images of particles or cells within the sample flowstream 1440a at the imaging axis 1450a, or at an image capture site associated with the imaging axis 1450a. In some cases, the particles can be illuminated with an illumination source or lamp 1426a. Images of the sample flowstream 1440a can be obtained as particles approach the imaging axis 1450a, as the particles traverse the imaging axis 1450a, and/or as the particles flow away from the imaging axis 1450a.

FIG. 20B depicts aspects of an alternative flowcell configuration, where the imaging target 1470b has a position fixed relative to a viewport window 1482b of the flowcell 1430b. For example, the imaging target 1470b can be embedded within or fixed upon the window 1482b. As shown here, the imaging method can include focusing an image capture device 1460b by imaging an imaging target 1470b having a position fixed relative to the flowcell 1430b. Further, the image capture device 1460b can be focused on the sample flowstream 1440b using a displacement distance. For example, the displacement distance can correspond to a distance D between the sample flowstream 1440b and the imaging target 1470b.

Figure 20C:
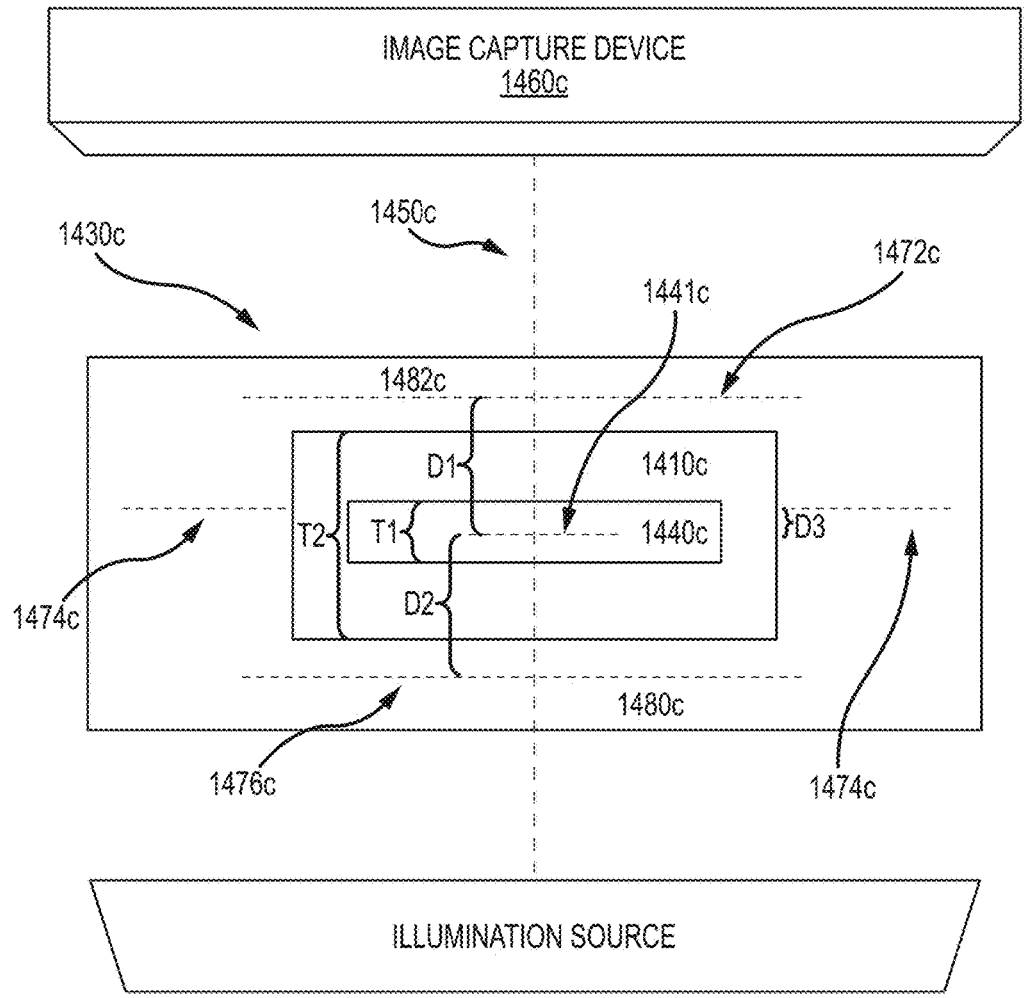
FIG. 20C depicts a cross-section end view of a flowcell according to embodiments of the present invention.

FIG. 20C depicts a cross-section end view of a flowcell 1430c, illustrating various alternative placement locations for an autofocus or imaging target. For example, an imaging target 1472c can be located at a viewport window 1482c of the flowcell 1430c. Optionally, an imaging target 1474c can be located at an illumination window 1480c of the flowcell 1430c. Further optionally, an imaging target 1476c can be located in a lateral flowcell wall (e.g. 1432c and/or 1434c). The image capture device 1460c can be focused on a sample flowstream 1440c, which is enveloped within a sheath fluid 1410c, a using the displacement distance. In some embodiments, the displacement distance can correspond to or be defined by a distance D1 along the imaging axis 1450c between the sample flowstream 1440c (or a central plane 1441c defined by the flowstream 1440c) and the viewport window imaging target 1472c. In some embodiments, the displacement distance can correspond to or be defined by a distance D2 along the imaging axis between the sample flowstream 1440a (or the central plane 1441c) and the illumination window imaging target 1476c. In some embodiments, the displacement distance can correspond to or be defined by a distance D3 along the imaging axis between the sample flowstream 1440a (or the central plane 1441c) and the flowcell lateral wall imaging target 1474c. In some cases, distance D3 has a value greater than zero. In some cases, distance D3 has a value of zero; that is, where the sample flowstream 1440a (or the central plane 1441c) is coplanar with the imaging target 1474c. In some cases, it is possible to define a displacement distance that is not calculated based on distance D1, distance D2, or distance D3. For example, a displacement distance may be a predetermined number or value that is provided by a flowcell or hematology analyzer manufacturer.

According to some embodiments, the sample flowstream 1440c can have a thickness T1 at the imaging axis within a range from about 2 μm to about 10 μm. In some cases, the flowpath or the sheath fluid 1410c can have a thickness T2 of about 150 μm at the imaging axis. As shown here, an imaging target 1472c can be located on a viewport window 1482c disposed between the sample flowstream 1440c and the image capture device 1460c. In some cases, an imaging target (e.g. 1474c) can be located between an illumination window 1480c and a viewport window 1482c. As discussed elsewhere herein, the process of acquiring a focused image can include adjusting a distance between the image capture device 1460c and the flowcell 1430c using the displacement distance. In some cases, as discussed elsewhere herein, the process of acquiring a focused image can include adjusting a focal distance of the image capture device 1460c using the displacement distance. In some cases, the process of acquiring a focused image can include adjusting the distance between the image capture device 1460c and the flowcell 1430c, and the process of adjusting the distance includes moving the flowcell 1430c, for example to a position closer to the image capture device 1460c, or to a position more distant from the image capture device 1460c.

Figure 20D:
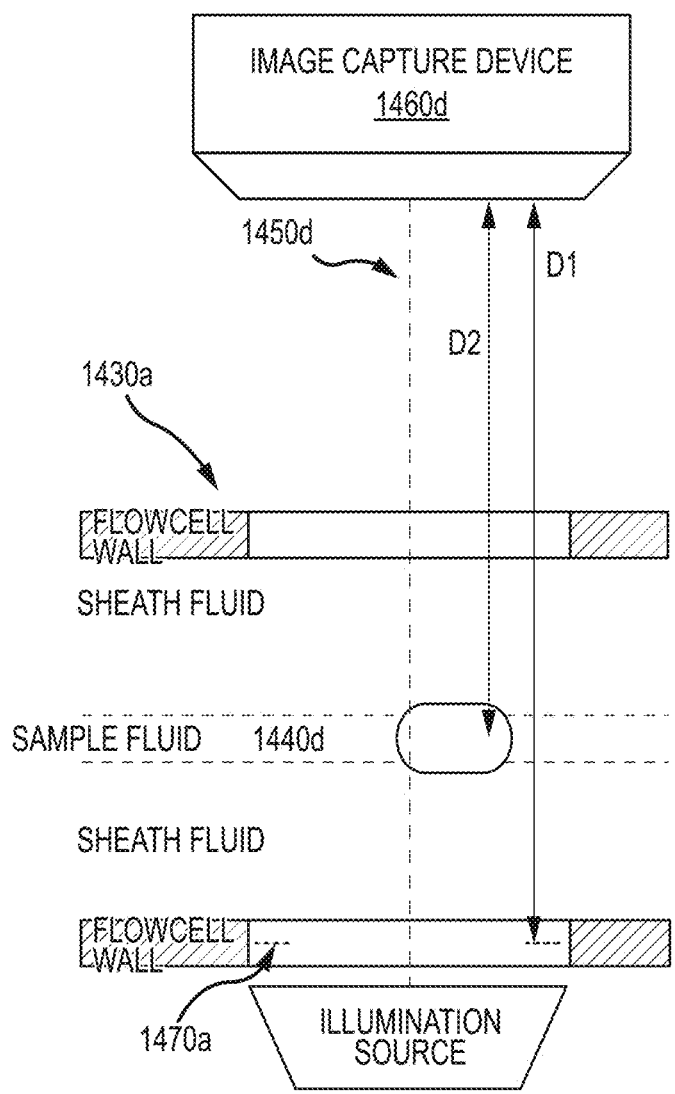
FIG. 20D shows a focal distance of the image capture device according to embodiments of the present invention.

As depicted in FIG. 20D, a first focal distance of the image capture device 1460d can correspond to a distance D1 (e.g. along the imaging axis 1450d) between the image capture device 1460d and the imaging target 1470d, and a second focal distance of the image capture device 1460d can correspond to a distance D2 (e.g. along the imaging axis 1450d) between the image capture device 1460d and the sample flow stream 1440d (or a central plane defined by the sample flow stream). In some cases, the imaging target may be located in another location in the flowcell, for example as depicted in FIG. 20C. According to some embodiments, the displacement distance can correspond to a distance difference between the first focal distance (or distance D1) and the second focal distance (or distance D2). The image capture device 1460d can be focused on the sample flowstream 1440d using this displacement distance (e.g. difference between D1 and D2).

FIG. 21 depicts an elevation view showing embodiments of an autofocus pattern (or imaging target), which for example can be located on illuminating orifices or window, on a viewing portal or window, or at another flowcell location. The target can fade as the distance or position of the high optical resolution imaging device is moved relative to the ribbon-shaped sample stream. As depicted in FIGS. 9-12B, an imaging or focus target (autofocus pattern) can reside on the periphery of the area of view in which the sample is to appear. With returning reference to FIG. 21, it can be seen that it is also possible that the focus target can be defined by contrasting shapes that reside in the field of view.

Figure 22A:
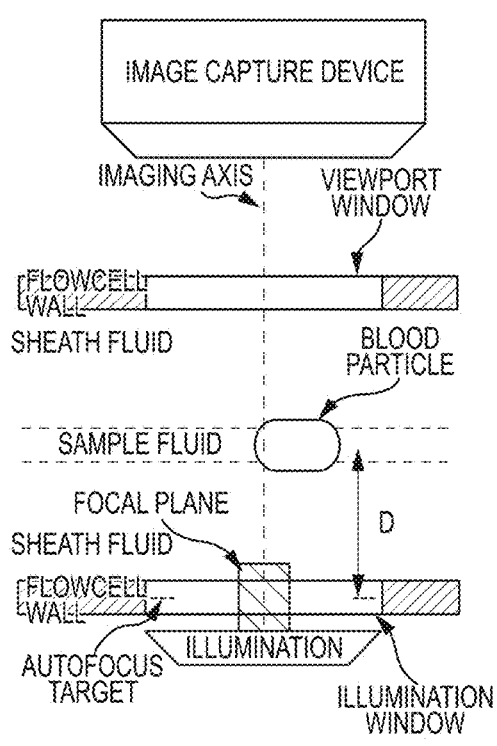
FIGS. 22A and 22B show focus configurations according to embodiments of the present invention.

When the imaging device is in focus on the autofocus pattern (target) (panel B in FIG. 21), the shapes as imaged by the device are well defined and can be used for autofocusing as described herein, namely to seek the distance between the target and the imaging device at which the shapes produce the highest contrast in amplitude between adjacent pixels located along lines that cross over the shapes, such as the lines shown as arrow heads. The focus configuration depicted in panel B corresponds to an analogous focus configuration depicted in FIG. 22A. As illustrated in FIG. 22A, the focal plane of the image capture device is aligned with the autofocus target, and hence the image capture device is in a position to obtain sharp images of the autofocus target.

Figure 22B:
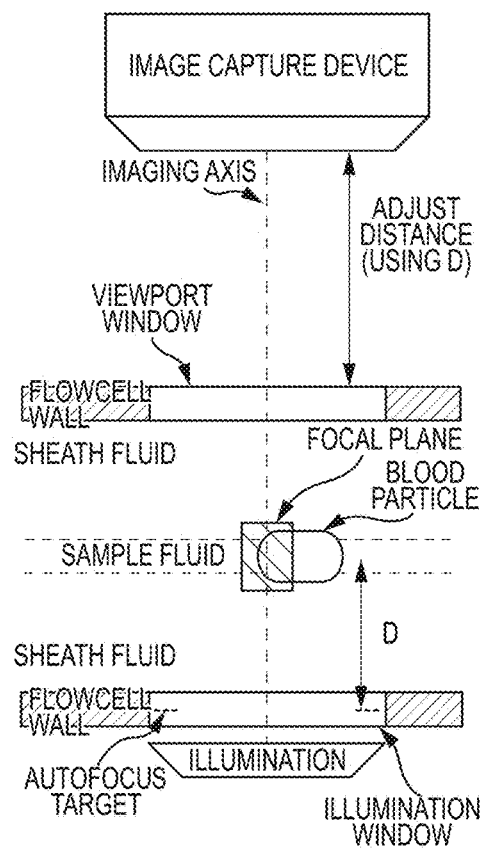

With returning reference to FIG. 21, when the working location (e.g. focal plane of imaing device) is moved away from the autofocus pattern (shown in panels A and C, shown left and right of autofocus pattern in FIG. 21), for example by adjusting the working distance of the objective or the distance between the objective and its focal plane, the focus target shapes now go out of focus, and at the position where the high optical resolution imaging device is focused on the ribbon-shaped sample stream, the focus target shapes are no longer discernable at all (see panel D in FIG. 21). The focus configuration depicted in panel D can corresponds to an analogous focus configuation depicted in FIG. 22B. As illustrated in FIG. 22B, the focal plane of the image capture device is aligned with the sample fluid stream, and hence the image capture device is in a position to obtain sharp images of particles in the sample flowstream. The focal plane of FIG. 22A is separated from the focal plane of FIG. 22B by a distance D. As shown in FIG. 22B, by moving the image capture device a distance D it is possible to also move the focal plane a distance D, and hence move the focal plane from the autofocus target to the sample flowstream. In some cases, the focal plane can be moved from the autofocus target to the sample flowstream by internally adjusting the focal distance of the image capture device while keeping the image capture device in a fixed position relative to the flowcell. In some cases, the focal plane can be moved from the autofocus target to the sample flowstream by internally adjusting the focal distance of the image capture device in combination with adjusting the position of the image capture device relative to the flowcell. The autofocus shapes can be provided at any location that is within view and is fixed relative to the flowcell, such as on the illumination opening or window, or on the front or back of the viewing port or window through which the high optical resolution imaging device is directed, or at a fixture attached to the photocell to hold a target in position to be imaged.

According to some embodiments, when the high optical resolution imaging device is moved over the displacement distance and the autofocus pattern goes out of focus, the features that appear in focus are the blood cells as opposed to the autofocus pattern. In the embodiment of FIG. 21, the autofocus pattern is defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 µm in a flowcell dimensioned for hematology (blood cell) imaging applications. In some embodiments, the autofocus feature maintains the high optical resolution imaging device within 1 µm of the optimal focus distance.

Accordingly, the features described in FIG. 21 provide an exemplary technique for determining a displacement distance. For example, a method of determining a displacement distance may include an autofocusing process that involves injecting a test fluid sample into a sheath fluid to form a test sample flowstream within a flow cell, and obtaining a first focused image of the imaging target using an image capture device. The first focused image can correspond to panel B in FIG. 21, where the focused imaging target and the image capture device define a first focal distance. As depicted here, the focal plane or working distance/location of the image capture device is positioned at the imaging target. The autofocusing process can also include obtaining a second focused image of the test sample flowstream using the image capture device. The second focused image can correspond to panel D in FIG. 21, where the focused test sample flow stream and the image capture device define a second focal distance. As depicted here, the focal plane or working distance/location of the image capture device is positioned at the imaging target. The autofocusing procees may further include obtaining the displacement distance by calculating a difference between the first focal distance and the second focal distance. In some cases, the test fluid sample is the same as the blood fluid sample and the test sample flowstream is the same as the sample flowstream. In some cases, the autofocusing process establishes a focal plane associated with the image capture device, and the focal plane remains stationary relative to the image capture device. In some cases, the process of autofocusing the image capture device includes determining an optimal focus position from among a plurality of focus positions.

According to some embodiments, the image capture device can be focused on the sample flowstream without using temperature data. For example, a process of focusing the image capture device on the sample flowstream can be performed independently of a temperature of the image capture device. In some cases, an imaging target can include a scale (e.g. as depicted in FIG. 12B) for use in positioning the imaging axis of the image capture device relative to the sample flowstream. In some cases, the imaging target can include an iris aligned relative to the imaging axis, such that the imaged particles are disposed within an aperture defined by the iris, and one or more edge portions of the iris are imaged during autofocusing.

In exemplary embodiments, autofocusing techniques can position the flowcell to within ±1 μm from an optimal focal position of the sample stream. In some cases, embodiments encompass autofocus techniques that can automatically focus the imaging system without the need for a separate focusing liquid or solution or any user intervention. Exemplary autofocusing techniques can also acount for mechanical causes of suboptimal focusing performance, such as drift or thermal expansion which can cause fluctuations in the distance between the imaging device objective and flowcell. In some cases, it was observed that the location of the sample flow within the flowcell can be very stable and temperature independent. Hence, exemplary imaging techniques can involve focusing on an imaging target in the flowcell, and using a fixed offset to achieve optimal focus on the sample stream.

According to some embodiments, the microscope objective that is used on an imaging system has a numerical aperture of 0.75, resulting in a theoretical depth of field (DoF) of ±0.5 μm. In certain experimental trials, it was observed that good image quality could be obtained at ±1.25 μm from an optimal focal point. It was also observed that a practical or experimental depth of field could be different from the theoretical depth of field. For example, in certain experimental trials it was observed that the depth of field was around 2.5 to 3 μm. Based on certain experimental studies, it was determined that autofocus performance for positioning the flowcell within ±1.25 μm could ensure good image quality. In some embodiments, an autofocus system can operate to position the flowcell within ±1 μm from an optimal focus position of the sample stream. In certain experimental trials, it was observed that autofocus techniques as disclosed herein can repeatedly locate a target in a flowcell with a standard deviation of less than 0.3 μm. In some cases, trial autofocus system runs demonstrated excellent repeatability (standard deviation ≤0.23 μm) and were able to determine the focus position of the sample stream to within <0.6 μm from an optimized metric position which is within a ±1 μm positional tolerance. Additional autofocus trial runs at a variety of temperature conditions also exhibited excellent positioning performance (e.g. flowcell positioning within a required ±1 μm tolerance of and optimal focus position). This degree of accuracy in an automated analyzer system is well suited for consistently and reliably obtaining high quality images of particles from a blood fluid sample flowing in a thin ribbon flowstream as disclosed elsewhere herein, over an operational temperature range corresponding to standard laboratory conditions.

Figure 23:
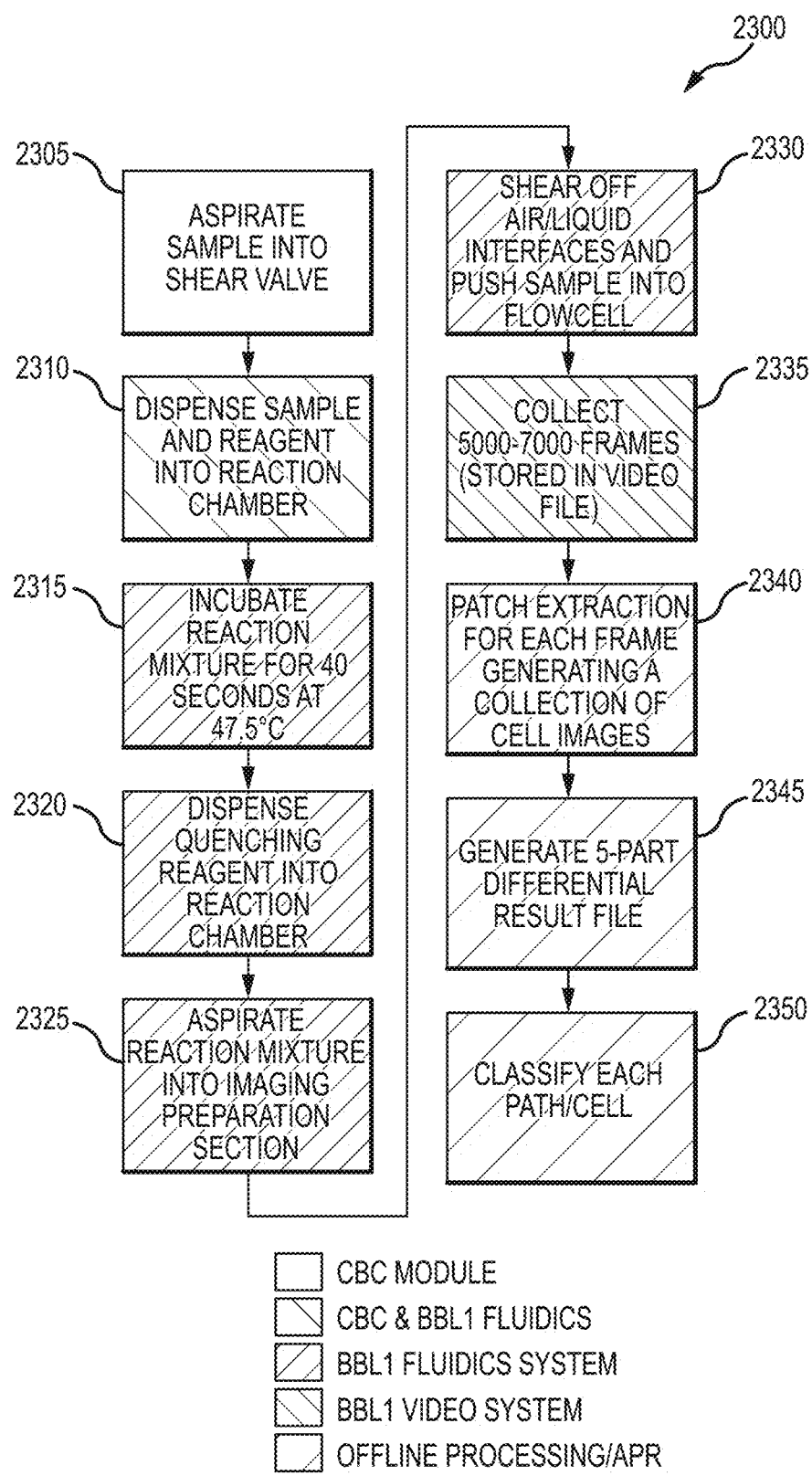
FIG. 23 depicts aspects of sample processing techniques, according to embodiments of the present invention.

FIG. 23 depicts aspects of a sample processing methods 2300 according to embodiments of the present invention. As shown here, sample processing methods may include aspirating a sample into a shear valve, as indicated by step 2305. This step can be performed by a CBC module. Methods may also include dispensing sample and reagent into a reaction chamber, as depicted in step 2310. This step can be performed by a CBC module and a first fluidics system (e.g. BBL1 Fluidics). Further, methods may include incubating the reaction mixture for a desired time duration at a desired temperature (e.g. for 40 seconds at 47.5° C.), as indicated by step 2315. Methods may also include dispensing a quenching reagent into the reaction chamber, as indicated by step 2320, aspirating the reaction mixture into an imaging preparation section, as indicated by step 2325, and shearing off air/liquird interfaces and pushing sample into the flowcell, as indicated by step 2330. According to some embodiments, steps 2315, 2320, 2325, and 2330 can be performed by a fluidics system (e.g. BBL Fluidics). According to some embodiments, methods may include collecting images, as indicated in step 2335. For example, an imaging collection process may include collecting 5000-7000 frames, and the images can be stored in a video file. In some cases, step 2335 can be performed by a video system (e.g. BBL Video). What is more, methods may include performing a patch extraction for each frame generating a collection of images, as indicated by step 2340, generating a 5-part differential or other diagnostic result file, as indicated by step 2345, and classifying each patch/cell, as indicated by step 2350. In some cases, steps 2340, 2345, and 2350 can be performed with offline processing using hematology automated particle recognition (APR) software.

The PIOAL has a suitable viscosity and density, and flow rates at the point of introduction to the flowcell of the sample are such that the sample fluid flattens into a thin ribbon. The ribbon-shaped sample stream is carried along with the PIOAL, to pass in front of a viewing port where an objective lens and a light source are arranged to permit viewing of the ribbon-shaped sample stream. The sample fluid is introduced, for example, injected at a point where the flowpath of the PIOAL narrows symmetrically. As a result, the sample fluid stream is flattened and stretched into a thin ribbon. A PIOAL of this disclosure may be used as the sheath fluid with any visual analyzer of this disclosure. In one embodiment, the PIOAL can be introduced into an end of the flowcell to carry along the sample fluid toward the discharge.

The dimension of the ribbon-shaped sample stream in the viewing zone is affected by geometric thinning of the PIOAL flowpath and differential linear velocity of the sample fluid and PIOAL resulting in thinning and stretching of the ribbon-shaped sample stream. The initial differential linear velocity of the sample to PIOAL may range from 0.5:1 to 5:1. The PIOAL flowpath cross section may be thinned by reducing the depth by a factor of about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, or 200:1. In one embodiment, the geometric thinning is 40:1. In one embodiment, the geometric thinning is 30:1. Factors taken into account are transit time through the flowcell, desired rate of sample throughput, achieving a ribbon-shaped sample stream thickness comparable to particle size, obtaining alignment of particles and organelles, achieving in focus content of particles, balancing pressure, flow, and viscosity within operational limits, optimizing ribbon-shaped sample stream thickness, obtaining a desired linear velocity, manufacturability considerations, and volumes of sample and PIOAL required.

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flowcell is 1, 2, 3, or 4 seconds, or any range in between any two of those times. In some embodiments the transit time may be less than 4, 3 or 2 seconds.

The viscosities and the flow rates of the sample fluid and the PIOAL and the contour of the flowcell are arranged such that the PIOAL flow flattens and stretches the sample flow into a flat ribbon consistently through the viewing zone at a dependable location corresponding to an image capture site. The sample fluid stream may be compressed to approximately 2 to 3 µm in fluid flow thickness. Several blood cell types have diameters larger than the stream thickness. Shear forces in the direction parallel to the direction of the flow cause an increase of an image projection of the particles under imaging conditions in the focal plane of the high optical resolution imaging device and/or causing the intraparticle structures, for example, intracellular structures, organelles or lobes, to be positioned, repositioned, and/or better-positioned to be substantially parallel to the direction of flow. The high optical resolution imaging device depth of field is up to 7 µm, for example, 1-4 µm.

The flow cross section of the PIOAL, with the ribbon-shaped sample stream carried along, is constant through a viewing zone in front of a viewing port through which the objective lens is directed. The objective lens may be the objective component of a high optical resolution imaging device or the digital image capture device. The ribbon-shaped sample stream follows a path across the viewing zone at a known and repeatable position within the flowcell, for example, at a known and repeatable distance from two walls of the flowcell, being discharged downstream.

Optical information from the particles in the sample are detected by a detecting section in the analyzer, when the ribbon-shaped sample stream is carried through the viewing zone in front of the viewing port, thereby generating data from the particles/cells contained in the sample. The use of this analyzer allows capture, processing, categorization and subcategorization and counting of cells and/or particles contained in samples. The PIOAL liquid can be prepared by the addition of viscosity modifying agent, buffer agent, pH adjusting agent, antimicrobial agent, ionic strength modifier, surfactant, and/or a chelating agent. Exemplary functional components and/or features of the analyzer in the present disclosure can include, for example, the ability to acquire and/or process data from image analysis, sample staining processing, image processing, and/or particle image identification, counting, and/or categorization and subcategorization.

In one embodiment this disclosure was based on the surprising and unexpected discovery that the addition of a suitable amount of a viscosity agent in the PIOAL significantly improves particle/cell alignment in a flowcell, leading to a higher percentage of aligned cells, or cellular components in focus, and higher quality images of cells and/or particles in flow. A viscosity differential in combination with a geometric focusing effect of a narrowing transition zone can achieve enhanced alignment and focus results. The addition of the viscosity agent increases the shear forces on cells like RBCs, which improves the alignment of the cells in a plane substantially parallel to the flow direction, which results in image optimization. This also results in positioning, repositioning, and/or better-positioning of intraparticle structures such as intracellular structures, organelles or lobes substantially parallel to the direction of flow, which results in image optimization. The viscosity agent also reduces misalignment of cells, generally, but not limited to cells that are smaller in diameter than the flow stream.

Alignment of cells that are smaller in diameter than the flow stream, for example, red blood cells may be obtained by for example, increasing the viscosity of the PIOAL, or by increasing the flow speed ratio. This results in alignment of the RBCs parallel to the direction of the flow and to the focal plane FP (e.g. as depicted in FIG. 4K). In some embodiments, a reduction in RBC misalignment and/or increase in RBC alignment is achieved by increasing the viscosity of the PIOAL.

The ribbon-shaped sample stream thickness can be affected by the relative viscosities and flow rates of the sample fluid and the PIOAL. The source of the sample and/or the source of the PIOAL, for example comprising precision displacement pumps, can be configured to provide the sample and/or the PIOAL at controllable flow rates for optimizing the dimensions of the ribbon-shaped sample stream, namely as a thin ribbon at least as wide as the field of view of the high optical resolution imaging device or the digital image capture device.

The flow cross section of the PIOAL, with the ribbon-shaped sample stream carried along, is constant through a viewing zone in front of a viewing port through which the high optical resolution imaging device is directed. The ribbon-shaped sample stream follows a path across the viewing zone at a known and repeatable distance from either of the front and rear walls of the flowcell, being discharged downstream of that.

The present disclosure provides a technique for automatically achieving a correct working position of the high optical resolution imaging device for focusing on the ribbon-shaped sample stream. The flowcell structure is configured such that the ribbon-shaped sample stream has a fixed and repeatable location between the walls of the flowcell defining the flow path of sample fluid, in a thin ribbon between layers of PIOAL, passing through a viewing zone in the flowcell. In the flowcell embodiments disclosed, for example in FIG. 1-4G, the cross section of the flowpath for the PIOAL can narrow symmetrically at a transition zone, and a sample can be inserted through a flattened orifice such as a tube with a rectangular lumen at the orifice. The narrowing flowpath (for example geometrically narrowing in cross sectional area by a ratio of 20:1 to 40:1) and also due to an optionally greater linear velocity of the PIOAL compared to the flow of the sample, cooperate to flatten the sample cross section by a ratio of about 20:1 to 70:1. According to some embodiments, the ratio can be within a range from 10:1 to 100:1, within a range from 50:1 to 100:1, within a range from 70:1 to 80:1. According to some embodiments, the ratio is 75:1. Effectively, due to the combination of flow rate, viscosity, and geometry, the sample is formed into a thin ribbon. The narrowing flowpath (for example geometrically narrowing in cross sectional area by a ratio of 40:1, or by a ratio between 20:1 to 70:1) and a difference in linear speed of the PIOAL compared to the flow of the sample, cooperate to compress the sample cross section by a ratio of about 20:1 to 70:1. In some embodiments the cross section thickness ratio may be 40:1. In some embodiments the cross section thickness ratio may be 30:1.

As a result, process variations such as the specific linear velocities of the sample and the PIOAL, do not tend to displace the ribbon-shaped sample stream from its location in the flow. Relative to the structure of the flowcell, the ribbon-shaped sample stream location is stable and repeatable.

In another aspect, this invention relates to a kit comprising the particle contrast agent compositions of this invention. The kit may also contain instructions on the use of particle contrast agent composition according to any of the methods described herein. The kit may also include a particle and/or intracellular organelle alignment liquid (PIOAL). The kit may also contain a programmable storage medium and related software for image based identification of particles such as neutrophil, lymphocytes, monocyte, eosinophils, basophils, platelets, reticulocytes, nucleated RBCs, blasts, promyelocytes, myelocytes, metamyelocytes, bacteria, fungi, protists, protozoa, or parasites. The kit may also comprise one or more buffers, which may include isotonic buffers and/or diluents. The kit and or buffer may further comprise a surfactant, a pH adjusting agent, and/or an antimicrobial agent. In other embodiments, the kit may also comprise a cleaning or flushing solution. The kit may also comprise standards for positive and negative controls. In some embodiments the standard may comprise a standard stained cell reagent. The kit may also comprise disposables such as disposable micropipettes, tips or tubes for transferring the components of the kit. The kit may contain any one, or any combination of two or more of these kit components.

The discrimination of blood cells in a blood sample is an exemplary application for which embodiments of the instant invention are particularly well suited. The sample is prepared by automated techniques and presented to a high optical resolution imaging device as a thin ribbon-shaped sample stream to be imaged periodically while the ribbon-shaped sample stream flows across a field of view. The images of the particles (such as blood cells) can be distinguished from one another, categorized, subcategorized, and counted, using pixel image data programmed processing techniques, either exclusively automatically or with limited human assistance, to identify and count cells or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cells of each distinguished category and/or subcategory in the sample as a whole. The sample used for visual discrimination can be diluted, but the proportions of cells in each category and/or subcategory are represented in the diluted sample, particularly after a number of images have been processed.

The apparatus, compositions, and methods disclosed herein are useful in discriminating and quantifying cells in samples based on visual distinctions. The sample can be a biological sample, for example, a body fluid sample comprising white blood cells, including without limitation, blood, serum, bone marrow, lavage fluid, effusions, exudates, cerebrospinal fluid, pleural fluid, peritoneal fluid, and amniotic fluid. In some embodiments, the sample can be a solid tissue sample, e.g., a biopsy sample that has been treated to produce a cell suspension. The sample may also be a suspension obtained from treating a fecal sample. A sample may also be a laboratory or production line sample comprising particles, such as a cell culture sample. The term sample may be used to refer to a sample obtained from a patient or laboratory or any fraction, portion or aliquot thereof. The sample can be diluted, divided into portions, or stained in some processes.

In one aspect, the systems, compositions and methods of this disclosure provide surprisingly high quality images of cells in a flow. In one aspect, the visual analyzer can be used in methods of this disclosure to provide automated image based WBC differential counting. In certain embodiments, the methods of this disclosure relate to automated identification of visual distinctions, including morphological features and/or abnormalities for determining, diagnosing, prognosing, predicting, and/or supporting a diagnosis of whether a subject is healthy or has a disease, condition, abnormality and/or infection and/or is responsive or non-responsive to treatment. The system may further comprise a particle counter in some embodiments. Applications include categorizing and/or subcategorizing, and counting cells in a fluid sample, such as a blood sample. Other similar uses for counting additional types of particles and/or particles in other fluid samples are also contemplated. The system, compositions, and methods of this invention can be used for real-time categorization and subcategorization and viewing of images using any suitable automated particle recognition algorithm. The captured images for each sample can be stored to be viewed at a later date.

In another aspect, the apparatus, compositions, and methods of this invention provide surprisingly more accurate image based cell categorization and subcategorization and flagging which reduces the manual review rate compared to the manual review rate when using current automated analyzers. The systems, compositions, and methods reduce the manual review rate and permit the manual review to be performed on the instrument. In addition, the systems, compositions, and methods of this disclosure also reduce the percentage of samples flagged during automated analysis as requiring manual review.

The present disclosure further relates to systems, methods and compositions for combining a complete blood count (CBC) counter with an analyzer, such as a visual analyzer, in order to obtain a CBC and an image based expanded white blood cell differential count and an image based expanded platelet count, thereby extending the effective detection range for counting platelets.

Accordingly, in some embodiments, the present disclosure provides an apparatus and a method for analyzing a sample containing particles, for example, blood cells. According to this disclosure, a visual analyzer is provided for obtaining images of a sample comprising particles suspended in a liquid. In some embodiments, the visual analyzer comprises a flowcell and an autofocus component, in which a liquid sample containing particles of interest is caused to flow through a flowcell having a viewport through which a camera coupled to an objective lens captures digital images of particles. Exemplary autofocus techniques which can be implemented using embodiments of the present invention are disclosed in co-pending U.S. patent application Ser. No. 14/216,811 filed Mar. 17, 2014, the content of which is incorporated herein by reference. The flowcell is coupled to a source of sample fluid, such as a diluted and/or treated blood sample or other bodily fluid sample as described herein, and to a source of a clear sheath fluid, or particle and/or intracellular organelle alignment liquid (PIOAL).

In one embodiment, the apparatus also comprises a particle counter having at least one detection range, as well as an analyzer, and a processor. The analyzer and the processor are configured to provide additional information to correct counting, categorization, and subcategorization errors associated with the particle counter, and further determine accurate particle count or concentration of different categories and/or subcategories of particles in the sample.

The instant disclosure provides methods and compositions useful for particle and/or intracellular organelle alignment in conducting image-based sample analysis. In some embodiments, this disclosure relates to methods and compositions for combined counting and imaging system with the ability to perform a complete blood count (CBC) and an image based expanded white blood cell (WBC) differential able to identify and count cell types, such as WBCs, RBCs, and/or platelets, including, for example, neutrophils, lymphocytes, monocytes, eosinophils, basophils, reticulocytes, nucleated RBCs, blasts, promyelocytes, myelocytes, or metamyelocytes, and to provide image based information for WBC counts and morphologies, red blood cell (RBC) counts and morphologies and platelet (PLT) counts and morphologies.

In other embodiments, this disclosure relates to a PIOAL that can be used in image based analysis of particles as described herein. Cell category and/or subcategory count in blood samples is used in this disclosure as nonlimiting examples of the sort of samples that may be analyzed. In some embodiments, cells present in samples may also include bacterial or fungal cells as well as white blood cells, red blood cells and/or platelets. In some embodiments, particle suspensions obtained from tissues or aspirates may be analyzed.

The discrimination of blood cells in a blood sample is an exemplary application for which the subject matter is particularly well suited. The sample is prepared by automated techniques and presented to a high optical resolution imaging device as a ribbon-shaped sample stream to be imaged periodically while the sample flows across a field of view. The images of the particles (such as blood cells) can be distinguished from one another, categorized, subcategorized, and/or counted, using pixel image data programmed processing techniques, either exclusively automatically or with limited human assistance, to identify and count cells or particles. In addition to the cell images, which can be stored and made available in the case of unusual or critical features, the output data includes a count of the occurrences of each particular category and/or subcategory of cell or particle distinguished in the recorded sample images. The counts of the different particles found in each image can be processed further, for example used to accumulate accurate and statistically significant proportionate ratios, or functions thereof of cells of each distinguished category and/or subcategory in the sample as a whole. The sample used for visual discrimination can also be highly diluted, but the proportions of cells in each category and/or subcategory are represented in the distribution for the diluted sample, particularly after a number of images have been processed.

In some aspects, samples are presented, imaged and analyzed in an automated manner. In the case of blood samples, the sample may be substantially diluted with a suitable diluent or saline solution, which reduces the extent to which the view of some cells might be hidden by other cells in an undiluted or less-diluted sample. The cells can be treated with agents that enhance the contrast of some cell aspects, for example using permeabilizing agents to render cell membranes permeable, and histological stains to adhere in and to reveal features, such as granules and the nucleus. In some embodiments it may be desirable to stain an aliquot of the sample for counting and characterizing particles which include reticulocytes, nucleated red blood cells, and platelets, and for white blood cell differential, characterization and analysis. In other embodiments, samples containing red blood cells may be diluted before introduction to the flowcell and imaging.

According to some embodiments, the particulars of sample preparation apparatus and methods for sample dilution, permeabilizing and histological staining, generally are accomplished using precision pumps and valves operated by one or more programmable controllers, and are not central to this disclosure. Examples can be found in patents assigned to International Remote Imaging Systems, Inc., such as U.S. Pat. No. 7,319,907, concerning programmable controls. Likewise, techniques for distinguishing among certain cell categories and/or subcategories by their attributes such as relative size and color can be found in U.S. Pat. No. 5,436,978 in connection with white blood cells. The disclosures of these patents are hereby incorporated by reference. According to some embodiments, sample preparation techniques may include staining, lysing, permeabilizing, and other processing modalities such as those described in co-pending U.S. patent application Ser. No. 14/216,339 filed Mar. 17, 2014, (now U.S. Pat. No. 9,279,750 issued Mar. 8, 2016), the content of which is incorporated herein by reference.

The term high optical resolution imaging device can include devices that are capable of obtaining particles images with sufficient visual distinctions to differentiate morphological features and/or changes. Exemplary high optical resolution imaging devices can include devices with an optical resolution of 1 µm or lower, including for example, 0.4 to 0.5 µm, such as for example, 0.46 µm In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using a visual analyzer comprising a flowcell, a high optical resolution imaging device or the digital image capture device, optionally with an autofocus feature.

In one embodiment, the images provide information relating to the cytosolic, cell nucleus and/or nuclear components of the cell. In one embodiment, the images provide information relating to the granular component and/or other morphological features of the cell. In one embodiment, the images provide information relating to cytosolic, nuclear and/or granular components of the cell. The granular and/or nuclear images and/or features are determinative for cell categorization and subcategorization both independently or in combination with each other.

In one aspect of the methods of this invention, the cells contacted with particle contrast agent composition and/or imaged are nucleated red blood cells. In yet another aspect, the methods of this invention relate to a method for performing image-based red blood cell categorization and subcategorization comprising: a) imaging a portion of the red blood cells; and b) determining the morphology of the imaged red blood cells. As used herein, red blood cells (RBC) can include, for example, normal or abnormal red blood cells, reticulocytes, nucleated red blood cells, and/or malaria-infected cells. In some embodiments, the imaging is performed using the apparatus of this disclosure such as an apparatus comprising a particle counter, a visual analyzer and a processor.

As used herein, an exemplary complete blood count (CBC) can include a test panel typically requested by a doctor or other medical professional that provides information about the particles and/or cells in a patient's blood sample. Exemplary cells that circulate in the bloodstream can be generally divided into three types: including but not limited to, for example, white blood cells (e.g., leukocytes), red blood cells (e.g., erythrocytes), and platelets (e.g., thrombocytes).

As used herein, abnormally high or low counts may indicate the presence of disease, disorder, and/or condition. Thus, a CBC is one of the commonly performed blood tests in medicine, as it can provide an overview of a patient's general health status. Accordingly, a CBC is routinely performed during annual physical examinations.

As used herein, typically a phlebotomist collects the blood sample from the subject, the blood is generally drawn into a test tube typically containing an anticoagulant (e.g., EDTA, sometimes citrate) to stop it from clotting. The sample is then transported to a laboratory. Sometimes the sample is drawn off a finger prick using a Pasteur pipette for immediate processing by an automated counter. In one embodiment, the particle image is acquired while the particle is enveloped in a sheath fluid or PIOAL. In certain embodiments, the blood sample may be viewed on a slide prepared with a sample of the patient's blood under a microscope (a blood film, or peripheral smear). In certain embodiments, the complete blood count is performed by an automated analyzer.

As used herein, in general, blood analyzers can aspirate a very small amount of the specimen through narrow tubing. Sensors can detect the count and/or the number of cells passing through the tubing, and can identify the type of cell. Exemplary sensors may include detectors of light (e.g., visible, UV or IR) and/or electrical impedance. Exemplary detection parameters may include size, volume, and/or cellular features. In certain embodiments, the sensors can detect visible and non-visible light in a wavelength spectrum ranging from about 200 nm to about 10000 nm. In certain embodiments, the sensors can detect a wavelength of between about between 380 nm and about 760 nm.

As used herein, data/parameters of a blood count can include, for example, total red blood cells; hemoglobin—the amount of hemoglobin in the blood; hematocrit or packed cell volume (PCV); mean corpuscular volume (MCV)—the average volume of the red cells (anemia is classified as microcytic or macrocytic based on whether this value is above or below the expected normal range. Other conditions that can affect MCV include thalassemia, reticulocytosis and alcoholism); mean corpuscular hemoglobin (MCH)—the average amount of hemoglobin per red blood cell, in picograms; mean corpuscular hemoglobin concentration (MCHC)—the average concentration of hemoglobin in the cells; red blood cell distribution width (RDW)—the variation in cellular volume of the RBC population; total white blood cells; neutrophil granulocytes (may indicate bacterial infection, typically increased in acute viral infections). Due to the segmented appearance of the nucleus, neutrophils are sometimes referred to as "segs." The nucleus of less mature neutrophils is not segmented, but has a band or elongated shape. Less mature neutrophils—those that have recently been released from the bone marrow into the bloodstream—are known as "bands". Other data/parameters for a blood count can also include, for example, lymphocytes (e.g., increased with some viral infections such as glandular fever, and in chronic lymphocytic leukemia (CLL), or decreased by HIV infection); monocytes (may be increased in bacterial infection, tuberculosis, malaria, Rocky Mountain spotted fever, monocytic leukemia, chronic ulcerative colitis and regional enteritis; eosinophil granulocytes (e.g., increased in parasitic infections, asthma, or allergic reaction); basophil granulocytes (e.g., increased in bone marrow related conditions such as leukemia or lymphoma.

As used herein, data/parameters of a blood count can also include, for example, data associated with platelets, including platelet numbers, information about their size and the range of sizes in the blood; mean platelet volume (MPV)—a measurement of the average size of platelets.

In another aspect of the methods of this invention, the cells contacted with particle contrast agent composition and/or imaged are abnormal cells, such as malaria-infected cells, atypical lymphocytes. In some aspects of this invention, the cells are abnormal cells which can be used to identify, predict, diagnose, prognose, or support a diagnosis of a condition, disease, infection and/or syndrome.

In another aspect of the methods of this invention, the cells are platelets.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape and any size. In certain embodiments, particles can comprise cells. Examples of particles include but are not limited to cells, including blood cells, fetal cells, epithelials, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes and blasts. In addition to mature RBCs, members of RBCs may include nucleated RBCs (NRBCs) and reticulocytes. PLTs may include "giant" PLTs and PLT clumps. Blood cells and formed elements are further described elsewhere in this disclosure.

Exemplary particles can include formed elements in biological fluid samples, including for example, spherical and non-spherical particles. In certain embodiments, the particles can comprise non-spherical components. The image projection of non-spherical components can be maximized in the focal plane of the high optical resolution imaging device. In certain embodiments, the non-spherical particles are aligned in the focal plane of the high optical resolution imaging device (aligned in a plane substantially parallel to the direction of the flow). In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles.

As used herein, detectable and measurable particle parameters can include, for example, visual and/or non-image based indices of size, shape, symmetry, contour and/or other characteristics.

In another embodiment, this disclosure relates to a method for imaging particles using, for example, the kits of this invention, in methods comprising, for example: 1) illuminating the particles with light in a visual analyzer; 2) obtaining a digitized image of sample particles enveloped in a PIOAL; and 3) analyzing particle containing samples based on the image information. In other embodiments, the method may further comprise contacting the sample containing particles with a particle contrast agent composition prior to illuminating the treated sample.

In one embodiment, the particles analyzed comprise at least one of a spherical particle, a non-spherical particle, or both. In another embodiment, the particles comprise at least one spherical particle. In still another embodiment, the particles comprise at least one nonspherical particle. In another embodiment, an image projection of non-spherical particles or particles having non-spherical components is maximized in a plane substantially parallel to the flow direction. The particles may be, for example, WBCs, RBCs, and/or platelets. In one embodiment, at least 50% of the non-spherical particles are aligned in a plane substantially parallel to the direction of flow. In another aspect, use of the PIOALs of this invention in a flowcell permits at least 90% of the non-spherical particles to be aligned in a plane substantially parallel to the direction of flow.

Flow of the cells smaller than the thickness of the ribbon-shaped sample stream enveloped in PIOAL, results in alignment of those cells parallel to the direction of the flow. In one embodiment of this disclosure, at least 92% of the non-spherical particles are aligned in a plane substantially parallel to the direction of flow. In yet another embodiment, at least 90% of the non-spherical particles are aligned a plane substantially parallel to the direction of flow. In another embodiment, at least 75%, 80%, 85%, 86%, 87%, 88%, 89%, 90%, 91%, 92%, 93%, 94% or at least 95% of the particles are substantially aligned, namely within 20 degrees from a plane substantially parallel to the direction of flow. In another embodiment, the percentage of non-spherical and/or spherical particles are aligned in a plane substantially parallel to the direction of flow may be any range between any two of the recited percentages, for example, at least 75-85%, 75-80%, and other ranges such as 75-92%.

Shear forces in the direction parallel to the direction of the flow as a result of flow of larger cells in the sample enveloped in the PIOAL, such as WBCs, results in positioning, repositioning, and/or better positioning of nuclear structures, cytosolic structures or granules or other intracellular components or structures closer to a plane parallel to the direction of the flow In one embodiment, the non-spherical particles comprise red blood cells. In another aspect of this invention, the spherical particles comprise white blood cells or nucleated red blood cells.

In one embodiment of the methods of this invention, the particles are non-spherical particles. In one embodiment, the particles analyzed comprise at least one of a spherical particle, a non-spherical particle, or both. In another embodiment, the particles comprise at least one spherical particle. In still another embodiment, the particles comprise at least one nonspherical particle. In another embodiment, an image projection of non-spherical particles or particles having non-spherical components is maximized in a plane substantially parallel to the direction of flow. The particles may be, for example, RBCs, including reticulocytes and nucleated RBCs, platelets and/or WBC, including a neutrophil, lymphocyte, monocyte, eosinophil, basophil, or immature WBC including a blast, promyelocyte, myelocyte, or metamyelocyte. In one embodiment, at least 50% of the non-spherical particles are aligned in a plane substantially parallel to the direction of flow. In another aspect, use of the PIOALs of this invention in a flowcell permits at least 90% of the non-spherical particles to be aligned in a plane substantially parallel to the direction of flow.

In one embodiment of this disclosure, the image cross-section comprises at least one of differentially stained nuclear structure, differentially stained cytosolic structure or differentially stained granules in a WBC, including a neutrophil, lymphocyte, monocyte, eosinophil, basophil, or immature WBC including a blast, promyelocyte, myelocyte, or metamyelocyte. In another embodiment, at least 50%, 55%, 60%, 65%, 70%, 75%, 80%, 85%, 86%, 87%, 88%, 89%, 90%, 91%, 92%, 93%, 94% or at least 95% of the spherical and/or non-spherical particles have nuclear structures, cytosolic structures or granules in the focal plane or depth of field of the high optical resolution imaging device.

In some embodiments of the methods of this invention, the image information is the image cross-section of a particle. In some aspects, the image cross-section comprises at least one of a differentially stained nuclear structure, a differentially stained cytosolic structure or differentially stained granules in a WBC, including a neutrophil, lymphocyte, monocyte, eosinophil, basophil, or immature WBC including a blast, promyelocyte, myelocyte, or metamyelocyte.

In one embodiment, the methods of this invention provide surprisingly high quality images of cells with a high percentage of particles and particle content in-focus in flow, which are useful in obtaining automated, image based WBC differentials, as well as automated identification of morphological abnormalities useful in determining, diagnosing, prognosing, predicting, or supporting a diagnosis of whether a subject is healthy or has a disease, condition, abnormality or infection and/or is responsive or non-responsive to treatment.

In another aspect, the compositions and methods of this invention provide more accurate image based cell categorization and subcategorization and flagging which greatly reduces the manual review rate compared to current analyzers.

As used herein, exemplary white blood cells (WBC) can include, for example, neutrophils, lymphocytes, monocytes, eosinophils, basophils, immature granulocytes including meta-myelocyes, myelocytes, pro-myelocytes and blasts, and abnormal white blood cells. As used herein, red blood cells (RBC) can include, for example, normal or abnormal red blood cells, reticulocytes, and nucleated red blood cells.

As used herein, viscosity agent can include viscosity agents or viscosity modifiers. An exemplary viscosity agent/modifier has a characteristic viscosity that is different from the viscosity of the sample such that when the PIOAL and the viscosity agent are mixed, the viscosity of the PIOAL is altered or and/or increased in order to maximize the alignment of particles. In certain embodiments, the viscosity difference and/or a speed difference between the ribbon-shaped sample stream and the PIOAL can introduce shear forces to act on the particles while in flow thereby reducing the misalignment and/or causing the particles to align.

As used herein, the particle contrast agent compositions can be adapted for use in combination with a particle and/or intracellular organelle alignment liquid (PIOAL) in a visual analyzer for analyzing particles in a sample from a subject. The exemplary PIOAL is useful, as an example, in methods for automated recognition of different types of particles in a sample from a subject.

In another aspect, the cells may be enveloped in PIOAL when images are obtained. Suitable exemplary intracellular organelle alignment liquids are described herein.

In one embodiment, this disclosure relates to a PIOAL for use in a visual analyzer. In certain embodiments, the PIOAL may comprise at least one of a buffer; a pH adjusting agent; a buffer; a viscosity agent/modifier; ionic strength modifier, a surfactant, a chelating agent, and/or an antimicrobial agent.

In one aspect, the PIOAL may comprise two or more viscosity agents/modifiers.

In one aspect, the PIOAL of this invention may have a viscosity of between about 1 to about 10 centipoise. In one embodiment, the PIOAL of this invention may comprise a viscosity agent/modifier. In one embodiment, the PIOAL comprises up to 100% of a viscosity agent.

As used herein, the viscosity agent and/or viscosity modifier can include any substance suitable to achieve a viscosity of about 1 to about 10 centipoise, with optical characteristics, including optical clarity, appropriate for use in an imaging system. Generally, the viscosity agent or modifier is non-toxic, biocompatible and leaves the cellular structure and contents substantially intact. The viscosity agent and/or viscosity modifier may comprise at least one of glycerol; glycerol derivative; ethylene glycol; propylene glycol (dihydroxypropane); polyethylene glycol; water soluble polymer and/or dextran. In one aspect, the viscosity agent/modifier in the PIOAL may be glycerol. As an example, in one aspect, the viscosity agent/modifier in the PIOAL may be a glycerol derivative. As an example, in one aspect, the viscosity agent/modifier in the PIOAL may be polyvinylpyrrolidone (PVP). As another example, the viscosity agent/modifier in the PIOAL may be ethylene glycol. As another example, the viscosity agent/modifier in the PIOAL may be propylene glycol (dihydroxypropane). As another example, the viscosity agent/modifier in the PIOAL may be polyethylene glycol. As another example, the viscosity agent/modifier in the PIOAL may be water soluble polymer or dextran. In other aspects, the viscosity agent/modifier in the PIOAL may comprise two or more of glycerol, glycerol derivative; ethylene glycol; propylene glycol (dihydroxypropane); polyvinylpyrrolidone (PVP); polyethylene glycol; water soluble polymer or dextran. Viscosity agent/modifying agents may include any agent suitable to provide a viscosity of about 1 to about 10 centipoise, with optical characteristics, including optical clarity, appropriate for use in an imaging system.

As used herein, other exemplary viscosity agents/modifiers can include, for example, natural hydrocolloids (and derivatives), such as Acacia, tragacanth, alginic acid, carrageenan, locust bean gum, guar gum, xanthan gum, gum arabic, guar gum, gelatin, cellulose, alginates, starches, sugars, dextrans; gelatin; sugars (and derivatives), such as dextrose, fructose; polydextrose; dextrans; polydextrans; saccharides; and polysaccharides; semisynthetic hydrocolloids (and derivatives), such as glycerol, methylcellulose, hydroxyethyl starch (hetastarch), sodium carboxymethylcellulose, hydroxyethylcellulose, hydroxypropylmethylcellulose, polyvinylpyrrolidone (PVP); synthetic hydrocolloids (and derivatives), such as Polyvinyl alcohol (PVA) and/or Carbopol®. Other cell compatible viscosity agents/modifiers are also considered useful for this purpose.

In another aspect, the viscosity agent/modifier in the PIOAL may be glycerol present at a concentration of about 1 to about 50% (v/v) of the PIOAL. As an example, in one embodiment, the viscosity agent/modifier may be present in the PIOAL at a concentration of about 5.0% to about 8.0% (v/v). In another aspect, the viscosity agent/modifier may be present at a concentration of about 6.5% (v/v). In one embodiment, the viscosity agent/modifier is glycerol present at a concentration of about 6.5% (v/v).

In yet another embodiment, the PIOAL can comprise a glycerol viscosity agent/modifier present at a concentration of about 30% (v/v).

In another aspect, the viscosity agent/modifier in the PIOAL may be PVP present at a concentration of about 0.5 to about 2.5% (w/v). As an example, in one embodiment, the viscosity agent/modifier PVP may be present in the PIOAL at a concentration of about 1.0 to about 1.6% (w/v). In one embodiment, the PVP is present at a concentration of about 1.0% (w/v).

In another aspect, the viscosity agent/modifier in the PIOAL may be PVP and glycerol. As an example, in one embodiment, the glycerol may be present in the PIOAL at a concentration of about 5% (v/v) in combination with about 1% (w/v) of PVP.

In one embodiment, the PIOAL of this invention may be used in a visual analyzer to image particles. In one aspect, the visual analyzer comprises a flowcell with a symmetrical flow path, and an autofocus component.

A viscosity agent and/or viscosity modifying/adjusting agents, such as glycerol, may be included in the PIOAL. The viscosity agent, or viscosity modifying agent when introduced, can appropriately adjust the viscosity of the PIOAL to the desired range. Any suitable viscosity agent may be used which sufficiently increases the viscosity of the PIOAL, which has suitable optical characteristics to permit high quality imaging of cells in flow. The PIOAL will have a suitable viscosity to align cells and/or cellular structures into a single plane that is substantially parallel to the direction of the flow, thereby, in part, increasing the in-focus contents of the particles.

The PIOAL may be used with any analyzer of this disclosure.

As used herein, the term "glycerols" encompasses glycerol and a derivative of glycerol (hereinafter referred to as glycerol derivative). Examples of a glycerol derivative include thioglycerol, polyglycerol, and the like. Usable examples of polyglycerol may include diglycerol, POLYGLYCERIN #310 (Sakamoto Yakuhin Kogyo Co., Ltd.), POLYGLYCERIN #750 (Sakamoto Yakuhin Kogyo Co., Ltd.), POLYGLYCERIN #500 (Sakamoto Yakuhin Kogyo Co., Ltd.), and the like.

In another embodiment, the PIOAL of this disclosure further comprises a pH adjusting agent. In one aspect, the final pH of the PIOAL and/or the sample is between about 6.0 to about 8.0. In another aspect, the final pH of the PIOAL and/or the sample is between about 6.6 to about 7.4. In one aspect, the final pH of the PIOAL may be the same pH as the prepared sample 12B (referring to FIG. 8).

Exemplary pH adjusting agents can include, for example, acids (exemplars include organic acids and mineral acids), bases (exemplars include organic bases and hydroxides of alkaline metals and alkaline earth metals). Exemplary organic acids can include acetic, lactic, formic, citric, oxalic, and uric acids. Exemplary mineral acids can include, for example, hydrochloric, nitric, phosphoric, sulphuric, boric, hydrofluoric, hydrobromic and perchloric acids. Exemplary organic bases can include, for example, pyridine, methylamine, imidazole, benzimidazole, histidine, phosphazene, and hydroxides of cations. Exemplary hydroxides of alkali metal and alkaline earth metals can include, for example, Potassium hydroxide (KOH), Barium hydroxide ($Ba(OH)_2$), Caesium hydroxide (CsOH), Sodium hydroxide (NaOH), Strontium hydroxide ($Sr(OH)_2$), Calcium hydroxide ($Ca(OH)_2$), Lithium hydroxide (LiOH), and Rubidium hydroxide (RbOH).

In some embodiments, using a buffer, the pH of PIOAL is preferably maintained from about 6.0 to about 8.5, more preferably from about 7.0 to about 8.0. In some embodiments it is preferable to add a buffer agent to the PIOAL in order to adjust the pH of PIOAL. Any suitable buffer agent or agents may be used as long as the agent or agents adjust the pH of the PIOAL to the proper range. Examples of such a buffer agent include PBS, Good's buffers (specifically, tris buffer, MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, and the like), disodium hydrogenphosphate, sodium dihydrogen phosphate, monobasic potassium phosphate, veronal sodium-HCl, collidine-HCl, tris(hydroxymethyl)aminomethane-maleic acid, tris(hydroxymethyl)aminomethane-HCl, which may be used alone or in combination.

In another embodiment, the PIOAL of this invention comprises an ionic strength modifier to adjust the ionic strength of the resulting formulation. Exemplary ionic strength modifiers may include $Li^+$, $Na^+$, $K^+$, $Mg^{++}$, $Ca^{++}$, $Cl^-$, $Br^-$, $HCO^-_3$, sulphates, pyrosulphates, phosphates, pyrophosphates (e.g., potassium pyrophosphate), citrates, cacodylates or other suitable salts. In one embodiment, the PIOAL may be isotonic.

Surfactants may be added to the PIOAL. The kinds of surfactants are not particularly limited as long as they are compatible with other components of the PIOAL, and compatible with the ribbon-shaped sample stream and the particles in the sample. Surfactants may include, for example, cationic, anionic, nonionic, and ampholytic surfactants. Exemplary surfactants may include polyoxyethylenealkyl ether-type surfactants, polyoxyethylenealkylphenyl ether-type surfactants, (for example, NISSAN NONION NS-240 (NOF CORPORATION, registered trademark)), polyoxyethylenesorbitan alkyl ester-type surfactants (for example, RHEODOL TW-0120 (Kao Corporation, registered trademark)), polyol copolymers (for example, PLURONIC F-127, F-123, F-109, F-87, F-86, F-68, T-1107, T-1102 (BASF Corporation, registered trademark)), MEGA-8, sucrose monocaprate, deoxy-BIGCHAP, n-octyl-β-D-thioglucoside, n-nonyl-β-D-thiomaltoside, n-heptyl-β-D-thioglucoside, n-octyl-β-D-thioglucoside, CHAPS, CHAPSO, and the like may be used. Other surfactants may include Triton-X-100 and Tween 20 at sample and ribbon-shaped sample stream compatible concentrations.

The concentration of the surfactant in PIOAL is preferably the concentration level at which particles such as cells in the sample are not affected and/or remain substantially intact. Specifically, the concentration is preferably from 5 to 5000 mg/L, more preferably from 100 to 3000 mg/L.

When particles contained in the sample are analyzed with the analyzer, amorphous salts such as ammonium phosphate, magnesium phosphate, calcium carbonate may precipitate in the sample. Chelating agents may be added to the PIOAL in order to dissolve these amorphous salts. The addition of chelating agents enables not only dissolving amorphous salts, but also inhibiting the oxidation of PIOAL. Usable examples of a chelating agent include EDTA salts, CyDTA, DHEG, DPTA-OH, EDDA, EDDP, GEDTA, HDTA, HIDA, Methyl-EDTA, NTA, NTP, NTPO, EDDPO, and the like. The concentration of the chelating agent in the PIOAL is preferable within the range of 0.05 to 5 g/L.

In another embodiment, the PIOAL may further comprise one or more antimicrobial agents. In some aspects, the antimicrobial agent may be, for example, substances which have fungicidal activity (fungicidal agents) and/or substances which have bactericidal activity (bactericidal agents). In certain embodiments, suitable antimicrobial agents can include, for example, parebens, isothiazolinone, phenolics, acidic preservatives, halogenated compounds, quarternia, and alcohol. Exemplary parabens can include Parabens and Paraben salts. Exemplary isothiazolinones can include methylchloroisothiazolinone, methylisothiazolinone, benzisothiazolinone ProClin 150, ProClin 200, ProClin 300, and ProClin 950. Exemplary phenolic types can include phenoxyethanol, benzyl alcohol, and phenethyl alcohol. Exemplary acidic preservatives can include dehydroacetic acid, benzoic acid, sorbic acid, salicylic acid, formic acid, propionic acid. Exemplary halogenated compounds can include 2-bromo-2-nitropropane-1, 3-diol, chloroacetamide, chlorobutanol, chloroxylenol, chlorphenesin, dichlorobenzyl alcohol, iodopropynyl butylcarbamate, methyldibromo glutaronitrile. Exemplary quaternia can include benzalkonium chloride, benzethonium chloride, chlorhexidine, hexamidine diisethionate, and polyaminopropyl biguanide. Exemplary alcohols can include ethyl alcohol and isopropyl alcohol. Examples thereof include triazine antimicrobial agents, thiazole bactericidal agents (for example, benzisothiazolone etc.), pyrithione, pyridine bactericidal agents (for example, 1-hydroxy pyridine-2-thiosodium etc.), 2-phenoxyethanol, and the like. Specifically, Proxel GXL (Avecia), TOMICIDE S (API Corporation), and the like may be used. The bactericidal and/or fungicidal agents help improve the stability of the PIOAL.

In one embodiment, the concentration of the antimicrobial agent may be 0.01% to 0.5% (w/v). The concentration may be 0.03 to 0.05% (w/v).

The sample which is subjected to analysis using the analyzer with the PIOAL in the embodiment is not particularly limited. Samples obtained from the living body (biological samples) are normally used. Alternatively, those samples can be diluted, purified, contacted with a contrast agent, or the like for use. Specifically, examples of such a sample may include blood, semen, cerebrospinal fluid, and the like. Samples may also include particle suspensions derived from tissue samples. The PIOAL in the embodiment is suitably used when particles (red blood cell, white blood cell, bacteria, etc.) are analyzed.

The PIOAL of this invention may be used in a visual analyzer that images particles. In one aspect, the visual analyzer comprises a flowcell capable of maintaining the flow of a ribbon-shaped sample stream with predetermined dimensional characteristics, such as an advantageous ribbon-shaped sample stream thickness. In some embodiments, the flowcell may have a symmetrical flow path, and be used in combination with an autofocus component.

This disclosure relates to a method for imaging a particle comprising: 1) contacting the sample with a particle contrast agent composition; 2) illuminating the prepared particle; 3) obtaining a digitized image of the particle in a ribbon-shaped sample stream enveloped in a PIOAL; and; 4) analyzing the image information to categorize or subcategorize the particles. In some embodiments, the particle may be at least one of, a WBC, RBC, and/or platelet, including, for example, a neutrophil, lymphocyte, monocyte, eosinophil, basophil, reticulocyte, nucleated RBC, blast, promyelocyte, myelocyte, or metamyelocyte, cell, bacteria, parasites, particulate matter, cell clump, cellular component, and immature granulocyte. In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed based on particle image information.

In some embodiments the visual analyzer comprises a flowcell with a symmetrical or an asymmetrical flowpath, and an autofocus component.

In a general aspect, the exemplary PIOAL and methods of use thereof are useful when employed in combination with an automated analyzer found in research and/or medical laboratories. Exemplary automated analyzers are instrument designed to measure different formed elements and/or other characteristics in a number of biological samples, quickly, including, for example, human body fluid samples, with minimal human assistance. Exemplary automated analyzers can include, for example, hematology analyzers and/or cell counters, which can perform for example, complete blood count (CBC) determination. The exemplary analyzers can process samples singly, in batches, or continuously.

In one aspect, the exemplary analyzer/system comprises an automated particle counter configured to detect a plurality of particles that meet one or more selection criteria, and to provide a particle count thereof, wherein the selection criteria encompasses members of at least two categories within said particles. An analyzer, which may comprise a processor, which may include components of the counter, is programmed to distinguish the particles of the at least two categories. A distribution of each of the particles is determined using the analyzer. The processor uses the distribution to correct the particle count for the members of at least one of the at least two categories and/or subcategories. In some embodiments, the particle counter comprises at least one channel configured to provide the particle count of the at least one category and/or subcategory of particles based on a predetermined range based on volume, size, shape, and/or other criterion. For example, the members of the at least one category and/or subcategory comprise at least one type of particle selected from a group consisting of subcategories of white blood cells (WBCs), red blood cells (RBCs), giant platelets (PLTs), and nucleated red blood cells (NRBCs). On a particle counter, due to similar size or other measured characteristic, cells such as giant PLTs and NRBC's may be counted as WBCs. By operating the apparatus as described herein, particle count or concentration of giant PLTs and NRBC's can be measured accurately.

The sample can be an isolated and/or prepared biological sample, including for example, a body fluid sample, a blood, serum, cerebrospinal fluid, pleural fluid, peritoneal fluid, saliva, seminal fluid, tears, sweat, milk, amniotic fluid, lavage fluid, bone marrow asirate, effusions, exudates, or other sample obtained from a subject (e.g., biopsy sample that has been treated to produce a cell suspension, or a laboratory or production line sample comprising particles). In some embodiments, the sample can be a solid tissue sample, e.g., a biopsy sample that has been treated to produce a cell suspension. The sample may also be a suspension obtained from treating a fecal sample. A sample may also be a laboratory, chemical, industrial or production line sample comprising particles, such as a cell culture sample. The term sample may be used to refer to a sample obtained from a patient or laboratory or any fraction, portion or aliquot thereof. The sample can be diluted, divided into portions, or treated with a contrast agent in some processes.

The methods disclosed herein are applicable to samples from a wide range of organisms, including mammals, e.g., humans, non-human primates (e.g., monkeys), horses, cows or other livestock, dogs, cats or other mammals kept as pets, rats, mice, or other laboratory animals; birds, e.g., chickens; reptiles, e.g., alligators; fish, e.g., salmon and other farmed species; and amphibians.

The samples can be obtained by any conventional method, e.g., excretion, draw, harvesting, aspirate, or a biopsy. The sample can be from a subject considered to be healthy, for example, a sample collected as part of a routine physical examination. The sample can also be from a subject who has, who is at risk for, or who is suspected of having a disorder. The disorder can be the result of a disease, a genetic abnormality, an infection, an injury or unknown causes. Alternatively or in addition, the methods can be useful for monitoring a subject during the course of treatment for a disorder. Where there are signs of non-responsiveness to treatment and/or therapy, a clinician can choose an alternative or adjunctive agent. Depending upon the condition of the subject and the particular disorder, if any, samples can be collected once (or twice, three times, etc.) daily, weekly, monthly, or yearly.

The particles can vary depending upon the sample. The particles can be biological cells, for example, blood cells, fetal cells, stem cells, tumor cells or fragments thereof. In some embodiments the particles can be an infectious agent, for example, a virus or bacterium.

Reference to "blood cells" made in this disclosure will be understood to encompass any normal or abnormal, mature or immature cells which potentially exist in a biological fluid, for example, red blood cells (RBCs), white blood cells (WBCs), platelets (PLTs) and other cells. In general, normal RBCs, PLTs, and WBCs have a particle diameter in the range of 6-8 µm, 2-3 µm, and 8-15 µm, respectively. Normal RBCs, PLTs and WBCs are present in whole blood samples from normal patients in an approximate concentration range of $3.9\text{-}5.7 \times 10^{12}$ cells/L, $1.4\text{-}4.5 \times 10^{11}$ cells/L, $3.5\text{-}11 \times 10^{9}$ cells/L, respectively. See, Barbara J. Bain, Blood Cells, A Practical Guide, 4th ed., Blackwell Publishing, 2007, 34-36.

Reference to a "formed element" will be understood to encompass non-fluid elements present in biological fluid samples. Formed elements include, for example, classes of blood cells based on scientific classification or physiological function including erythrocytes (RBCs), leukocytes (WBCs) and platelets (PLTs), WBC clumps, subclasses of leukocytes, which include mature lymphocytes, and immature leukocytes such as monocytes, neutrophils, eosinophils, basophils. "Formed elements" for use herein will also include particles such as microorganisms, bacteria, fungi, parasites, or fragments thereof or other cell fragments. Major members of WBCs include but are not limited to neutrophils, lymphocytes, monocytes, eosinophils, and basophils. The members also include immature or abnormal cells. For example, immature WBCs may include metamyelocytes, myelocytes, pro-myelocytes. In addition to mature RBCs, members of RBCs may include nucleated RBCs (NRBCs) and reticulocytes. PLTs may include regular PLTs, and "giant" PLTs whose size is close to that of regular WBCs. Reference to a "member" or "members" of a category and/or subcategory of particles made in this disclosure will be understood to encompass individual particles within a category or sub-category of particles.

Unless expressly indicated otherwise, reference to a "category" of particles made in this disclosure will be understood to encompass a group of particles detected using at least one detection criterion measured, detected or derived such as size, shape, texture, or color. In some embodiments the members of at least one category and/or subcategory of particles counted by the apparatus of this disclosure will be the same type of formed element.

Such particles may be detected in a "channel." Reference to "channel" made in this disclosure will be understood to encompass a portion of the particle counter comprising a detector coupled to a signal source, providing an output that varies with greater or lesser detection of particles that meet at least one channel detection criterion. For example, a channel detection criterion can be based on size or volume of the particles. In some embodiments, the number of channels in a particle counter is one. In some other embodiments, the number of the channels in a particle counter is two or more.

One category and/or subcategory of particles detected in one channel of particle counter may comprise different classes and subclasses of particles, and grouped members of particles in two or more subclasses. Reference to a "category" of particles made in this disclosure will be understood to encompass a grouping of particles corresponding to criteria measured, detected or derived such as size, shape, texture, or color. In some embodiments the members of at least one category and/or subcategory of particles counted by the apparatus of this disclosure will be the same type of formed element.

As used herein, "alignment" can be characterized in part by the alignment of spherical and/or non-spherical particles. For example, particles such as non-spherical particles may be aligned in a plane substantially parallel to the direction of the flow. In certain embodiments, alignment of the non-spherical particles is characterized by the orientation of the particles increase an image projection of the non-spherical particles under imaging conditions in the focal plane of the high optical resolution imaging device. Particles such as spherical particles may have an increase in the amount of the in focus intraparticle contents of the particles and cells which is effective to generate visual distinctions for particle categorization and subcategorization. The intraparticle structures of particles such as spherical particles may be positioned, repositioned and/or better-positioned to be substantially parallel to the direction of flow. For example, intracellular structures, organelles or lobes may also be positioned, repositioned, and/or better-positioned to be substantially parallel to the direction of flow.

Reference to a "class" of particles made in this disclosure will be understood to encompass a group of particles based on scientific classification. For example, three major classes of blood cells exist in a whole blood sample, including RBCs, WBCs and PLTs.

Reference to a "member" or "members" of particles made in this disclosure will be understood to encompass particles in one category or subcategory of particles. For example, each category of blood cells can be further divided into subcategories or members. Major members of WBCs include but are not limited to neutrophils, lymphocytes, monocytes, eosinophils, and basophils. The members also include immature or abnormal cells. For example, immature WBCs may include metamyelocytes, myelocytes, and promyelocytes. In addition to mature RBCs, members of RBCs may include nucleated RBCs (NRBCs) and reticulocytes. PLTs may include regular PLTs, and "giant" PLTs whose size is close to that of regular WBCs.

Reference to "immature cells" will be understood to encompass cells in a certain developmental stage, for example, inside the bone marrow or shortly after release from bone marrow but before full development into a mature cell.

Reference to "abnormal cells" will be understood to encompass cells with irregular morphological characteristics or cells associated with a certain disease or condition, or irregularities associated which may in some instances be associated with certain diseases or conditions. Examples of certain disease include but are not limited to erythrocytosis, polycythemia, anemia, erythroblastopenia, leukocytosis, leukopenia, lymphocytosis, lymphocytopenia, granulocytosis, granulocytopenia or agranulocytosis, neutrophilia, neutropenia, eosinophilia, eosinopenia, basophilia, basopenia, thrombocytosis, thrombocytopenia, and pancytopenia. A class of cells may increase or decrease in the bloodstream. In some conditions, abnormal cells much larger than regular white cells exist at a small concentration in a blood sample. Variations in size, shape, color, and/or intracellular structures may be associated with certain diseases or conditions.

Reference to "count" of particles or "particle count" made in this disclosure will be understood to encompass the numbers of particles obtained from one channel of a particle counter. Reference to "concentration" of a class or a member of particles made in this disclosure will be understood to mean the numbers of the particles per unit volume (e.g., per liter) or per sample of a known volume. For example, a particle counter may provide counts or concentrations or other count based function for categories of particles, while a visual analyzer may provide counts, concentrations, ratios or other concentration based parameters for each category or subcategory of particles.

Reference to "ratio" made in this disclosure will be understood to encompass any quantitative and/or proportionate ratio of two categories/subcategories, classes or members of particles. Examples of such a ratio include but are not limited to a ratio by concentration, weight, and/or by numbers of particles. Typically the ratio concerns the numerical fraction of the count of one category, class or member over the count of another such category, class or member. In some embodiments, determinations using weighted counts or weighted and/or proportionate ratios may also be made.

Hence, embodiments of the present invention encompass hybrid systems and methods, for example which combine electronic cell counting and photographic cell imaging techniques, for example to analyze cells that might be difficult to distinguish electrically, or to analyze cells present in amounts that make it difficult to obtain an accurate electronic count thereof.

The present disclosure also relates to a surprising and unexpected particle contrast agent composition for rapidly generating visual distinctions in a sample. The particle contrast agent composition can be especially useful in automated flow cytometry systems. The particle contrast agent composition is comprised of a combination of a particle contrast agent, a permeabilizing agent, and a fixing agent. In one embodiments, the particle contrast agent composition is a mixture of Crystal Violet, New Methylene Blue, Saponin, and Gluteraldehyde. In an embodiment that is surprisingly effective, under staining condutions, the Crystal Violet is present in amounts sufficient to result in concentrations of about 7.8 μM, the New Methylene Blue is present in amounts sufficient to result in concentrations of about 735 μM, the Saponin is present in amounts sufficient to result in concentrations between about 50 mg/L and about 750 mg/L, the composition futher includes Eosin-Y present in amounts sufficient to result in concentrations of about 27 μM, and the Gluteraldehyde is present in amounts sufficient to result in concentrations at or below 0.1%.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may be drawn not to scale.

The particle contrast agent composition of the invention, when applied to a blood fluid sample, causes the staining of cells in such sample similar to that of a blood smear treated with a standard blood smear stain, and in particular similar to a blood smear stain with Wright's stain. Wright's stain is a histologic stain that facilitates the differentiation of blood cell types (e.g. WBC). It is used primarily to stain peripheral blood smears and bone marrow aspirates which are examined under a light microscope. In cytogenetics it is used to stain chromosomes to facilitate diagnosis of syndromes and diseases. There are related stains known as the buffered Wright stain, the Wright-Giemsa stain, and the buffered Wright-Giemsa stain. Because the Wright's stain process involves alcohol solvent, this staining procedure is destructive to viable cells and does not result in substantially intact cells. The May-Grunwald stain, which produces a more intense coloration, also takes a longer time to perform.

Aspects and embodiments of the present invention are based on the surprising and unexpected discovery that certain particle contrast agent compositions, including for example, stain/dye compositions, and/or combinations thereof, have unexpected properties and efficacy when used to perform automated, image-based sample analysis, such as blood analysis.

The compositions and method disclosed herein can be used with many different types of hematology imaging systems. In particular, the compositions and methods described herein can be used with image-based sample analysis, such as flowcell analysis. An example of such a flowcell analysis can include traditional, known methods of flow cytometry. Additionally, the compositions and methods described herein can be advantageously used with the flow-cell analysis systems and methods described in brief detail below and described further in the co-filed applications entitled "Flowcell Systems And Methods For Particle Analysis In Blood Samples," U.S. patent application Ser. No. 14/216,533, filed Mar. 17, 2014, (now U.S. Pat. No. 9,322,752 issued Apr. 26, 2016), and "Hematology Systems and Methods," PCT Patent Application No. PCT/US2014/030942, filed Mar. 18, 2014, both of which are hereby incorporated by reference.

Particle Contrast Agent Composition

Figure 24:
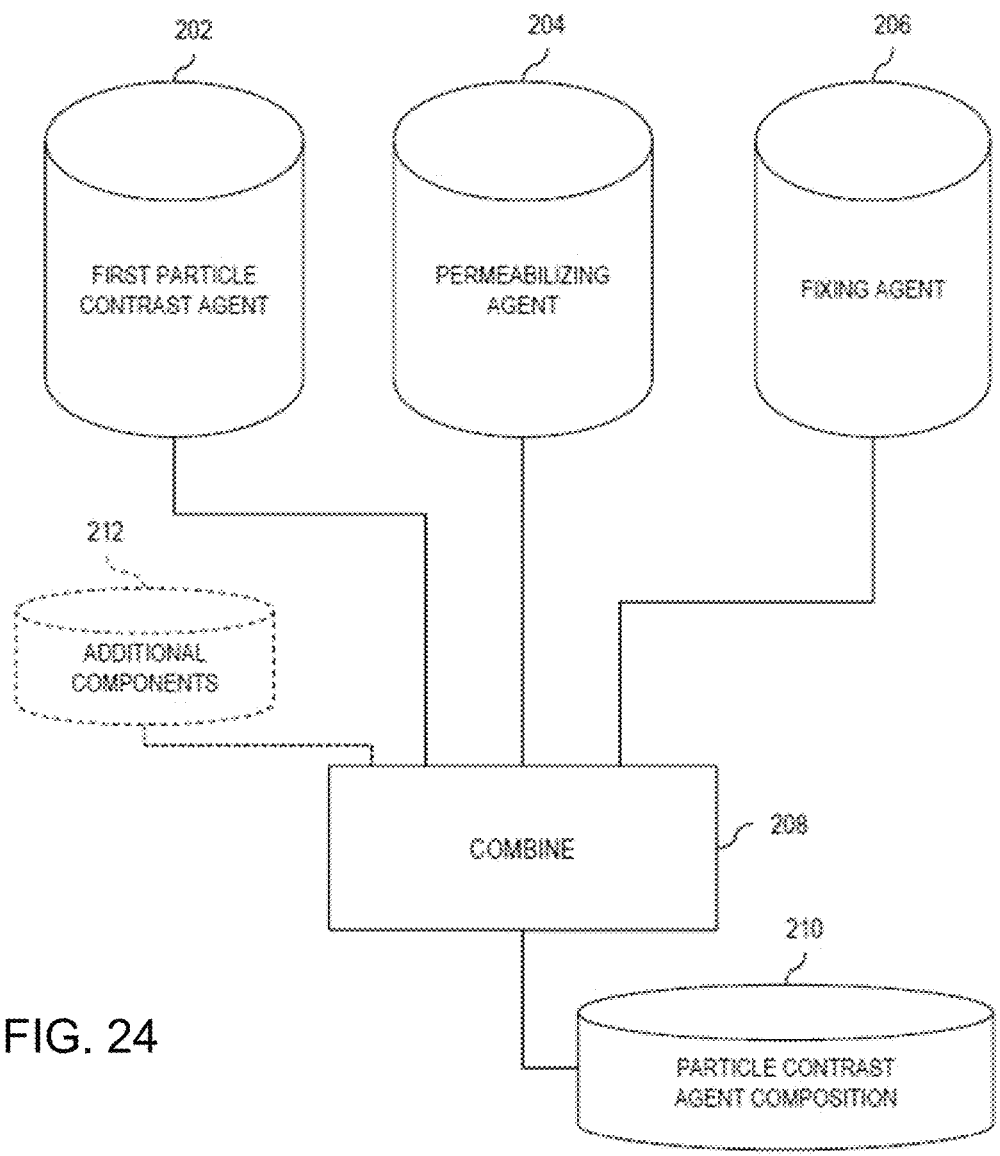
FIG. 24 is a schematic diagram of the preparation of a particle contrast agent composition according to one embodiment.

FIG. 24 is a schematic diagram of the preparation of a particle contrast agent composition according to one embodiment. At block 208, a particle contrast agent 202, a permeabilizing agent 204, and a fixing agent 206 are combined to create the particle contrast agent composition 210. In one embodiment, the particle contrast agent 202, permeabilizing agent 204, and fixing agent 206 are combined at the same time. In other embodiments, one of the particle contrast agent 202, permeabilizing agent 204, and fixing agent 206 is combined with another one of the particle contrast agent 202, permeabilizing agent 204, and fixing agent 206, which is then combined with the last of the particle contrast agent 202, permeabilizing agent 204, and fixing agent 206, in any order. The combination at block 208 can be performed in any order and in any suitable way.

In alternate embodiments, one of the permeabilizing agent 204 and fixing agent 206 is not included in the particle contrast agent composition 210. In still further embodiments, additional materials are combined at block 208 as part of the particle contrast agent composition 210, as described in further detail below.

The particle contrast agent composition 210 can be provided as part of a kit. The particle contrast agent composition 210 can be provided already prepared or as one or more components that must be combined.

Particle Contrast Agent

The particle contrast agent 202 can be any contrast agent capable of producing visible distinctions, such as those similar to a Wright stain. Examples of such contrast agents include Alcian Blue and Alcian Blue 86 (PAS neutral and acidic mucosubstances); Alizarin Red S; Allura Red AC (azodye red dye #40); Analine Blue (cilia intensified with oxalic acid); Auramine O; Azure B; Azure C; Bismarck Brown; Brilliant Blue FCF (Comassie blue); Brilliant cresyl blue; Brilliant green; Carmium (red nuclear dye composed of Carminic acid and Potassium alum); Congo red; Chlorozol black E (nuclei black, cyto gray, glycogen pink); Cresyl violet acetate; Darrow red; Eosin bluish; Erythrosin B (red dye #3); Ethyl eosin; Fast Green FCF (green dye #3); Fuchin basic-(nuclei and flagella); Fluorescein-(Mercurochrome); Giemsa-peripheral blood smears; Harris hematoxylin-regressive nuclear stain; Indigo Carmine (Blue dye #2); Janus Green B (mitochondria); Jenner Stain-(peripheral blood smears); Light Green SF yellowish; MacNeal-(tetrachrome blood stain); Malachite green; Methyl orange; Martius yellow; Mayer's Hematoxylin-progressive nuclear stain; Methyl violet 2B; Methenamine Silver-Peroidic acid; Methylene violet; May Grunwald-hematological stain; MTT-formazan stain; Mucicarmine-primary tumor stain; Neutral red; Nigrosin; Nile Blue A; Nuclear Fast red C.I. 60760; Napthal AS; Nitro-Blue Tetrazolium-fast formazan dye; Orange G; Orange II; Orcein; Papanicolaou Stain EAS-brilliant cytoplasmic staining; Pararosanilin; Pararosanaline; Periodic Acid Schiff-(PAS, specific carbohydrate stain); Phyloxine B; Protargol S; Pyronin B; Pyronin Y; Resazurin; Romanowsky-Giemsa; Rose Bengal; Safranin O; Sudan Black B; Sudan III- (with alpha-napthol stains myeloid granules); Sudan IV-stains triglycerides; Tartrazine-(azo dye Yellow #5); Thionin-stains meta chromatin; Triphenyl Tetrazolium; TTC-Formazan red dye; Toluidine BlueO; Wright's Stain-(fixative, buffer and stain for conventional blood smears); and Wright Giemsa.

Through non-trivial efforts and experimentation, it has been found that surprisingly effective results can be achieved in the particle contrast agent composition 210, as described in further detail herein, with the use of a particle contrast agent 202 that includes at least one of Crystal Violet, New Methylene Blue, Safranin O, Eosin Y and Methyl Green. The particle contrast agent 202 is added in an amount effective to stain viable and/or substantially intact cells for image-based categorization and subcategorization. The particle contrast agent 202 can be any combination of two or more of the aforementioned particle contrast agents. The particle contrast agent 202 can be selected to efficaciously obtain "Wright-like" stained images of vital and/or substantially intact cells.

In one embodiment, the particle contrast agent 202 includes Crystal Violet. The Crystal Violet can be present in amounts sufficient to achieve between about 1 µM to about 100 µM under staining conditions. As used herein, the term "under staining conditions" refers to when the component is mixed with the sample. The Crystal Violet can be present in amounts sufficient to achieve between about 6 µM to about 10 µM under staining conditions. The Crystal Violet can be present in amounts sufficient to achieve about 7.8 µM under staining conditions. The Crystal Violet can be present in amounts sufficient to achieve very nearly 7.8 µM under staining conditions. The Crystal Violet can be purified to at least 90% pure. The Crystal Violet can be purified to at least 91%, 92%, 93%, 94%, 95%, 96%, 97%, or 98% pure. The Crystal Violet can be purified to at least 99% pure. The particle contrast agent 202 can be solely Crystal Violet, or can be Crystal Violet combined with one or more additional particle contrast agents.

In one embodiment, the particle contrast agent 202 includes New Methylene Blue. The New Methylene Blue can be present in amounts sufficient to achieve between about 70 µM to about 2.4 mM under staining conditions. The New Methylene Blue can be present in amounts sufficient to achieve between about 500 µM to about 950 µM under staining conditions. The New Methylene Blue can be present in amounts sufficient to achieve about 735 μM under staining conditions. The New Methylene Blue can be present in amounts sufficient to achieve very nearly 735 μM under staining conditions. The New Methylene Blue can be purified to at least 70% pure. The New Methylene Blue can be purified to at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% pure. The New Methylene Blue can be purified to at least 100% pure.

In some embodiments, surprisingly effective results are achieved when the particle contrast agent 202 includes both Crystal Violet and New Methylene Blue. The ratio of Crystal Violet to New Methylene Blue can be between about 1:1 to about 1:500 (molar/molar). The ratio of Crystal Violet to New Methylene Blue can be between about 1:50 to about 1:160 (molar/molar). The ratio of Crystal Violet to New Methylene Blue can be between about 1:90 to about 1:110 (molar/molar).

In one embodiment, the particle contrast agent 202 includes Eosin Y. The Eosin Y can be present in amounts sufficient to achieve between about 3 μM to about 300 μM under staining conditions. The Eosin Y can be present in amounts sufficient to achieve between about 10 μM to about 50 μM under staining conditions. The Eosin Y can be present in amounts sufficient to achieve about 27 μM under staining conditions. The Eosin Y can be present in amounts sufficient to achieve very nearly 27 μM under staining conditions. The Eosin Y can be purified to at least 80% pure. The Eosin Y can be purified to at least 81%, 82%, 83%, 84%, 85%, 86%, 87%, 88%, 89%, 90%, 91%, 92%, 93%, 94%, 95%, 96%, 97%, 98%, or 99% pure. The Eosin Y can be purified to at least 100% pure.

In some embodiments, surprisingly effective results are achieved when the particle contrast agent 202 is a combination of Crystal Violet, New Methylene Blue, and Eosin Y, each having any combination of concentrations and purities as described above. In some embodiments, the particle contrast agent 202 is specifically Crystal Violet present in amounts sufficient to achieve about 7.8 μM, New Methylene Blue present in amounts sufficient to achieve about 735 μM, and Eosin Y present in amounts sufficient to achieve about 27 μM. In some embodiments, the particle contrast agent 202 is specifically at least 99% pure Crystal Violet present in amounts sufficient to achieve about 7.8 μM at least 99% pure New Methylene Blue present in amounts sufficient to achieve about 735 μM, and at least 99% pure Eosin Y present in amounts sufficient to achieve about 27 μM.

In one embodiment, the particle contrast agent 202 includes Safranin O. The Safranin O can be present in amounts sufficient to achieve between about 1 μM to about 100 μM under staining conditions. The Safranin O can be present in amounts sufficient to achieve between about 3 μM to about 30 μM under staining conditions. The Safranin O can be present in amounts sufficient to achieve about 9 μM under staining conditions. The Safranin O can be present in amounts sufficient to achieve very nearly 9 μM under staining conditions. The Safranin O can be purified to at least 80% pure. The Safranin O can be purified to at least 81%, 82%, 83%, 84%, 85%, 86%, 87%, 88%, 89%, 90%, 91%, 92%, 93%, 94%, 95%, 96%, 97%, 98%, or 99% pure. The Safranin O can be purified to at least 100% pure.

In one embodiment, the particle contrast agent 202 includes Methyl Green. The Methyl Green can be present in amounts sufficient to achieve about 0.1 g/L under staining conditions. The Methyl Green can be present in amounts sufficient to achieve very nearly 0.1 g/L under staining conditions. The Methyl Green can be purified to at least 80% pure. The Methyl Green can be purified to at least 81%, 82%, 83%, 84%, 85%, 86%, 87%, 88%, 89%, 90%, 91%, 92%, 93%, 94%, 95%, 96%, 97%, 98%, or 99% pure. The Methyl Green can be purified to at least 100% pure.

In some embodiments, the particle contrast agent 202 includes one or more of Crystal Violet, New Methylene Blue, Safranin O, Eosin Y and Methyl Green in amounts effective to generate visual distinctions in particles, for example, by enhancing intracellular content features of particles in a sample when presented for imaging. The particle contrast agent 202 can be present in amounts sufficient to enhance and/or stain subcellular structures of neutrophils, lymphocytes, monocytes, eosinophils, and basophils as well as reticulocytes, nucleated red blood cells, platelets, blast, promyelocyte, myelocyte, metamyelocyte, or cell fragments. Visualizable or visual distinctions can include any particle or intraparticle features that may be visualizable or otherwise detectable using any light source (e.g., UV, visible, IR).

In embodiments where the particle contrast agent composition 210 includes two or more particle contrast agents 202, the amounts of each of the particle contrast agents 202 can be adjusted appropriately, depending on whether the particle contrast agents 202 have independent, competitive and/or enhancing effects on the generation of visual distinctions for particle categorization and subcategorization.

Permeabilizing Agent

In some embodiments, the permeabilizing agent 204 can include a surfactant. In some embodiments, the permeabilizing agent 204 can include a saponin. In alternate embodiments, the permeabilizing agent 204 can include at least one of a quarternary ammonium salt, a nonionic surfactant, and a zwitterionic surfactant. The permeabilizing agent can alter the permeability of a cell in order to increase accessibility of the particle contrast agent 202 to the intracellular contents. The permeabilizing agent can be selected and included in quantities sufficient to permit a rapid, one-step staining procedure.

Examples of a nonionic surfactant can include (1) polyoxyethylene alkyl or aryl ethers (polyethoxylates), including straight-chain aliphatic hydrophobes etherified to polyethylene glycol or polyoxyethylene ethanol, e.g., Brij® 35; (2) branched-chain aliphatic/aromatic (e.g., octylphenol) hydrophobes etherified to polyethylene glycol, e.g., Triton X®-100; (3) straight-chain aliphatic/aromatic (e.g., n-nonylphenol) hydrophobes etherified to polyethylene glycol, e.g., Igepal® C0897; and (4) straight-chain aliphatic (e.g., carboxylic acid) hydrophobes esterified to polyethylene glycol, e.g., Myrj® 53, and others. Examples of nonionic polyoxyethylene alkyl or aryl ethers (polyethoxylates) surfactants can include polyoxyethylene(4) lauryl ether (Brij® 30); polyoxyethylene(23) lauryl ether (Brij® 35); polyoxyethylene(2) cetyl ether (Brij® 52); polyoxyethylene(20) cetyl ether (Brij® 58); polyoxyethylene(2) stearyl ether (Brij® 72); polyoxyethylene(10)stearyl ether (Brij® 76); polyoxyethylene(20) stearyl ether (Brij® 78); polyoxyethylene(2) oleyl ether (Brij® 92); polyoxyethylene(10) oleyl ether (Brij® 96); polyoxyethylene(20) oleyl ether (Brij® 98); polyoxyethylene(21) stearyl ether (Brij® 721); polyoxyethylene(100) stearyl ether (Brij® 700); and others. Further examples of nonionic surfactants can include Triton X®-100 (non-reduced or reduced), Triton®X-114 non-reduced or reduced), Triton X®-165, and Triton X®-305 (non-reduced and reduced), and others.

In an embodiment, the permeabilizing agent 204 can include Brij® 35 at amounts sufficient to result in concentrations of about 0.10 g/L to about 0.20 g/L under staining conditions. The Brij® 35 can be present in amounts sufficient to result in concentrations of about 0.10 g/L to about 0.16 g/L under staining conditions. The Brij® 35 can be present in amounts sufficient to result in concentrations of about 0.012 g/L to about 0.14 g/L.

Examples of zwitterionic surfactants can include TDAPS (tetradecyldimethylammoniopropanesulfonate), CHAP SO (3-[(3-cholamidopropyl) dimethylammonio]-2-hydroxy-1-propanesulfonate), alkyl N, N-dimethyl N-oxides having from about 12 to about 16 carbon atoms, lauryl dimethylamine N-oxide (LO), DDAPS (N-dodecyl-N, N-dimethyl-3-ammonio-1-propanesulfonate), and others.

In some embodiments, the permeabilizing agent 204 includes an agent sufficient to lyse red blood cells. In some embodiments, the permeabilizing agent 204 includes an agent sufficient to lyse red blood cells other than reticulocytes or nucleated red blood cells. In some embodiments, the permeabilizing agent 204 includes an agent sufficient to lyse red blood cells while white blood cells, reticulocytes, nucleated red blood cells, platelets, and other cells remain substantially intact. In some embodiments, the permeabilizing agent 204 renders the members and/or nuclear membranes of white blood cells, reticulocytes, nucleated red blood cells, and/or platelets more permeable and/or porous to facilitate access by the particle contrast agent 202.

In some embodiments, the permeabilizing agent 204 is selected to be able to quickly create the pores or openings necessary to allow the particle contrast agent 202 to enter cells in the sample.

Through non-trivial efforts and experimentation, it has been found that surprisingly effective results can be achieved in some embodiments of the particle contrast agent composition 210 with the use of a permeabilizing agent 204 that includes 5PD-Lytic available from Clinical Diagnostic Solutions (CDS) in Ft. Lauderdale, Fla. 5PD-Lytic includes saponin. 5PD-Lytic is generally described in U.S. Pat. No. 6,632,676, herein incorporated by reference.

Through non-trivial efforts and experimentation, it has been found that surprisingly effective results can be achieved in some embodiments of the particle contrast agent composition 210 with the use of a permeabilizing agent 204 includes a saponin present in amounts sufficient to result in concentrations of about 10 mg/L to about 1000 mg/L under staining conditions. In some embodiments, the saponin is present in amounts sufficient to result in concentrations of about 50 mg/L to about 750 mg/L. In some embodiments, the saponin can be a quarternary ammonium-substituted saponin ether.

Fixing Agent

In some embodiments, the fixing agent 206 can be selected to ensure the white blood cells do not degrade during staining and imaging. In some embodiments, the fixing agent 206 can ensure other cells and cell structures do not degrade. Examples of fixing agents can include glutaraldyde; formaldehyde; cross-linking agents; ammonia picrate in isotonic saline (e.g., for methylene blue staining); ethyl alcohol; methanol (e.g., at room temperature, −20° C. or −70° C.); Heidenhain's Susa—$HgCl_2$, NaCl Trichloroacetic acid, formalin; Bouin's—Picric acid, Formalin, acetic acid; Duboseq-Brazil—Bouins with 80% EtOH; Carnoy's—EtOH, Chloroform, acetic acid; Zenker's—$HgC_{12}$, $K_2CrO_7$, $NaSO_4.H_2O$; acetocarmine; Gatensby's—Chromic acid, Osmium tetroxide, NaCl; Baker's—Formalin, $CaCl_2$; Smith's—$K_2Cr_2O_7$, formalin, acetic acid; 1% methyl green, 1% acetic acid; Phenol, formalin, glycerol, Genetian violet; Schaudin—$HgCl_2$, EtOH, acetic acid; Champy's—Chromic acid, $K_2CrO_7$, $OsO_4$; Fleming's—Cromic acid, OsO4, acetic acid; Formol-Silver—Formaldehyde, $AgNO_3$; Streck's Tissue Fixative—Bronopol, Diazolidinyl urea, $ZnSO_4.7H_2O$, sodium citrate; 1% imidazolidnyl urea in PBS; Glyoxal: Glyofix, Prefer, Safefix, Histochoice; Glydant-Hydantoin; Dimethylol urea; Sodium hydroxymethylglycinate; Karnovsky's; Mecuric chloride (B-5); Hollande's; and others. In addition, suitable exemplary fixative can include any of the following either alone or in combination.

In some embodiments, the fixing agent 206 can be an oxidizing agent, a mercurial, a picrate, a hepes-glutamic acid buffer-mediated organic solvent protection effect (HOPE) fixative, or a water soluble preservative. Examples of oxidizing agents include Potassium dichromate, chromic acid, potassium permanganate, and others. Examples of mercurial include B-5, Zernker's fixative, and others. Examples of water-soluble preservatives include methyl paraben, propyl paraben, dimethylolurea, 2-pyridinethiol-1-oxide, sorbic acid, potassium sorbate, and others.

Through non-trivial efforts and experimentation, it has been found that surprisingly effective results can be achieved in some embodiments of the particle contrast agent composition 210 with the use of a fixing agent 206 that includes at least one of Gluteraldehyde and Formaldehyde.

In some embodiments, surprisingly effective results can be achieved by using a fixing agent 206 that includes Gluteraldehyde at or below 0.1% by weight.

Additional Components

In some embodiments, optional additional components 212 can be optionally combined at block 208 into the particle contrast agent composition 210. Examples of additional components 212 can include buffer components, viscosity modifying agents, an antimicrobial agent, an osmotic adjusting agent, an ionic strength modifier, a surfactant, a chelating agent, and others. In some embodiments, surprisingly effective results can be achieved when the particle contrast agent composition 210 includes a phosphate buffered saline.

Exemplary viscosity modifying agents include natural hydrocolloids (and derivatives), such as carrageenan, locust bean gum, guar gum, and gelatin; sugars (and derivatives), such as dextrose, fructose; polydextrose; dextrans; polydextrans; saccharides; and polysaccharides; semi-synthetic hydrocolloids (and derivatives), such as Methylcellulose, Carboxymethylcellulose; Synthetic hydro colloids (and derivatives), such as Carbopol®; and Clays (and derivatives), such as Bentonite and Veegum®.

Rapid, One-Step Staining Process

Figure 25:
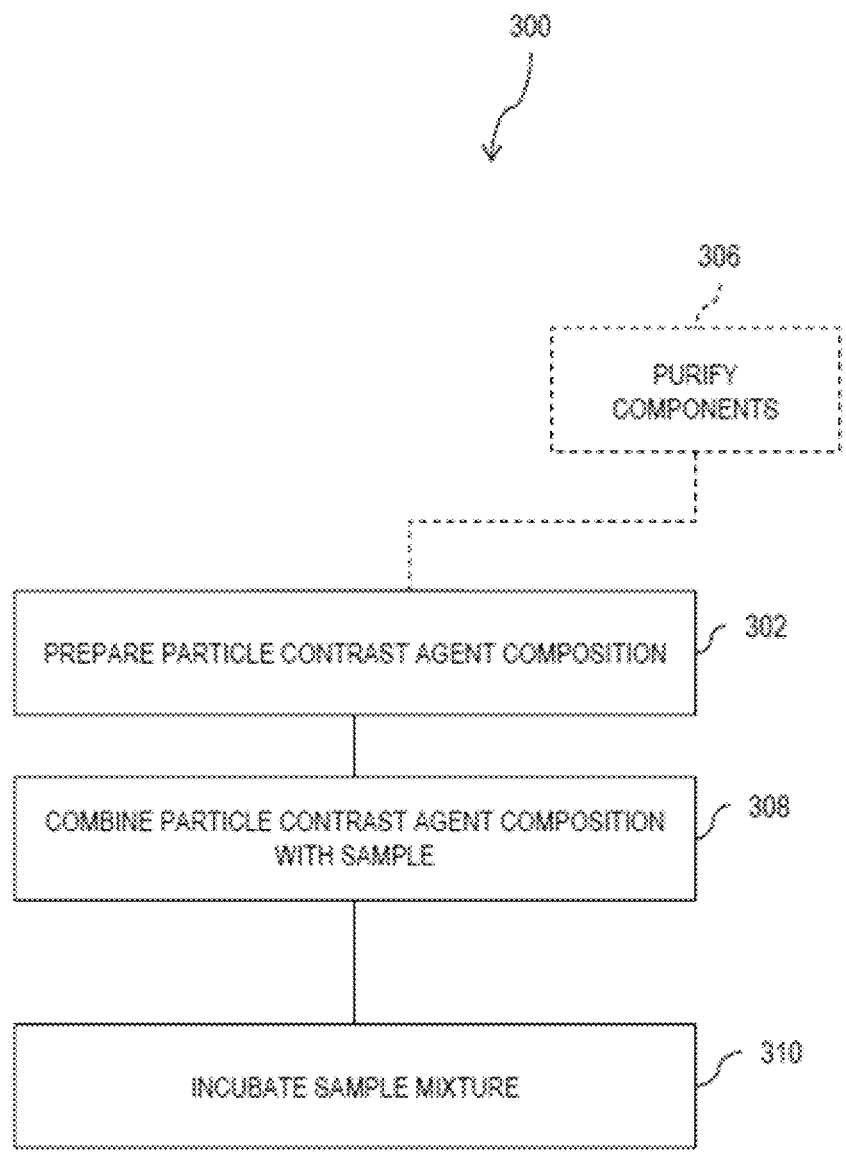
FIG. 25 is a flowchart of a rapid, one-step staining process according to one embodiment.

FIG. 25 is a flowchart of a rapid, one-step staining process 300 according to one embodiment. While the rapid, one-step staining process 300 can contain several sub-steps, the term "one-step" is used to identify that the sample need not be introduced to multiple, different solutions during the staining procedure. The particle contrast agent composition 210 is prepared at block 302, as described above with reference to FIG. 24. Optionally, in some embodiments, components, such as any particle contrast agents 202, can be purified at block 306. Purifying particle contrast agents 202 can reduce the level of precipitates formed upon contact with a sample, thereby reducing the background and improving the results of image-based blood sample analysis with a decreased need for further review of images or slides, or manually prepared microscopy.

At block 308, the particle contrast agent composition 210 is combined with the sample. The particle contrast agent composition 210 can be combined with the sample in any suitable way, including mixing together. Combining at block 308 can include diluting the sample with a certain amount of particle contrast agent composition 210. The sample can be diluted with particle contrast agent composition 210. The amount of dilution can be selected to provide an optimal number of cells per frame during an image-based analysis. The amount of dilution can be selected to provide an optimal number of white blood cells per frame during an image-based analysis. The amount of dilution can be otherwise selected to provide an optimal volume for any other non-image-based analysis.

Through non-trivial efforts and experimentation, it has been found that surprisingly effective results can be achieved in some embodiments of the particle contrast agent composition 210 with the use of a ratio of the particle contrast agent composition 210 to the sample at between about 2:1 to about 20:1. The ratio of the particle contrast agent composition 210 to the sample can be between about 3:1 to about 10:1. The ratio of the particle contrast agent composition 210 to the sample can be between about 3:1 to about 4:1. The ratio of the particle contrast agent composition 210 to the sample can be between about 3:1 or about 4:1. In some embodiments, surprisingly effective results can be achieved using a ratio of the particle contrast agent composition 210 to the sample at very nearly 3:1 or very nearly 4:1.

Surprisingly effective results can be achieved by using particle contrast agent with 40 mL of 5PD-Lytic and 50 mL of Phosphate Buffered Saline with a dilution ratio of 10:1 particle contrast agent composition 210 to sample. Surprisingly effective results can be achieved by using particle contrast agent with 40 mL of 5PD-Lytic, extra saponin, and 40 mL of Phosphate Buffered Saline with a dilution ratio of 5:1 particle contrast agent composition 210 to sample. Surprisingly effective results can be achieved by using particle contrast agent with 40 mL of 5PD-Lytic, extra saponin, and 36 mL of Phosphate Buffered Saline with a dilution ratio of 4:1 particle contrast agent composition 210 to sample.

In some embodiments, the sample is combined with the particle contrast agent composition 210 at elevated temperatures, such as any of the temperatures described below with reference to incubating.

As used herein, the combined sample and particle contrast agent composition 210 is referred to as the sample mixture.

At block 310, the sample mixture is incubated for a certain amount of time at a certain temperature. Incubation can increase the permeability of the cells or their internal structures, allowing the particle contrast agent 202 to better infiltrate the cells or cellular structures. The time and temperature of incubation can be selected to enable the particle contrast agent composition 210 to properly permeate, fix, and stain the sample. The time and temperature of incubation can be selected to ensure lysing of red blood cells while keeping white blood cells, platelets, and nucleated red blood cells substantially intact.

Through non-trivial efforts and experimentation, it has been found that surprisingly effective results can be achieved in some embodiments of the particle contrast agent composition 210 with incubation of the sample mixture at temperatures between about 37° C. and about 60° C. for about 1 to 60 seconds. The sample mixture can be heated to temperatures between about 46° C. and about 49° C. The sample mixture can be incubated for between 40 and 50 seconds. The sample mixture can be incubated up to an hour. In some embodiments, surprisingly effective results can be achieved by incubating the sample mixture at about 48° C. for about 45 seconds. In some embodiments, surprisingly effective results can be achieved by incubating the sample mixture at about 47° C. for about 45 seconds.

In some embodiments, the combining at block 308 and the incubating at block 310 complete in approximately the same amount of time or less time than the time it takes for a sample mixture to be processed in the imaging equipment and for the lines of the imaging equipment to be flushed and/or cleaned. In this way, a first sample mixture can be imaged while a second sample mixture is being combined and incubated. Once the first sample mixture has been imaged and the imaging equipment has been cleaned, the second sample mixture can immediately be imaged.

In alternate embodiments, the combining at block 308 and the incubating at block 310 complete in less than twice the time it takes for a sample mixture to be processed in the imaging equipment and for the lines of the imaging equipment to be flushed and/or cleaned. In this way, while a first sample mixture is being imaged, a second sample mixture can be ready to be imaged, and a third sample mixture and fourth sample mixture can be in the process of being combined and incubated. Once the first sample mixture has been imaged and the imaging equipment has been cleaned, the second sample mixture can immediately be imaged. The third sample mixture can be finishing its combining and incubating and the fourth sample mixture can still be combining and incubating. Once the second sample mixture has been imaged and the imaging equipment has been cleaned, the third sample mixture can immediately be imaged, while the fourth sample mixture begins to finish combining and incubating and a fifth sample mixture begins combining and incubating. The process can continue indefinitely to continually image sample mixtures.

Through non-trivial efforts and experimentation, it has been found that surprisingly effective results can be achieved through a combination of certain embodiments of the particle contrast agent composition 210, certain ways of combining the particle contrast agent composition 210 with the sample, and certain ways of incubating the sample mixture.

Specifically, surprisingly effective results can be achieved by using a particle contrast agent composition 210 including 90% pure or greater Crystal Violet at about 7.8 µM under staining conditions, 70% pure or greater New Methylene Blue at about 735 µM under staining conditions, 80% pure or greater Eosin-Y at about 27 µM under staining conditions, pre-treated saponin at about 50 mg/L to about 750 mg/L under staining conditions, and gluteraldehyde at about 0.1% or less under staining conditions; where the particle contrast agent 210 is combined with the sample at a ratio of particle contrast agent 210 to sample between about 3:1 and about 4:1; and where the resulting sample mixture is incubated at about 48° C. for about 45 seconds.

Certain effective particle contrast agent compositions 210 and staining procedures enable "Wright-like" stained images of vital and/or substantially intact cells to be efficaciously obtained with an automated visual analyzer using dyes in a non-alcohol based solvent system. Certain effective particle contrast agent compositions 210 and staining procedures enable rapid staining of samples such that various cellular components, nuclear lobes, and granular structures are clearly distinguishable. Certain effective particle contrast agent compositions 210 and staining procedures are suitable for supravital staining. Certain effective particle contrast agent compositions 210 and staining procedures are generate visual distinctions for particle categorization and subcategorization. Certain effective particle contrast agent compositions 210 and staining procedures are effective to enhance intracellular content features of particles in a serum, cerebrospinal fluid, pleural fluid, synovial fluid, seminal fluid, peritoneal fluid, amniotic fluid, lavage fluid, bone marrow aspirate fluid, effusions, exudates, or blood samples. Certain effective particle contrast agent compositions 210 and staining procedures are effective to stain neutrophils, lymphocytes, monocytes, eosinophils, basophils, platelets, reticulocytes, nucleated red blood cells, blasts, promyelocytes, myelocytes, metamyelocytes, casts, bacteria, epithelials, and/or parasites. Certain effective particle contrast agent compositions 210 and staining procedures are effective to generate visual distinctions for particle categorization and subcategorization, for example, by providing for differential staining of primary and secondary granules in cells, such as to aid in sub-categorization of immature granulocytes and their age determination based on the differential staining or enhancement of primary and secondary granules. Certain effective particle contrast agent compositions 210 and staining procedures are effective to generate visual distinctions for counting and characterizing red blood cells, reticulocytes, nucleated red blood cells, and platelets, as well as for white blood cell differential counting and white blood characterization and analysis. Certain effective particle contrast agent compositions 210 and staining procedures are effective to generate visual distinctions in vital and/or viable cells and/or cells with structures that remain substantially intact. Certain effective particle contrast agent compositions 210 and staining procedures are effective for staining subcellular structures of neutrophils, lymphocytes, monocytes, eosinophils, and basophils as well as reticulocytes, nucleated red blood cells, platelets, blast, promyelocyte, myelocyte, metamyelocyte, or cell fragments.

The rapid staining enabled by certain effective particle contrast agent compositions 210 and staining procedures described herein can be used with manual or semi-automated imaging and/or analysis procedures.

Through non-trivial efforts and experimentation, it has been found that surprisingly effective results can be achieved with certain embodiments of the particle contrast agent composition 210 comprising particle contrast agents in a non-alcohol based solvent system that are able, for the first time to the inventors' knowledge, to generate "Wright-like" stain images of vital and/or substantially intact cells which can reveal various cellular components, nuclear lobes, and granular structures, and make these particle and/or cellular features visually distinct.

Through non-trivial efforts and experimentation, it has been found that surprisingly effective results can be achieved when using a particle contrast agent composition 210 composed as listed in Table A1, where the Working Stain Reagent is made by mixing 40 mL of New Methyl Blue and 5 mL of Crystal Violet.

TABLE A1

| | |
|---|---|
| 50 mL | Phosphate Buffered Saline |
| 40 mL | Working Stain Reagent |
| 40 mL | 0.09% New Methyl Blue in CDS 5PD-Lytic |
| 5 mL | 0.009% Crystal Violet in CDS 5PD-Lytic |
| 10 mL | 0.5% Saponin |
| an amount sufficient to achieve 0.1% under staining conditions | Gluteraldehyde |

Figure 26:
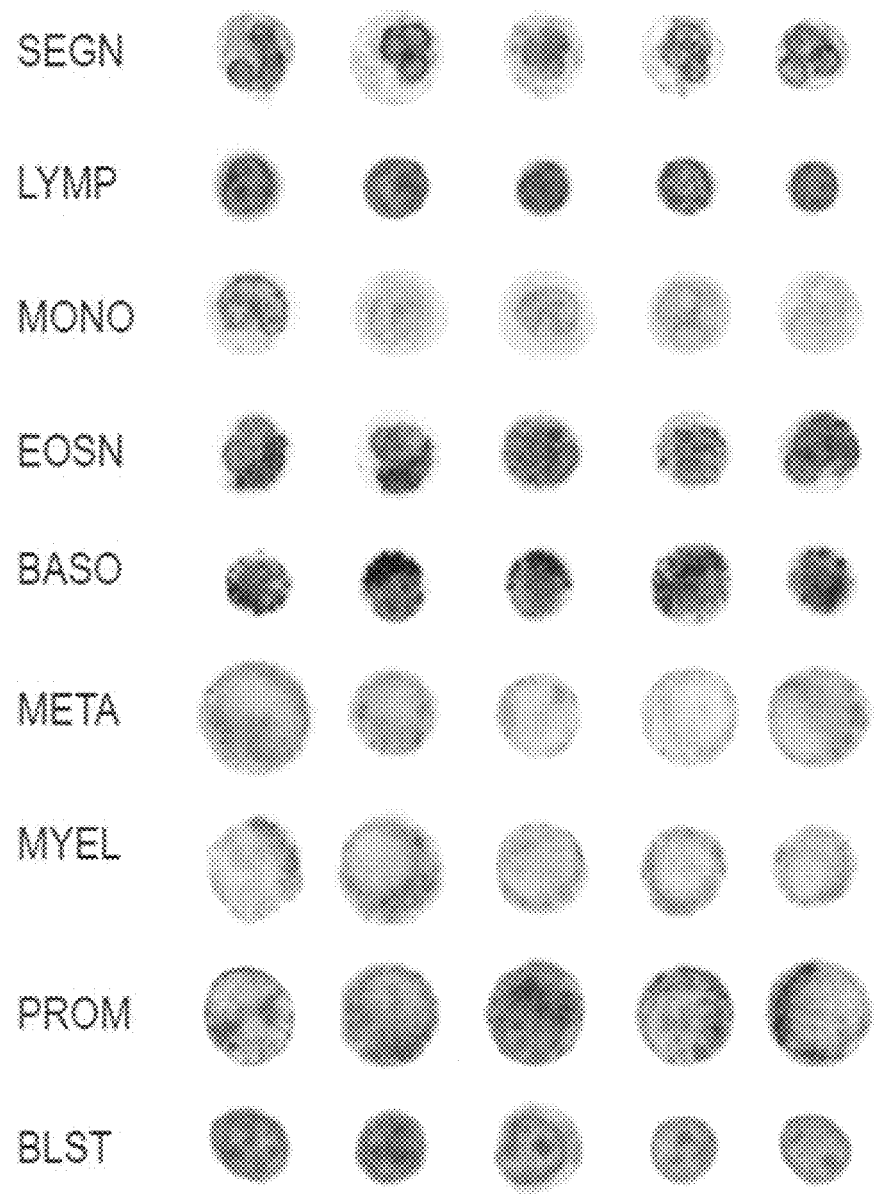
FIG. 26 is a representative illustration of selected white blood cells stained according to the rapid, one-step staining process according to one embodiment.

FIG. 26 is a representative illustration of selected white blood cells from a sample stained with the particle contrast agent composition 210 set forth in Table A1 and stained using the rapid, one-step staining procedures set forth above. The white blood cells are intact and show staining characteristics of a Wright stain. The various types of white blood cells (e.g., neutrophils, lymphocytes, monocytes, eosinophils, basophils, etc) are visually differentiable.

In some embodiments, features of cells stained by the particle contrast agent compositions of this disclosure are noted in Table A2.

TABLE A2

| Cell Type/ Cell Substructure | Size (relative to RBC) | Shape | Color | Details |
|---|---|---|---|---|
| RBC | Standard | Round | | Central Pallor |
| Nucleated RBC | Standard | Round | Stained Nucleus | |
| NEUT | Large | Round to Oval | Nucleus Stained | Cytoplasmic Granules |
| NEUT: Nucleus | Interm. % | Segmented | Colored by Stain | Multiple Lobes |
| LYMP | Standard to small | Round to Ovoid | Nucleus Stained | Small Cytoplasm |
| LYMP: Nucleus | Large % | Round | Colored by Stain | Single Lobed |
| MONO | Large | Round | Nucleus Stained Lightly Colored cytoplasm | Large Cytoplasm |
| MONO: Nucleus | Interm % | Irregular | Colored by Stain | Nucleus Stains Light |
| EOS | Intermediate | Round | Stained Nucleus and Granules | Coarse large granules |
| EOS: Nucleus | Small to Interm. % | Segmented | Colored by Stain | Multiple Large Lobes |
| BASO | Standard to Small | Round | Nucleus and Granules stained | Coarse dense granules in Cytoplasm |
| BASO: Nucleus | Large % | Segmented | Colored by Stain | May be Obscured by Dark Granules |

In certain embodiments, the stain/dye composition is formulated for stability, ease of storage, disposal, and/or limited toxicity.

Figure 27:
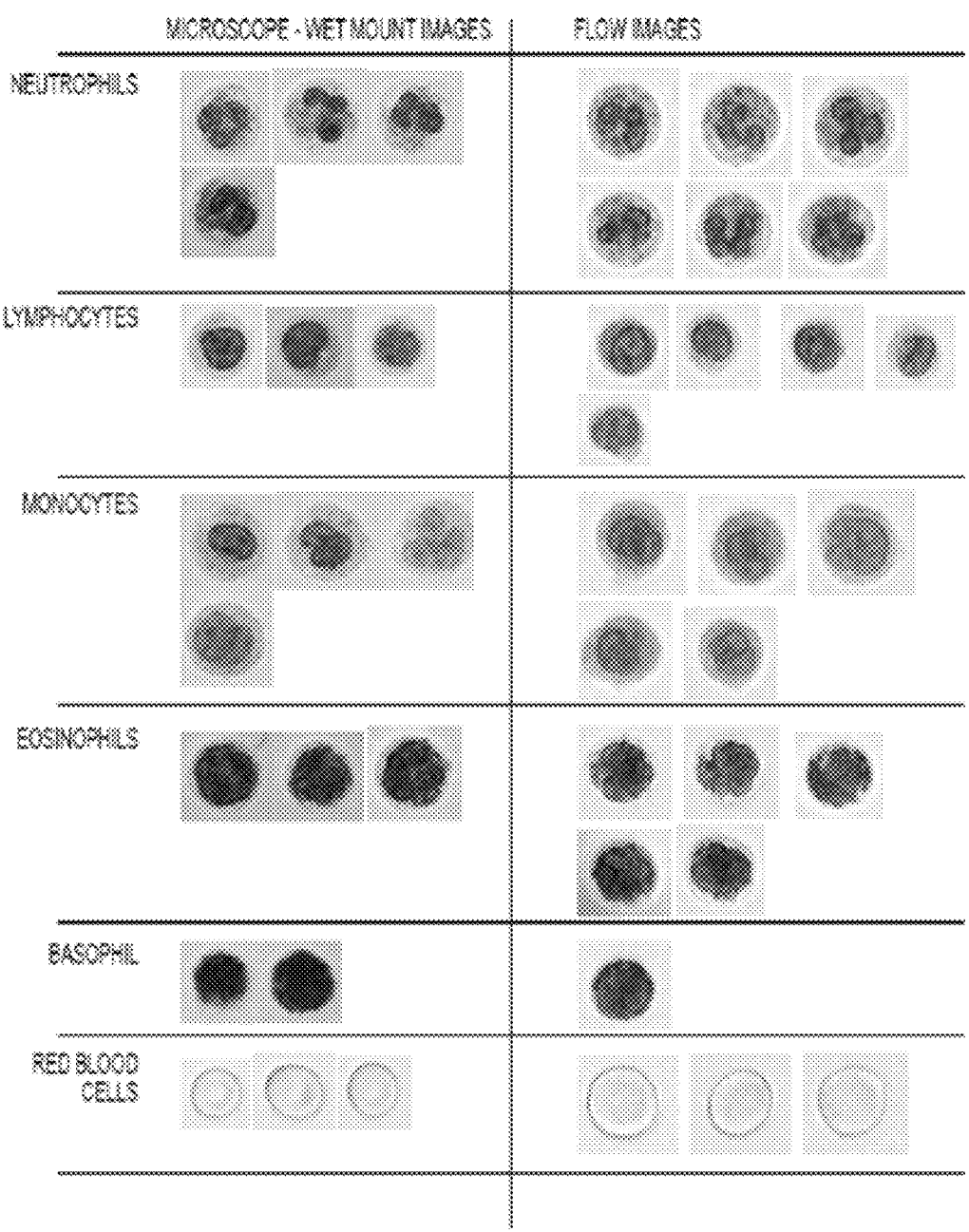
FIG. 27 is a representative illustration of selected while blood cells from a sample stained with a particle contrast agent composition according to one embodiment.

FIG. 27 is a representative illustration of selected white blood cells from a sample stained with the particle contrast agent composition 210 according to one embodiment, including cells imaged through manual, wet mount imaging and automatic flow imaging.

Early Experimentation

As described with reference to the examples below, numerous staining compositions and methods were tested and modified in order to result in the embodiments disclosed above.

Figure 28:
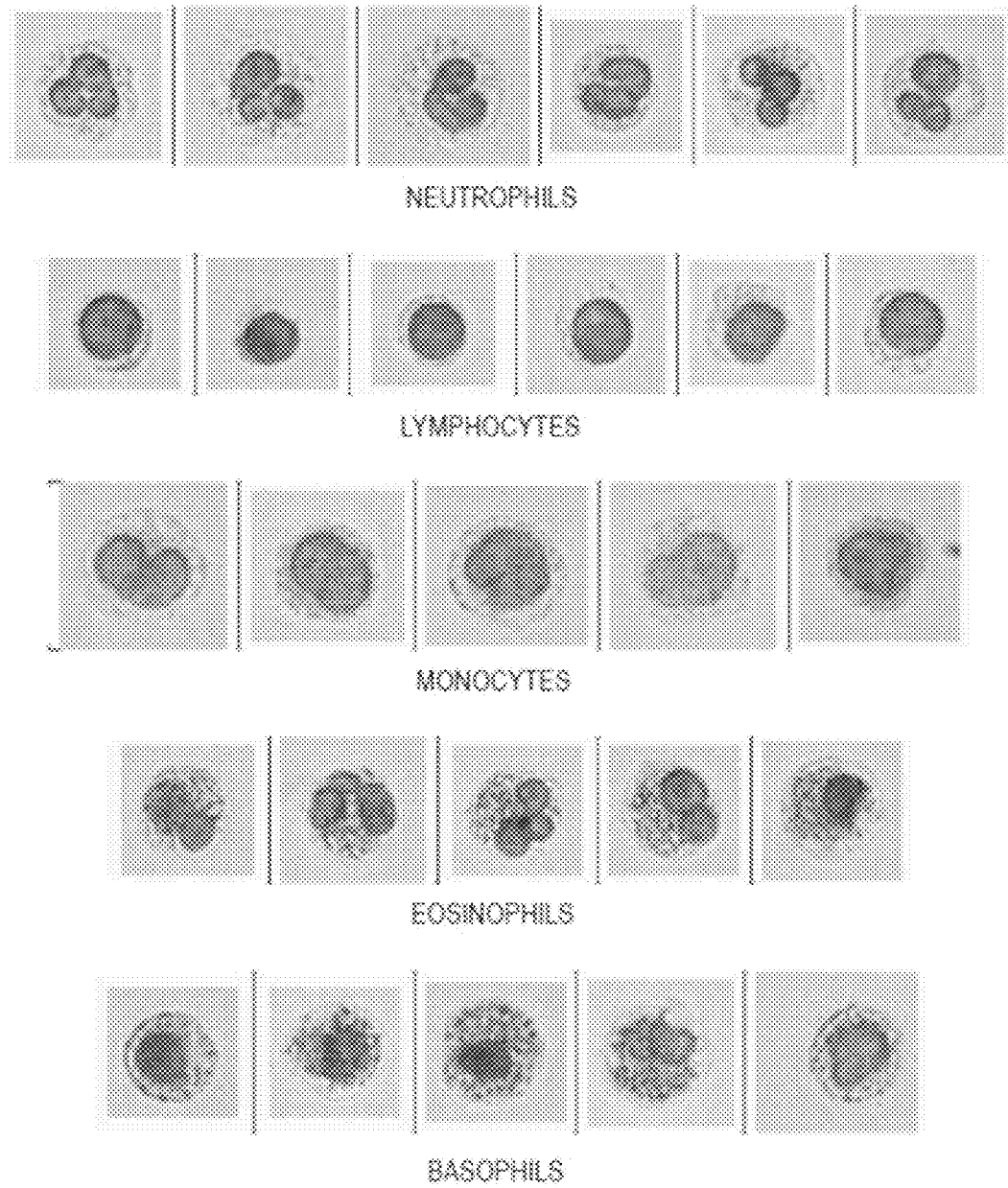
FIG. 28 is a representative illustration of stained cells according to an early Example 1.

In an early Example 1, a two-step staining method existed where a sample and an early embodiment of a particle contrast agent composition were combined and incubated for 40 seconds at 47.5° C., and then a quenching reagent was applied to the sample mixture. The particle contrast agent composition included Coulter LH Series Dilutent, Coulter Lyse S III diff Lytic Reagent, Coulter LH Series Pak Reagent Kit, and Coulter LH Series RETIC PAK Reagent Kit. The results are seen in FIG. 28.

Figure 29:
FIG. 29 is a representative illustration of stained cells according to an early Example 2.
Figure 29:

In an early Example 2 after Example 1, the two-step staining method of Example 1 was replaced by a one-step staining method. The improved results of Basophils are seen in FIG. 29 as compared to the results of Example 1.

In an early Example 3, a particle contrast agent composition without including gluteraldehyde resulted in weakened white blood cells that would break apart because of the shear forces in the flowcell. Images of the results of Example 3 showing damaged membranes are shown in FIG. 30.

In an early Example 4 after Example 3, gluteraldehyde was added to the particle contrast agent composition. The white blood cell membranes were more intact in Example 4, but the nucleus membranes were still damaged. After making adjustment to the PIOAL to reduce the glycerol content, the morphology of the white blood cells were mostly unchanged during imaging, as shown in FIG. 31.

In early examples with two-dye stains using particle contrast agent compositions of New Methylene Blue and Crystal Violet, most cell types were well distinguishable except for eosinophils, which were somewhat inconsistent and not always easy to distinguish from neutrophils, as shown in FIG. 32. In a subsequent Examples 5 and 6, a third particle contrast agent was added to the particle contrast agent composition.

In Example 5, Methyl Green was added to the particle contrast agent composition. The methyl green helped stain the eosinophils better, but the nucleus of the cells no longer stains with the desired purple, but blue. FIG. 33 depicts images of Example 5 neutrophils with blue-stained nuclei, but lost granular detail.

Figure 34:
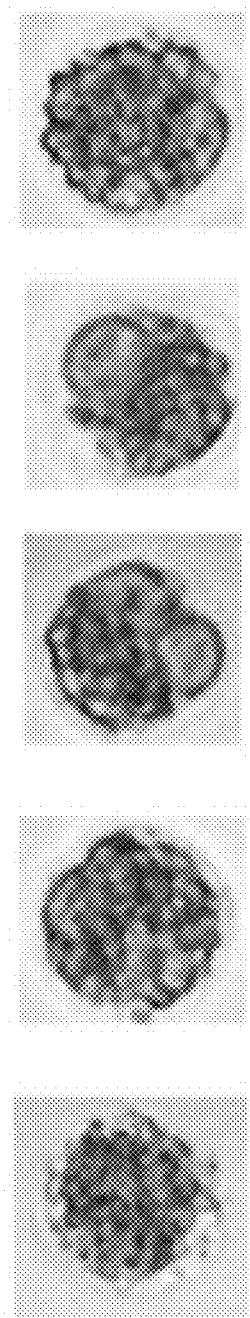
FIG. 34 is a representative illustration of stained cells according to an early Example 6.

In Example 6, Eosin-Y was used instead of Methyl Green as a third particle contrast agent in the particle contrast agent composition. The Eosin-y retained a purple stain of the nucleus and the granules stain consistently with a slightly orange shine, as seen in FIG. 34.

Through the experimentation mentioned above and additional experimentation, it has been determined that the disclosed embodiments and claimed embodiments provide preferential results.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A method for imaging particles using a particle analysis system configured for combined viscosity and geometric hydrofocusing, the particles included within a blood fluid sample, the method comprising:
   injecting a sheath fluid along a flowpath of a flowcell of the particle analyzer, the sheath fluid having a viscosity that is different from a viscosity of the blood fluid sample;
   injecting the blood fluid sample from a sample fluid injection tube at a flow rate into the flowing sheath fluid within the flowcell so as to provide a sample fluid stream having a first thickness adjacent the injection tube, the flowpath of the flowcell having a decrease in flowpath size such that thickness of the sample fluid stream decreases from the initial thickness to a second thickness adjacent an image capture site; and
   imaging a first plurality of the particles from the sample at the image capture site of the flowcell;
   wherein the decrease in flowpath size is defined by a proximal flowpath transition zone portion having a proximal thickness, and distal flowpath transition zone portion having a distal thickness less than the proximal thickness, and,
   wherein the viscosity difference between the sheath and blood fluid samples, in combination with the decrease in flowpath size and the flow rate of the sample, is effective to deliver cells in the sample from the sample fluid injection tube to the image capture site in a nonzero transit time that is four seconds or less.

2. The method according to claim 1, wherein the imaging step is performed along an imaging axis, and wherein a distance between the distal flowpath transition zone portion and the imaging axis is within a range from about 16 mm to about 26 mm.

3. The method according to claim 1, wherein the imaging step is performed along an imaging axis, and wherein a distance between the distal flowpath transition zone portion and the imaging axis is about 21 mm.

4. The method according to claim 1, wherein the imaging step is performed along an imaging axis, and wherein a distance between the distal flowpath transition zone portion and the imaging axis is about 8.24 mm.

5. The method according to claim 1, wherein the sample fluid injection tube has an exit port, and wherein a distance between the exit port and the distal flowpath transition zone portion is about 12.54 mm.

6. The method according to claim 1, wherein the flowcell defines a sheath fluid entrance, and wherein a distance between the sheath fluid entrance and the distal flowpath transition zone portion is about 12.7 mm.

7. The method according to claim 1, wherein the sample fluid injection tube has an exit port, and wherein a distance between the exit port and the proximal flowpath transition zone portion is about 0.73 mm.

8. The method according to claim 1, wherein the sample fluid injection tube has an exit port, and wherein the exit port is disposed proximal to the proximal flowpath transition zone portion and the distal flowpath transition zone portion.

9. The method according to claim 1, wherein the sample fluid injection tube has an exit port, and wherein the exit port is disposed distal to the proximal flowpath transition zone portion and proximal to the distal flowpath transition zone portion.

10. The method according to claim 1, wherein the decrease in flowpath size is defined by opposed walls of the flowpath angling radially inwardly along the flowpath generally symmetric about a transverse plane that bisects the sample fluid stream initial and second thicknesses.

11. The method according to claim 1, wherein the initial thickness is about 150 μm and the second thickness is about 2 μm.

12. The method according to claim 1, wherein the sample fluid stream has a compression ratio of 75:1.

13. The method according to claim 1, wherein the initial thickness is within a range from about 50 μm to about 250 um and the second thickness is within a range from about 2 μm to about 10 μm.

14. The method according to claim 1, wherein the second thickness is smaller than at least some of the particles.

15. The method according to claim 1, wherein a velocity of the sheath fluid traveling between the proximal flowpath transition zone portion and the distal flowpath transition zone portion is greater than a velocity of the sheath fluid traveling at the proximal flowpath transition zone portion.

16. The method according to claim 1, wherein the image capture site has a field of view of between about 150 μm×150 μm and 400 μm×400 μm.

17. The method according to claim 1, wherein the image capture site has a field of view of about 275 μm×275 μm.

18. The method according to claim 1, wherein the sample fluid injection tube comprises an exit port having a height of about 150 μm and a width of about 1350 μm.

19. The method according to claim 1, wherein the blood fluid sample exiting the sample fluid injection tube has a first width, and wherein the blood fluid sample at the image capture site has a second width that is equal to the first width.

20. The method according to claim 1, wherein the blood fluid sample exiting the sample fluid injection tube has a width of about 1350 μm, and wherein the blood fluid sample at the image capture site has a width of about 1350 μm.

* * * * *